(12) United States Patent
Aono et al.

(10) Patent No.: US 11,186,588 B2
(45) Date of Patent: Nov. 30, 2021

(54) 6H-THIENO[2,3-E][1,2,4]TRIAZOLO[3,4-C][1,2,4]TRIAZEPINE DERIVATIVE

(71) Applicant: AYUMI PHARMACEUTICAL CORPORATION, Tokyo (JP)

(72) Inventors: Hiroyuki Aono, Kyoto (JP); Iwao Seki, Kyoto (JP); Miwa Imamura, Kyoto (JP); Tomomi Tanaka, Kyoto (JP); Satoshi Shirae, Kyoto (JP); Kenji Kawashima, Ikoma (JP); Yusuke Yamazaki, Ikoma (JP); Minoru Yamamoto, Ikoma (JP)

(73) Assignee: AYUMI PHARMACEUTICAL CORPORATION, Tokyo (JP)

( * ) Notice: Subject to any disclaimer, the term of this patent is extended or adjusted under 35 U.S.C. 154(b) by 35 days.

(21) Appl. No.: 16/617,201

(22) PCT Filed: May 31, 2018

(86) PCT No.: PCT/JP2018/021040
§ 371 (c)(1),
(2) Date: Nov. 26, 2019

(87) PCT Pub. No.: WO2018/221679
PCT Pub. Date: Dec. 6, 2018

(65) Prior Publication Data
US 2021/0130367 A1 May 6, 2021

(30) Foreign Application Priority Data
May 31, 2017 (JP) .............................. JP2017-108401

(51) Int. Cl.
C07D 495/14 (2006.01)
A61P 37/06 (2006.01)
A61P 19/02 (2006.01)

(52) U.S. Cl.
CPC ............ *C07D 495/14* (2013.01); *A61P 19/02* (2018.01); *A61P 37/06* (2018.01)

(58) Field of Classification Search
CPC .................................................. C07D 495/14
See application file for complete search history.

(56) References Cited

U.S. PATENT DOCUMENTS

| | | | |
|---|---|---|---|
| 4,455,307 A | 6/1984 | Hester, Jr. | |
| 5,807,850 A * | 9/1998 | Nakamura | C07D 255/04 514/183 |
| 8,044,042 B2 * | 10/2011 | Adachi | A61P 37/08 514/219 |
| 2012/0157428 A1 | 6/2012 | Albrecht et al. | |
| 2016/0375032 A1 | 12/2016 | Riveiro et al. | |

FOREIGN PATENT DOCUMENTS

| | | |
|---|---|---|
| EP | 0934940 A1 | 8/1999 |
| JP | S58118513 A | 7/1983 |
| JP | H11228576 A | 8/1999 |
| JP | 2013544847 A | 12/2013 |
| JP | 2016538307 A | 12/2016 |
| WO | 9616062 A1 | 5/1996 |
| WO | WO9616062 * | 5/1996 |
| WO | 9747622 A1 | 12/1997 |
| WO | WO9747622 * | 12/1997 |
| WO | 2015078928 A1 | 6/2015 |
| WO | 2016207204 A1 | 12/2016 |

OTHER PUBLICATIONS

Deepak, V. et al., "In silico design and bioevaluation of selective benzotriazepine BRD4 inhibitors with potent antiosteoclastogenic activity", Chemical Biology Drug Design, vol. 90, Issue 1, pp. 97-111, 2017.
Ding, N. et al., "BRD4 is a novel therapeutic target for liver fibrosis", Proc Natl Acad Sci, vol. 112, No. 51, pp. 15713-15718, Dec. 22, 2015.
Filippakopoulos, P. et al., "Benzodiazepines and benzotriazepines as protein interaction inhibitors targeting bromodomains of the BET family", Bioorganic & Medicinal Chemistry, 20 (6), pp. 1878-1886, 2012.
International Search Report (PCT/ISA/210) dated Aug. 14, 2018, by the Japan Patent Office as the International Searching Authority for International Application No. PCT/JP2018/021040.
Jahagirdar, R. et al., "A novel BET bromodomain inhibitor, RVX-208, shows reduction of atherosclerosis in hyperlipidemic ApoE deficient mice", Atherosclerosis, 236 (1), pp. 91-100, Sep. 2014.
Klein, K. et al., "The bromodomain protein inhibitor I-BET151 suppresses expression of inflammatory genes and matrix degrading enzymes in rheumatoid arthritis synovial fibroblasts", Ann Rheum Dis, 75 (2), pp. 422-429, Feb. 2016.
Li, Z. et al., "The BET bromodomain inhibitor JQ1 activates HIV latency through antagonizing Brd4 inhibition of Tat-transactivation", Nucleic Acids Research, vol. 41, No. 1, pp. 277-287, Jan. 2013.
Magistri, M. et al., "The BET-Bromodomain Inhibitor JQ1 Reduces Inflammation and Tau Phosphorylation at Ser396 in the Brain of the 3xTg Model of Alzheimer's Disease", Current Alzheimer Research, 13 (9), pp. 985-995, 2016.
Matzuk, M. et al., "Small-Molecule Inhibition of BRDT for Male Contraception", Cell, 150 (4), pp. 673-684, Aug. 17, 2012.
Nadeem, A. et al., "Imiquimod-induced psoriasis-like skin inflammation is suppressed by BET bromodomain inhibitor in mice through RORC/IL-17A pathway modulation", Pharmacological Research, 99, pp. 248-257, Sep. 2015.
Nicodeme, E. et al., "Suppression of inflammation by a synthetic histone mimic", Nature, vol. 468, 7327, pp. 1119-1123, Dec. 2010.
Siebel, A. et al., "Effects of the BET-inhibitor, RVX-208 on the HDL lipidome and glucose metabolism in individuals with prediabetes: A randomized controlled trial", Metabolism, 65 (6), pp. 904-914, Jun. 2016.

(Continued)

*Primary Examiner* — Paul V Ward
(74) *Attorney, Agent, or Firm* — Buchanan Ingersoll & Rooney PC

(57) ABSTRACT

The 6H-thieno[2,3-e][1,2,4]triazolo[3,4-c][1,2,4]triazepine derivatives or salts thereof of the present invention have BRD4 inhibitory activity, and thus, they are useful as medicaments, in particular, as prophylaxis and/or therapeutic agents for diseases associated with BRD4.

9 Claims, No Drawings

(56) References Cited

OTHER PUBLICATIONS

Spiltoir, J. et al., "BET acetyl-lysine binding proteins control pathological cardiac hypertrophy", Journal of Molecular and Cellular Cardiology, 63, pp. 175-179, 2013.
Wei, S. et al., "Therapeutic targeting of BET protein BRD4 delays murine lupus", International Immunopharmacology, 29 (2), pp. 314-319, Dec. 2015.
Written Opinion (PCT/ISA/237) dated Aug. 14, 2018, by the Japan Patent Office as the International Searching Authority for International Application No. PCT/JP2018/021040.
Zhou, X. et al., "Therapeutic targeting of BET bromodomain protein, Brd4, delays cyst growth in ADPKD", Human Molecular Genetics, vol. 24, No. 14, pp. 3982-3993, Jul. 2015.
Examination Report dated Mar. 18, 2021, by the Indian Patent Office in corresponding Indian Patent Application No. 201947053070 and an English translation of the Report. (8 pages).
Elattar et al., "Advances in 1,2,4-triazepines chemistry," RSC Advances, 2015, vol. 5, pp. 106710-106753.

\* cited by examiner

6H-THIENO[2,3-E][1,2,4]TRIAZOLO[3,4-C][1,2,4]TRIAZEPINE DERIVATIVE

TECHNICAL FIELD

The present invention relates to novel 6H-thieno[2,3-e][1,2,4]triazolo[3,4-c][1,2,4]triazepine derivatives of formula (I):

[Chem. 1]

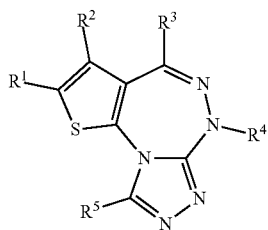

wherein $R^1$ to $R^5$ are as defined in the present specification or salts thereof. 6H-thieno[2,3-e][1,2,4]triazolo[3,4-c][1,2,4]triazepine derivatives of formula (I) or salts thereof of the present invention (hereinafter also referred to as the present compounds) have BRD4 inhibitory activity, and thus, they are useful as medicaments, in particular, for the prophylaxis or treatment of diseases associated with BRD4.

BACKGROUND ART

Bromodomain is a protein domain that is known to have the functions of recognizing acetylated lysine of histone, and controlling chromatin structure and gene expression by collecting regulatory proteins. BRD2, BRD3, BRD4 and BRDT are known as BET (bromodomain and extra-terminal) family protein that has a bromo domain repeat sequence and a specific terminal sequence, and it plays an important role in various intracellular processes such as inflammation related gene expression, cell division, virus/host interaction.

Patent Literature 1 describes that 6H-thieno[3,2-f][1,2,4]triazolo[4,3-a][1,4]diazepine derivatives inhibit binding of acetylated histone H4 to a transcriptional regulator family containing tandem bromodomain (BRD) that has been known as a BET protein (including BRD2, BRD3 and BRD4).

Non-Patent Literature 1 describes that a bromo domain protein inhibitor I-BET151 is useful for rheumatoid arthritis. Non-Patent Literatures 2-10 report that a BRD4 inhibitor JQ1 is useful for systemic lupus erythematosus, lupus nephritis, psoriasis, proliferative diseases, hepatic fibrosis, hypertrophic cardiomyopathy, viral infections, contraception, Alzheimer's disease and cystic disease of kidney. Non-Patent Literatures 11 and 12 report that a BET inhibitor RVX-208 is useful for type II diabetes and atherosclerosis.

PRIOR ART DOCUMENTS

Patent Literatures

Patent Literature 1: WO2015/078928

Non-Patent Literatures

Non-Patent Literature 1: Ann Rheum Dis. 2016 February; 75(2): 422-9.

Non-Patent Literature 2: Int immunopharmacol. 2015 December; 29(2): 314-9.

Non-Patent Literature 3: Pharmacol Res. 2015 September; 99: 248-57.

Non-Patent Literature 4: Nature 468, 7327

Non-Patent Literature 5: Proc Natl Acad Sci USA. 2015 Dec. 22; 112(51): 15713-8.

Non-Patent Literature 6: J Mol Cell Cardiol. 2013 October; 63: 175-9.

Non-Patent Literature 7: Nucleic Acids Res. 2013 Jan. 7; 41 (1): 277-87.

Non-Patent Literature 8: Cell. 2012 Aug. 17; 150(4): 673-684.

Non-Patent Literature 9: Curr Alzheimer Res. 2016; 13(9): 985-95.

Non-Patent Literature 10: Hum Mol Genet. 2015 Jul. 15; 24(14): 3982-3993.

Non-Patent Literature 11: Atherosclerosis. 2014 September; 236(1)

Non-Patent Literature 12: Metabolism. 2016 June; 65(6): 904-14.

SUMMARY OF THE INVENTION

Technical Problem

An object of the present invention is to provide novel 6H-thieno[2,3-e][1,2,4]triazolo[3,4-c][1,2,4]triazepine derivatives or salts thereof.

Solution to Problem

The present inventors have conducted synthetic study of 6H-thieno[2,3-e][1,2,4]triazolo[3,4-c][1,2,4]triazepine derivatives or salts thereof, and succeeded in producing new compounds. Further, as a result of the pharmacological action research of the compounds, we have found that 6H-thieno[2,3-e][1,2,4]triazolo[3,4-c][1,2,4]triazepine derivatives or salts thereof have BRD4 inhibitory activity and are useful as medicaments, whereby the present invention is completed.

The present invention relates to novel compounds of formula (I):

[Chem. 2]

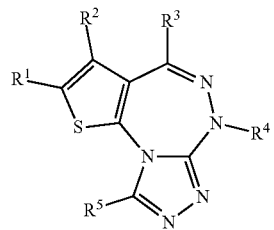

wherein
  $R^1$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy;
  $R^2$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy;
  $R^3$ is unsubstituted or substituted aryl, unsubstituted or substituted heteroaryl or bicyclopentane, wherein the substituted aryl or the substituted heteroaryl is substituted with at least one substituent(s) selected from the group consisting of halogen, hydroxy, amino, nitro, cyano, carboxy, $C_{1-6}$ alkyl, halo-$C_{1-6}$ alkyl, hydroxy- $C_{1-6}$ alkyl, $C_{1-6}$ alkoxy, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$;

$R^4$ is H, unsubstituted or substituted aryl-$C_{1-6}$ alkyl, unsubstituted or substituted heteroaryl-$C_{1-6}$ alkyl, unsubstituted or substituted aryl-$NR^bC(O)$—, unsubstituted or substituted heteroaryl-NRC(O)—, unsubstituted or substituted aryl-$C_{1-6}$ alkyl-$NR^bC(O)$—, or unsubstituted or substituted heteroaryl-$C_{1-6}$ alkyl-$NR^bC(O)$—, wherein the substituted aryl and the substituted heteroaryl are substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$;

$R^5$ is H, halogen, $C_{1-6}$ alkyl, halo-$C_{1-6}$ alkyl, hydroxy-$C_{1-6}$ alkyl, $C_{1-6}$ alkoxy, halo-$C_{1-6}$ alkoxy or hydroxy-$C_{1-6}$ alkoxy;

$R^a$ is H, $C_{1-6}$ alkyl or halo-$C_{1-6}$ alkyl; and $R^b$ is H, $C_{1-6}$ alkyl or halo-$C_{1-6}$ alkyl or salts thereof (hereinafter also referred to as "the present compound"), use of the compounds of formula (I) or salts thereof for the prophylaxis and/or treatment of diseases associated with BRD4, and methods of the prophylaxis and/or treatment of diseases associated with BRD4 comprising administering the compounds of formula (I) or salts thereof. The present invention also relates to medicaments comprising the compounds of formula (I) or salts thereof, and methods for producing the compounds of formula (I) or salts thereof and medicaments comprising the same.

Effects of Inventions

The present invention can provide novel 6H-thieno[2,3-e][1,2,4]triazolo[3,4-c][1,2,4]triazepine derivatives or salts thereof. The present compounds have BRD4 inhibitory activity, and are useful as medicaments, in particular, for the prophylaxis and/or treatment of diseases associated with BRD4 inhibition, i.e. for example, autoimmune diseases, inflammatory diseases, proliferative diseases, metabolic diseases, fibrotic diseases, cardiomyopathy, virus infectious diseases, neurodegenerative diseases, or for contraception.

DESCRIPTION OF EMBODIMENTS

The present invention is hereinbelow described in detail.

In the present invention, "halogen" indicates fluorine, chlorine, bromine or iodine.

In the present invention, "hydroxy" indicates —OH group.

In the present invention, "amino" indicates —$NH_2$ group.

In the present invention, "cyano" indicates —CN group.

In the present invention, "nitro" indicates —$NO_2$ group.

In the present invention, "lower alkyl" indicate a linear or branched alkyl group having 1 to 8 carbon atoms, preferably 1 to 6 carbon atoms, particularly preferably 1 to 4 carbon atoms. Specific examples include methyl, ethyl, n-propyl, n-butyl, n-pentyl, n-hexyl, n-heptyl, n-octyl, isopropyl, isobutyl, sec-butyl, tert-butyl, isopentyl.

In the present invention, "lower cycloalkyl" indicate a cycloalkyl group having 3 to 8 carbon atoms, preferably 3 to 6 carbon atoms. Specific examples include cyclopropyl, cyclobutyl, cyclopentyl, cyclohexyl, cycloheptyl, cyclooctyl.

In the present invention, "aryl" indicates a residue wherein one hydrogen atom is removed from a monocyclic aromatic hydrocarbon having 6 to 14 carbon atoms, or bicyclic or tricyclic fused polycyclic aromatic hydrocarbon. Specific examples include phenyl, naphthyl, anthryl, phenanthryl.

In the present invention, "heteroaryl" indicates a 5- or 6-membered aromatic ring having 1, 2, 3 or 4 heteroatoms selected from N, S or O. Specific examples include pyridinyl, pyrimidinyl, pyridazinyl, pyrazinyl, imidazolyl, pyrazolyl, thiazolyl, 1,3,4-oxadiazolyl, 1,2,4-oxadiazolyl, 1,2,4-triazolyl, 1,2,3-triazolyl, isoxazolyl, tetrazolyl, 1,2,4-thiadiazolyl, isothiazolyl, oxazolyl, thienyl.

In the present invention, N-heteroatom in the heteroaryl group can be oxidized to $N^+$—$(O^-)$.

In the present invention, "lower alkoxy" indicate a group wherein the hydrogen atom of the hydroxyl group is substituted with a lower alkyl group. Specific examples include methoxy, ethoxy, n-propoxy, n-butoxy, n-pentoxy, n-hexyloxy, n-heptyloxy, n-octyloxy, isopropoxy, isobutoxy, sec-butoxy, tert-butoxy, isopentoxy.

In the present invention, the term "hydroxy-lower alkyl" means a group wherein the lower alkyl is as defined above, and at least one hydrogen atom is substituted with a hydroxy group.

In the present invention, the term "halo-lower alkyl" means a group wherein the lower alkyl is as defined above, and at least one hydrogen atom is substituted with a halogen atom.

In the present invention, the terms "hydroxy-lower alkoxy" mean a group wherein the lower alkoxy is as defined above, and at least one hydrogen atom is substituted with a hydroxy group.

In the present invention, the terms "halo-lower alkoxy" mean a group wherein the lower alkoxy is as defined above, and at least one hydrogen atom is substituted with a halogen atom.

In the present invention, the "salt" is not particularly limited as long as it is a pharmaceutically acceptable salt. The "salt" includes, for example a salt with an inorganic acid or an organic acid, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid. In the present invention, the salt of the present compound is preferably a salt of the present compound with hydrochloric acid, succinic acid, fumaric acid, p-toluenesulfonic acid or maleic acid, and more preferably a salt of the present compound with hydrochloric acid.

In the present invention, when a geometric isomer and/or an optical isomer exist in the present compound, these isomers are also included in the present invention.

In the present invention, when proton tautomerism exists in the present compound, these tautomers (keto, enol) are also included in the present invention.

In the present invention, when a hydrate and/or a solvate exist in the present compound, these hydrate and/or solvate are also included in the present invention.

In the present invention, when a crystal polymorph and/or a crystal polymorph group (crystal polymorph system) is/are exist in the present compound, these crystal polymorphs and/or crystal polymorph groups (crystal polymorph system) are also included in the present invention. Here, the crystal polymorph group (crystal polymorph system) refers to a crystal form and/or the whole thereof in each step when the form of the crystal variously changes depending on the conditions and/or states (incidentally, a formulated state is also included in said states), such as production, crystallization, storage, of these crystals. In the present invention, the crystal polymorph and/or crystal polymorph group of the present compound, for example, is preferably, a crystal of a salt of the present compound with hydrochloric acid, succinic acid, fumaric acid, p-toluenesulfonic acid or maleic acid, and more preferably a crystal of a salt of the present compound with hydrochloric acid.

In the present invention, the present invention also encompasses pharmaceutically acceptable prodrugs of the compounds of formula (I) or salts thereof.

The pharmaceutically acceptable prodrugs refer to compounds having a group that can be converted to, for example an amino group, a hydroxy group, a carboxy group by solvolysis or under physiological conditions. Examples of the group that can form a prodrug include, for example, groups described in Progress in Medicine, Vol. 5, pp. 2157-2161, 1995 and "Development of pharmaceuticals" (Hirokawa-Shoten Ltd., 1990), Vol. 7, Molecular Design 163-198.

In the present invention, the present compound itself may be a prodrug.

In the present invention, "pharmaceutical composition" means a composition that can be use as a medicament. The pharmaceutical composition of the present invention may contain the present compound or a salt thereof and a pharmaceutically acceptable additives (for example, an excipient, a binder, a disintegrator, a coating agent, a stabilizer, a corrigent (for example a sweetener, an acidifier, a flavoring agent), an isotonizing agent, a buffering agent, a surfactant, a stabilizer, a preservative, a pH adjusting agent, an analgesic), which can be used and prepared in a necessary amount, where necessary.

In the present invention, "BRD4 inhibitor" refers to a compound having an inhibitory action on binding of BRD4 to histone by binding to BRD4.

In the present invention, diseases associated with BRD4 are not particularly limited as long as they can be prophylaxis and/or treated with a BRD4 inhibitor.

In the present invention, examples of the "disease associated with BRD4" include, for example, autoimmune diseases, inflammatory diseases, proliferative diseases, metabolic diseases, fibrotic diseases, cardiomyopathy, virus infectious diseases, neurodegenerative diseases.

In the present invention, autoimmune diseases and/or inflammatory diseases include, for example, rheumatoid arthritis, systemic lupus erythematosus, osteoarthritis, juvenile idiopathic arthritis, ankylosing spondylitis, chronic obstructive pulmonary disease, Crohn's disease, ulcerative colitis, Sjoegren's disease, multiple sclerosis, psoriasis, psoriatic arthritis, septicemia, uveitis, scleritis, retinitis, age-related macular degeneration, proliferative vitreoretinopathy, proliferative diabetic retinopathy, optic neuromyelitis, Behcet's disease, Castleman's disease, atherosclerosis, acute gout, Kawasaki disease, Hashimoto's disease, lupus nephritis, glomerular nephritis, multiple myositis, multiple dermatitis, scleroderma, atopic dermatitis, Wegener's granulomatosis, polyarteritis nodosa, Takayasu's arteritis, pulmonary arterial hypertension, tissue graft versus host disease, acute rejection of transplanted organs, type I diabetes, sarcoidosis, Addison's disease, encephalitis, vasculitis, hypophysitis, thyroiditis, asthma, pneumonia, hepatitis, myocarditis, pericarditis, non-alcoholic steatohepatitis.

In the present invention, proliferative diseases may include, for example, cancer, in particular renal cell cancer, glioblastoma, rhabdomyosarcoma, malignant melanoma, epidermoid cancer, lung cancer, renal cancer, pancreatic ductal cancer, breast adenocarcinoma, breast cancer, breast ductal carcinoma, pancreatic cancer, cervical cancer, squamous cell carcinoma, acute lymphatic leukemia, colorectal cancer, medulloblastoma, colon adenocarcinoma, prostatic cancer, colon cancer, transitional cell cancer, leukemia, chronic myeloid leukemia, myelogenous osteosarcoma, non-small cell lung cancer, small cell lung cancer, ovarian cancer, ovarian teratoma, bladder papilloma, ganglioneuroblastoma, large-cell immunoblastic lymphoma, T-lymphoblastic lymphoma, thyroid cancer, astrocytoma, glioblastoma multiforme, epithelial cancer, NUT midline cancer, liver cancer and hepatocellular carcinoma, preferably renal cell cancer, renal cell cancer, rhabdomyosarcoma, lung cancer, pancreatic ductal cancer, breast cancer, breast ductal carcinoma, pancreatic cancer, cervical cancer, squamous cell carcinoma, acute lymphatic leukemia, colorectal cancer, medulloblastoma, colon adenocarcinoma, prostatic cancer, colon cancer, transitional cell cancer, leukemia, chronic myeloid leukemia, myelogenous osteosarcoma, non-small cell lung cancer, ovarian cancer, ovarian teratoma, large-cell immunoblastic lymphoma, T-lymphoblastic lymphoma, thyroid cancer, epithelial cancer and NUT midline cancer, more preferably renal cell cancer, pancreatic ductal cancer, breast ductal carcinoma, pancreatic cancer, cervical cancer, acute lymphatic leukemia, colorectal cancer, leukemia, chronic myeloid leukemia, ovarian cancer, ovarian teratoma, large-cell immunoblastic lymphoma, T-lymphoblastic lymphoma, thyroid cancer, epithelial cancer and NUT midline cancer, and still more preferably breast ductal carcinoma, acute lymphatic leukemia, leukemia, chronic myeloid leukemia, ovarian teratoma, large-cell immunoblastic lymphoma, T-lymphoblastic lymphoma and NUT midline cancer.

In the present invention, the cancer is, for example, renal cancer, in particular renal cell cancer.

In the present invention, the cancer is, for example, lung cancer, in particular non-small cell lung cancer and small cell lung cancer.

In the present invention, the cancer is, for example, pancreatic cancer, in particular pancreatic ductal cancer.

In the present invention, the cancer is, for example, liver cancer, in particular hepatocellular carcinoma.

In the present invention, the cancer is, for example, colon cancer, colorectal cancer and colon adenocarcinoma, in particular colorectal cancer.

In the present invention, the cancer is, for example, breast cancer, breast adenocarcinoma and breast ductal carcinoma, in particular breast ductal carcinoma.

In the present invention, the cancer is, for example, cervical cancer, ovarian cancer and ovarian teratoma, in particular ovarian teratoma.

In the present invention, the cancer is, for example, prostatic cancer and bladder papilloma.

In the present invention, the cancer is, for example, rhabdomyosarcoma and myelogenous osteosarcoma.

In the present invention, the cancer is, for example, epithelial cancer, epidermoid cancer, squamous cell carcinoma, transitional cell cancer, malignant melanoma, in particular epithelial cancer.

In the present invention, the cancer is, for example, ganglioneuroblastoma, glioblastoma, glioblastoma multiforme, astrocytoma and medulloblastoma.

In the present invention, the cancer is, for example, leukemia, acute lymphatic leukemia, chronic myeloid leukemia, large-cell immunoblastic lymphoma and T-lymphoblastic lymphoma.

In the present invention, the cancer is, for example, thyroid cancer.

In the present invention, the cancer is, for example, NUT midline cancer.

In the present invention, metabolic diseases include, for example, atherosclerosis, hyperlipidemia, obesity, hepatic steatosis, osteoporosis, type II diabetes, amyloidosis, gout and pseudogout.

In the present invention, fibrotic diseases include, for example, pulmonary fibrosis, hepatic fibrosis, renal fibrosis, myelofibrosis, cystic fibrosis, scarring, myocardial fibrosis and postoperative stenosis.

In the present invention, cardiomyopathy includes, for example, hypertrophic cardiomyopathy, dilated cardiomyopathy, diabetic cardiomyopathy, cardiac sarcoidosis, cardiac amyloidosis and ischemic cardiomyopathy.

In the present invention, viral infections include, for example, infectious diseases with human immunodeficiency virus, human papilloma virus, herpes virus, Epstein-Barr virus, hepatitis B virus and hepatitis C virus.

In the present invention, contraception includes, for example, contraception in male.

In the present invention, neurodegenerative diseases include, for example, Alzheimer's disease, Parkinson's disease, amyotrophic lateral sclerosis, Huntington's disease and glaucoma.

In the present invention, cystic disease of kidney includes, for example, congenital renal cysts, acquired renal cysts, simple renal cysts, pararenal cysts and multilobular renal cyst.

In the present invention, "therapeutic agent" referred to an agent used for the treatment of diseases. In addition, "prophylaxis agent" in the present invention referred to an agent used for the prophylaxis of diseases.

(A) As one embodiment of the present invention, the compound of formula (I) or a salt thereof includes a compound or a salt thereof wherein each group is as described below.
In the formula (I):

[Chem. 3]

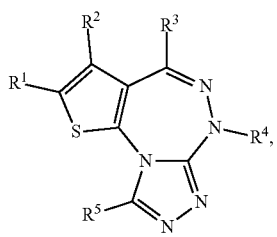

a compound wherein
(a1) $R^1$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy; and/or
(a2) $R^2$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy; and/or
(a3) $R^3$ is unsubstituted or substituted aryl, unsubstituted or substituted heteroaryl, or bicyclopentane, wherein the substituted aryl or substituted heteroaryl is substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$; and/or
(a4) $R^4$ is H, unsubstituted or substituted aryl-$C_{1-6}$ alkyl, unsubstituted or substituted heteroaryl-$C_{1-6}$ alkyl, unsubstituted or substituted aryl-NRC(O)—, unsubstituted or substituted heteroaryl-$NR^bC(O)$—, unsubstituted or substituted aryl-$C_{1-6}$ alkyl-$NR^bC(O)$—, or unsubstituted or substituted heteroaryl-$C_{1-6}$ alkyl-$NR^bC(O)$—, wherein the substituted aryl or substituted heteroaryl is substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NRC(O)$—$R^a$, —C(O)—$OR^a$ and —C(O)—$NR^bR^a$; and/or
(a5) $R^5$ is H, halogen, $C_{1-6}$ alkyl, halo-$C_{1-6}$ alkyl, hydroxy-$C_{1-6}$ alkyl, $C_{1-6}$ alkoxy, halo-$C_{1-6}$ alkoxy or hydroxy-$C_{1-6}$ alkoxy, and/or
(a6) $R^a$ is H, $C_{1-6}$ alkyl or halo-$C_{1-6}$ alkyl, and/or
(a7) $R^b$ is H, $C_{1-6}$ alkyl or halo-$C_{1-6}$ alkyl,
or a salt thereof, i.e. in the compound of formula (I), a compound or a salt thereof consisting of each combination of the above-mentioned (a1) to (a7).

(B) As one embodiment of the present invention, the compound of formula (I) or a salt thereof includes a compound or a salt thereof wherein each group is as described below.

In the above-mentioned formula (I), a compound wherein
(b1) R is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy; and/or
(b2) $R^2$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy; and/or
(b3) $R^3$ is unsubstituted or substituted phenyl, wherein the substituted phenyl is substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NRC(O)$—$R^a$, —C(O)—$OR^a$ and —C(O)—$NR^bR^a$; and/or
(b4) $R^4$ is unsubstituted or substituted aryl-$C_{1-6}$ alkyl, unsubstituted or substituted heteroaryl-$C_{1-6}$ alkyl, wherein the substituted aryl or substituted heteroaryl is substituted phenyl, substituted pyridyl, substituted indolyl or substituted thienyl, and is substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NRC(O)$—$R^a$, —C(O)—$OR^a$ and —C(O)—$NR^bR^a$; and/or
(b5) $R^5$ is H, halogen, $C_{1-6}$ alkyl, halo-$C_{1-6}$ alkyl, $C_{1-6}$ alkoxy, halo-$C_{1-6}$ alkoxy or hydroxy $C_{1-6}$ alkoxy; and/or
(b6) $R^a$ is H, $C_{1-6}$ alkyl or halo-$C_{1-6}$ alkyl; and/or
(b7) $R^b$ is H, $C_{1-6}$ alkyl or halo-$C_{1-6}$ alkyl, or a salt thereof, i.e. in the compound of formula (I), a compound or a salt thereof consisting of each combination of the above-mentioned (b1) to (b7).

(C) As one embodiment of the present invention, the compound of formula (I) or a salt thereof includes a compound or a salt thereof wherein each group is as described below.

In the above-mentioned formula (I), a compound wherein
(c1) $R^1$ is H, $C_{1-6}$ alkyl, halo-$C_{1-6}$ alkyl or hydroxy$C_{1-6}$ alkyl; and/or
(c2) $R^2$ is H, Cu alkyl, halo-$C_{1-6}$ alkyl or hydroxy$C_{1-6}$ alkyl; and/or
(c3) $R^3$ is unsubstituted or substituted phenyl, wherein the substituted phenyl is substituted with at least one substituent(s) selected from the group consisting of halogen, hydroxy, amino, nitro, $C_{1-6}$ alkyl, halo-$C_{1-6}$ alkyl, $C_{1-6}$ alkoxy, halo-$C_{1-6}$ alkoxy, —$NR^aR^b$ and —$NR^bC(O)$—$R^a$; and/or
(c4) $R^4$ is unsubstituted or substituted phenyl-$C_{1-6}$ alkyl, unsubstituted or substituted pyridyl-$C_{1-6}$ alkyl, wherein the substituted phenyl and substituted pyridyl are substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR$, —OC(O)—$R^a$, —$NR^bC(O)$—$R^a$, —C(O)—$OR^a$ and —C(O)—$NR^bR^a$; and/or (c5) $R^5$ is H, halogen, $C_{1-6}$ alkyl, halo-$C_{1-6}$ alkyl, or hydroxy$C_{1-6}$ alkyl; and/or (c6) $R^a$ is H, $C_{1-6}$ alkyl or halo-$C_{1-6}$ alkyl; and/or (c7) $R^b$ is H, $C_{1-6}$ alkyl or halo-$C_{1-6}$ alkyl or a salt thereof, i.e. in the compound of formula (I), a compound or a salt thereof consisting of each combination of the above-mentioned (c1) to (c7).

(D) As one embodiment of the present invention, the compound of formula (I) or a salt thereof includes a compound or a salt thereof wherein each group is as described below.

In the above-mentioned formula (I), a compound wherein (d1) $R^1$ is $C_{1-6}$ alkyl or halo-$C_{1-6}$ alkyl; and/or (d2) R is $C_{1-6}$ alkyl or halo-$C_{1-6}$ alkyl; and/or (d3) $R^3$ is unsubstituted phenyl or substituted phenyl, wherein the substituted phenyl is substituted with at least one substituent(s) selected from the group consisting of halogen and —$NR^bC(O)$—$R^a$; and/or (d4) $R^4$ is unsubstituted pyridyl or substituted pyridyl-$C_{1-6}$ alkyl, wherein the substituted pyridyl is substituted with halogen; and/or (d5) $R^5$ is H, halogen, $C_{1-6}$ alkyl, halo-$C_{1-6}$ alkyl, or hydroxyl-$C_{1-6}$ alkyl; and/or (d6) $R^a$ is $C_{1-6}$ alkyl or halo-$C_{1-6}$ alkyl; and/or (d7) $R^b$ is H or a salt thereof, i.e. in the compound of formula (I), a compound or a salt thereof consisting of each combination of the above-mentioned (d1) to (d7) (preferably it is not
4-(4-chlorophenyl)-6-(4-methoxybenzyl)-2,3,9-trimethyl-6H-thieno[2,3-e][1,2,4]t riazolo[3,4-c][1,2,4]triazepine
4-(4-chlorophenyl)-2,3,9-trimethyl-6-(pyridin-3-ylmethyl)-6H-thieno[2,3-e][1,2,4]triazolo[3,4-c][1,2,4]triazepine
6-(4-methoxybenzyl)-2,3,9-trimethyl-4-phenyl-6H-thieno[2,3-e][1,2,4]triazolo[3,4-c][1,2,4]triazepine
2,3,9-trimethyl-4-phenyl-6-(pyridin-3-ylmethyl)-6H-thieno[2,3-e][1,2,4]triazolo[3,4-c][1,2,4]triazepine
2,3,9-trimethyl-4-phenyl-6-(pyridin-4-ylmethyl)-6H-thieno[2,3-e][1,2,4]triazolo[3,4-c][1,2,4]triazepine
4-(2-chlorophenyl)-2,3,9-trimethyl-6-(pyridin-3-ylmethyl)-6H-thieno[2,3-e][1,2,4]triazolo[3,4-c][1,2,4]triazepine and
4-(4-methoxyphenyl)-2,3,9-trimethyl-6-(pyridin-3-ylmethyl)-6H-thieno[2,3-e][1,2,4]triazolo[3,4-c][1,2,4]triazepine).

(E) As one embodiment of the present invention, in the compound of formula (I) or a salt thereof, a compound wherein (e-1) $R^1$ is H, and $R^2$ is H, (e-2) $R^1$ is H, and R is $C_{1-6}$ alkyl, (e-3) $R^1$ is $C_{1-6}$ alkyl, and $R^2$ is H, (e-4) $R^1$ is H, and R is hydroxyl-$C_{1-6}$ alkyl, or (e-5) $R^1$ is hydroxyl-$C_{1-6}$ alkyl, and $R^2$ is H, or a salt thereof, i.e. in the compound of formula (I), a compound or a salt thereof consisting of each combination of the above-mentioned (e1) to (e5).

(F) As one embodiment of the present invention, in the compound of formula (I) or a salt thereof, a compound wherein (f-1) $R^3$ is unsubstituted or substituted aryl, unsubstituted or substituted heteroaryl, or bicyclopentane, wherein the substituted aryl or substituted heteroaryl is substituted with at least one substituent(s) selected from the group consisting of hydroxy, amino, nitro, cyano, carboxy, $C_{1-6}$ alkyl, halo-$C_{1-6}$ alkyl, hydroxy-$C_{1-6}$ alkyl, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$, (f-2) $R^3$ is phenyl or substituted phenyl, or pyridyl or substituted pyridyl, wherein the substituted phenyl or substituted pyridyl is substituted with at least one substituent(s) selected from the group consisting of hydroxy, amino, dimethylamino, acetylamino, nitro, cyano, carboxy, methoxycarbonyl, $C_{1-6}$ alkyl, halo-$C_{1-6}$ alkyl, hydroxy-$C_{1-6}$ alkyl and halo-$C_{1-6}$ alkoxy, (f-3) $R^3$ is phenyl, 2-chlorophenyl, 3-chlorophenyl, 4-chlorophenyl, 4-aminophenyl, 2-methoxyphenyl, 3-methoxyphenyl, 4-methoxyphenyl or 4-acetylaminophenyl, or (f-4) $R^3$ is 4-aminophenyl or 4-acetylaminophenyl, or a salt thereof, i.e. in the compound of formula (I), a compound or a salt thereof consisting of each combination of the above-mentioned (f-1) to (f-4).

(G) As one embodiment of the present invention, in the compound of formula (I) or a salt thereof, a compound wherein (g-1) $R^4$ is substituted heteroaryl-$C_{1-6}$ alkyl, substituted heteroaryl-$NR^bC(O)$—, or substituted heteroaryl-$C_{1-6}$ alkyl-$NR^bC(O)$—, wherein the heteroaryl is substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$, (g-2) $R^4$ is phenyl-$C_{1-6}$ alkyl or substituted phenyl-$C_{1-6}$ alkyl, or pyridyl-$C_{1-6}$ alkyl or substituted pyridyl-$C_{1-6}$ alkyl, wherein the substituted phenyl or substituted pyridyl is substituted with at least one substituent(s) selected from the group consisting of hydroxy, amino, dimethylamino, acetylamino, nitro, cyano, carboxy, methoxycarbonyl, $C_{1-6}$ alkyl, halo-$C_{1-6}$ alkyl, hydroxy-$C_{1-6}$ alkyl, $C_{1-6}$ alkoxy and halo-$C_{1-6}$ alkoxy, (g-3) $R^4$ is benzyl, 2-fluorobenzyl, 3-fluorobenzyl, 2-chlorobenzyl, 3-chlorobenzyl, 2-methylbenzyl, 3-methylbenzyl, 4-methylbenzyl, 4-(tert-butyl)benzyl, 2-(trifluoromethyl)benzyl, 3-(trifluoromethyl)benzyl, 4-(trifluoromethyl)benzyl, 3-methoxybenzyl or 4-methoxybenzyl, or (g-4) $R^4$ is pyridin-2-ylmethyl, pyridin-3-ylmethyl, pyridin-4-ylmethyl, (2-fluoropyridin-4-yl)methyl, (2-fluoropyridin-3-yl)methyl, (3-fluoropyridin-2-yl)methyl, (3-fluoropyridin-4-yl)methyl, (5-fluoropyridin-2-yl)methyl, (6-fluoropyridin-2-yl)methyl, (6-fluoropyridin-3-yl)methyl, (2-chloropyridin-3-yl)methyl, (3-chloropyridin-2-yl)methyl, (4-chloropyridin-2-yl)methyl, (4-chloropyridin-3-yl)methyl, (5-chloropyridin-2-yl)methyl, (5-chloropyridin-3-yl)methyl, (6-chloropyridin-3-yl)methyl, (2-bromopyridin-3-yl)methyl, (2-hydroxypyridin-3-yl)methyl, (4-hydroxypyridin-3-yl)methyl, (5-hydroxypyridin-3-yl)methyl, (6-hydroxypyridin-3-yl)methyl, (2-aminopyridin-3-yl)methyl, (2-aminopyridin-4-yl)methyl, (2-nitropyridin-3-yl)methyl, (2-methoxypyridin-3-yl)methyl, (3-methoxypyridin-2-yl)methyl, (4-methoxypyridin-3-yl)methyl, (4-methoxypyridin-2-yl)methyl, (5-methoxypyridin-2-yl)methyl, (2-ethoxypyridin-3-yl)methyl, (2-hydroxymethylpyridin-3-yl)methyl, (2-(trifluoromethyl)pyridin-3-yl)methyl, (2,5-difluoropyridin-3-yl)methyl, (5-fluoro-2-methoxypyridin-3-yl)methyl, (2-acetylaminopyridin-3-yl)methyl or (2-acetylaminopyridin-4-yl)methyl, or a salt thereof, i.e. in the compound of formula (I), a compound or a salt thereof consisting of each combination of the above-mentioned (g-1) to (g-4).

(H) As one embodiment of the present invention, in the compound of formula (I) or a salt thereof, compounds wherein $R^3$ is unsubstituted phenyl, 3-chlorophenyl, 4-chlorophenyl or 4-methoxyphenyl, and $R^4$ is unsubstituted pyridyl-3-ylmethyl, unsubstituted pyridyl-4-ylmethyl, 4-fluorobenzyl, 4-methoxybenzyl, 4-cyanobenzyl, 3,4-dichlorobenzyl or 3,4-difluorobenzyl or salts thereof are excluded.

(J) As one embodiment of the present invention, in the compound of formula (I) or a salt thereof, the compounds selected from:

2,9-dimethyl-4-phenyl-6H-thieno[2,3-e][1,2,4]triazolo[3,4-c][1,2,4]triazepine 2-ethyl-9-methyl-4-phenyl-6H-thieno[2,3-e][1,2,4]triazolo[3,4-c][1,2,4]triazepine 2,3,9-trimethyl-4-phenyl-6H-thieno[2,3-e][1,2,4]triazolo[3,4-c][1,2,4]triazepine 4-(4-chlorophenyl)-2-ethyl-9-methyl-6H-thieno[2,3-e][1,2,4]triazolo[3,4-c][1,2,4]triazepine 4-(4-chlorophenyl)-2,3,9-trimethyl-6H-thieno[2,3-e][1,2,4]triazolo[3,4-c][1,2,4]triazepine 4-(4-methoxyphenyl)-2,3,9-trimethyl-6H-thieno[2,3-e][1,2,4]triazolo[3,4-c][1,2,4]triazepine 2,9-dimethyl-4-phenyl-6-(pyridin-3-ylmethyl)-6H-thieno[2,3-e][1,2,4]triazolo[3,4-c][1,2,4]triazepine 2,9-dimethyl-4-phenyl-6-(pyridin-4-ylmethyl)-6H-thieno[2,3-e][1,2,4]triazolo[3,4-c][1,2,4]triazepine 2,9-dimethyl-4-phenyl-6-(pyridin-3-ylmethyl)-6H-thieno[2,3-e][1,2,4]triazolo[3,4-c][1,2,4]triazepine toluenesulfonate 4-((2,9-dimethyl-4-phenyl-6H-thieno[2,3-e][1,2,4]triazolo[3,4-c][1,2,4]triazepin-6-yl)methyl)benzonitrile 2-ethyl-9-methyl-4-phenyl-6-(pyridin-3-ylmethyl)-6H-thieno[2,3-e][1,2,4]triazolo[3,4-c][1,2,4]triazepine 2-ethyl-9-methyl-4-phenyl-6-(pyridin-4-ylmethyl)-6H-thieno[2,3-e][1,2,4]triazolo[3,4-c][1,2,4]triazepine 6-(4-methoxybenzyl)-2,9-dimethyl-4-phenyl-6H-thieno[2,3-e][1,2,4]triazolo[3,4-c][1,2,4]triazepine 6-(4-chlorobenzyl)-2,9-dimethyl-4-phenyl-6H-thieno[2,3-e][1,2,4]triazolo[3,4-c][1,2,4]triazepine 4-((2-ethyl-9-methyl-4-phenyl-6H-thieno[2,3-e][1,2,4]triazolo[3,4-c][1,2,4]triazepin-6-yl)methyl)benzonitrile 2,3,9-trimethyl-4-phenyl-6-(pyridin-3-ylmethyl)-6H-thieno[2,3-e][1,2,4]triazolo[3,4-c][1,2,4]triazepine 2,3,9-trimethyl-4-phenyl-6-(pyridin-4-ylmethyl)-6H-thieno[2,3-e][1,2,4]triazolo[3,4-c][1,2,4]triazepine 4-((2,9-dimethyl-4-phenyl-6H-thieno[2,3-e][1,2,4]triazolo[3,4-c][1,2,4]triazepin-6-yl)methyl)pyridine 1-oxide 2-ethyl-6-(4-methoxybenzyl)-9-methyl-4-phenyl-6H-thieno[2,3-e][1,2,4]triazolo[3,4-c][1,2,4]triazepine 3-((2,9-dimethyl-4-phenyl-6H-thieno[2,3-e][1,2,4]triazolo[3,4-c][1,2,4]triazepin-6-yl)methyl)pyridine 1-oxide 6-(4-(1H-tetrazol-5-yl)benzyl)-2,9-dimethyl-4-phenyl-6H-thieno[2,3-e][1,2,4]triazolo[3,4-c][1,2,4]triazepine 6-(4-methoxybenzyl)-2,3,9-trimethyl-4-phenyl-6H-thieno[2,3-e][1,2,4]triazolo[3,4-c][1,2,4]triazepine 2,9-dimethyl-6-(4-(2-methyl-2H-tetrazol-5-yl)benzyl)-4-phenyl-6H-thieno[2,3-e][1,2,4]triazolo[3,4-c][1,2,4]triazepine 4-(4-chlorophenyl)-2-ethyl-9-methyl-6-(pyridin-3-ylmethyl)-6H-thieno[2,3-e][1,2,4]triazolo[3,4-c][1,2,4]triazepine 4-(4-chlorophenyl)-2-ethyl-9-methyl-6-(pyridin-4-ylmethyl)-6H-thieno[2,3-e][1,2,4]triazolo[3,4-c][1,2,4]triazepine 4-((4-(4-chlorophenyl)-2-ethyl-9-methyl-6H-thieno[2,3-e][1,2,4]triazolo[3,4-c][1,2,4]triazepin-6-yl)methyl)benzonitrile 2,9-dimethyl-6-(4-(1-methyl-1H-tetrazol-5-yl)benzyl)-4-phenyl-6H-thieno[2,3-e][1,2,4]triazolo[3,4-c][1,2,4]triazepine 4-(4-chlorophenyl)-6-(4-fluorobenzyl)-2,3,9-trimethyl-6H-thieno[2,3-e][1,2,4]triazolo[3,4-c][1,2,4]triazepine 6-(4-chlorobenzyl)-4-(4-chlorophenyl)-2,3,9-trimethyl-6H-thieno[2,3-e][1,2,4]triazolo[3,4-c][1,2,4]triazepine 4-(4-methoxyphenyl)-2,3,9-trimethyl-6-(pyridin-3-ylmethyl)-6H-thieno[2,3-e][1,2,4]triazolo[3,4-c][1,2,4]triazepine 4-(4-methoxyphenyl)-2,3,9-trimethyl-6-(pyridin-4-ylmethyl)-6H-thieno[2,3-e][1,2,4]triazolo[3,4-c][1,2,4]triazepine 6-(4-(1H-tetrazol-5-yl)benzyl)-4-(4-chlorophenyl)-2,9-dimethyl-6H-thieno[2,3-e][1,2,4]triazolo[3,4-c][1,2,4]triazepine 4-(4-chlorophenyl)-2-ethyl-6-(4-methoxybenzyl)-9-methyl-6H-thieno[2,3-e][1,2,4]triazolo[3,4-c][1,2,4]triazepine 4-((4-(4-chlorophenyl)-2,3,9-trimethyl-6H-thieno[2,3-e][1,2,4]triazolo[3,4-c][1,2,4]triazepin-6-yl)methyl)benzonitrile 4-((4-(4-methoxyphenyl)-2,3,9-trimethyl-6H-thieno[2,3-e][1,2,4]triazolo[3,4-c][1,2,4]triazepin-6-yl)methyl)benzonitrile 4-(4-chlorophenyl)-2,3,9-trimethyl-6-(pyridin-3-ylmethyl)-6H-thieno[2,3-e][1,2,4]triazolo[3,4-c][1,2,4]triazepine 4-(4-chlorophenyl)-2,3,9-trimethyl-6-(pyridin-4-ylmethyl)-6H-thieno[2,3-e][1,2,4]triazolo[3,4-c][1,2,4]triazepine 6-(4-methoxybenzyl)-4-(4-methoxyphenyl)-2,3,9-trimethyl-6H-thieno[2,3-e][1,2,4]triazolo[3,4-c][1,2,4]triazepine 4-(4-chlorophenyl)-6-(4-methoxybenzyl)-2,3,9-trimethyl-6H-thieno[2,3-e][1,2,4]triazolo[3,4-c][1,2,4]triazepine 4-((4-(4-chlorophenyl)-2-ethyl-9-methyl-6H-thieno[2,3-e][1,2,4]triazolo[3,4-c][1,2,4]triazepin-6-yl)methyl)pyridine 1-oxide 3-((4-(4-chlorophenyl)-2-ethyl-9-methyl-6H-thieno[2,3-e][1,2,4]triazolo[3,4-c][1,2,4]triazepin-6-yl)methyl)pyridine 1-oxide 4-(2-chlorophenyl)-2,3,9-trimethyl-6-(pyridin-4-ylmethyl)-6H-thieno[2,3-e][1,2,4]triazolo[3,4-c][1,2,4]triazepine 4-(2-chlorophenyl)-2,3,9-trimethyl-6-(pyridin-3-ylmethyl)-6H-thieno[2,3-e][1,2,4]triazolo[3,4-c][1,2,4]triazepine 4-(4-chlorophenyl)-6-(3,4-dichlorobenzyl)-2-ethyl-9-methyl-6H-thieno[2,3-e][1,2,4]triazolo[3,4-c][1,2,4]triazepine 3-((4-(4-chlorophenyl)-2,3,9-trimethyl-6H-thieno[2,3-e][1,2,4]triazolo[3,4-c][1,2,4]triazepin-6-yl)methyl)pyridine 1-oxide 4-(4-chlorophenyl)-6-(3,4-difluorobenzyl)-2,3,9-trimethyl-6H-thieno[2,3-e][1,2,4]triazolo[3,4-c][1,2,4]triazepine 4-(4-chlorophenyl)-6-(3,4-dichlorobenzyl)-2,3,9-trimethyl-6H-thieno[2,3-e][1,2,4]triazolo[3,4-c][1,2,4]triazepine 4-((4-(2-chlorophenyl)-2,3,9-trimethyl-6H-thieno[2,3-e][1,2,4]triazolo[3,4-c][1,2,4]triazepin-6-yl)methyl)pyridine 1-oxide and 2-(4-((4-(4-chlorophenyl)-2,9-dimethyl-6H-thieno[2,3-e][1,2,4]triazolo[3,4-c][1,2,4]triazepin-6-yl)methyl)phenoxy)-N,N-dimethylethane-1-amine are excluded.

One embodiment of the present invention is, in the compound of formula (I) or a salt thereof, a compound or a salt thereof consisting of each combination of the abovementioned (A) to (J).

As one embodiment of the present invention, the following compounds or salts thereof are exemplified:

6-benzyl-4-(4-chlorophenyl)-2,3,9-trimethyl-6H-thieno[2,3-e][1,2,4]triazolo[3,4-c][1,2,4]triazepine
4-(4-chlorophenyl)-2,3,9-trimethyl-6-(pyridin-2-ylmethyl)-6H-thieno[2,3-e][1,2,4]triazolo[3,4-c][1,2,4]triazepine
4-(4-chlorophenyl)-6-(3-methoxybenzyl)-2,3,9-trimethyl-6H-thieno[2,3-e][1,2,4]triazolo[3,4-c][1,2,4]triazepine
6-(4-(tert-butyl)benzyl)-4-(4-chlorophenyl)-2,3,9-trimethyl-6H-thieno[2,3-e][1,2,4]triazolo[3,4-c][1,2,4]triazepine
4-(4-chlorophenyl)-6-(2-fluorobenzyl)-2,3,9-trimethyl-6H-thieno[2,3-e][1,2,4]triazolo[3,4-c][1,2,4]triazepine
4-(4-chlorophenyl)-6-(3-fluorobenzyl)-2,3,9-trimethyl-6H-thieno[2,3-e][1,2,4]triazolo[3,4-c][1,2,4]triazepine
6-(2-chlorobenzyl)-4-(4-chlorophenyl)-2,3,9-trimethyl-6H-thieno[2,3-e][1,2,4]triazolo[3,4-c][1,2,4]triazepine
4-(4-chlorophenyl)-2,3,9-trimethyl-6-(2-methylbenzyl)-6H-thieno[2,3-e][1,2,4]triazolo[3,4-c][1,2,4]triazepine
4-(4-chlorophenyl)-2,3,9-trimethyl-6-(3-methylbenzyl)-6H-thieno[2,3-e][1,2,4]triazolo[3,4-c][1,2,4]triazepine
4-(4-chlorophenyl)-2,3,9-trimethyl-6-(4-methylbenzyl)-6H-thieno[2,3-e][1,2,4]triazolo[3,4-c][1,2,4]triazepine
4-(4-chlorophenyl)-2,3,9-trimethyl-6-(4-(trifluoromethyl)benzyl)-6H-thieno[2,3-e][1,2,4]triazolo[3,4-c][1,2,4]triazepine
4-(4-chlorophenyl)-2,3,9-trimethyl-N-phenyl-6H-thieno[2,3-e][1,2,4]triazolo[3,4-c][1,2,4]triazepine-6-carboxamide
6-(3-chlorobenzyl)-4-(4-chlorophenyl)-2,3,9-trimethyl-6H-thieno[2,3-e][1,2,4]triazolo[3,4-c][1,2,4]triazepine
4-(4-chlorophenyl)-2,3,9-trimethyl-6-(2-(trifluoromethyl)benzyl)-6H-thieno[2,3-e][1,2,4]triazolo[3,4-c][1,2,4]triazepine
4-(4-chlorophenyl)-2,3,9-trimethyl-6-(3-(trifluoromethyl)benzyl)-6H-thieno-[2,3-e][1,2,4]triazolo[3,4-c][1,2,4]triazepine
4-(4-chlorophenyl)-2,3,9-trimethyl-6-phenethyl-6H-thieno[2,3-e][1,2,4]triazolo[3,4-c][1,2,4]triazepine
4-(4-chlorophenyl)-2,3,9-trimethyl-6-(3-phenylpropyl)-6H-thieno[2,3-e][1,2,4]triazolo[3,4-c][1,2,4]triazepine
4-(4-chlorophenyl)-6-((6-fluoropyridin-2-yl)methyl)-2,3,9-trimethyl-6H-thieno[2,3-e][1,2,4]triazolo[3,4-c][1,2,4]triazepine
4-(4-chlorophenyl)-6-((5-fluoropyridin-2-yl)methyl)-2,3,9-trimethyl-6H-thieno[2,3-e][1,2,4]triazolo[3,4-c][1,2,4]triazepine
4-(4-chlorophenyl)-6-((3-fluoropyridin-2-yl)methyl)-2,3,9-trimethyl-6H-thieno[2,3-e][1,2,4]triazolo[3,4-c][1,2,4]triazepine
4-(4-chlorophenyl)-6-((3-chloropyridin-2-yl)methyl)-2,3,9-trimethyl-6H-thieno[2,3-e][1,2,4]triazolo[3,4-c][1,2,4]triazepine
4-(4-chlorophenyl)-6-((2-fluoropyridin-3-yl)methyl)-2,3,9-trimethyl-6H-thieno[2,3-e][1,2,4]triazolo[3,4-c][1,2,4]triazepine
4-(4-chlorophenyl)-6-((6-fluoropyridin-3-yl)methyl)-2,3,9-trimethyl-6H-thieno[2,3-e][1,2,4]triazolo[3,4-c][1,2,4]triazepine
2,3,9-trimethyl-4-phenyl-6H-thieno[2,3-e][1,2,4]triazolo[3,4-c][1,2,4]triazepine
6-benzyl-2,3,9-trimethyl-4-phenyl-6H-thieno[2,3-e][1,2,4]triazolo[3,4-c][1,2,4]triazepine
2,3,9-trimethyl-4-phenyl-6-(pyridin-2-ylmethyl)-6H-thieno[2,3-e][1,2,4]triazolo[3,4-c][1,2,4]triazepine
6-(3-methoxybenzyl)-2,3,9-trimethyl-4-phenyl-6H-thieno[2,3-e][1,2,4]triazolo[3,4-c][1,2,4]triazepine
4-(4-chlorophenyl)-6-(2-methoxybenzyl)-2,3,9-trimethyl-6H-thieno[2,3-e][1,2,4]triazolo[3,4-c][1,2,4]triazepine
N-benzyl-4-(4-chlorophenyl)-2,3,9-trimethyl-6H-thieno[2,3-e][1,2,4]triazolo[3,4-c][1,2,4]triazepine-6-carboxamide
4-(4-chlorophenyl)-6-((5-chloropyridin-2-yl)methyl)-2,3,9-trimethyl-6H-thieno[2,3-e][1,2,4]triazolo[3,4-c][1,2,4]triazepine
4-(4-chlorophenyl)-6-((6-chloropyridin-3-yl)methyl)-2,3,9-trimethyl-6H-thieno[2,3-e][1,2,4]triazolo[3,4-c][1,2,4]triazepine
4-(4-chlorophenyl)-6-((2-chloropyridin-3-yl)methyl)-2,3,9-trimethyl-6H-thieno[2,3-e][1,2,4]triazolo[3,4-c][1,2,4]triazepine
4-(4-chlorophenyl)-6-((5-chloropyridin-3-yl)methyl)-2,3,9-trimethyl-6H-thieno[2,3-e][1,2,4]triazolo[3,4-c][1,2,4]triazepine
4-(4-chlorophenyl)-6-((4-chloropyridin-2-yl)methyl)-2,3,9-trimethyl-6H-thieno[2,3-e][1,2,4]triazolo[3,4-c][1,2,4]triazepine
4-(4-chlorophenyl)-6-((3-fluoropyridin-4-yl)methyl)-2,3,9-trimethyl-6H-thieno[2,3-e][1,2,4]triazolo[3,4-c][1,2,4]triazepine
4-(4-chlorophenyl)-6-((2-fluoropyridin-4-yl)methyl)-2,3,9-trimethyl-6H-thieno[2,3-e][1,2,4]triazolo[3,4-c][1,2,4]triazepine
4-(4-chlorophenyl)-6-((4-chloropyridin-3-yl)methyl)-2,3,9-trimethyl-6H-thieno[2,3-e][1,2,4]triazolo[3,4-c][1,2,4]triazepine
6-(2-(1H-indol-3-yl)ethyl)-4-(4-chlorophenyl)-2,3,9-trimethyl-6H-thieno[2,3-e][1,2,4]triazolo[3,4-c][1,2,4]triazepine
4-(4-chlorophenyl)-2,3,9-trimethyl-6-(thiophen-2-ylmethyl)-6H-thieno[2,3-e][1,2,4]triazolo[3,4-c][1,2,4]triazepine
4-(4-chlorophenyl)-6-((6-methoxypyridin-2-yl)methyl)-2,3,9-trimethyl-6H-thieno[2,3-e][1,2,4]triazolo[3,4-c][1,2,4]triazepine
4-(4-chlorophenyl)-6-((5-methoxypyridin-2-yl)methyl)-2,3,9-trimethyl-6H-thieno[2,3-e][1,2,4]triazolo[3,4-c][1,2,4]triazepine
4-(4-chlorophenyl)-6-((4-methoxypyridin-2-yl)methyl)-2,3,9-trimethyl-6H-thieno[2,3-e][1,2,4]triazolo[3,4-c][1,2,4]triazepine
4-(4-chlorophenyl)-6-((2-methoxypyridin-3-yl)methyl)-2,3,9-trimethyl-6H-thieno[2,3-e][1,2,4]triazolo[3,4-c][1,2,4]triazepine
4-(4-chlorophenyl)-6-((6-methoxypyridin-3-yl)methyl)-2,3,9-trimethyl-6H-thieno[2,3-e][1,2,4]triazolo[3,4-c][1,2,4]triazepine
4-(4-chlorophenyl)-6-((4-methoxypyridin-3-yl)methyl)-2,3,9-trimethyl-6H-thieno[2,3-e][1,2,4]triazolo[3,4-c][1,2,4]triazepine
3-((4-(4-chlorophenyl)-2,3,9-trimethyl-6H-thieno[2,3-e][1,2,4]triazolo[3,4-c][1,2,4]triazepin-6-yl)methyl)aniline
3-((4-(4-chlorophenyl)-2,3,9-trimethyl-6H-thieno[2,3-e][1,2,4]triazolo[3,4-c][1,2,4]triazepin-6-yl)methyl)phenol
4-(4-chlorophenyl)-6-((3-methoxypyridin-2-yl)methyl)-2,3,9-trimethyl-6H-thieno[2,3-e][1,2,4]triazolo[3,4-c][1,2,4]triazepine
3-((4-(4-chlorophenyl)-2,3,9-trimethyl-6H-thieno[2,3-e][1,2,4]triazolo[3,4-c][1,2,4]triazepin-6-yl)methyl)-N,N-dimethylaniline
N-(4-((4-(4-chlorophenyl)-2,3,9-trimethyl-6H-thieno[2,3-e][1,2,4]triazolo[3,4-c][1,2,4]triazepin-6-yl)methyl)pyridin-2-yl)acetamide
4-((4-(4-chlorophenyl)-2,3,9-trimethyl-6H-thieno[2,3-e][1,2,4]triazolo[3,4-c]-[1,2,4]triazepin-6-yl)methyl)pyridin-2-amine 4-(4-chlorophenyl)-6-(4-methoxybenzyl)-9-methyl-6H-thieno[2,3-e][1,2,4]triazolo[3,4-c][1,2,4]triazepine 4-(4-chlorophenyl)-9-methyl-6H-thieno[2,3-e][1,2,4]triazolo[3,4-c][1,2,4]triaz epine 6-benzyl-4-(4-chlorophenyl)-9-methyl-6H-thieno[1,2,4]triazolo[3,4-c][1,2,4]triazepine 4-(4-chlorophenyl)-9-methyl-6-(pyridin-3-ylmethyl)-6H-thieno[2,3-e][1,2,4]triazolo[3,4-c][1,2,4]triazepine 4-(4-chlorophenyl)-9-methyl-6-(pyridin-2-ylmethyl)-6H-thieno[2,3-e][1,2,4]triazolo[3,4-c][1,2,4]triazepine 4-(4-chlorophenyl)-9-methyl-6-(pyridin-4-ylmethyl)-6H-thieno[2,3-e][1,2,4]triazolo[3,4-c][1,2,4]triazepine 4-(4-chlorophenyl)-6-(3-methoxybenzyl)-9-methyl-6H-thieno[2,3-e][1,2,4]triazolo[3,4-c][1,2,4]triazepine 4-(4-chlorophenyl)-6-(4-methoxybenzyl)-2,9-dimethyl-6H-thieno[2,3-e][1,2,4]triazolo[3,4-c][1,2,4]triazepine 4-(4-chlorophenyl)-6-(4-methoxybenzyl)-3,9-dimethyl-6H-thieno[2,3-e][1,2,4]triazolo[3,4-c][1,2,4]triazepine 5-(4-chlorophenyl)-7-(4-methoxybenzyl)-10-methyl-7H-pyrido[2,3-e][1,2,4]triazolo[3,4-c][1,2,4]triazepine (4-(4-chlorophenyl)-6-(4-methoxybenzyl)-2,3-dimethyl-6H-thieno[2,3-e][1,2,4]triazolo[3,4-c][1,2,4]triazepin-9-yl)methanol 4-(4-chlorophenyl)-6-(4-methoxybenzyl)-2,3-dimethyl-9-(trifluoromethyl)-6H-thieno[2,3-e][1,2,4]triazolo[3,4-c][1,2,4]triazepine 2,3,9-trimethyl-4-(4-nitrophenyl)-6-(pyridin-3-ylmethyl)-6H-thieno[2,3-e][1,2,4]triazolo[3,4-c][1,2,4]triazepine N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide 4-(3-chlorophenyl)-2,3,9-trimethyl-6-(pyridin-3-ylmethyl)-6H-thieno[2,3-e][1,2,4]triazolo[3,4-c][1,2,4]triazepine 4-(2-methoxyphenyl)-2,3,9-trimethyl-6-(pyridin-3-ylmethyl)-6H-thieno[2,3-e][1,2,4]triazolo[3,4-c][1,2,4]triazepine 4-(3-methoxyphenyl)-2,3,9-trimethyl-6-(pyridin-3-ylmethyl)-6H-thieno[2,3-e][1,2,4]triazolo[3,4-c][1,2,4]triazepine 3-((4-(4-chlorophenyl)-2,3,9-trimethyl-6H-thieno[2,3-e][1,2,4]triazolo[3,4-c]-[1,2,4]triazepin-6-yl)methyl)picolinonitrile 4-(4-chlorophenyl)-2,3,9-trimethyl-6-((2-(trifluoromethyl)pyridin-3-yl)methyl)-6H-thieno[2,3-e][1,2,4]triazolo[3,4-c][1,2,4]triazepine 6-((2-bromopyridin-3-yl)methyl)-4-(4-chlorophenyl)-2,3,9-trimethyl-6H-thieno[2,3-e][1,2,4]triazolo[3,4-c][1,2,4]triazepine 4-(4-chlorophenyl)-2,3,9-trimethyl-6-((2-nitropyridin-3-yl)methyl)-6H-thieno[2,3-e][1,2,4]triazolo[3,4-c][1,2,4]triazepine 3-((4-(4-chlorophenyl)-2,3,9-trimethyl-6H-thieno[2,3-e][1,2,4]triazolo[3,4-c][1,2,4]triazepin-6-yl)methyl)pyridin-2-amine N-(3-((4-(4-chlorophenyl)-2,3,9-trimethyl-6H-thieno[2,3-e][1,2,4]triazolo[3,4-c][1,2,4]triazepin-6-yl)methyl)pyridin-2-yl)acetamide Methyl 3-((4-(4-chlorophenyl)-2,3,9-trimethyl-6H-thieno[2,3-e][1,2,4]triazolo[3,4-c][1,2,4]triazepin-6-yl)methyl)picolinate 3-((4-(4-chlorophenyl)-2,3,9-trimethyl-6H-thieno[2,3-e][1,2,4]triazolo[3,4-c][1,2,4]triazepin-6-yl)methyl)picolinic acid 3-((4-(4-chlorophenyl)-2,3,9-trimethyl-6H-thieno[2,3-e][1,2,4]triazolo[3,4-c][1,2,4]triazepin-6-yl)methyl)-N-ethylpicolinamide (3-((4-(4-chlorophenyl)-2,3,9-trimethyl-6H-thieno[2,3-e][1,2,4]triazolo[3,4-c][1,2,4]triazepin-6-yl)methyl)pyridin-2-yl)methanol 4-(4-chlorophenyl)-6-((2-ethoxypyridin-3-yl)methyl)-2,3,9-trimethyl-6H-thieno[2,3-e][1,2,4]triazolo[3,4-c][1,2,4]triazepine 4-(4-chlorophenyl)-6-((2,5-difluoropyridin-3-yl)methyl)-2,3,9-trimethyl-6H-thieno[2,3-e][1,2,4]triazolo[3,4-c][1,2,4]triazepine 4-(4-chlorophenyl)-6-((5-fluoro-2-methoxypyridin-3-yl)methyl)-2,3,9-trimethyl-6H-thieno[2,3-e][1,2,4]triazolo[3,4-c][1,2,4]triazepine 6-((2-fluoropyridin-3-yl)methyl)-2,3,9-trimethyl-4-phenyl-6H-thieno[2,3-e][1,2,4]triazolo[3,4-c][1,2,4]triazepine 4-(4-chlorophenyl)-2,3,9-trimethyl-N-phenyl-6H-thieno[2,3-e][1,2,4]triazolo[3,4-c][1,2,4]triazepine-6-carboxamide 4-(2,3,9-trimethyl-6-(pyridin-3-ylmethyl)-6H-thieno[2,3-e][1,2,4]triazolo[3,4-c][1,2,4]triazepin-4-yl)aniline N-(4-(9-(hydroxymethyl)-2,3-dimethyl-6-(pyridin-3-ylmethyl)-6H-thieno[2,3-e][1,2,4]triazolo[3,4-c][1,2,4]triazepin-4-yl)phenyl)acetamide N-(4-(2,3,9-trimethyl-6H-thieno[2,3-e][1,2,4]triazolo[3,4-c][1,2,4]triazepin-4-yl)phenyl)acetamide N-(4-(2-(hydroxymethyl)-3,9-dimethyl-6-(pyridin-3-ylmethyl)-6H-thieno[2,3-e][1,2,4]triazolo[3,4-c][1,2,4]triazepin-4-yl)phenyl)acetamide N-(4-(3-(hydroxymethyl)-2,9-dimethyl-6-(pyridin-3-ylmethyl)-6H-thieno[2,3-e][1,2,4]triazolo[3,4-c][1,2,4]triazepin-4-yl)phenyl)acetamide N-(4-(6-((2-hydroxypyridin-3-yl)methyl)-2,3,9-trimethyl-6H-thieno[2,3-e][1,2,4]triazolo[3,4-c][1,2,4]triazepin-4-yl)phenyl)acetamide N-(4-(6-((4-hydroxypyridin-3-yl)methyl)-2,3,9-trimethyl-6H-thieno[2,3-e][1,2,4]triazolo[3,4-c][1,2,4]triazepin-4-yl)phenyl)acetamide N-(4-(6-((5-hydroxypyridin-3-yl)methyl)-2,3,9-trimethyl-6H-thieno[2,3-e][1,2,4]triazolo[3,4-c][1,2,4]triazepin-4-yl)phenyl)acetamide N-(4-(6-((6-hydroxypyridin-3-yl)methyl)-2,3,9-trimethyl-6H-thieno[2,3-e][1,2,4]triazolo[3,4-c][1,2,4]triazepin-4-yl)phenyl)acetamide 3-((4-(4-aminophenyl)-2,3,9-trimethyl-6H-thieno[2,3-e][1,2,4]triazolo[3,4-c][1,2,4]triazepin-6-yl)methyl)pyridin-2-ol 3-((4-(4-aminophenyl)-2,3,9-trimethyl-6H-thieno[2,3-e][1,2,4]triazolo[3,4-c][1,2,4]triazepin-6-yl)methyl)pyridin-4-ol 5-((4-(4-aminophenyl)-2,3,9-trimethyl-6H-thieno[2,3-e][1,2,4]triazolo[3,4-c][1,2,4]triazepin-6-yl)methyl)pyridin-3-ol 5-((4-(4-aminophenyl)-2,3,9-trimethyl-6H-thieno[2,3-e][1,2,4]triazolo[3,4-c][1,2,4]triazepin-6-yl)methyl)pyridin-2-ol (4-(4-aminophenyl)-2,3-dimethyl-6-(pyridin-3-ylmethyl)-6H-thieno[2,3-e][1,2,4]triazolo[3,4-c][1,2,4]triazepin-9-yl)methanol (4-(4-aminophenyl)-3,9-dimethyl-6-(pyridin-3-ylmethyl)-6H-thieno[2,3-e][1,2,4]triazolo[3,4-c][1,2,4]triazepin-2-yl)methanol (4-(4-aminophenyl)-2,9-dimethyl-6-(pyridin-3-ylmethyl)-6H-thieno[2,3-e][1,2,4]triazolo[3,4-c][1,2,4]triazepin-3-yl)methanol 2-(4-(4-aminophenyl)-9-methyl-6-(pyridin-3-ylmethyl)-6H-thieno[2,3-e][1,2,4]triazolo[3,4-c][1,2,4]triazepin-3-yl)ethane-1-ol N-(4-(3-(2-hydroxyethyl)-9-methyl-6-(pyridin-3-ylmethyl)-6H-thieno[2,3-e][1,2,4]triazolo[3,4-c][1,2,4]triazepin-4-yl)phenyl)acetamide.

The compounds of formula (I) and salts thereof of the present invention can be prepared by methods known in the art.

The preparations of the compounds of formula (I) of the present invention can be carried out by the continuous or convergent synthetic routes. Synthesis of the compounds of formula (I) of the present invention is shown in the following Schemes.

The methods required for the reaction and purification of the resulting products are known in the art.

The compounds of formula (I) of the present invention can be produced by the following methods, by the methods of Examples, or by analogous methods thereof.

The reaction conditions suitable for the individual reaction steps (Step) are known to the person skilled in the art. The order of the reaction is not limited to that represented in Schemes, and is determined by starting materials and their respective reactivities. The order of the reaction step (Step) can be freely changed. Starting materials are either commercially available, or can be prepared by methods analogous to the methods given below, by the methods of Examples or by methods known in the art.

Scheme 1

[Chem. 4]

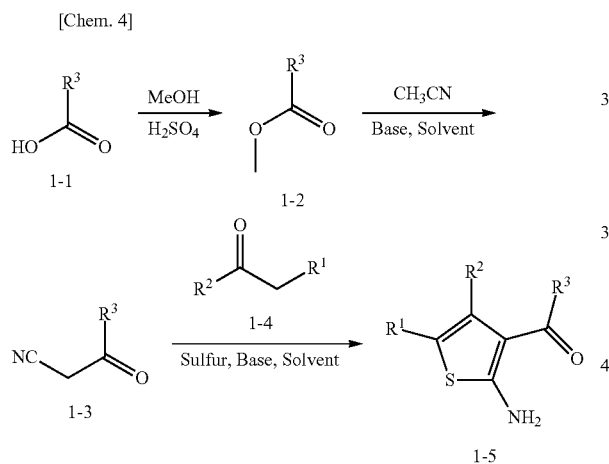

A compound of formula 1-2 can be obtained by using a compound of formula 1-1 and sulfuric acid in methanol. A compound of formula 1-3 can be obtained by using a compound of formula 1-2, CH3CN and a base in a solvent. A compound of formula 1-5 can be obtained by using a compound of formula 1-3, a compound of formula 1-4, sulfur and a base in a solvent. In the formula 1-1 to 1-5, $R^1$ to $R^3$ are as defined above.

Scheme 2

[Chem. 5]

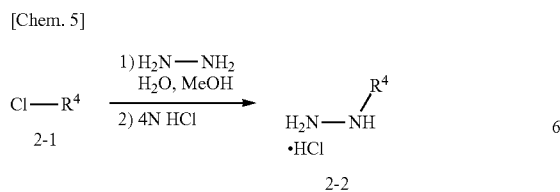

A compound of formula 2-2 can be obtained by using a hydrazine hydrated solution, a compound of formula 2-1 and hydrochloric acid in methanol. In the formula 2-1 and 2-2, $R^4$ is as defined above.

Scheme 3

[Chem. 6]

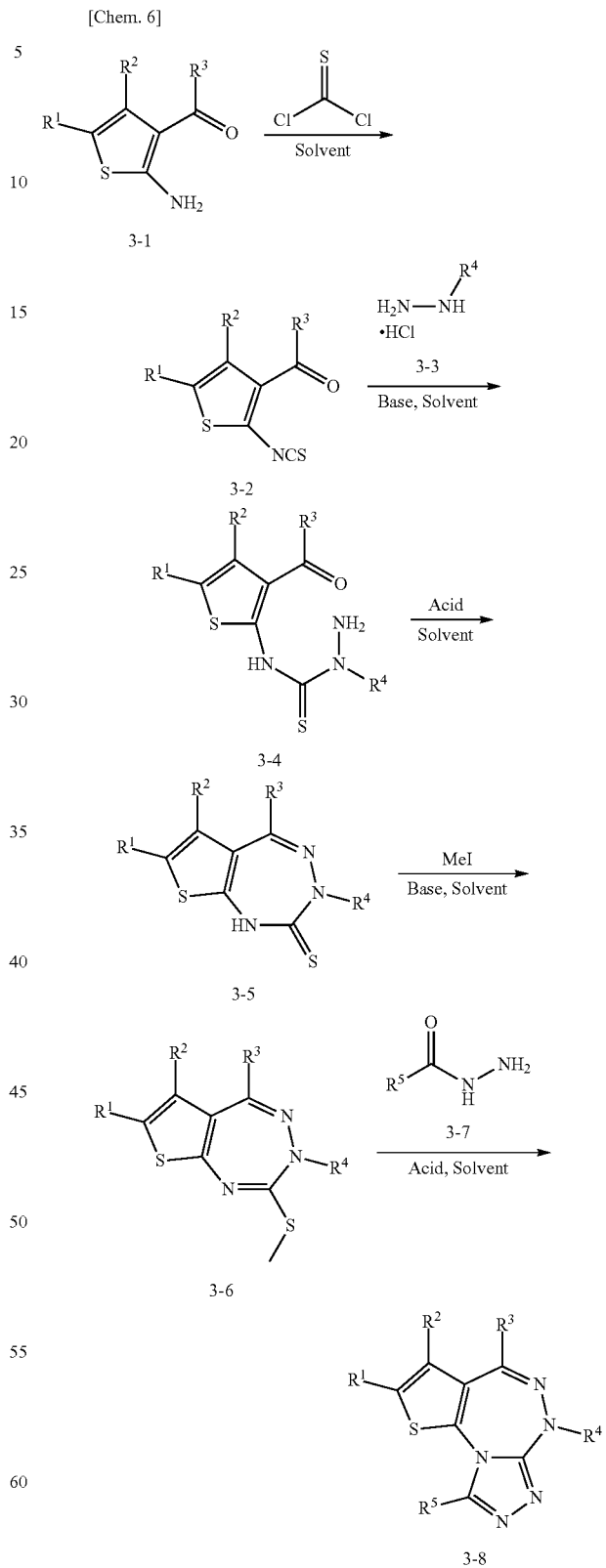

A compound of formula 3-2 can be obtained by using a compound of formula 3-1 (the above-mentioned compound of formula 1-5) and CSCl$_2$ in a solvent. A compound of formula 3-4 can be obtained by using a compound of formula 3-2, a compound of formula 3-3 (the above-mentioned compound of formula 2-2) and a base in a solvent. A compound of formula 3-5 can be obtained by using a compound of formula 3-4 and an acid in a solvent. A compound of formula 3-6 can be obtained by using a compound of formula 3-5, methyl iodide and a base. A compound of formula 3-8 can be obtained by using a compound of formula 3-6 and a compound of formula 3-7 in a solvent. In the formula 3-1 to 3-8, R to R$^5$ are as defined above.

Scheme 4

[Chem. 7]

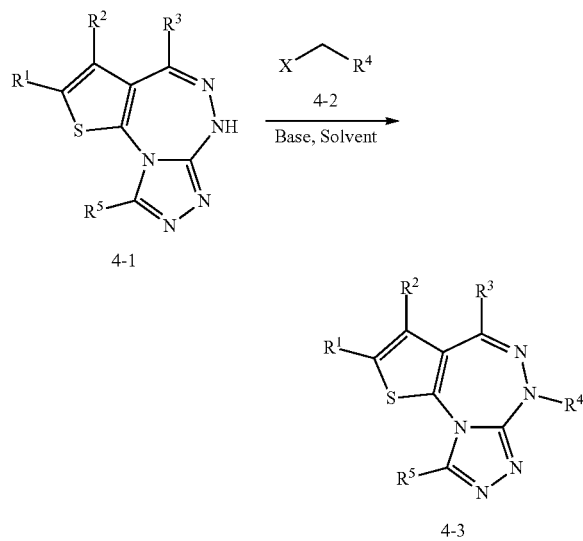

A compound of formula 4-3 can be obtained by using a compound of formula 4-1, a compound of formula 4-2 and abase in a solvent. In the formula 4-1 to 4-3, R$^1$ to R$^5$ are as defined above.

The present compounds produced by the above-mentioned synthetic routes can also be, by using generally used techniques, in the form of the above-mentioned salt, hydrate or solvate.

In order to find out usefulness of the present compounds as medicaments, the following pharmacological tests were carried out. The same assays were also carried out using the compounds known in literatures, and these were compared with the test results of the present compounds; whereby the present compounds are confirmed to be particularly useful as medicaments.

In order to evaluate BRD4 inhibitory activity of the present compounds, BRD4-H4KAc4 binding assay was carried out by an amplified luminescence proximity homogeneous assay. The present compounds showed BRD4 binding activity.

Since the present compounds have BRD4 inhibition action, these are particularly useful as BRD4 inhibitors, and useful for diseases that BRD4 inhibitors are to be effective, in particular, the prophylaxis and/or treatment of autoimmune diseases, inflammatory diseases, proliferative diseases, metabolic diseases, fibrotic diseases, cardiomyopathy, virus infectious diseases and neurodegenerative diseases, or for contraception.

One embodiment of the present invention includes a prophylaxis and/or therapeutic agent comprising the present compound(s), for diseases associated with BRD4 inhibition.

One embodiment of the present invention includes a pharmaceutical composition comprising the present compound(s), for the prophylaxis and/or treatment of diseases associated with BRD4 inhibition.

One embodiment of the present invention includes the present compound(s) for use in the prophylaxis and/or treatment of diseases associated with BRD4 inhibition.

One embodiment of the present invention includes the use of the present compound(s) for the manufacture of medicaments for the prophylaxis and/or treatment of diseases associated with BRD4 inhibition.

One embodiment of the present invention includes a method of the prophylaxis and/or treatment of diseases associated with BRD4 inhibition comprising administering a therapeutically effective amount of the present compound(s) to a subject in need thereof.

The present compound can be administered either orally or parenterally. Administration forms includes, for example oral administration, intravenous administration, intramuscular administration, intraarticular administration, intranasal administration, inhalation administration, transdermal administration. Preferred is a parenteral administration form including, for example intravenous administration, intramuscular administration, intraarticular administration, intranasal administration, inhalation administration, transdermal administration.

Dosage forms of the present compounds include, for example tablets, capsules, granules, powders, enteric agents, injections, eye drops, suppositories, transdermal preparations, ointments, aerosols (including inhalants), and these can be formulated using generally used techniques.

For example, oral preparations such as tablets, capsules, granules and powders can be prepared by using, depending on necessity, for example, an excipient such as lactose, mannitol, starch, crystal cellulose, light anhydrous silicic acid, calcium carbonate, calcium hydrogen phosphate, a lubricant such as stearic acid, magnesium stearate, talc, a binder such as starch, hydroxypropyl cellulose, hydroxypropyl methyl cellulose, polyvinyl pyrrolidone, a disintegrator such as carboxymethyl cellulose, low-substituted hydroxypropyl methyl cellulose, calcium citrate, a coating agent such as hydroxypropyl methyl cellulose, macrogol, silicone resin, a stabilizer such as ethyl paraoxybenzoate, benzyl alcohol, a corrigent such as sweetener, acidifier, flavoring agent, with a necessary amount.

Parenteral agents such as injections can be prepared by using, depending on necessity, for example, an isotonizing agent such as sodium chloride, conc. glycerin, propylene glycol, polyethylene glycol, potassium chloride, sorbitol, mannitol, a buffering agent such as sodium phosphate, sodium hydrogen phosphate, sodium acetate, citric acid, glacial acetic acid, trometamol, a surfactant such as polysorbate 80, polyoxyl 40 stearate, polyoxyethylene hydrogenated castor oil 60, a stabilizer such as sodium citrate, sodium edetate, a preservative such as benzalkonium chloride, paraben, benzothonium chloride, paraoxybenzoic acid ester, sodium benzoate, chlorobutanol, a pH adjusting agent such as hydrochloric acid, citric acid, phosphoric acid, glacial acetic acid, sodium hydroxide, sodium carbonate, sodium hydrogen carbonate, an analgesic such as benzyl alcohol, with a necessary amount.

An administration dose of the present compound can be appropriately selected and used depending on, for example the symptoms, age, dosage form. For example, an oral preparation can be generally administered in a dose of 0.01 to 1,000 mg per day, preferably 1 to 100 mg per day, in singly or in several times.

In the following, Production Examples, Pharmacological tests and Preparation Examples of the present compounds are shown. These are to better understanding the present invention, and do not limit the scope of the present invention.

PRODUCTION EXAMPLES

Synthesis of Intermediate 1

[Chem. 8]

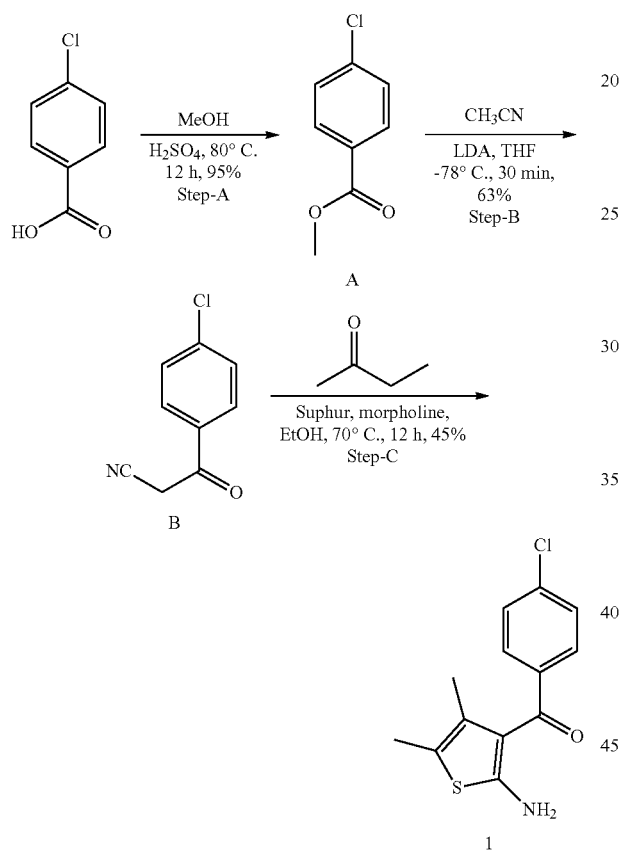

Step-A: Synthesis of methyl 4-chlorobenzoate (Compound A)

To a stirred solution of a compound 1 (1.25 kg, 8,012 mmol) in methanol (12 L) was added conc. sulfuric acid (700 mL, 1,314 mmol) at 0° C., and the mixture was heated at 90° C. for 12 hours. Next, the reaction mixture was allowed to cool at room temperature, and the solvent was distilled off under reduced pressure. The reaction mixture was diluted with water, extracted with ethyl acetate (4 times). The organic layer was separated, washed with a bicarbonate solution and brine, dried over sodium sulfate and concentrated to provide a crude product, to obtain Compound A (1.3 kg, 95.58%).

$^1$H-NMR (400 MHz, CDCl$_3$): δ 7.99 (d, 2H), 7.42 (d, 2H), 3.94 (s, 3H); LCMS: 171.1 (M+1).

Step-B: Synthesis of 3-(4-chlorophenyl)-3-oxopropanenitrile (Compound B)

To a stirred solution of dry CH3CN (14.5 g, 35 mmol) and dry tetrahydrofuran (300 mL) was added lithium diisopropylamide (220 mL, 441 mmol, 2M solution, in tetrahydrofuran) at −78° C., and the mixture was stirred at the same temperature for 1 hour under nitrogen atmosphere. Compound A (50 g, 29.4 mmol) in tetrahydrofuran (10 mL) was added dropwise, and the mixture was stirred at the same temperature for 30 minutes. Next, the reaction mixture was allowed to cool at room temperature, and quenched with an ammonium chloride solution. The precipitated solid was filtered, washed with water, ether and pentane, and dried to obtain Compound B (0.7 g, 63.1%). The same batch was repeated with the scales of 50 g×20.

$^1$H-NMR (400 MHz, CDCl$_3$): δ 7.89 (d, 2H), 7.45 (d, 1H), 4.02 (s, 2H); LCMS: 180.1 (M+1).

Step-C: Synthesis of (2-amino-4,5-dimethylthiophen-3-yl)(4-chlorophenyl)methanone (Intermediate 1)

To a stirred solution of Compound B (50 g, 280 mmol) in ethanol (300 mL) were added sulfur (8.9 g, 280 mmol), morpholine (24.3 g, 280 mmol) and butan-2-one (20 g, 280 mmol), and the reaction liquid was heated to reflux for 12 hours. The progress of the reaction was monitored by TLC. After the reaction completed, the solvent was distilled off under reduced pressure. The reaction liquid was diluted with water and extracted with ethyl acetate (4 times). The organic layer was separated, washed with brine, dried over sodium sulfate and concentrated to obtain a crude product. The crude product was triturated with IPA and n-pentane to purify the same to obtain pure Compound 1. The remaining crude compound was purified by column chromatography with silica gel of 100-200 mesh using 20% ethyl acetate-hexane to obtain Compound 1 (0.51 g, 45.9%). The same batch was repeated with the scales of 100 g and 600 g.

$^1$H NMR (400 MHz, DMSO-d$_6$): δ 7.93 (d, 2H), 7.56-7.42 (m, 2H), 7.4-7.38 (m, 2H), 2.04 (s, 3H), 1.42 (s, 3H); LCMS: 266.05 (M+1).

Synthesis of Intermediate C

[Chem. 9]

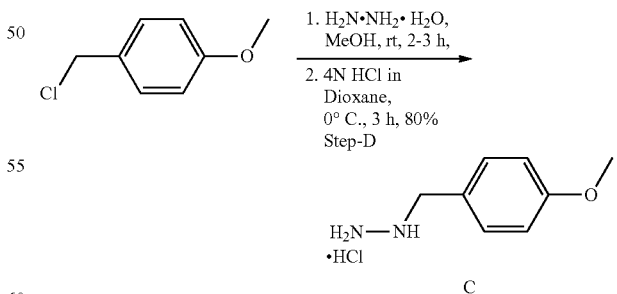

Step-D: Synthesis of (4-methoxybenzyl)hydrazine hydrochloride (Intermediate C)

To a stirred solution of hydrazinehydrate (3.19 mL, 63.8 mmol) in methanol (5 mL) was added 1-(chloromethyl)-4- methoxybenzene (1 g, 6.38 mmol) at 0° C., and the mixture was stirred at room temperature for 2 hours. The progress of the reaction was monitored by TLC. After the reaction completed, the reaction mixture was distilled off under reduced pressure and extracted with ether. The combined organic extracts were washed with water and brine, dried over anhydrous sodium sulfate, and distilled off under reduced pressure. The crude compound was taken in dioxane (5 mL), 4.0 M dioxane hydrochloric acid (2 mL) was added thereto, and the mixture was stirred at room temperature for 3 hours. The precipitated solid was filtered, washed with ether and dried to obtain Compound C (1 g, 80%). The same batch was repeated with the scales of 1 g, 50 g, 100 g and 350 g.

$^1$H NMR (400 MHz, DMSO-$d_6$): δ 7.68 (brs, 2H), 7.38 (dd, 2H), 6.85 (dd, 2H), 3.98 (s, 2H), 3.78 (s, 3H).

Synthetic Schemes of Compounds of Examples 1 to 26

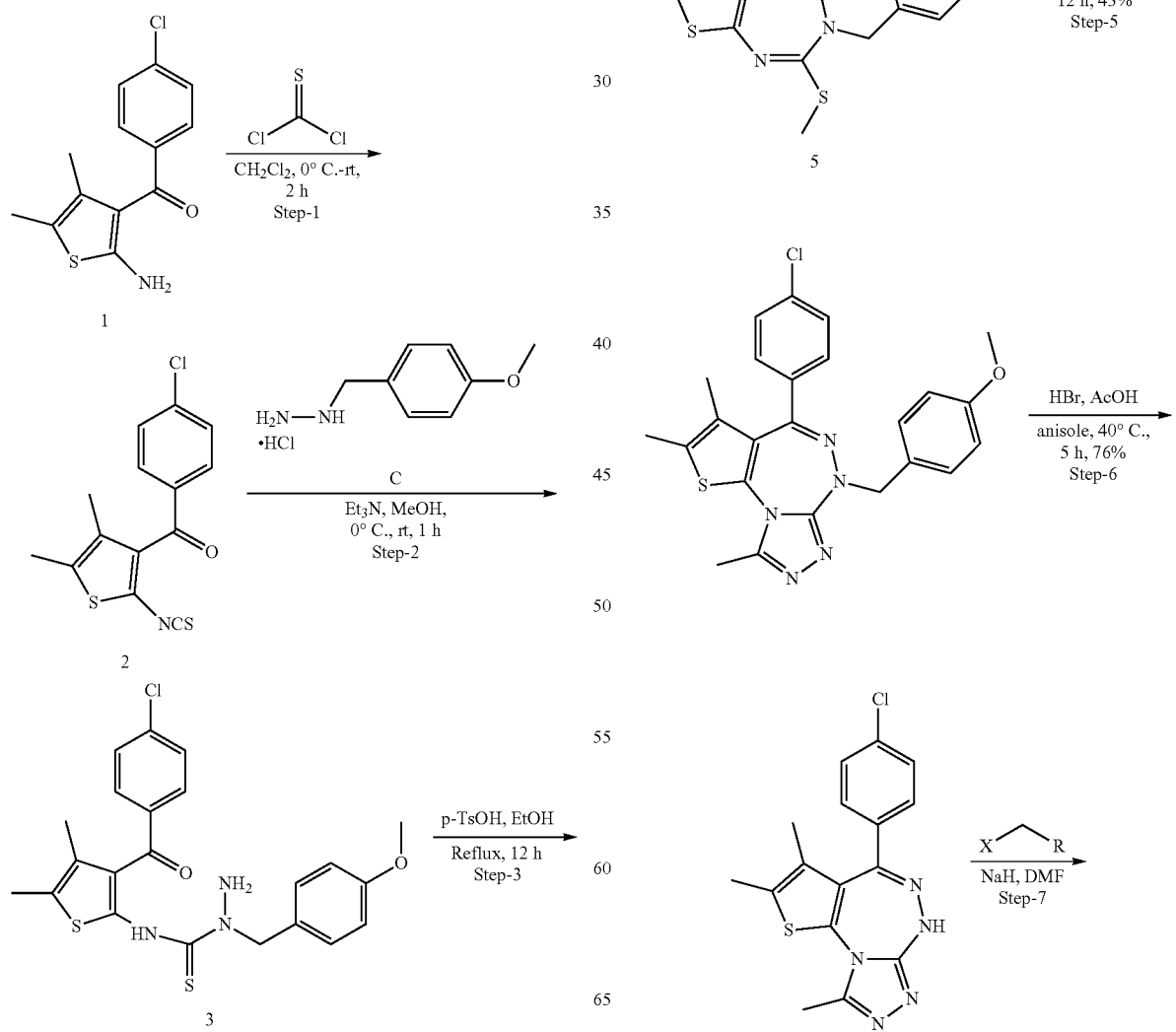

-continued

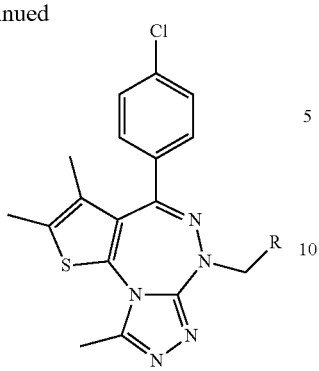

Step-1: Synthesis of (4-chlorophenyl)(2-isothiocyanato-4,5-dimethylthiophen-3-yl)methanone (Intermediate 2)

To a stirred solution of thiophosgene (25 mL, 326 mmol) in water (100 mL) was added dropwise Intermediate 1 (50 g, 188.6 mmol) in dichloromethane (150 mL) at 0° C. The reaction mixture was stirred at room temperature for one hour. The progress of the reaction was monitored by TLC. After the reaction completed, the reaction mixture was diluted with water and extracted with dichloromethane (3 times). The combined organic extracts were washed with brine, dried over anhydrous sodium sulfate, and distilled off under reduced pressure to obtain a crude Intermediate 2. The crude product was used in the next Step (52 g, crude). The same batch was repeated with the scales of 150 g×3.

LCMS: 307.15 (M+1).

Step-2: Synthesis of N-(3-(4-chlorobenzoyl)-4,5-dimethylthiophen-2-yl)-1-(4-methoxybenzyl)hydrazine-1-carbothioamide (Intermediate 3)

To a mixture of Compound C (40 g, 212.7 mmol) in methanol (350 mL) was added triethylamine (100 mL) at 0° C. Compound 2 (52 g, 169.9 mmol) in tetrahydrofuran (350 mL) was added dropwise thereto at the same temperature. The progress of the reaction was monitored by TLC. After the reaction completed, the reaction mixture was distilled off under reduced pressure to obtain a crude Compound 3. The crude product was used in the next Step (88 g, crude).

LCMS: 191.15 (M+1).

Step-3: Synthesis of 5-(4-chlorophenyl)-3-(4-methoxybenzyl)-6,7-dimethyl-1,3-dihydro-2H-thieno[2,3-e][1,2,4]triazepine-2-thione (Intermediate 4)

To a stirred solution of Compound 3 (88 g, 463 mmol) in ethanol (100 mL) was added p-toluenesulfonic acid (15 g, 87.2 mmol), and the reaction mixture was heated at 80° C. for 12 hours. The progress of the reaction was monitored by TLC.

After the reaction completed, the reaction mixture was concentrated. The crude product was diluted with water, and extracted with ethyl acetate (3 times). The combined organic extracts were washed with saturated sodium bicarbonate and brine, dried over anhydrous sodium sulfate, and distilled off under reduced pressure. The crude product was purified by column chromatography with silica gel of 100-200 mesh using 40% ethyl acetate-hexane to obtain Compound 4 (16 g, 19%, total yield from Step-1 to Step-3).

$^1$H NMR (400 MHz, DMSO-d$_6$): δ 7.64-7.60 (m, 2H), 7.38-7.27 (m, 4H), 6.85 (dd, 2H), 3.73 (s, 3H), 3.39 (dt, J=3.8, 2.0 Hz, 1H), 2.21 (s, 3H), 1.41 (s, 3H), 1.08-1.06 (m, 2H); LCMS: 443.25 (M+1).

Step-4: Synthesis of 5-(4-chlorophenyl)-3-(4-methoxybenzyl)-6,7-dimethyl-2-(methylthio)-3H-thieno[2,3-e][1,2,4]triazepine (Intermediate 5)

To a stirred solution of Compound 4 (10 g, 22.6 mmol) in acetone (110 mL) were added potassium carbonate (31 g, 224.6 mmol) and methyl iodide (3.8 g, 26.76 mmol), and the reaction mixture was stirred at room temperature for 2 hours. The progress of the reaction was monitored by TLC. After the reaction completed, the reaction mixture was filtered and washed with acetone. The solvent was distilled off under reduced pressure and diluted with ethyl acetate. The combined organic extracts were washed with water and brine, dried over anhydrous sodium sulfate, and distilled off under reduced pressure. The crude product was used in the next Step (10.3 g, crude). The same batch was repeated with the scales of 50 g and 130 g.

$^1$H NMR (400 MHz, DMSO-d6): δ 7.43-7.40 (m, 2H), 7.23-7.16 (m, 4H), 6.93-6.84 (m, 2H), 4.70 (s, 2H), 3.75 (s, 3H), 2.56 (s, 3H), 2.21 (s, 3H), 1.4 (s, 3H); LCMS: 457.15 (M+1).

Step-5: Synthesis of 4-(4-chlorophenyl)-6-(4-methoxybenzyl)-2,3,9-trimethyl-6H-thieno[2,3-e][1,2,4]triazolo[3,4-c][1,2,4]triazepine (Compound of Example 2)

To a stirred solution of Compound 5 (10.3 g, 22.5 mmol) in n-butanol (30 mL) were added p-toluenesulfonic acid (0.42 g, 2.25 mmol) and acetylhydrazine (3.35 g, 45.1 mmol), and the reaction mixture was heated at 110° C. for 12 hours. The progress of the reaction was monitored by TLC. After the reaction completed, the reaction mixture was distilled off under reduced pressure. The crude product was washed with ether and purified to obtain the compound of Example 2 (4.5 g, 43%).

The same batch was repeated with the scales of 50 g and 130 g.

$^1$H NMR (400 MHz, DMSO-d$_6$): δ 7.53-7.46 (m, 2H), 7.38-7.27 (m, 4H), 6.93-6.84 (m, 2H), 4.93 (d, J=13.7 Hz, 1H), 4.69 (d, J=13.5 Hz, 1H), 3.73 (d, J=1.4 Hz, 3H), 2.50 (dt, J=3.8, 2.0 Hz, 3H), 2.35 (s, 3H), 1.46 (s, 3H); LCMS: 464.40 (M+1); HPLC: 95.12%.

Step-6: Synthesis of 4-(4-chlorophenyl)-2,3,9-trimethyl-6H-thieno[2,3-e][1,2,4]triazolo[3,4-c][1,2,4]triazepine (Compound of Example 1)

To a stirred solution of the compound of Example 2 (30 g, 64.6 mmol) in anisole (15 mL) were added hydrogen bromide (150 mL, 47% aqueous solution) and acetic acid (30 mL), and the reaction mixture was heated at 55° C. for 10 hours. The progress of the reaction was monitored by TLC. After the reaction completed, the reaction mixture was quenched with a sodium bicarbonate solution and extracted with ethyl acetate. The combined organic extracts were washed with brine, dried over anhydrous sodium sulfate, and distilled off under reduced pressure. The crude product was purified by repeat washing with ether and pentane to obtain the compound of Example 1 (51.1 g, 76.8%).

$^1$H NMR (400 MHz, methanol-d$_4$): δ 7.50-7.38 (m, 4H), 2.61 (s, 3H), 2.39 (s, 3H), 1.59 (s, 3H); LCMS: 344.15 (M+1); HPLC: 95.60%.

General Procedure for Coupling Reaction

Step-7

To a stirred solution of the compound of Example 1 (1 eq.) in DMF was added sodium hydride (3 eq.) at 0° C., and the mixture was stirred for 15 minutes. R—X compound (1.2 eq.) was added thereto, and the reaction mixture was stirred at the same temperature for one hour. The progress of the reaction was monitored by TLC. After the reaction completed, the reaction mixture was diluted with water and extracted with ethyl acetate. The combined organic extracts were washed with brine, dried over anhydrous sodium sulfate, and distilled off under reduced pressure. The crude product was purified by preparative TLC/column chromatography/preparative HPLC to obtain a desired product.

Example 3

Step-7: Synthesis of 6-benzyl-4-(4-chlorophenyl)-2,3,9-trimethyl-6H-thieno[2,3-e][1,2,4]triazolo[3,4-c][1,2,4]triazepine (Compound of Example 3)

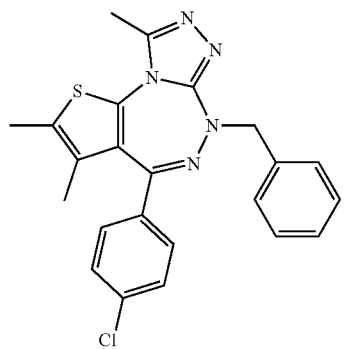

[Chem. 11]

The title compound was synthesized according to the general method of coupling reaction using the compound of Example 1 and (bromomethyl)benzene (60 mg, 31.7%).

$^1$H NMR (400 MHz, CDCl$_3$): δ 7.42 (d, J=7.5 Hz, 2H), 7.39-7.20 (m, 7H), 5.15 (d, J=13.8 Hz, 1H), 4.92 (d, J=14.1 Hz, 1H), 2.62 (s, 3H), 2.37 (s, 3H), 1.54 (s, 3H); LCMS: 434.15 (M+1); HPLC: 97.39%.

Example 4

Step-7: Synthesis of 4-(4-chlorophenyl)-2,3,9-trimethyl-6-(pyridin-3-ylmethyl)-6H-thieno[2,3-e][1,2,4]triazolo[3,4-c][1,2,4]triazepine (Compound of Example 4)

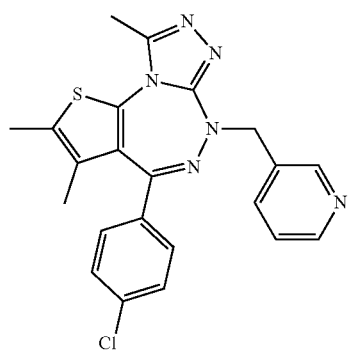

[Chem. 12]

The title compound was synthesized according to the general method of coupling reaction using the compound of Example 1 and 3-(bromomethyl)pyridine (75 mg, 39.5%).

$^1$H NMR (400 MHz, DMSO-d$_6$): δ 8.63 (d, J=2.3 Hz, 1H), 8.49 (dd, J=4.7, 1.7 Hz, 1H), 7.81 (dt, J=7.8, 1.9 Hz, 1H), 7.50 (d, J=8.5 Hz, 2H), 7.41-7.27 (m, 3H), 5.03 (d, J=13.9 Hz, 1H), 4.82 (d, J=14.2 Hz, 1H), 2.54 (s, 3H), 2.35 (s, 3H), 1.46 (s, 3H); LCMS: 435.15 (M+1); HPLC: 99.64%.

Example 5

Step-7: Synthesis of 4-(4-chlorophenyl)-2,3,9-trimethyl-6-(pyridin-2-ylmethyl)-6H-thieno[2,3-e][1,2,4]triazolo[3,4-c][1,2,4]triazepine (Compound of Example 5)

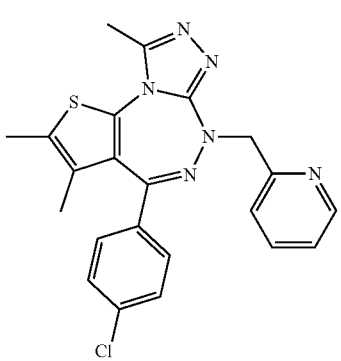

[Chem. 13]

The title compound was synthesized according to the general method of coupling reaction using the compound of Example 1 and 2-(bromomethyl)pyridine (78 mg, 40%).

$^1$H NMR (400 MHz, CDCl$_3$): δ 8.64-8.57 (m, 1H), 7.70-7.61 (m, 1H), 7.46 (d, J=7.9 Hz, 1H), 7.37-7.15 (m, 5H), 5.28 (d, J=14.6 Hz, 1H), 5.06 (d, J=15.1 Hz, 1H), 2.62 (s, 3H), 2.36 (s, 3H), 1.56 (s, 3H); LCMS: 435.15 (M+1); HPLC: 98.10%.

Example 6

Step-7: Synthesis of 4-(4-chlorophenyl)-6-(3-methoxybenzyl)-2,3,9-trimethyl-6H-thieno[2,3-e][1,2,4]triazolo[3,4-c][1,2,4]triazepine (compound of Example 6)

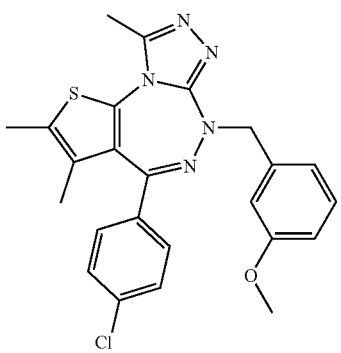

[Chem. 14]

The title compound was synthesized according to the general method of coupling reaction using the compound of Example 1 and 1-(bromomethyl)-3-methoxybenzene compound (80 mg, 70%).

¹H NMR (400 MHz, CDCl₃): δ 7.33-7.20 (m, 5H), 7.04-6.94 (m, 2H), 6.81 (dd, J=8.1, 2.6 Hz, 1H), 5.14 (d, J=13.5 Hz, 1H), 4.90 (d, J=14.4 Hz, 1H), 3.78 (s, 3H), 2.63 (s, 3H), 2.37 (s, 3H), 1.56 (s, 3H); LCMS: 464.15 (M+1); HPLC: 96.46%.

Example 7

Step-7: Synthesis of 6-(4-(tert-butyl)benzyl)-4-(4-chlorophenyl)-2,3,9-trimethyl-6H-thieno[2,3-e][1,2,4]triazolo[3,4-c][1,2,4]triazepine (Compound of Example 7)

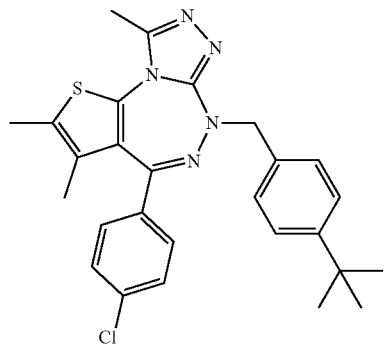

[Chem. 15]

The title compound was synthesized according to the general method of coupling reaction using the compound of Example 1 and 1-(bromomethyl)-4-(tert-butyl)benzene (60 mg, 28.0%).

¹H NMR (400 MHz, CDCl₃): δ 7.39-7.26 (m, 8H), 5.15 (d, J=13.9 Hz, 1H), 4.89 (d, J=12.9 Hz, 1H), 2.62 (s, 3H), 2.37 (s, 3H), 1.56 (s, 3H), 1.32 (s, 9H); LCMS: 490.20 (M+1); HPLC: 99.55%.

Example 8

Step-7: Synthesis of 4-(4-chlorophenyl)-6-(2-fluorobenzyl)-2,3,9-trimethyl-6H-thieno[2,3-e][1,2,4]triazolo[3,4-c][1,2,4]triazepine (Compound of Example 8)

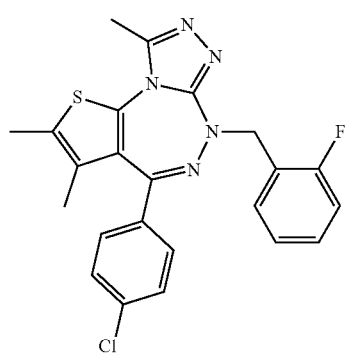

[Chem. 16]

The title compound was synthesized according to the general method of coupling reaction using the compound of Example 1 and 1-(bromomethyl)-2-fluorobenzene (47 mg, 72.3%).

¹H NMR (400 MHz, CDCl₃): δ 7.53-7.44 (m, 1H), 7.30 (t, J=8.3 Hz, 5H), 7.19-7.01 (m, 2H), 5.17 (d, J=14.4 Hz, 1H), 5.02 (d, J=14.0 Hz, 1H), 2.62 (s, 3H), 2.36 (s, 3H), 1.53 (s, 3H). LCMS: 452.20 (M+1); HPLC: 97.11%.

Example 9

Step-7: Synthesis of 4-(4-chlorophenyl)-6-(3-fluorobenzyl)-2,3,9-trimethyl-6H-thieno[2,3-e][1,2,4]triazolo[3,4-c][1,2,4]triazepine (Compound of Example 9)

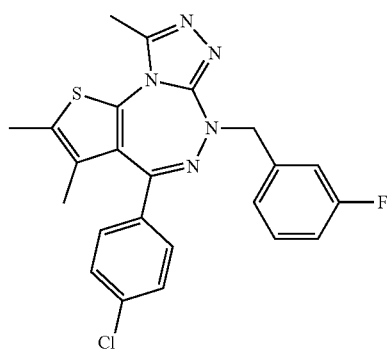

[Chem. 17]

The title compound was synthesized according to the general method of coupling reaction using the compound of Example 1 and 1-(bromomethyl)-3-fluorobenzene (16 mg, 24.4%).

¹H NMR (400 MHz, CDCl₃): δ 7.25 (dq, J=23.7, 8.1, 7.6 Hz, 6H), 7.11 (d, J=10.2 Hz, 1H), 6.97 (t, J=8.6 Hz, 1H), 5.14 (d, J=14.5 Hz, 1H), 4.91 (d, J=14.4 Hz, 1H), 2.63 (s, 3H), 2.39 (s, 3H), 1.59 (s, 3H); LCMS: 452.20 (M+1); HPLC: 98.11%.

Example 10

Step-7: Synthesis of 6-(2-chlorobenzyl)-4-(4-chlorophenyl)-2,3,9-trimethyl-6H-thieno[2,3-e][1,2,4]triazolo[3,4-c][1,2,4]triazepine (Compound of Example 10)

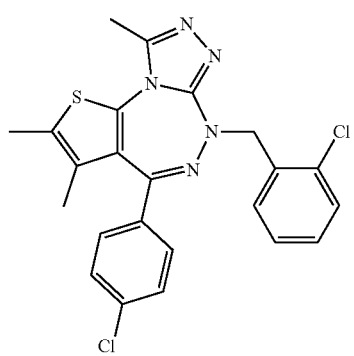

[Chem. 18]

The title compound was synthesized according to the general method of coupling reaction using the compound of Example 1 and 1-(bromomethyl)-2-chlorobenzene (18 mg, 26.4%).

$^1$H NMR (400 MHz, CDCl$_3$): δ 7.50-7.43 (m, 1H), 7.42-7.18 (m, 7H), 5.33-5.23 (m, 1H), 5.08 (d, J=14.5 Hz, 1H), 2.63 (s, 3H), 2.38 (s, 3H), 1.56 (s, 3H); LCMS: 468.15 (M+1); HPLC: 99.34%.

Example 11

Step-7: Synthesis of 4-(4-chlorophenyl)-2,3,9-trimethyl-6-(2-methylbenzyl)-6H-thieno[2,3-e][1,2,4]triazolo[3,4-c][1,2,4]triazepine (Compound of Example 11)

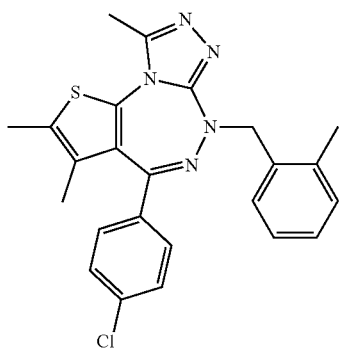

[Chem. 19]

The title compound was synthesized according to the general method of coupling reaction using the compound of Example 1 and 1-(bromomethyl)-2-methylbenzene (21 mg, 32.2%).

$^1$H NMR (400 MHz, CDCl$_3$): δ 7.44-7.36 (m, 1H), 7.33-7.13 (m, 7H), 5.14 (d, J=14.2 Hz, 1H), 4.94 (d, J=14.1 Hz, 1H), 2.62 (s, 3H), 2.36 (d, J=9.0 Hz, 6H), 1.53 (s, 3H); LCMS: 448.25 (M+1); HPLC: 99.6%.

Example 12

Step-7: Synthesis of 4-(4-chlorophenyl)-2,3,9-trimethyl-6-(3-methylbenzyl)-6H-thieno[2,3-e][1,2,4]triazolo[3,4-c][1,2,4]triazepine (Compound of Example 12)

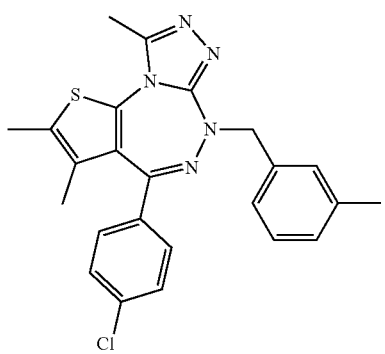

[Chem. 20]

The title compound was synthesized according to the general method of coupling reaction using the compound of Example 1 and 1-(bromomethyl)-3-methylbenzene (25 mg, 38.4%).

$^1$H NMR (400 MHz, CDCl$_3$): δ 7.25 (d, J=25.3, 6.4 Hz, 7H), 7.12-7.05 (m, 1H), 5.11 (d, J=14.0 Hz, 1H), 4.89 (d, J=14.0 Hz, 1H), 2.63 (d, J=3.1 Hz, 3H), 2.36 (dd, J=13.0, 3.6 Hz, 6H), 1.59 (d, J=3.6 Hz, 3H); LCMS: 448.25 (M+1); HPLC: 99.94%.

Example 13

Step-7: Synthesis of 4-(4-chlorophenyl)-2,3,9-trimethyl-6-(4-methylbenzyl)-6H-thieno[2,3-e][1,2,4]triazolo[3,4-c][1,2,4]triazepine (Compound of Example 13)

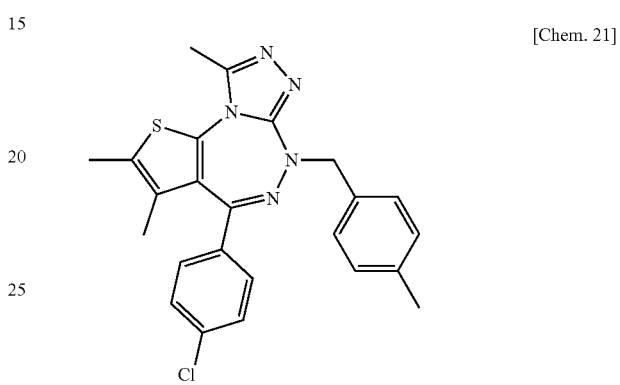

[Chem. 21]

The title compound was synthesized according to the general method of coupling reaction using the compound of Example 1 and 1-(bromomethyl)-4-methylbenzene (14 mg, 20.8%).

$^1$H NMR (400 MHz, CDCl$_3$): δ 7.35-7.22 (m, 6H), 7.13 (d, J=7.6 Hz, 2H), 5.11 (d, J=13.9 Hz, 1H), 4.88 (d, J=13.8 Hz, 1H), 2.62 (s, 3H), 2.36 (d, J=9.2 Hz, 6H), 1.54 (s, 3H); LCMS: 448.15 (M+1); HPLC: 95.82%.

Example 14

Step-7: Synthesis of 4-(4-chlorophenyl)-2,3,9-trimethyl-6-(4-(trifluoromethyl)benzyl)-6H-thieno[2,3-e][1,2,4]triazolo[3,4-c][1,2,4]triazepine (Compound of Example 14)

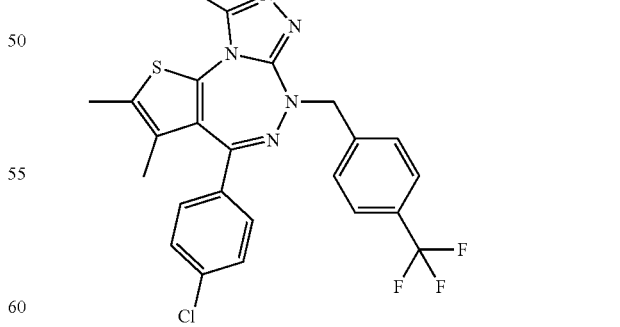

[Chem. 22]

The title compound was synthesized according to the general method of coupling reaction using the compound of Example 1 and 1-(bromomethyl)-4-(trifluoromethyl)benzene (14 g, 18.6%).

$^1$H NMR (400 MHz, DMSO-d$_6$): δ 7.71 (d, J=8.1 Hz, 2H), 7.61 (d, J=8.0 Hz, 2H), 7.49 (d, J=8.3 Hz, 2H), 7.32 (d, J=8.5

Hz, 2H), 5.10 (s, 1H), 4.89 (d, J=14.6 Hz, 1H), 2.54 (s, 3H), 2.37 (s, 3H), 1.50 (s, 3H); LCMS: 502 (M+1); HPLC: 99.89%.

Example 15

Step-7: 4-(4-Chlorophenyl)-2,3,9-trimethyl-N-phenyl-6H-thieno[2,3-e][1,2,4]triazolo[3,4-c][1,2,4]triazepine-6-carboxamide (Compound of Example 15)

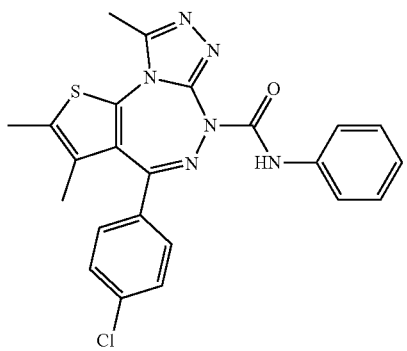

[Chem. 23]

The title compound was synthesized according to the general method of coupling reaction using the compound of Example 1 and phenylcarbamic acid bromide (16 mg, 23.1%).

¹H NMR (400 MHz, CDCl₃) δ 8.85 (s, 1H), 7.61 (d, J=8.0 Hz, 2H), 7.53 (d, J=8.3 Hz, 2H), 7.44 (d, J=8.3 Hz, 2H), 7.36 (t, J=7.8 Hz, 2H), 7.13 (t, J=7.4 Hz, 1H), 2.69 (s, 3H), 2.40 (s, 3H), 1.63 (s, 3H); LCMS: 463 (M+1); HPLC: 98.09%.

Example 16

Step-7: Synthesis of 6-(3-chlorobenzyl)-4-(4-chlorophenyl)-2,3,9-trimethyl-6H-thieno[2,3-e][1,2,4]triazolo[3,4-c][1,2,4]triazepine (Compound of Example 16)

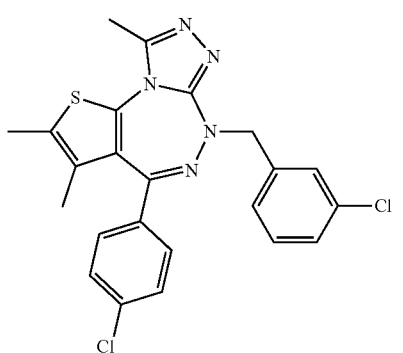

[Chem. 24]

The title compound was synthesized according to the general method of coupling reaction using the compound of Example 1 and 1-(bromomethyl)-3-chlorobenzene (24 mg, 35%).

¹H NMR (400 MHz, CDCl₃): δ 7.65 (dd, J=13.0, 8.1 Hz, 1H), 7.48 (t, J=7.6 Hz, 3H), 7.42-7.21 (m, 4H), 5.15 (d, J=14.9 Hz, 1H), 4.85 (d, J=14.8 Hz, 1H), 2.63 (s, 3H), 2.38 (s, 3H), 1.56 (s, 3H); LCMS: 468.10 (M+1); HPLC: 96.82%.

Step-7: Synthesis of 4-(4-chlorophenyl)-2,3,9-trimethyl-6-(2-(trifluoromethyl)benzyl)-6H-thieno[2,3-e][1,2,4]triazolo[3,4-c][1,2,4]triazepine (Compound of Example 17)

Example 17

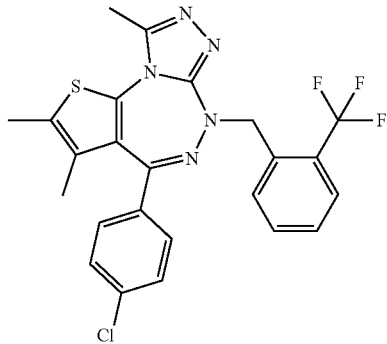

[Chem. 25]

The title compound was synthesized according to the general method of coupling reaction using the compound of Example 1 and 1-(bromomethyl)-2-(trifluoromethyl)benzene compound (20 mg, 27%).

¹H NMR (400 MHz, CDCl₃): δ 7.65 (dd, J=13.0, 8.1 Hz, 2H), 7.48 (t, J=7.6 Hz, 1H), 7.42-7.21 (m, 5H), 5.39 (d, J=14.9 Hz, 1H), 5.15 (d, J=14.8 Hz, 1H), 2.63 (s, 3H), 2.38 (s, 3H), 1.56 (s, 3H); LCMS: 502 (M+1); HPLC: 96.39%.

Example 18

Step-7: Synthesis of 4-(4-chlorophenyl)-2,3,9-trimethyl-6-(3-(trifluoromethyl)benzyl)-6H-thieno[2,3-e][1,2,4]triazolo[3,4-c][1,2,4]triazepine (Compound of Example 18)

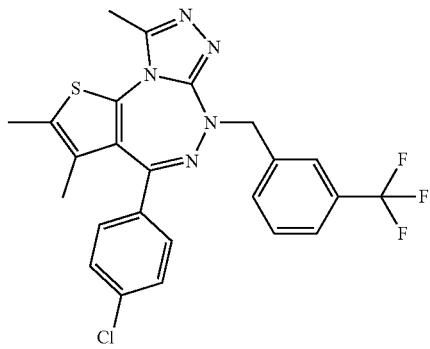

[Chem. 26]

The title compound was synthesized according to the general method of coupling reaction using the compound of Example 1 and 1-(bromomethyl)-3-(trifluoromethyl)benzene (26 mg, 36%).

¹H NMR (400 MHz, CDCl₃): δ 7.68 (s, 1H), 7.61 (d, J=7.6 Hz, 1H), 7.54 (d, J=7.9 Hz, 1H), 7.46 (t, J=7.8 Hz, 1H), 7.33-7.15 (m, 4H), 5.16 (d, J=14.3 Hz, 1H), 4.99 (d,

J=15.0 Hz, 1H), 2.64 (s, 3H), 2.39 (s, 3H), 1.56 (s, 3H); LCMS: 502.35 (M+1); HPLC: 95.8%.

Example 19

Step-7: Synthesis of 4-(4-chlorophenyl)-2,3,9-trimethyl-6-phenethyl-6H-thieno[2,3-e][1,2,4]triazolo[3,4-c][1,2,4]triazepine (Compound of Example 19)

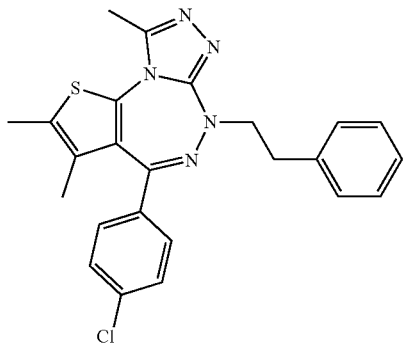

[Chem.27]

The title compound was synthesized according to the general method of coupling reaction using the compound of Example 1 and (2-bromoethyl)benzene (24 mg, 36%).

$^1$H NMR (400 MHz, CDCl$_3$): δ 7.41-7.31 (m, 3H), 7.29-7.15 (m, 6H), 4.12-4.02 (m, 2H), 3.11 (d, J=7.6 Hz, 2H), 2.60 (s, 3H), 2.38 (s, 3H), 1.62 (s, 3H); LCMS: 448.30 (M+1); HPLC: 94.1%.

Example 20

Step-7: Synthesis of 4-(4-chlorophenyl)-2,3,9-trimethyl-6-(3-phenylpropyl)-6H-thieno[2,3-e][1,2,4]triazolo[3,4-c][1,2,4]triazepine (Example 20)

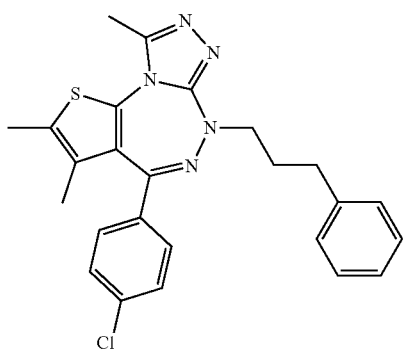

[Chem. 28]

The title compound was synthesized according to the general method of coupling reaction using the compound of Example 1 and (3-bromopropyl)benzene (18 mg, 27%).

$^1$H NMR (400 MHz, CDCl$_3$): δ 7.45-7.31 (m, 4H), 7.25 (d, J=9.0 Hz, 3H), 7.18 (d, J=7.4 Hz, 2H), 3.86 (q, J=9.3, 8.9 Hz, 2H), 2.73 (d, J=10.2 Hz, 2H), 2.61 (s, 3H), 2.37 (s, 3H), 2.14 (d, J=17.9 Hz, 2H), 1.56 (s, 3H); LCMS: 462.35 (M+1); HPLC: 99.26%.

Example 21

Step-7: Synthesis of 4-(4-chlorophenyl)-6-((6-fluoropyridin-2-yl)methyl)-2,3,9-trimethyl-6H-thieno[2,3-e][1,2,4]triazolo[3,4-c][1,2,4]triazepine (Compound of Example 21)

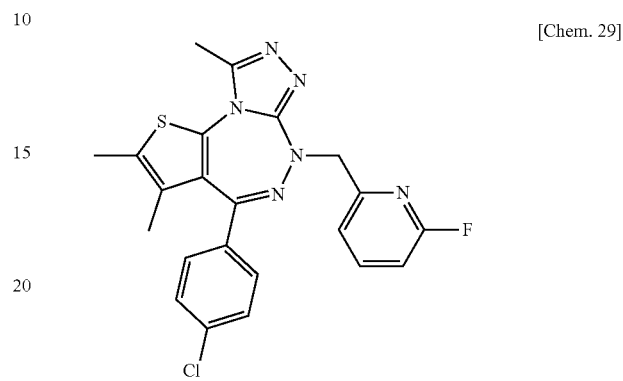

[Chem. 29]

The title compound was synthesized according to the general method of coupling reaction using the compound of Example 1 and 2-(bromomethyl)-6-fluoropyridine (23 mg, 35%).

$^1$H NMR (400 MHz, CDCl$_3$): δ 7.75 (q, J=8.0 Hz, 1H), 7.30 (m, J=8.7 Hz, 5H), 6.88-6.80 (m, 1H), 5.23 (d, J=14.2 Hz, 1H), 4.99 (d, J=15.2 Hz, 1H), 2.62 (s, 3H), 2.37 (s, 3H), 1.27 (d, J=12.3 Hz, 1H); LCMS: 453.20 (M+1); HPLC: 94.16%.

Example 22

Step-7: Synthesis of 4-(4-chlorophenyl)-6-((5-fluoropyridin-2-yl)methyl)-2,3,9-trimethyl-6H-thieno[2,3-e][1,2,4]triazolo[3,4-c][1,2,4]triazepine (Compound of Example 22)

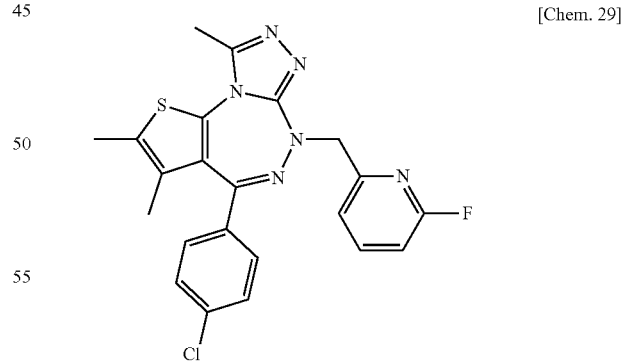

[Chem. 29]

The title compound was synthesized according to the general method of coupling reaction using the compound of Example 1 and 2-(bromomethyl)-5-fluoropyridine (20 mg, 30%).

$^1$H NMR (400 MHz, CDCl$_3$): δ 8.46 (d, J=2.9 Hz, 1H), 7.43-7.19 (m, 6H), 5.25 (d, J=14.3 Hz, 2H), 2.62 (s, 3H), 2.36 (s, 3H), 1.45 (s, 3H); LCMS: 453.15 (M+1); HPLC: 90.33%.

Example 23

Step-7: Synthesis of 4-(4-chlorophenyl)-6-((3-fluoropyridin-2-yl)methyl)-2,3,9-trimethyl-6H-thieno[2,3-e][1,2,4]triazolo[3,4-c][1,2,4]triazepine (Compound of Example 23)

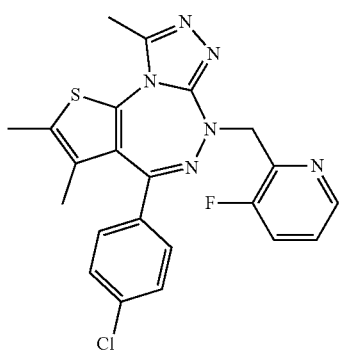
[Chem. 31]

The title compound was synthesized according to the general method of coupling reaction using the compound of Example 1 and 2-(bromomethyl)-3-fluoropyridine (24 mg, 36.8%).

$^1$H NMR (400 MHz, CDCl$_3$): δ 8.46 (d, J=2.9 Hz, 1H), 7.53-7.27 (m, 5H), 7.24 (s, 1H), 5.25 (d, J=14.3 Hz, 1H), 5.04 (d, J=14.2 Hz, 1H), 2.62 (s, 3H), 2.36 (s, 3H), 1.55 (s, 3H); LCMS: 453.15 (M+1); HPLC: 99%.

Example 24

Step-7: Synthesis of 4-(4-chlorophenyl)-6-((3-chloropyridin-2-yl)methyl)-2,3,9-trimethyl-6H-thieno[2,3-e][1,2,4]triazolo[3,4-c][1,2,4]triazepine (Compound of Example 24)

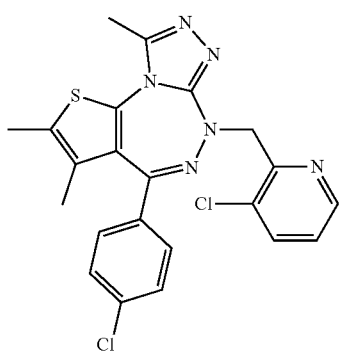
[Chem. 32]

The title compound was synthesized according to the general method of coupling reaction using the compound of Example 1 and 2-(bromomethyl)-3-chloropyridine (17 mg, 25%).

$^1$H NMR (400 MHz, CDCl$_3$): δ 8.47 (d, J=2.4 Hz, 1H), 7.76 (dd, J=8.1, 2.4 Hz, 1H), 7.36-7.22 (m, 5H), 5.08 (s, 2H), 2.62 (s, 3H), 2.37 (s, 3H), 1.28 (d, J=14.0 Hz, 3H); LCMS: 469.25 (M+1); HPLC: 98.16%.

Example 25

Step-7: Synthesis of 4-(4-chlorophenyl)-6-((2-fluoropyridin-3-yl)methyl)-2,3,9-trimethyl-6H-thieno[2,3-e][1,2,4]triazolo[3,4-c][1,2,4]triazepine (Compound of Example 25)

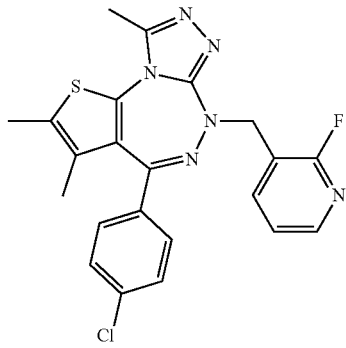
[Chem. 33]

The title compound was synthesized according to the general method of coupling reaction using the compound of Example 1 and 3-(bromomethyl)-2-fluoropyridine (15 mg, 23%).

$^1$H NMR (400 MHz, CDCl$_3$): δ 8.15 (d, J=4.6 Hz, 1H), 7.98 (t, J=8.3 Hz, 1H), 7.31 (q, J=8.5 Hz, 4H), 7.17 (t, J=6.1 Hz, 1H), 5.16 (d, J=14.3 Hz, 1H), 4.97 (d, J=14.5 Hz, 1H), 2.62 (s, 3H), 2.37 (s, 3H), 1.56 (s, 3H); LCMS: 453.15 (M+1); HPLC: 95.18%.

Example 26

Step-7: Synthesis of 4-(4-chlorophenyl)-6-((6-fluoropyridin-3-yl)methyl)-2,3,9-trimethyl-6H-thieno[2,3-e][1,2,4]triazolo[3,4-c][1,2,4]triazepine (Compound of Example 26)

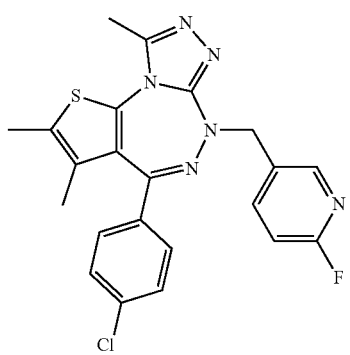
[Chem. 34]

The title compound was synthesized according to the general method of coupling reaction using the compound of Example 1 and 5-(bromomethyl)-2-fluoropyridine (14 mg, 21.3%).

$^1$H NMR (400 MHz, CDCl$_3$): δ 8.31 (d, J=2.2 Hz, 1H), 7.89 (td, J=7.9, 2.4 Hz, 1H), 7.32 (d, J=8.4 Hz, 4H), 6.91 (dd, J=8.4, 2.9 Hz, 1H), 5.10 (d, J=13.9 Hz, 1H), 4.93 (s, 1H), 2.63 (s, 3H), 2.37 (s, 3H), 1.54 (s, 3H); LCMS: 453.20 (M+1); HPLC: 95.84%.

Synthetic Scheme of the Compounds of Examples 27 to 33

[Chem. 35]

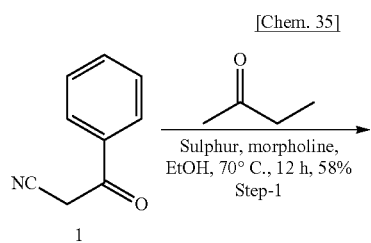

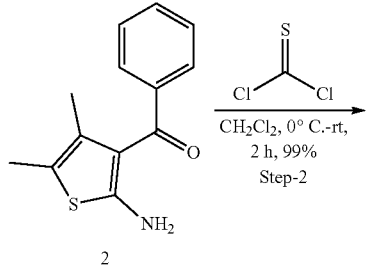

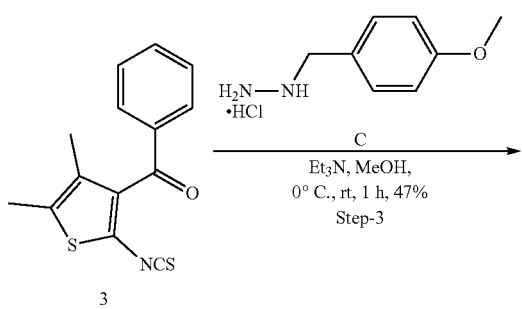

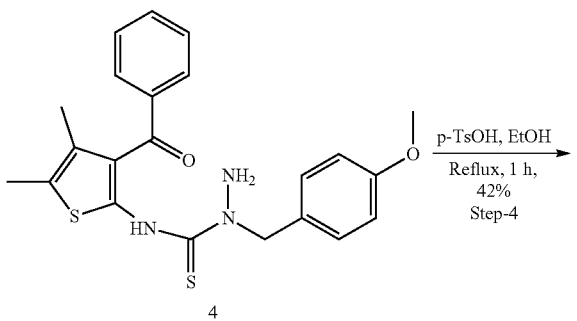

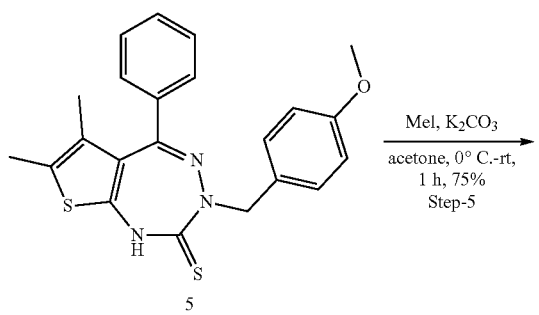

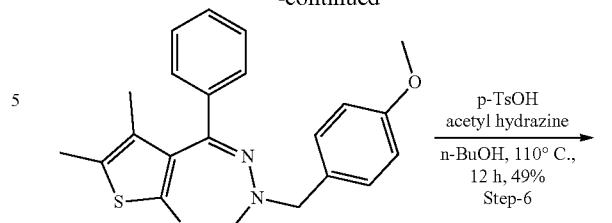

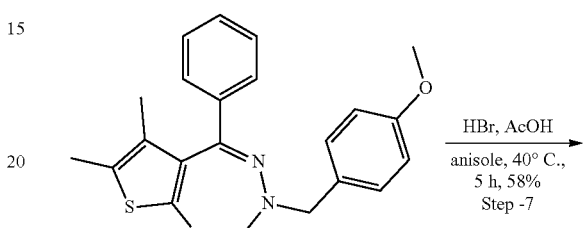

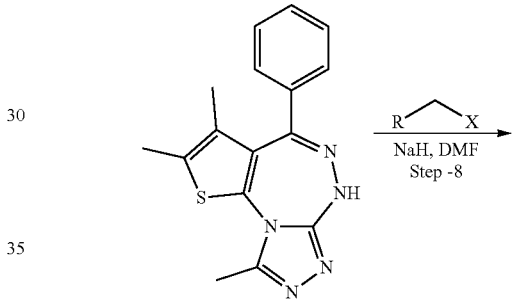

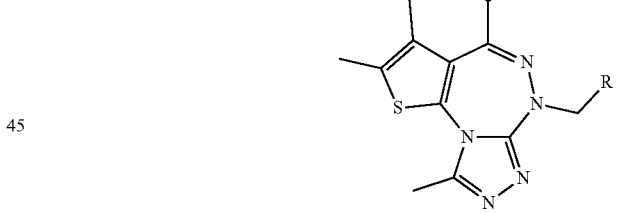

Step-1: Synthesis of (2-amino-4,5-dimethylthiophen-3-yl)(phenyl)methanone (Intermediate 2)

To a stirred solution of Compound 1 (15 g, 104 mmol) in ethanol (50 mL) were added sulfur (3.3 g, 104 mmol), morpholine (9 g, 104 mmol) and butan-2-one (7 g, 104 mmol), and the reaction liquid was heated to reflux for 12 hours. The progress of the reaction was monitored by TLC. After the reaction completed, the solvent was distilled off under reduced pressure. The reaction liquid was diluted with water and extracted with ethyl acetate (4 times). The organic layer was separated, washed with brine, dried over sodium sulfate and concentrated to obtain a crude product. The crude product was purified by column chromatography with silica gel of 100-200 mesh using 20% ethyl acetate-hexane to obtain Compound 1 (14 g, 58.5%).

¹H NMR (400 MHz, CDCl₃): δ 7.59-7.38 (m, 5H), 6.42-6.25 (m, 2H), 2.14 (s, 3H), 1.54 (s, 3H); LCMS: 232.1 (M+1).

Step-2: Synthesis of (2-isothiocyanato-4,5-dimethylthiophen-3-yl)(phenyl)methanone (Intermediate 3)

To a stirred solution of thiophosgene (1 mL, 12.97 mmol) in water (5 mL) was added dropwise Compound 2 (2 g, 8.6 mmol) in dichloromethane (5 mL) at 0° C. The reaction mixture was stirred at room temperature for one hour. The progress of the reaction was monitored by TLC. After the reaction completed, the reaction mixture was diluted with water and extracted with dichloromethane (3 times). The combined organic extracts were washed with brine, dried over anhydrous sodium sulfate, and distilled off under reduced pressure to obtain a crude Intermediate 3 (2 g, crude). The crude product was used in the next Step. The same batch was repeated with the scale of 6 g.
LCMS: 274.15 (M+1).

Step-3: Synthesis of N-(3-benzoyl-4,5-dimethylthiophen-2-yl)-1-(4-methoxybenzyl)hydrazine-1-carbothioamide (Intermediate 4)

To a mixture of Compound C (1.55 g, 8.8 mmol) in methanol (5 mL) was added triethylamine (1.2 mL, 8.8 mmol) at 0° C. Compound 3 (2 g, 7.3 mmol) in tetrahydrofuran (5 mL) was added to the reaction mixture at the same temperature. The progress of the reaction was monitored by TLC. After the reaction completed, the reaction mixture was distilled off under reduced pressure to obtain a crude Intermediate 4. The crude product was used in the next Step (2 g, crude). The same batch was repeated with the scale of 6 g.
LCMS: 426.4 (M+1).

Step-4: Synthesis of 3-(4-methoxybenzyl)-6,7-dimethyl-5-phenyl-1,3-dihydro-2H-thieno[2,3-e][1,2,4]triazepine-2-thione (Intermediate 5)

To a stirred solution of Intermediate 4 (2 g, 4.7 mmol) in ethanol (20 mL) was added p-toluenesulfonic acid (50 mg, catalytic amount), and the reaction mixture was heated at 80° C. for 3 hours. The progress of the reaction was monitored by TLC. After the reaction completed, the reaction mixture was diluted with water and extracted with ethyl acetate (3 times). The combined organic extracts were washed with brine, dried over anhydrous sodium sulfate, and distilled off under reduced pressure. The crude product was purified by column chromatography with silica gel of 100-200 mesh using 15% ethyl acetate-hexane to obtain Intermediate 5 (0.8 g, 42%). The same batch was repeated with the scale of 6 g.
¹H NMR (400 MHz, CDCl₃): δ 7.59 (s, 1H), 7.41-7.21 (m, 5H), 7.16 (d, 2H), 6.82 (d, 2H), 5.38-5.21 (m, 2H), 3.8 (s, 3H), 2.21 (s, 3H), 1.21 (s, 3H); LCMS: 408.25 (M+1).

Step-5: Synthesis of 3-(4-methoxybenzyl)-6,7-dimethyl-2-(methylthio)-5-phenyl-3H-thieno[2,3-e][1,2,4]triazepine (Intermediate 6)

To a stirred solution of Intermediate 5 (0.8 g, 1.97 mmol) in acetone (15 mL) were added potassium carbonate (2.71 g, 19.7 mmol) and methyl iodide (0.15 mL, 2.36 mmol), and the reaction mixture was stirred at room temperature for 3 hours. The progress of the reaction was monitored by TLC. After the reaction completed, the reaction mixture was filtered and washed with acetone. The solvent was distilled off under reduced pressure and diluted with ethyl acetate. The combined organic extracts were washed with water and brine, dried over anhydrous sodium sulfate, and distilled off under reduced pressure. The crude product was purified by column chromatography with silica gel of 100-200 mesh using 10% ethyl acetate-hexane to obtain Intermediate 6 (0.62 g, 74.8%). The same batch was repeated with the scale of 3.5 g.
¹H NMR (400 MHz, CDCl₃): δ 7.59-7.18 (m, 7H), 6.82 (d, 2H), 4.95-4.40 (m, 2H), 3.82 (s, 3H), 2.42 (s, 3H), 2.22 (s, 3H), 1.21 (s, 3H); LCMS: 422.4 (M+1).

Example 28

Step-6: Synthesis of 6-(4-methoxybenzyl)-2,3,9-trimethyl-4-phenyl-6H-thieno[2,3-e][1,2,4]triazolo[3,4-c][1,2,4]triazepine (Compound of Example 28)

[Chem. 36]

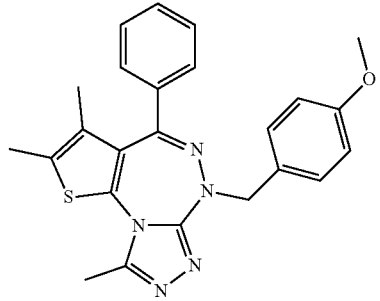

To a stirred solution of Intermediate 6 (0.62 g, 1.47 mmol) in n-butanol (5 mL) were added p-toluenesulfonic acid (28 mg, 0.147 mmol) and acetylhydrazine (0.218 g, 2.94 mmol), and the reaction mixture was heated at 110° C. for 12 hours. The progress of the reaction was monitored by TLC. After the reaction completed, the reaction mixture was distilled off under reduced pressure. The crude product was washed with ether and purified to obtain the compound of Example 28 (0.31 g, 49%). The same batch was repeated with the scale of 3 g.
¹H NMR (400 MHz, DMSO-d₆): δ 7.52-7.28 (m, 7H), 6.94-6.85 (m, 2H), 4.92 (d, J=13.6 Hz, 1H), 4.69 (d, J=13.5 Hz, 1H), 3.74 (s, 3H), 2.54 (s, 2H), 2.35 (s, 3H), 1.44 (s, 3H); LCMS: 430.15 (M+1); HPLC: 97.87%.

Example 27

Step-7: Synthesis of 2,3,9-trimethyl-4-phenyl-6H-thieno[2,3-e][1,2,4]triazolo[3,4-c][1,2,4]triazepine (Compound of Example 27)

[Chem. 37]

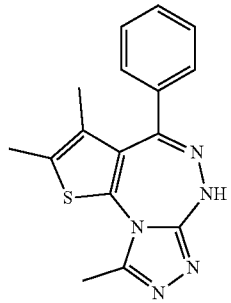

To a stirred solution of the compound of Example 28 (0.31 g, 0.7 mmol) in anisole (1 mL, 9.25 mmol) was added hydrogen bromide (3 mL, 47%) in acetic acid, and the reaction mixture was heated at 50° C. for 12 hours. The progress of the reaction was monitored by TLC. After the reaction completed, the reaction mixture was quenched with a sodium bicarbonate solution and extracted with ethyl acetate. The combined organic extracts were washed with brine, dried over anhydrous sodium sulfate, and distilled off under reduced pressure. The crude product was purified by repeating washing with ether and pentane to obtain the compound of Example 27 (0.13 g, 58.2%).

$^1$H NMR (400 MHz, DMSO-$d_6$): δ 9.81 (s, 1H), 7.51-7.36 (m, 5H), 2.52 (s, 3H), 2.34 (s, 3H), 1.46 (s, 3H); LCMS: 310.05 (M+1); HPLC: 98.9%.

Step-8: General Procedure for Coupling Reaction

To a stirred solution of the compound of Example 27 (1 eq.) in DMF was added sodium hydride (3 eq.) at 0° C., and the mixture was stirred for 15 minutes. R—X compound (1.2 eq) was added thereto, and the reaction mixture was stirred at the same temperature for 1 to 2 hours. The progress of the reaction was monitored by TLC. After the reaction completed, the reaction mixture was diluted with water and extracted with ethyl acetate. The combined organic extracts were washed with brine, dried over anhydrous sodium sulfate, and distilled off under reduced pressure. The crude product was purified by preparative TLC/column chromatography/preparative HPLC to obtain a desired product.

Example 29

Step-8: Synthesis of 6-benzyl-2,3,9-trimethyl-4-phenyl-6H-thieno[2,3-e][1,2,4]triazolo[3,4-c][1,2,4]triazepine (compound of Example 29)

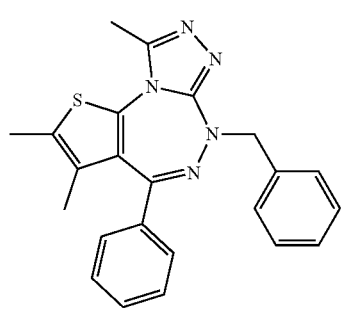

[Chem. 38]

The title compound was synthesized according to the general method of coupling reaction using the compound of Example 27 and (bromomethyl)benzene compound (81 mg, 52.3%).

$^1$H NMR (400 MHz, DMSO-$d_6$): δ 7.51-7.23 (m, 10H), 5.01 (d, J=13.9 Hz, 1H), 4.77 (d, J=14.0 Hz, 1H), 2.55 (s, 3H), 2.35 (s, 3H), 1.44 (s, 3H); LCMS: 400.15 (M+1); HPLC: 97.59%.

Example 30

Step-8: Synthesis of 2,3,9-trimethyl-4-phenyl-6-(pyridin-3-ylmethyl)-6H-thieno[2,3-e]-[1,2,4]triazolo[3,4-c][1,2,4]triazepine (Compound of Example 30)

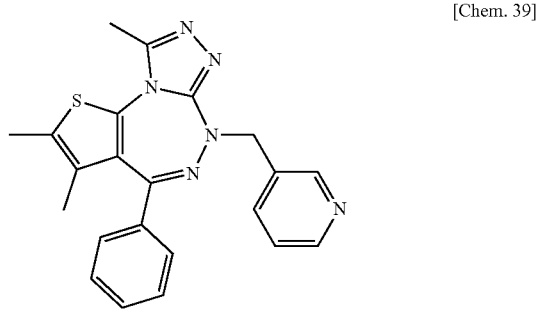 [SMILES: Cc1sc2c(c1C)C(c1ccccc1)=NN(Cc1cccnc1)c1nnc(C)n1-2]

[Chem. 39]

The title compound was synthesized according to the general method of coupling reaction using the compound of Example 27 and 3-(bromomethyl)pyridine (80 mg, 51.5%).

$^1$H NMR (400 MHz, DMSO-$d_6$): δ 8.64 (d, J=2.2 Hz, 1H), 8.49 (dd, J=4.7, 1.7 Hz, 1H), 7.82 (dt, J=7.9, 1.9 Hz, 1H), 7.52-7.25 (m, 6H), 5.06-4.97 (m, 1H), 4.82 (d, J=14.0 Hz, 1H), 2.55 (s, 3H), 2.35 (s, 3H), 1.43 (s, 3H); LCMS: 401.15 (M+1); HPLC: 96.69%.

Example 31

Step-8: Synthesis of 2,3,9-trimethyl-4-phenyl-6-(pyridin-2-ylmethyl)-6H-thieno[2,3-e][1,2,4]triazolo[3,4-c][1,2,4]triazepine (Compound of Example 31)

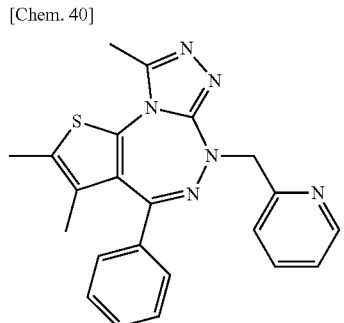

[Chem. 40]

The title compound was synthesized according to the general method of coupling reaction using the compound of Example 27 and 2-(bromomethyl)pyridine (110 mg, 70.7%).

$^1$H NMR (400 MHz, DMSO-$d_6$): δ 8.58-8.51 (m, 1H), 7.78 (td, J=7.7, 1.8 Hz, 1H), 7.51-7.24 (m, 7H), 5.11 (d, J=15.0 Hz, 1H), 4.88 (d, J=15.2 Hz, 1H), 2.56 (s, 3H), 2.37 (s, 3H), 1.47 (s, 3H); LCMS: 401.15 (M+1); HPLC: 99.69%.

Example 32

Step-8: 2,3,9-trimethyl-4-phenyl-6-(pyridin-4-ylmethyl)-6H-thieno[2,3-e][1,2,4]triazolo[3,4-c][1,2,4]triazepine (Compound of Example 32)

[Chem. 41]

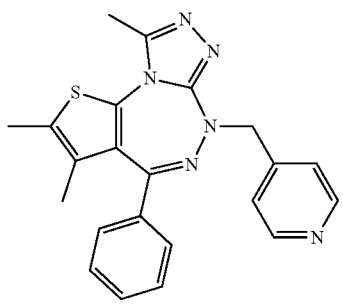

The title compound was synthesized according to the general method of coupling reaction using the compound of Example 27 and 4-(bromomethyl)pyridine (30 mg, 23.2%).

¹H NMR (400 MHz, DMSO-d₆): δ 8.52 (d, J=5.2 Hz, 2H), 7.50-7.33 (m, 5H), 7.30-7.22 (m, 2H), 5.03 (d, J=15.2 Hz, 1H), 4.81 (d, J=15.0 Hz, 1H), 2.54 (s, 3H), 2.35 (s, 3H), 1.46 (s, 3H); LCMS: 401.15 (M+1); HPLC: 99.29%.

Example 33

[Chem. 42]

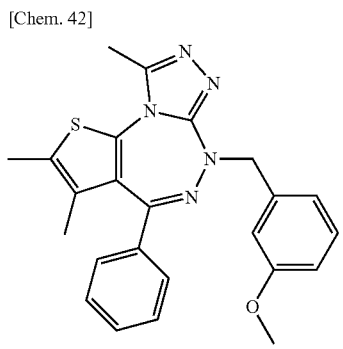

Step-8: Synthesis of 6-(3-methoxybenzyl)-2,3,9-trimethyl-4-phenyl-6H-thieno[2,3-e][1,2,4]triazolo[3,4-c][1,2,4]triazepine (Compound of Example 33)

The title compound was synthesized according to the general method of coupling reaction using the compound of Example 27 and 1-(bromomethyl)-3-methoxybenzene compound (66 mg, 39.6%).

¹H NMR (400 MHz, DMSO-d₆): δ 7.52-7.36 (m, 3H), 7.35-7.21 (m, 3H), 7.00-6.93 (n; 2H), 6.88-6.80 (m, 1H), 4.99 (d, J=14.3 Hz, 1H), 4.76 (d, J=14.3 Hz, 1H), 3.72 (d, J=1.0 Hz, 3H), 2.55 (s, 3H), 2.36 (s, 3H), 1.46 (s, 3H); LCMS: 430.10 (M+1); HPLC: 99.77%.

Synthesis of the Compounds of Examples 34 to 43

Example 34

Step-7: Synthesis of 4-(4-chlorophenyl)-6-(2-methoxybenzyl)-2,3,9-trimethyl-6H-thieno[2,3-e][1,2,4]triazolo[3,4-c][1,2,4]triazepine (Compound of Example 34)

[Chem. 43]

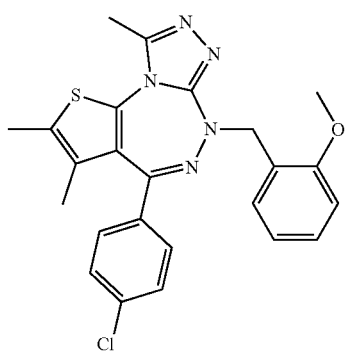

The title compound was synthesized according to the general method of coupling reaction using the compound of Example 1 and 1-(bromomethyl)-2-methoxybenzene (35 mg, 52%).

¹H NMR (400 MHz, CDCl₃): δ 7.37-7.20 (m, 6H), 6.89 (t, J=7.7 Hz, 2H), 5.19 (d, J=15.1 Hz, 1H), 5.02 (d, J=15.0 Hz, 1H), 3.82 (s, 3H), 2.62 (s, 3H), 2.37 (s, 3H), 1.58 (s, 3H); LCMS: 464.15 (M+1); HPLC: 99.46%.

Example 35

Step-7: N-benzyl-4-(4-chlorophenyl)-2,3,9-trimethyl-6H-thieno[2,3-e][1,2,4]triazolo[3,4-c][1,2,4]triazepine-6-carboxamide (Compound of Example 35)

[Chem. 44]

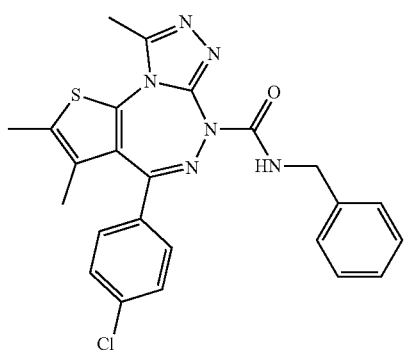

The title compound was synthesized according to the general method of coupling reaction using the compound of Example 1 and benzylcarbaic acid bromide (14 g, 20%).

¹H NMR (400 MHz, CDCl₃): δ 7.47-7.14 (m, 9H), 4.64 (d, J=5.7 Hz, 2H), 4.40 (d, J=5.8 Hz, 1H), 2.64 (s, 3H), 2.38 (s, 3H), 1.60 (s, 3H); LCMS: 477.25 (M+1); HPLC: 85%.

Example 36

Step-7: Synthesis of 4-(4-chlorophenyl)-6-((5-chloropyridin-2-yl)methyl)-2,3,9-trimethyl-6H-thieno[2,3-e][1,2,4]triazolo[3,4-c][1,2,4]triazepine (Compound of Example 36)

[Chem. 45]

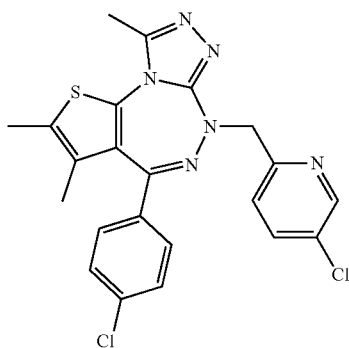

The title compound was synthesized according to the general method of coupling reaction using the compound of Example 1 and 2-(bromomethyl)-5-chloropyridine (15 mg, 18.5%).

$^1$H NMR (400 MHz, CDCl$_3$): δ 8.55 (d, J=2.4 Hz, 1H), 7.63 (dd, J=8.4, 2.4 Hz, 1H), 7.43 (d, J=8.4 Hz, 1H), 7.34-7.19 (m, 4H), 5.25 (d, J=14.6 Hz, 1H), 5.03 (d, J=14.4 Hz, 1H), 2.62 (s, 3H), 2.36 (s, 3H), 1.56 (s, 3H); LCMS: 453.15 (M+1); HPLC: 88.2%.

Example 37

Step-7: Synthesis of 4-(4-chlorophenyl)-6-((6-chloropyridin-3-yl)methyl)-2,3,9-trimethyl-6H-thieno[2,3-e][1,2,4]triazolo[3,4-c][1,2,4]triazepine (Compound of Example 37)

[Chem. 46]

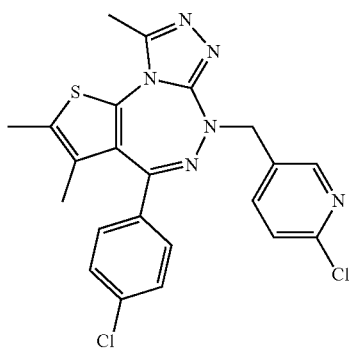

The title compound was synthesized according to the general method of coupling reaction using the compound of Example 1 and 5-(bromomethyl)-2-chloropyridine (16 mg, 23%).

$^1$H NMR (400 MHz, CDCl$_3$): δ 8.47 (d, J=2.4 Hz, 1H), 7.76 (dd, J=8.1, 2.4 Hz, 1H), 7.36-7.22 (m, 5H), 5.08 (s, 1H), 4.92 (s, 1H), 2.62 (s, 3H), 2.37 (s, 3H), 1.28 (s, 3H); LCMS: 469.05 (M+1); HPLC: 88.4%.

Example 38

Step-7: Synthesis of 4-(4-chlorophenyl)-6-((2-chloropyridin-3-yl)methyl)-2,3,9-trimethyl-6H-thieno[2,3-e][1,2,4]triazolo[3,4-c][1,2,4]triazepine (Compound of Example 38)

[Chem. 47]

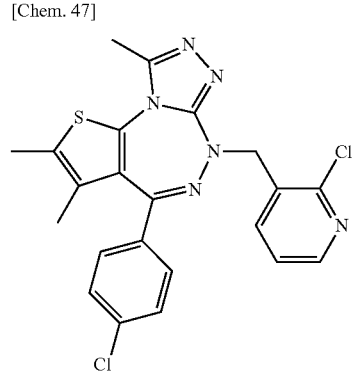

The title compound was synthesized according to the general method of coupling reaction using the compound of Example 1 and 3-(bromomethyl)-2-chloropyridine (21 mg, 30%).

$^1$H NMR (400 MHz, CDCl$_3$): δ 8.32 (dd, J=4.7, 2.1 Hz, 1H), 7.83 (dd, J=7.7, 1.9 Hz, 1H), 7.36-7.25 (m, 4H), 7.25-7.14 (m, 1H), 5.27 (d, J=14.7 Hz, 1H), 5.04 (d, J=14.7 Hz, 1H), 2.64 (d, J=13.8 Hz, 3H), 2.38 (s, 3H), 1.56 (s, 3H); LCMS: 469.15 (M+1); HPLC: 90.36%.

Example 39

Step-7: Synthesis of 4-(4-chlorophenyl)-6-((5-chloropyridin-3-yl)methyl)-2,3,9-trimethyl-6H-thieno[2,3-e][1,2,4]triazolo[3,4-c][1,2,4]triazepine (Compound of Example 39)

[Chem. 48]

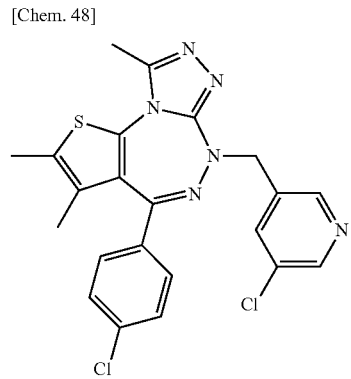

The title compound was synthesized according to the general method of coupling reaction using the compound of Example 1 and 3-(bromomethyl)-5-chloropyridine (12 mg, 17%).

$^1$H NMR (400 MHz, CDCl$_3$): δ 8.58 (d, J=1.9 Hz, 1H), 8.50 (d, J=2.3 Hz, 1H), 7.80-7.74 (m, 1H), 7.36-7.20 (m,

4H), 5.10 (s, 1H), 4.94 (s, 1H), 2.63 (s, 3H), 2.38 (s, 3H), 1.59 (s, 3H); LCMS: 469.15 (M+1); HPLC: 97.2%.

Example 40

Step-7: Synthesis of 4-(4-chlorophenyl)-6-((4-chloropyridin-2-yl)methyl)-2,3,9-trimethyl-6H-thieno[2,3-e][1,2,4]triazolo[3,4-c][1,2,4]triazepine (Compound of Example 40)

[Chem. 49]

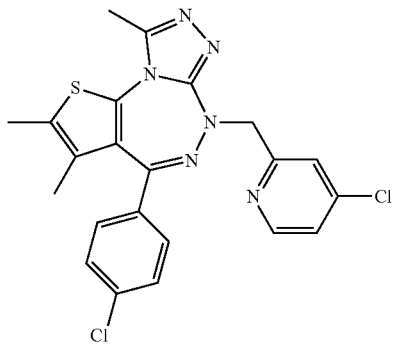

The title compound was synthesized according to the general method of coupling reaction using the compound of Example 1 and 2-(bromomethyl)-4-chloropyridine (20 mg, 29%).
$^1$H NMR (400 MHz, DMSO-d$_6$): δ 8.55 (s, 1H), 7.53-7.41 (m, 3H), 7.43-7.18 (m, 3H), 5.15 (d, J=14.6 Hz, 1H), 4.95 (d, J=14.4 Hz, 1H), 2.56 (s, 3H), 2.38 (s, 3H), 1.52 (s, 3H); LCMS: 469.15 (M+1); HPLC: 95.93%.

Example 41

Step-7: Synthesis of 4-(4-chlorophenyl)-6-((3-fluoropyridin-4-yl)methyl)-2,3,9-trimethyl-6H-thieno[2,3-e][1,2,4]triazolo[3,4-c][1,2,4]triazepine (Compound of Example 41)

[Chem. 50]

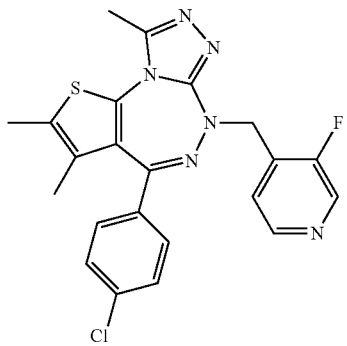

The title compound was synthesized according to the general method of coupling reaction using the compound of Example 1 and 4-(bromomethyl)-3-fluoropyridine (18 mg, 27.2%).
$^1$H NMR (400 MHz, DMSO-d$_6$): δ 9.12 (d, J=7.6 Hz, 1H), 8.70 (d, J=1.7 Hz, 1H), 8.54 (d, J=4.9 Hz, 1H), 7.63 (dd, J=6.2, 4.9 Hz, 1H), 7.30-7.21 (m, 2H), 7.12 (d, J=8.0 Hz, 2H), 5.70 (dd, J=17.1, 7.4 Hz, 1H), 2.44 (s, 3H), 2.24 (s, 3H), 1.95 (d, J=2.4 Hz, 3H); LCMS: 453.15 (M+1); HPLC: 95.33%.

Example 42

Step-7: Synthesis of 4-(4-chlorophenyl)-6-((2-fluoropyridin-4-yl)methyl)-2,3,9-trimethyl-6H-thieno[2,3-e][1,2,4]triazolo[3,4-c][1,2,4]triazepine (Compound of Example 42)

[Chem. 51]

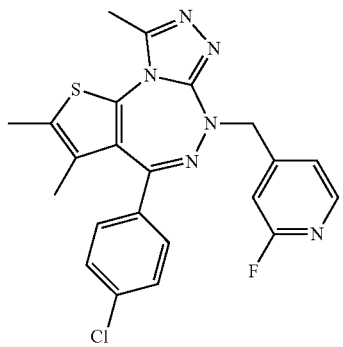

The title compound was synthesized according to the general method of coupling reaction using the compound of Example 1 and 4-(bromomethyl)-2-fluoropyridine (45 mg, 68.2%).
$^1$H NMR (400 MHz, DMSO-d$_6$): δ 8.21 (d, J=5.0 Hz, 1H), 7.54-7.41 (m, 2H), 7.43-7.22 (m, 3H), 7.14 (s, 1H), 5.11 (d, J=15.3 Hz, 1H), 4.91 (d, J=15.3 Hz, 1H), 3.51 (s, 3H), 2.38 (s, 3H), 1.51 (s, 3H); LCMS: 453.10 (M+1); HPLC: 88.36%.

Example 43

Step-7: Synthesis of 4-(4-chlorophenyl)-6-((4-chloropyridin-3-yl)methyl)-2,3,9-trimethyl-6H-thieno[2,3-e][1,2,4]triazolo[3,4-c][1,2,4]triazepine (Compound of Example 43)

[Chem. 52]

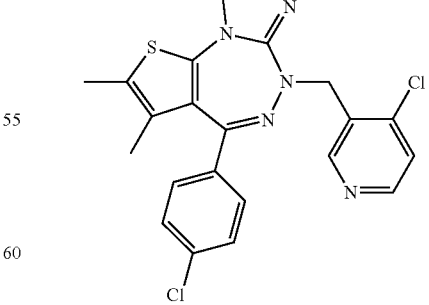

The title compound was synthesized according to the general method of coupling reaction using the compound of Example 1 and 3-(bromomethyl)-4-chloropyridine (45 mg, 65.8%).

$^1$H NMR (400 MHz, DMSO-d$_6$): δ 8.62 (s, 1H), 8.48 (d, J=5.2 Hz, 1H), 7.58 (d, J=5.4 Hz, 1H), 7.55-7.47 (m, 2H), 7.39-7.27 (m, 2H), 5.17 (d, J=14.6 Hz, 1H), 4.94 (d, J=14.3 Hz, 1H), 2.57 (s, 3H), 2.36 (s, 3H), 1.46 (s, 3H); LCMS: 433.15 (M+1); HPLC: 96.82%.

Synthetic Scheme of the Compound of Example 44

[Chem. 53]

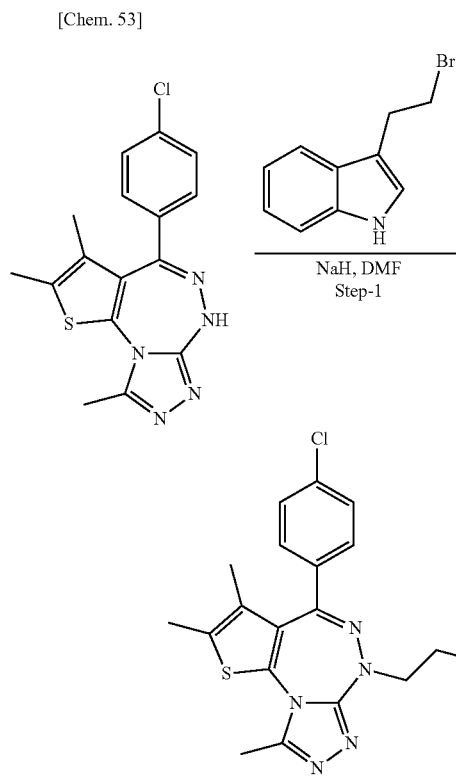

Step-1: 6-(2-(1H-indol-3-yl)ethyl)-4-(4-chlorophenyl)-2,3,9-trimethyl-6H-thieno[2,3-e][1,2,4]triazolo[3,4-c][1,2,4]triazepine (Compound of Example 44)

To a stirred solution of the compound of Example 1 (100 mg, 0.29 mmol) in DMF (2 mL) was added NaH (32 mg, 0.87 mmol) at 0° C., and the mixture was stirred for 15 minutes. 3-(2-Bromoethyl)-1H-indole compound (73 mg, 0.34 mmol) was added thereto, and the reaction mixture was stirred at the same temperature for one hour.

The progress of the reaction was monitored by TLC. After the reaction completed, the reaction mixture was diluted with water and extracted with ethyl acetate. The combined organic extracts were washed with brine, dried over anhydrous sodium sulfate, and distilled off under reduced pressure. The crude product was purified by preparative TLC to obtain an objective product (22 mg, 20%).

$^1$H NMR (400 MHz, DMSO-d$_6$): δ 10.80 (s, 1H), 7.58-7.43 (m, 5H), 7.37-7.27 (m, 1H), 7.15 (d, J=2.2 Hz, 1H), 7.05 (ddd, J=8.2, 7.0, 1.2 Hz, 1H), 6.92 (ddd, J=7.9, 7.0, 1.1 Hz, 1H), 3.94 (dt, J=27.3, 8.1 Hz, 2H), 3.24-3.08 (m, 2H), 2.52 (s, 3H), 2.37 (d, J=1.0 Hz, 3H), 1.55 (d, J=1.0 Hz, 3H); LCMS: 487.1 (M+1); HPLC: 98.48%.

Synthesis of the Compounds of Examples 45 to 57

[Chem. 54]

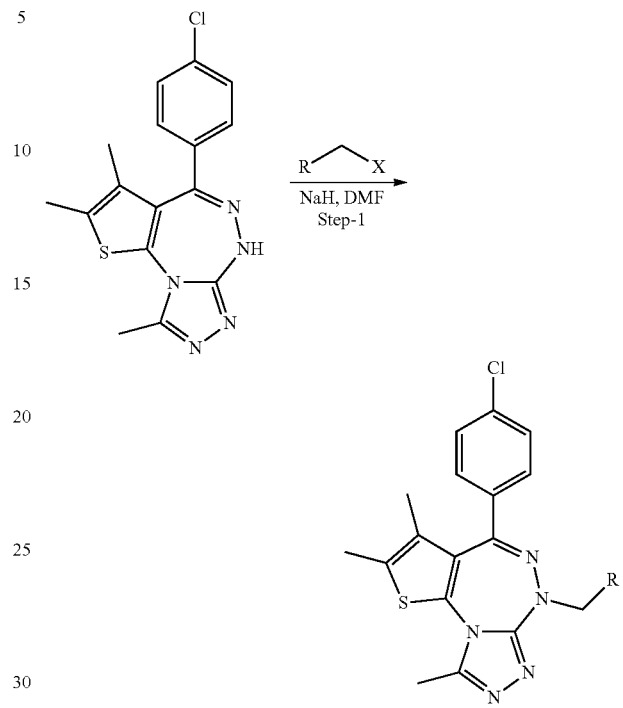

General Method of Coupling Reaction

To a stirred solution of the compound of Example 1 (1 eq.) in DMF was added NaH (3 eq.) at 0° C., and the mixture was stirred for 15 minutes. R—X compound (1.2 eq) was added thereto, and the reaction mixture was stirred at the same temperature for 1 to 2 hours. The progress of the reaction was monitored by TLC. After the reaction completed, the reaction mixture was diluted with water and extracted with ethyl acetate. The combined organic extracts were washed with brine, dried over anhydrous sodium sulfate, and distilled off under reduced pressure. The crude product was purified by preparative TLC/column chromatography/preparative HPLC to obtain an objective product.

Example 45

Step-1: Synthesis of 4-(4-chlorophenyl)-2,3,9-trimethyl-6-(thiophen-2-ylmethyl)-6H-thieno[2,3-e][1,2,4]triazolo[3,4-c][1,2,4]triazepine (Compound of Example 45)

[Chem. 55]

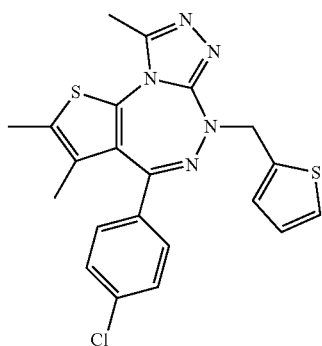

The title compound was synthesized according to the general method of coupling reaction using the compound of Example 1 and 2-(bromomethyl)thiphene (29 mg, 46%).

$^1$H NMR (400 MHz, DMSO-d$_6$): δ 8.34-8.22 (m, 2H), 7.59-7.43 (m, 3H), 7.30 (d, J=8.4 Hz, 2H), 5.09 (d, J=14.9 Hz, 1H), 4.94 (d, J=14.8 Hz, 1H), 2.56 (d, J=11.6 Hz, 3H), 2.36 (s, 3H), 1.50 (s, 3H), 1.22 (s, 2H), 0.86-0.74 (m, 1H); LCMS: 497.20 (M+1); HPLC: 90.5%.

Example 46

Step-1: Synthesis of 4-(4-chlorophenyl)-6-((6-methoxypyridin-2-yl)methyl)-2,3,9-trimethyl-6H-thieno[2,3-e][1,2,4]triazolo[3,4-c][1,2,4]triazepine (Compound of Example 46)

[Chem. 56]

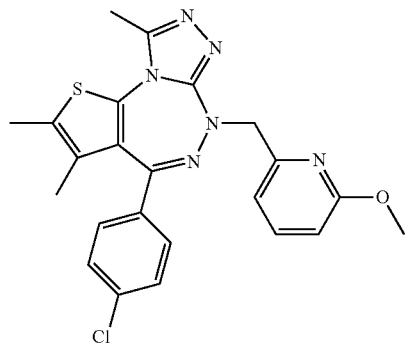

The title compound was synthesized according to the general method of coupling reaction using the compound of Example 1 and 2-(bromomethyl)-6-methoxypyridine (20 mg, 29%).

$^1$H NMR (400 MHz, DMSO-d$_6$): δ 7.67 (t, J=7.7 Hz, 2H), 7.49 (d, J=8.2 Hz, 4H), 7.41-7.27 (m, 4H), 6.89 (d, J=7.1 Hz, 2H), 6.70 (d, J=8.4 Hz, 2H), 5.07 (d, J=15.5 Hz, 2H), 4.82 (d, J=15.6 Hz, 2H), 3.82 (d, J=1.8 Hz, 6H), 2.56 (s, 5H), 2.37 (s, 5H), 1.52 (s, 5H), 1.23 (d, J=4.3 Hz, 1H), 0.85 (t, J=7.2 Hz, 1H); LCMS: 465.2 (M+1); HPLC: 98.67%.

Example 47

Step-1: Synthesis of 4-(4-chlorophenyl)-6-((5-methoxypyridin-2-yl)methyl)-2,3,9-trimethyl-6H-thieno[2,3-e][1,2,4]triazolo[3,4-c][1,2,4]triazepine (Compound of Example 47)

[Chem. 57]

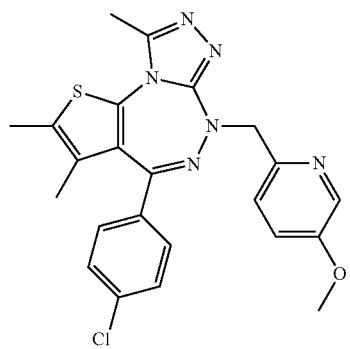

The title compound was synthesized according to the general method of coupling reaction using the compound of Example 1 and 2-(bromomethyl)-5-methoxypyridine (45 mg, 66%).

$^1$H NMR (400 MHz, DMSO-d$_6$): δ 8.25-8.19 (m, 1H), 7.47 (d, J=8.2 Hz, 2H), 7.39-7.24 (m, 5H), 5.03 (d, J=14.1 Hz, 1H), 4.86-4.74 (m, 1H), 3.79 (s, 3H), 2.54 (d, J=13.4 Hz, 3H), 2.34 (s, 3H), 1.47 (s, 3H), 1.27-1.18 (m, 1H), 0.87-0.77 (m, 1H); LCMS: 465.25 (M+1); HPLC: 99.86%.

Example 48

Step-1: Synthesis of 4-(4-chlorophenyl)-6-((4-methoxypyridin-2-yl)methyl)-2,3,9-trimethyl-6H-thieno[2,3-e][1,2,4]triazolo[3,4-c][1,2,4]triazepine (Compound of Example 48)

[Chem. 58]

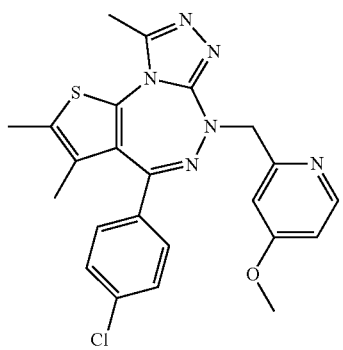

The title compound was synthesized according to the general method of coupling reaction using the compound of Example 1 and 2-(bromomethyl)-4-methoxypyridine (26 mg, 39%).

$^1$H NMR (400 MHz, DMSO-d$_6$): δ 8.35 (s, 1H), 7.50-7.47 (d, J=5.8 Hz, 2H), 7.34-7.31 (d, J=6 Hz, 2H), 6.89-6.85 (m, 2H), 5.08 (d, J=14.4 Hz, 1H), 4.82 (d, J=14.4 Hz, 1H), 3.75 (s, 3H), 2.55 (s, 3H), 2.37 (s, 3H), 1.51 (s, 3H); LCMS: 465.25 (M+1); HPLC: 99.86%.

Example 49

Step-1: Synthesis of 4-(4-chlorophenyl)-6-((2-methoxypyridin-3-yl)methyl)-2,3,9-trimethyl-6H-thieno[2,3-e][1,2,4]triazolo[3,4-c][1,2,4]triazepine (Compound of Example 49)

[Chem. 59]

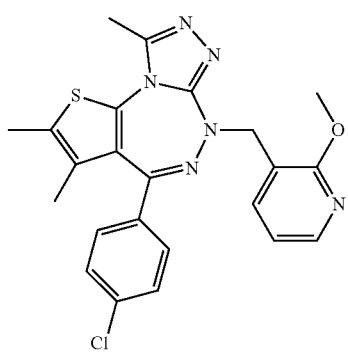

The title compound was synthesized according to the general method of coupling reaction using the compound of Example 1 and 3-(bromomethyl)-2-methoxypyridine (34 mg, 58%).

¹H NMR (400 MHz, DMSO-d₆): δ 8.10 (dd, J=5.0, 2.1 Hz, 1H), 7.58 (dd, J=7.3, 2.0 Hz, 1H), 7.53-7.45 (m, 2H), 7.33 (dd, J=8.6, 1.9 Hz, 2H), 7.02-6.92 (m, 1H), 4.98 (d, J=15.5 Hz, 1H), 4.75 (d, J=15.5 Hz, 1H), 3.90 (d, J=1.7 Hz, 3H), 2.61-2.50 (m, 5H), 2.36 (s, 3H), 1.50 (s, 3H), 0.90-0.78 (m, 1H); LCMS: 465.2 (M+1); HPLC: 90.37%.

Example 50

Step-1: Synthesis of 4-(4-chlorophenyl)-6-((6-methoxypyridin-3-yl)methyl)-2,3,9-trimethyl-6H-thieno[2,3-e][1,2,4]triazolo[3,4-c][1,2,4]triazepine (Compound of Example 50)

[Chem. 60]

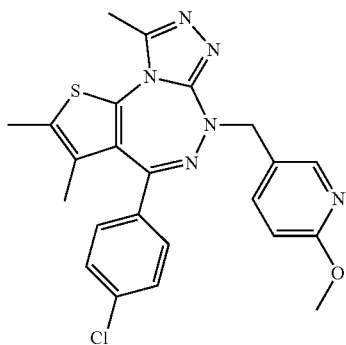

The title compound was synthesized according to the general method of coupling reaction using the compound of Example 1 and 5-(bromomethyl)-2-methoxypyridine (25 mg, 48%).

¹H NMR (400 MHz, DMSO-d₆): δ 8.22 (d, J=2.5 Hz, 1H), 7.78-7.70 (m, 1H), 7.54-7.46 (m, 2H), 7.35 (dd, J=8.7, 2.0 Hz, 2H), 6.79 (d, J=8.1 Hz, 1H), 4.93 (d, J=13.8 Hz, 1H), 4.72 (d, J=13.5 Hz, 1H), 3.83 (d, J=1.8 Hz, 3H), 2.59-2.46 (m, 4H), 2.43 (s, 2H), 2.34 (s, 3H), 1.46 (s, 2H), 1.23 (s, 1H), 0.90-0.73 (m, 1H); LCMS: 465.3 (M+1); HPLC: 86.09%.

Example 51

Step-1: 4-(4-chlorophenyl)-6-((4-methoxypyridin-3-yl)methyl)-2,3,9-trimethyl-6H-thieno[2,3-e][1,2,4]triazolo[3,4-c][1,2,4]triazepine (Compound of Example 51)

[Chem. 61]

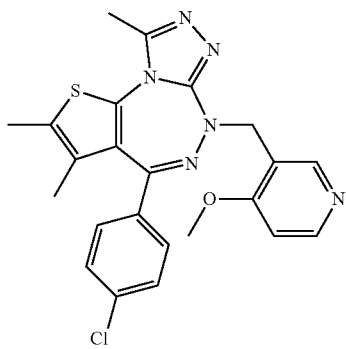

The title compound was synthesized according to the general method of coupling reaction using the compound of Example 1 and 3-(bromomethyl)-4-methoxypyridine (35 mg, 67%).

¹H NMR (400 MHz, DMSO-d₆): δ 8.42-8.34 (m, 1H), 8.32 (s, 1H), 7.53-7.45 (m, 2H), 7.33 (dd, J=9.0, 7.0 Hz, 2H), 7.06 (d, J=5.6 Hz, 1H), 5.00 (t, J=17.1 Hz, 1H), 4.78 (t, J=16.1 Hz, 1H), 3.85 (d, J=7.4 Hz, 3H), 3.32 (s, 1H), 3.23 (s, 1H), 2.55 (d, J=11.1 Hz, 3H), 2.35 (s, 5H), 1.46 (s, 7H), 1.37 (s, 2H), 1.22 (s, 1H), 0.80 (q, J=9.6, 7.5 Hz, 1H); LCMS: 465.1 (M+1); HPLC: 99.77%.

Example 52

Step-1B: Synthesis of 4-(4-chlorophenyl)-2,3,9-trimethyl-6-(3-nitrobenzyl)-6H-thieno[2,3-e][1,2,4]triazolo[3,4-c][1,2,4]triazepine (Compound 2B)

The title compound was synthesized according to the general method of coupling reaction using the compound of Example 1 and 1-(bromomethyl)-3-nitrobenzene compound (210 mg).

LC-MS: 479.1 (M+1)

Step-2B: Synthesis of 3-((4-(4-chlorophenyl)-2,3,9-trimethyl-6H-thieno[2,3-e][1,2,4]triazolo[3,4-c][1,2,4]triazepin-6-yl)methyl)aniline (Compound of Example 52)

[Chem. 62]

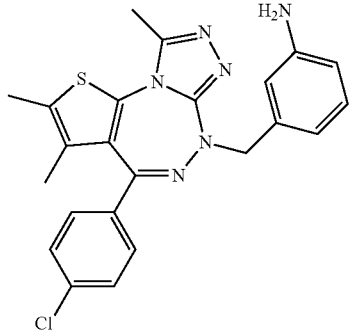

To a stirred solution of Compound 2B (100 mg, 0.20 mmol) in ethanol (5 mL) were added ammonium chloride (56 mg, 1.0 mmol) and iron powder (17.5 mg, 0.32 mmol). The reaction mixture was heated at 80° C. for 12 hours. The reaction mixture was concentrated under reduced pressure. The reaction mixture was diluted with dichloromethane and water. The organic layer was concentrated to obtain a crude compound. The crude compound was triturated with ether and pentane to obtain a pure compound (45 mg, 48%).

¹H NMR (400 MHz, DMSO-d₆): δ 7.50 (d, J=8.2 Hz, 2H), 7.35 (d, J=8.1 Hz, 2H), 6.95 (t, J=7.8 Hz, 1H), 6.58 (m, 1H), 6.51 (d, J=7.7 Hz, 1H), 6.49 (d, J=7.7 Hz, 1H), 5.03 (s, 2H), 4.87 (d, J=13.9 Hz, 1H), 4.59 (d, J=13.8 Hz, 1H), 2.53 (s, 3H), 2.36 (s, 3H), 1.49 (s, 3H); LC-MS: 449.3 (M+1); HPLC: 98.37%.

Example 53

Step-1A: Synthesis of 4-(4-chlorophenyl)-6-(3-methoxybenzyl)-2,3,9-trimethyl-6H-thieno[2,3-e][1,2,4]triazolo[3,4-c][1,2,4]triazepine (Compound 1A)

The title compound was synthesized according to the general method of coupling reaction using the compound of Example 1 and 3-(bromomethyl)phenol compound (200 mg).

LC-MS: 465.1 (M+1)

Step-2A: Synthesis of 3-((4-(4-chlorophenyl)-2,3,9-trimethyl-6H-thieno[2,3-e][1,2,4]triazolo[3,4-c][1,2,4]triazepin-6-yl)methyl)phenol (Compound of Example 53)

[Chem. 63]

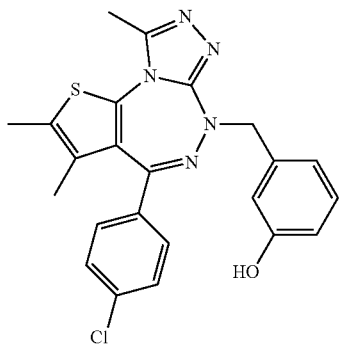

To a stirred solution of Compound 1A (75 mg, 0.161 mmol) in dichloromethane (10 mL) was added BBr$_3$ (1.0 M in dichloromethane) (2.4 mL, 0.242 mmol) at 0° C. The reaction mixture was stirred at room temperature for 4 hours. The reaction was monitored by TLC, and starting materials were not consumed so that BBr$_3$ (0.5 mL, 1.0 M in dichloromethane) was added again thereto. The reaction mixture was stirred again at room temperature for 2 hours. The reaction mixture was quenched with water. The organic layer was separated and concentrated under reduced pressure to obtain a crude compound of Example 53. The crude compound was purified by preparative TLC to obtain a pure compound of Example 53 (20 mg, 40%).
$^1$H NMR (400 MHz, DMSO-d$_6$): δ 9.34 (s, 1H), 7.53-7.45 (m, 2H), 7.37-7.29 (m, 2H), 7.11 (t, J=7.9 Hz, 1H), 6.83-6.75 (m, 2H), 6.68-6.60 (m, 1H), 4.95 (d, J=13.8 Hz, 1H), 4.68 (d, J=14.0 Hz, 1H), 2.54 (s, 3H), 2.36 (s, 3H), 1.49 (s, 3H); LC-MS: 450.2 (M+1); HPLC: 96.09%.

Example 54

Step-1: Synthesis of 4-(4-chlorophenyl)-6-((3-methoxypyridin-2-yl)methyl)-2,3,9-trimethyl-6H-thieno[2,3-e][1,2,4]triazolo[3,4-c][1,2,4]triazepine (Compound of Example 54)

[Chem. 64]

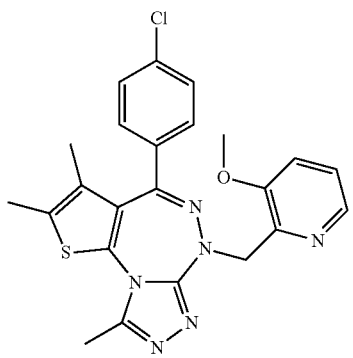

The title compound was synthesized according to the general method of coupling reaction using the compound of Example 1 and 2-(bromomethyl)-3-methoxypyridine compound (32 mg, 67%).

$^1$H NMR (400 MHz, DMSO-d$_6$): δ 8.06 (dd, J=4.8, 1.4 Hz, 1H), 7.52-7.40 (m, 4H), 7.35-7.24 (m, 3H), 5.08 (s, 1H), 5.03-4.91 (m, 1H), 3.83 (s, 3H), 2.54 (s, 3H), 2.35 (s, 3H), 1.45 (s, 3H), 1.27-1.20 (m, 1H); LCMS: 465.3 (M+1); HPLC: 97.84%.

Example 55

Step-1: Synthesis of 3-((4-(4-chlorophenyl)-2,3,9-trimethyl-6H-thieno[2,3-e][1,2,4]triazolo[3,4-c][1,2,4]triazepin-6-yl)methyl)-N,N-dimethylaniline (Compound of Example 55)

[Chem. 65]

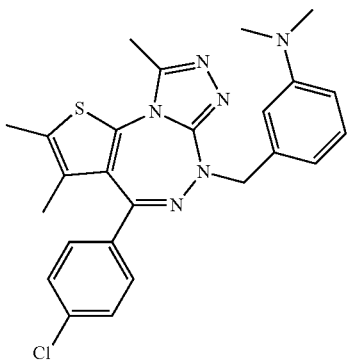

The title compound was synthesized according to the general method of coupling reaction using the compound of Example 1 and 3-(bromomethyl)-N,N-dimethylaniline (25 mg, 36%).
$^1$H NMR (400 MHz, DMSO-d$_6$): δ 7.50 (d, J=8.8 Hz, 2H), 7.34 (d, J=8.0 Hz, 2H), 7.12 (t, J=7.8 Hz, 1H), 6.74 (m, 1H), 6.66 (d, J=7.2 Hz, 1H), 6.61 (dd, J=8.0, 2.8 Hz, 1H), 4.98 (d, J=14.4 Hz, 1H), 4.73 (d, J=14.0 Hz, 1H), 2.84 (s, 6H), 2.54 (s, 3H), 2.35 (s, 3H), 1.48 (s, 3H); LC-MS: 477.2 (M+1); HPLC: 93.11%.

Example 56

Step-1: Synthesis of N-(4-((4-(4-chlorophenyl)-2,3,9-trimethyl-6H-thieno[2,3-e][1,2,4]triazolo[3,4-c][1,2,4]triazepin-6-yl)methyl)pyridin-2-yl)acetamide (Compound of Example 56)

[Chem. 66]

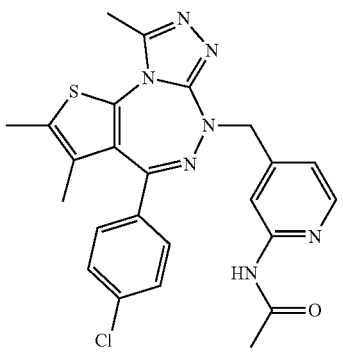

The title compound was synthesized according to the general method of coupling reaction using the compound of Example 1 and N-(4-(bromomethyl)pyridin-2-yl)acetamide (206 mg, 7%).

$^1$H NMR (400 MHz, DMSO-d$_6$): δ 10.42 (s, 1H), 8.23 (d, J=5.2 Hz, 1H), 8.11 (s, 1H), 7.47 (d, J=8.4 Hz, 2H), 7.33 (d, J=8.4 Hz, 2H), 7.07 (d, J=4.8 Hz, 1H), 5.02 (d, J=16 Hz, 1H), 4.82 (d, J=15.2 Hz, 1H), 2.55 (s, 3H), 2.37 (s, 3H), 2.05 (s, 3H), 1.54 (s, 3H); LC-MS: 492.3 (M+1); HPLC: 93.89%.

Example 57

Step-1A: Synthesis of 4-((4-(4-chlorophenyl)-2,3,9-trimethyl-6H-thieno[2,3-e][1,2,4]triazolo[3,4-c][1,2,4]triazepin-6-yl)methyl)pyridin-2-amine (Compound of Example 57)

[Chem. 67]

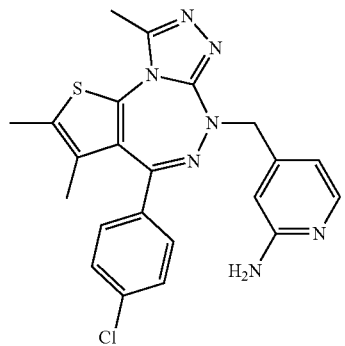

The compound of Example 56 (50 mg, 0.101 mmol) in stirred methanol:H$_2$O (3 mL, 10:1) was added NaOH (24 mg, 0.61 mmol). The reaction mixture was heated at 80° C. for 5 hours. The reaction mixture was concentrated, diluted with water, and extracted with 10% methanol in dichloromethane. The organic layer was separated and concentrated to obtain a crude compound. The crude compound was purified by preparative TLC to obtain the compound of Example 57 (15 mg, 30%).

$^1$H NMR (400 MHz, DMSO-d$_6$): δ 7.82 (d, J=4.8 Hz, 1H), 7.49 (d, J=8.8 Hz, 2H), 7.33 (d, J=8.8 Hz, 2H), 6.45 (d, J=5.2 Hz, 1H), 6.41 (s, 1H), 5.85 (s, 2H), 4.87 (d, J=14.8 Hz, 1H), 4.61 (d, J=14.8 Hz, 1H), 2.54 (s, 3H), 2.36 (s, 3H), 1.51 (s, 3H); LC-MS: 450.2 (M+1); HPLC: 99.19%.

Synthetic Scheme of the Compounds of Examples 58 and 60 to 64

[Chem. 68]

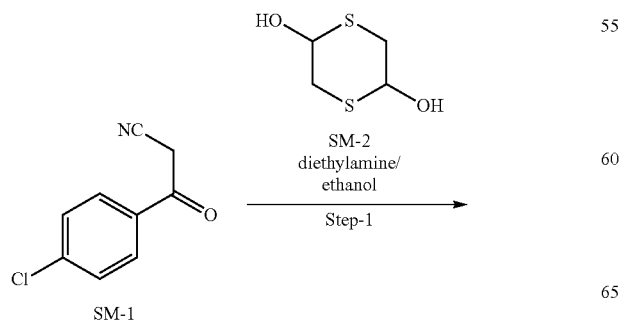

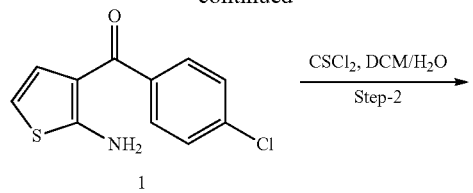

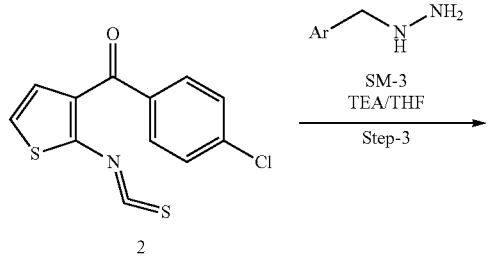

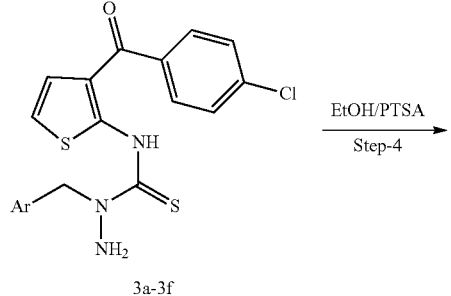

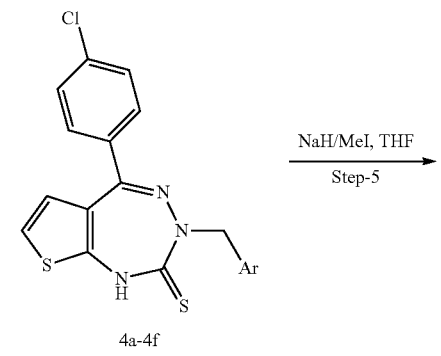

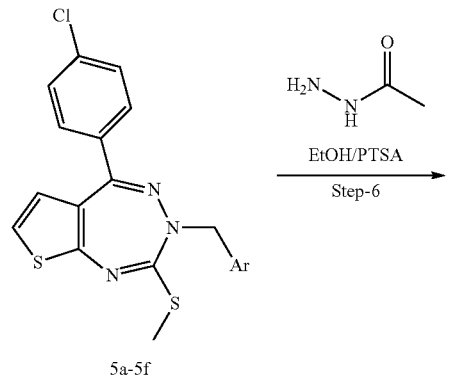

-continued

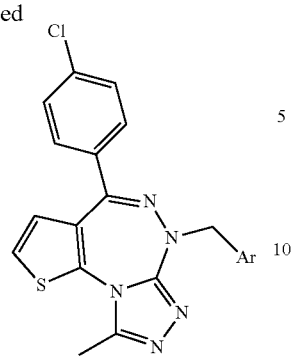

Step-1: Synthesis of (2-aminothiophen-3-yl)(4-chlorophenyl)methanone (Intermediate 1)

[Chem. 69]

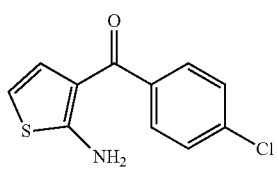

1

To a solution of SM-1 (1 g, 5.58 mmol) in ethanol (5 mL) were added diethylamine (0.6 mL) and SM-2 (424 mg, 2.79 mmol), and the mixture was stirred at 50° C. for 6 hours. After the reaction completed, yellow precipitates were filtered, washed with ethanol and dried under highly reduced pressure to obtain Intermediate 1 (750 mg).

Yield: 58%, $^1$H NMR (400 MHz, DMSO-$d_6$) δ 6.28 (d, J=5.87 Hz, 1H), 6.73 (d, J=5.87 Hz, 1H), 7.52-7.57 (m, 2H), 7.59-7.63 (m, 2H), 8.37 (brs, 2H) and LC-MS (M+1): 238.03

Step-2: Synthesis of (4-chlorophenyl)(2-isothiocyanatothiophen-3-yl)methanone (Intermediate 2)

[Chem. 70]

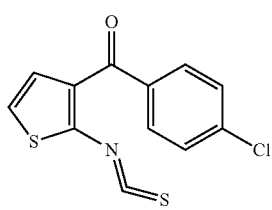

2

To a solution of thiophosgene (0.3 mL, 3.82 mmol) in water (10 mL) was added a solution of Intermediate 1 (700 mg, 2.94 mmol) in dichloromethane (50 mL) at 0° C., and the mixture was stirred at the same temperature for one hour and at room temperature for 4 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound (Intermediate 2) was confirmed by LC-MS, and used in the next Step without further purification. LC-MS (M+1): 280.04.

Step-3: Synthesis of Intermediate 3 (Intermediates 3a to 3f)

To a stirred solution of Intermediate 2 (1 equivalent) in tetrahydrofuran (15 mL) was added a corresponding hydrazine derivative SM-3 (1 equivalent), and the mixture was stirred at 0° C. for one hour and at room temperature for 4 hours. After the reaction completed, the reaction mixture was concentrated under reduced pressure to obtain a residue. The residue was triturated with hexane to obtain Intermediate 3 (Intermediates 3a to 3f).

Intermediate 3a: N-(3-(4-chlorobenzoyl)thiophen-2-yl)-1-(4-methoxybenzyl)hydrazine-1-carbothioamide

[Chem. 71]

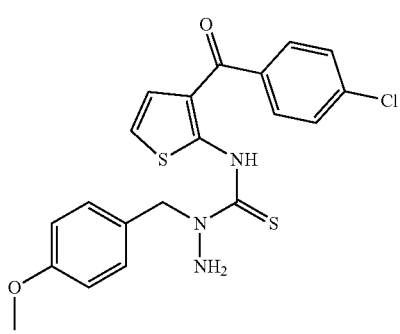

3a

Yield: 80%, $^1$H NMR (300 MHz, DMSO-$d_6$) δ 3.74 (s, 2H), 5.24 (s, 2H), 6.87-6.97 (m, 3H), 7.06 (d, J=5.87 Hz, 1H), 7.31 (d, J=8.80 Hz, 2H), 7.57-7.63 (m, 2H), 7.67-7.73 (m, 2H) and LC-MS (M+1): 432.15.

Intermediate 3b: 1-benzyl-N-(3-(4-chlorobenzoyl)thiophen-2-yl)hydrazinecarbothioamide

[Chem. 72]

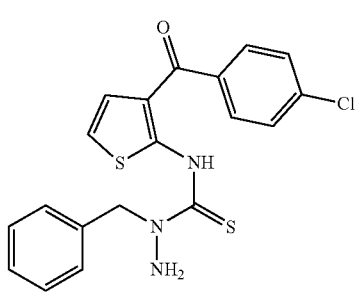

3b

The above-mentioned Intermediates were used in the next Step without purification.

Intermediate 3c: N-(3-(4-chlorobenzoyl)thiophen-2-yl)-1-(pyridin-3-ylmethyl)hydrazinecarbothioamide

[Chem. 73]

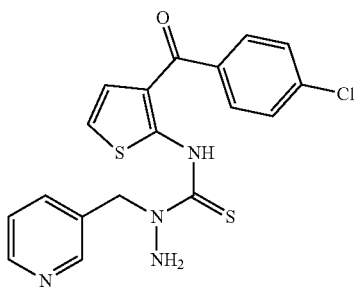

3c

Yield: 71%, H NMR (400 MHz, DMSO-d6) δ 5.34 (s, 2H), 6.91 (d, J=5.87 Hz, 1H), 7.07 (d, J=5.87 Hz, 1H), 7.40 (dd, J=7.83, 4.89 Hz, 1H), 7.58-7.64 (m, 2H), 7.68-7.73 (m, 2H), 7.75-7.80 (m, 1H), 8.52 (dd, J=4.89, 1.47 Hz, 1H), 8.59 (d, J=1.96 Hz, 1H) and LC-MS (M+1): 403.20.

Intermediate 3d: N-(3-(4-chlorobenzoyl)thiophen-2-yl)-1-(pyridin-2-ylmethyl)hydrazinecarbothioamide

[Chem. 74]

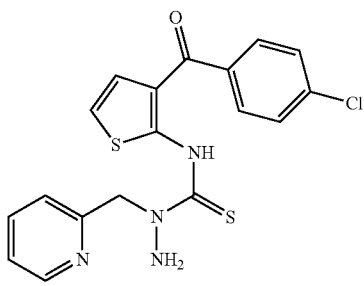

3d

Yield: 37%, $^1$H NMR (300 MHz, DMSO-d$_6$) δ 5.42 (s, 2H), 6.89 (d, J=5.87 Hz, 1H), 7.07 (d, J=5.87 Hz, 1H), 7.28-7.36 (m, 2H), 7.58-7.65 (m, 3H), 7.69-7.76 (m, 2H), 7.80 (td, J=7.61, 1.65 Hz, 1H), 8.54 (d, J=4.03 Hz, 1H) and LC-MS (M+1): 403.20.

Intermediate 3e: N-(3-(4-chlorobenzoyl)thiophen-2-yl)-1-(pyridin-4-ylmethyl)hydrazinecarbothioamide

[Chem. 75]

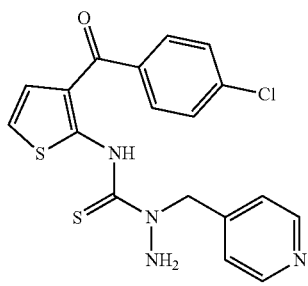

3e

Yield: 77%, $^1$H NMR (400 MHz, DMSO-d$_6$) δ 5.39 (s, 2H), 6.92 (d, J=6.36 Hz, 1H), 7.09 (d, J=5.87 Hz, 1H), 7.45 (d, J=5.38 Hz, 2H), 7.58-7.66 (m, 3H), 7.71-7.74 (m, 2H), 8.62 (d, J=5.38 Hz, 2H) and LC-MS (M+1): 403.20.

Intermediate 3f: N-(3-(4-chlorobenzoyl)thiophen-2-yl)-1-(3-methoxybenzyl)hydrazinecarbothioamide

[Chem. 76]

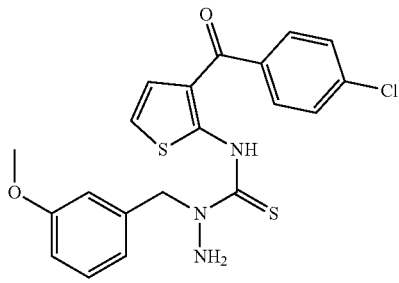

3f

The above-mentioned Intermediate was confirmed by LC-MS (M+1): 432.22, and used in the next Step without further purification.

Step-4: Synthesis of Intermediate 4 (Intermediates 4a to 4f)

To a stirred solution of Intermediate 3 (Intermediates 3a to 3f) (1 equivalent) in ethanol (20 mL) was added p-toluenesulfonic acid (0.1 equivalent), and the mixture was stirred at 100° C. for 16 hours. After the reaction completed, the reaction mixture was concentrated under reduced pressure to obtain a crude compound. The crude compound was purified by silica gel column chromatography (eluted with 30% ethyl acetate:hexane) to obtain Intermediate 4 (Intermediates 4a to 4f).

Intermediate 4a: 5-(4-chlorophenyl)-3-(4-methoxybenzyl)-1H-thieno[2,3-e][1,2,4]triazepine-2(3H)-thione

[Chem. 77]

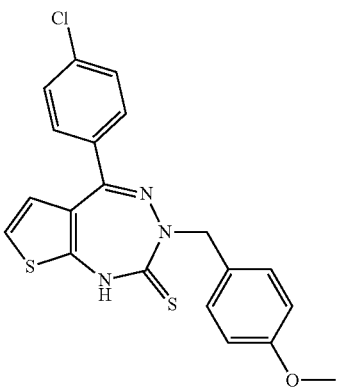

4a

Yield: 56%, $^1$H NMR (300 MHz, DMSO-d$_6$): δ 3.71 (s, 3H), 5.08 (s, 2H), 6.64 (d, J=5.87 Hz, 1H), 6.77-6.94 (m, 3H), 7.08-7.20 (m, 1H), 7.24-7.31 (m, 3H), 7.49 (d, J=8.44 Hz, 211), 11.17 (s, 1H) and LC-MS (M+1): 414.18.

Intermediate 4b: 3-benzyl-5-(4-chlorophenyl)-1H-thieno[2,3-e][1,2,4]triazepine-2(3H)-thione

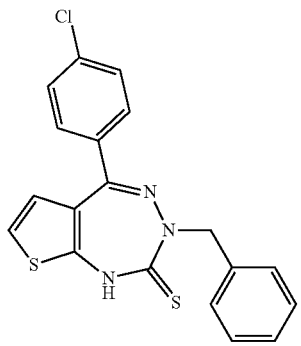

4b

The above-mentioned Intermediate was used in the next Step without further purification.

Intermediate 4c: 5-(4-chlorophenyl)-3-(pyridin-3-ylmethyl)-1H-thieno[2,3-e][1,2,4]triazepine-2(3H)-thione

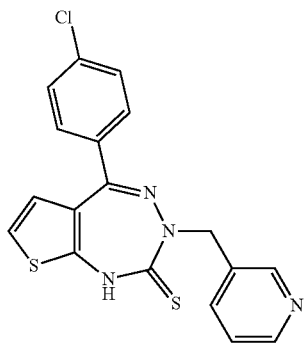

4c

Yield: 48%, H NMR (300 MHz, DMSO-$d_6$) δ 5.16 (s, 2H), 6.67 (d, J=5.87 Hz, 1H), 7.34 (dd, J=7.70, 4.77 Hz, 1H), 7.19 (d, J=5.87 Hz, 2H), 7.26 (d, J=8.44 Hz, 2H), 7.49 (d, J=8.80 Hz, 1H), 7.74 (d, J=7.70 Hz, 1H), 8.42-8.48 (m, 1H), 8.57 (d, J=1.47 Hz, 1H), 11.36 (s, 1H) and LC-MS (M+1): 385.11

Intermediate 4 d: 5-(4-chlorophenyl)-3-(pyridin-2-ylmethyl)-1H-thieno[2,3-e][1,2,4]triazepine-2(3H)-thione

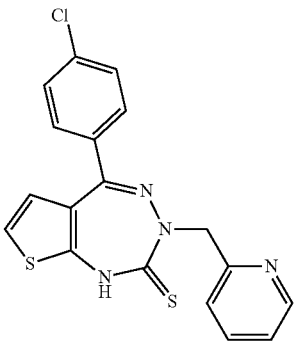

4d

Yield: 50%, $^1$H NMR (300 MHz, DMSO-$d_6$) δ 5.23 (s, 2H), 6.67 (d, J=5.85 Hz, 1H), 7.14-7.35 (m, 4H), 7.47 (d, J=8.41 Hz, 2H), 7.56-7.67 (m, 1H), 7.73 (td, J=7.68, 1.46 Hz, 1H), 8.51 (d, J=4.75 Hz, 1H), 11.28 (s, 1H) and LC-MS (M+1): 385.04

Intermediate 4e: 5-(4-chlorophenyl)-3-(pyridin-4-ylmethyl)-11H-thieno[2,3-e][1,2,4]triazepine-2(3H)-thione

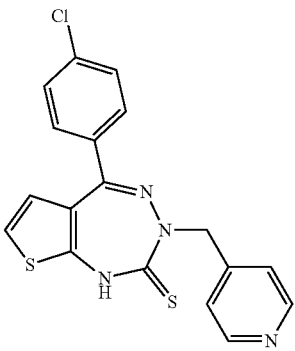

4e

Yield: 20%, $^1$H NMR (300 MHz, DMSO-$d_6$) δ 5.18 (s, 2H), 6.71 (d, J=5.87 Hz, 1H), 7.20-7.32 (m, 3H), 7.45-7.53 (m, 2H), 7.56-7.79 (m, 2H), 8.50 (brs, 2H), 11.41 (s, 1H) and LC-MS (M+1): 385.20.

Intermediate 4f: 5-(4-chlorophenyl)-3-(3-methoxy-benzyl)-11H-thieno[2,3-e][1,2,4]triazepine-2(3H)-thione

[Chem. 82]

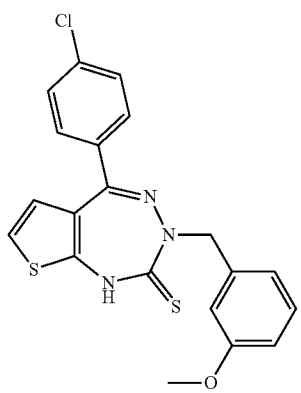

4f

Yield: 41%, ¹H NMR (300 MHz, DMSO-d₆) δ 3.64 (s, 3H), 5.15 (s, 2H), 6.69 (d, J=5.85 Hz, 1H), 6.75-6.92 (m, 3H), 7.16-7.29 (m, 4H), 7.48 (d, J=8.77 Hz, 2H), 11.24 (s, 1H) and LC-MS (M+1): 414.18.

Step-5: Synthesis of Intermediate 5 (Intermediates 5a to 5f)

To a stirred solution of Intermediate 4 (Intermediates 4a to 4f) (1 equivalent) in tetrahydrofuran (20 mL) was added NaH (2 equivalents) at 0° C., and the mixture was stirred at room temperature for one hour. Methyl iodide (1.2 equivalents) was added thereto at the same temperature, and the mixture was stirred at room temperature for one hour. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain Intermediate 5 (Intermediates 5a to 5f).

Intermediate 5a: 5-(4-chlorophenyl)-3-(4-methoxy-benzyl)-2-(methylthio)-3H-thieno[2,3-e][1,2,4]triazepine

[Chem. 83]

5a

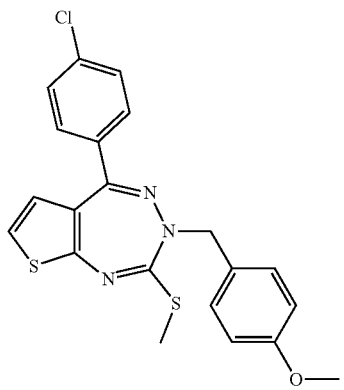

Yield: 88%, ¹H NMR (400 MHz, DMSO-d₆): δ 2.49 (s, 3H), 3.72 (s, 3H), 4.68 (s, 2H), 6.69 (d, J=5.6 Hz, 1H), 6.89 (d, J=8.4 Hz, 2H), 7.21 (d, J=6 Hz, 1H), 7.30-7.27 (m, 4H), 7.48 (d, J=8.4 Hz, 2H) and LC-MS (M+1): 428.19.

Intermediate 5b: 3-benzyl-5-(4-chlorophenyl)-2-(methylthio)-3H-thieno[2,3-e][1,2,4]triazepine

[Chem. 84]

5b

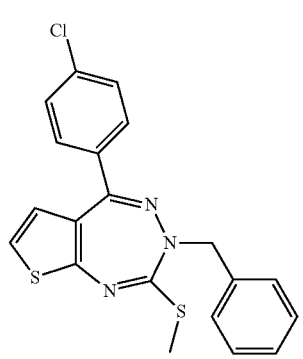

Yield: 90%, ¹H NMR (400 MHz, DMSO-d₆) δ 2.49 (s, 3H1), 4.76 (s, 2H1), 6.71 (d, J=5.38 Hz, 1H), 7.21-7.29 (m, 4H1), 7.30-7.39 (m, 4H), 7.44-7.50 (m, 2H) and LC-MS (M+1): 398.20.

Intermediate 5c: 5-(4-chlorophenyl)-2-(methylthio)-3-(pyridin-3-ylmethyl)-3H-thieno[2,3-e][1,2,4]triazepine

[Chem. 85]

5c

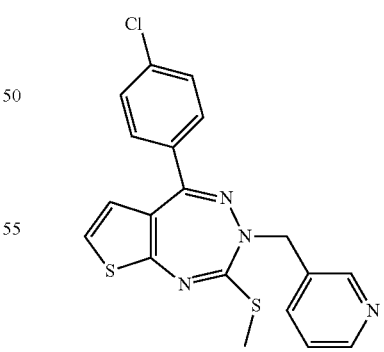

Yield: 85%, ¹H NMR (400 MHz, CDCl₃) δ 2.55 (s, 3H1), 4.81 (s, 2H), 6.59 (d, J=5.38 Hz, 1H), 6.86 (d, J=5.87 Hz, 1H), 7.18-7.22 (m, 2H), 7.24-7.29 (m, 4H), 7.71 (d, J=7.83 Hz, 1H), 8.53 (d, J=3.91 Hz, 1H), 8.67 (brs, 1H) and LC-MS (M+1): 399.21.

Intermediate 5d: 5-(4-chlorophenyl)-2-(methylthio)-3-(pyridin-2-ylmethyl)-3H-thieno[2,3-e][1,2,4]triazepine

[Chem. 86]

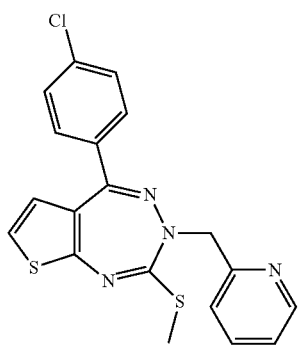

5d

Yield: 64%, $^1$H NMR (300 MHz, DMSO-d$_6$) δ 2.49 (s, 3H), 4.87 (s, 2H), 6.74 (d, J=5.50 Hz, 1H), 7.22-7.37 (m, 5H), 7.47 (d, J=8.44 Hz, 2H), 7.76 (td, J=7.70, 1.83 Hz, 1H), 8.54 (d, J=4.40 Hz, 1H) and LC-MS (M+1): 399.17.

Intermediate 5e: 5-(4-chlorophenyl)-2-(methylthio)-3-(pyridin-4-ylmethyl)-3H-thieno[2,3-e][1,2,4]triazepine

[Chem. 87]

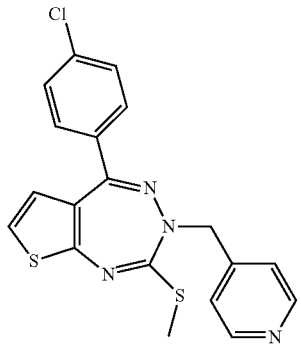

5e

Yield: 58%, $^1$H NMR (300 MHz, CDCl$_3$) δ 2.55 (s, 3H), 4.82 (s, 2H), 6.65 (d, J=5.85 Hz, 1H), 6.90 (d, J=5.48 Hz, 1H), 7.15-7.23 (m, 1H), 7.23-7.34 (m, 4H), 7.61 (s, 1H), 8.55 (brs, 2H) and LC-MS (M+1): 399.02

Intermediate 5f: 5-(4-chlorophenyl)-3-(3-methoxybenzyl)-2-(methylthio)-3H-thieno[2,3-e][1,2,4]triazepine

[Chem. 88]

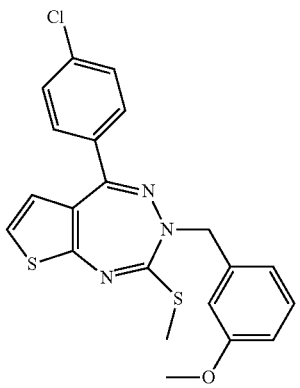

5f

Yield: 66%, $^1$H NMR (400 MHz, DMSO-d$_6$) δ 2.54 (s, 3H), 3.68 (s, 3H), 4.75 (s, 2H), 6.74 (d, J=5.87 Hz, 1H), 6.82 (dd, J=7.34, 1.47 Hz, 1H), 6.91-6.98 (m, 2H), 7.21-7.31 (m, 4H), 7.48 (d, J=8.31 Hz, 2H) and LC-MS (M+1): 428.15.

Step-6: Synthesis of the compounds of Examples 58 and 60 to 64

To a stirred solution of Intermediate 5 (Intermediates 5a to 5f) (1 equivalent) in ethanol (20 mL) were added acetic hydrazide (5 equivalent) and p-toluenesulfonic acid (0.1 equivalent), and the mixture was stirred at 100° C. for 16 hours. After the reaction completed, the reaction mixture was concentrated under reduced pressure to obtain a crude compound. The crude compound was purified by silica gel column chromatography (40% ethyl acetate:hexane) to obtain the compounds of Examples 58 and 60 to 64. Further, the compound of Example 59 was synthesized from the compound of Example 60.

Compound of Example 58: 4-(4-chlorophenyl)-6-(4-methoxybenzyl)-9-methyl-6H-thieno[2,3-e][1,2,4]triazolo[3,4-c][1,2,4]triazepine

[Chem. 89]

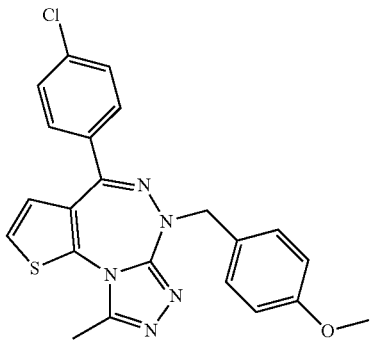

Yield: 20%, H NMR (400 MHz, DMSO-d₆) δ 2.54 (s, 3H), 3.73 (s, 3H), 4.83 (s, 2H), 6.84 (d, J=5.87 Hz, 1H), 6.89 (d, J=8.80 Hz, 2H), 7.34 (d, J=8.31 Hz, 2H), 7.38-7.44 (m, 2H), 7.47-7.52 (m, 2H), 7.60 (d, J=5.38 Hz, 1H) and LC-MS (M+1): 436.22

Compound of Example 60: 6-benzyl-4-(4-chlorophenyl)-9-methyl-6H-thieno[2,3-e][1,2,4]triazolo[3,4-c][1,2,4]triaz epine

[Chem. 90]

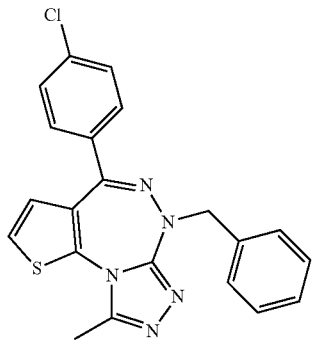

Yield: 30%, ¹H NMR (400 MHz, DMSO-d₆) δ 2.55 (s, 3H), 4.92 (s, 2H), 6.85 (d, J=5.48 Hz, 1H), 7.25-7.44 (m, 7H), 7.47-7.51 (m, 2H), 7.61 (d, J=5.85 Hz, 1H) and LC-MS (M+1): 406.09.

Compound of Example 61: 4-(4-chlorophenyl)-9-methyl-6-(pyridin-3-ylmethyl)-6H-thieno[2,3-e][1,2,4]triazolo[3,4-c][1,2,4]triazepine

[Chem. 91]

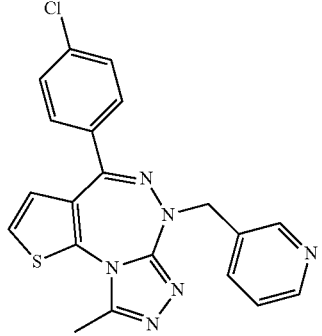

Yield: 19%, ¹H NMR (300 MHz, DMSO-d₆) δ 2.56 (s, 3H), 4.95 (s, 2H), 6.85 (d, J=5.85 Hz, 1H), 7.34-7.41 (m, 3H), 7.47-7.54 (m, 2H), 7.62 (d, J=5.48 Hz, 1H), 7.80-7.86 (m, 1H), 8.49 (dd, J=4.75, 1.46 Hz, 1H), 8.65 (d, J=1.46 Hz, 1H) and LC-MS (M+1): 407.00.

Compound of Example 62: 4-(4-chlorophenyl)-9-methyl-6-(pyridin-2-ylmethyl)-6H-thieno[2,3-e][1,2,4]triazolo[3,4-c][1,2,4]triazepine

[Chem. 92]

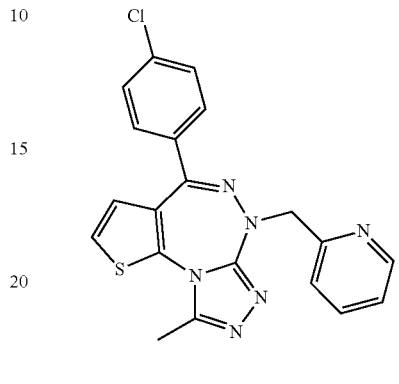

Yield: 10%, 1H NMR (400 MHz, CDCl₃) δ 2.65 (s, 3H), 5.19 (s, 2H), 6.77 (d, J=5.87 Hz, 1H), 7.17-7.21 (m, 2H), 7.30 (s, 3H), 7.48 (s, 1H), 7.68 (d, J=8.31 Hz, 1H), 8.61 (d, J=3.91 Hz, 1H) and LC-MS (M+1): 407.27.

Compound of Example 63: 4-(4-chlorophenyl)-9-methyl-6-(pyridin-4-ylmethyl)-6H-thieno[2,3-e][1,2,4]triazolo[3,4-c][1,2,4]triazepine

[Chem. 93]

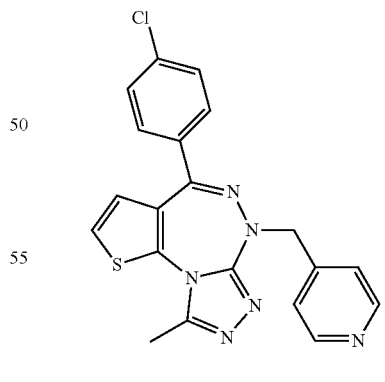

Yield: 16%, ¹H NMR (300 MHz, DMSO-d₆) δ 2.57 (s, 3H), 4.97 (s, 2H), 6.89 (d, J=5.85 Hz, 1H), 7.33-7.41 (m, 4H), 7.46-7.53 (m, 2H), 7.64 (d, J=5.48 Hz, 1H), 8.51-8.55 (m, 2H) and LC-MS (M+1): 407.11.

Compound of Example 64: 4-(4-chlorophenyl)-6-(3-methoxybenzyl)-9-methyl-6H-thieno[2,3-e][1,2,4]triazolo[3,4-c][1,2,4]triazepine

[Chem. 94]

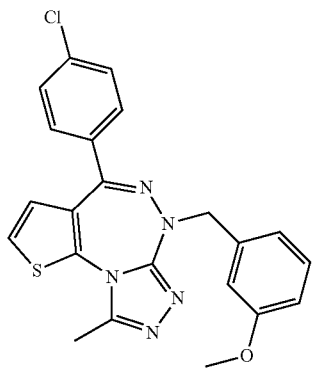

Yield: 41%, $^1$H NMR (300 MHz, DMSO-d$_6$) δ 2.56 (s, 3H), 3.71 (s, 3H), 4.90 (s, 2H), 6.80-6.89 (m, 2H), 6.93-7.00 (m, 2H), 7.21-7.30 (m, 1H), 7.36-7.44 (m, 2H), 7.49-7.52 (m, 2H), 7.62 (d, J=5.85 Hz, 1H) and LC-MS (M+1): 436.22.

Compound of Example 59: Synthesis of 4-(4-chlorophenyl)-9-methyl-6H-thieno[2,3-e][1,2,4]triazolo[3,4-c][1,2,4]triazepine

[Chem. 95]

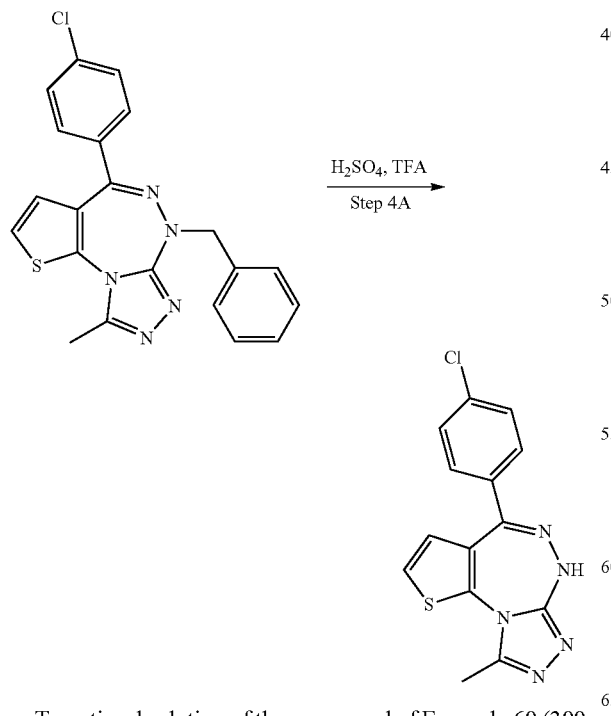

To a stirred solution of the compound of Example 60 (300 mg, 0.74 mmol) in TFA (3 mL) was added H$_2$SO$_4$ (3 mL), and the mixture was stirred at room temperature for 18 hours. After the reaction completed, the reaction mixture was poured into ice-cold water to make it basic with a sodium bicarbonate solution and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 3% methanol/dichloromethane) to obtain the compound of Example 59 (200 mg, LC-MS: 92%). This was further purified by preparative HPLC to obtain the compound of Example 59 (85 mg, yield: 36%) as a pale yellow solid.

Yield: 36%, $^1$H NMR (300 MHz, DMSO-d$_6$) δ 2.52 (s, 3H), 6.77 (d, J=5.87 Hz, 1H), 7.51 (s, 3H), 7.57 (d, J=5.50 Hz, 1H), 9.92 (s, 1H) and LC-MS (M+1): 316.08.

Synthetic Scheme of the Compound of Example 65

[Chem. 96]

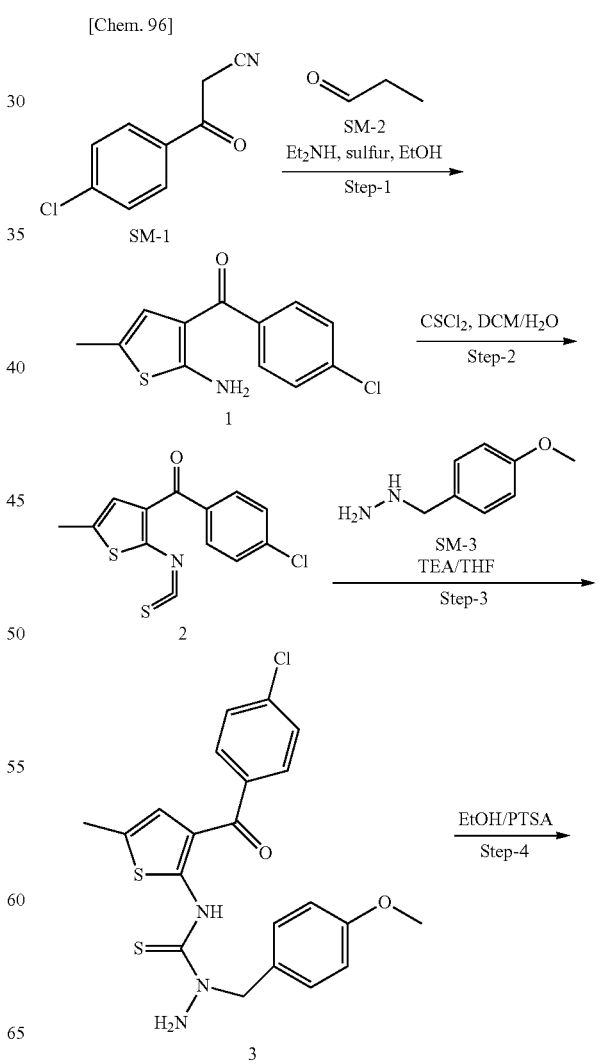

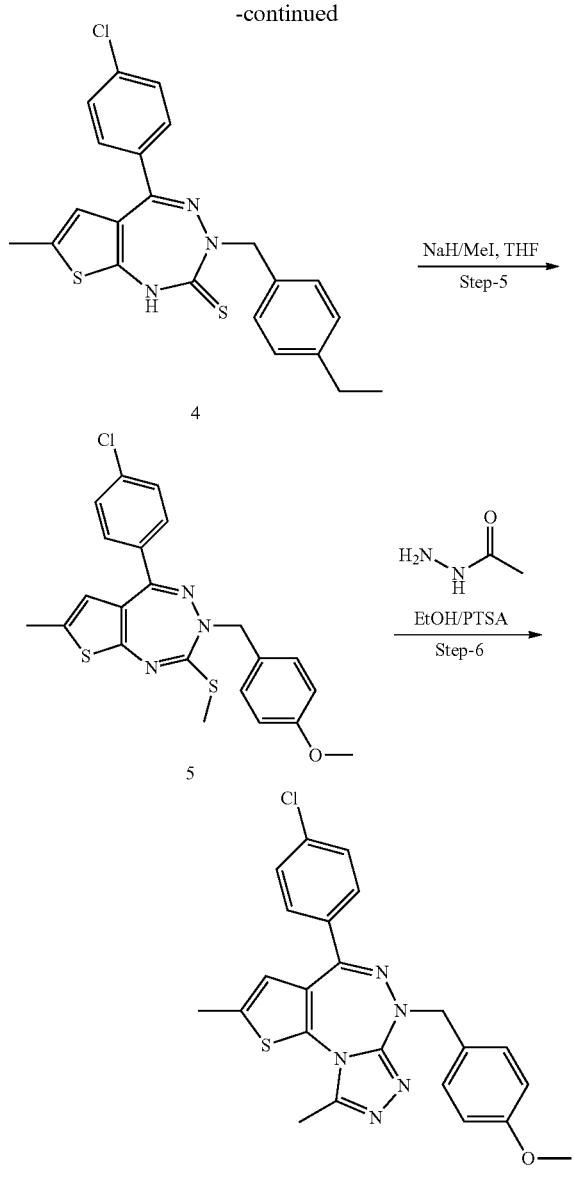

Step-1: Synthesis of (2-amino-5-methylthiophen-3-yl)(4-chlorophenyl)methanone (Intermediate 1)

[Chem. 97]

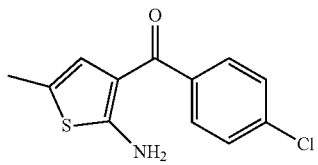

To a solution of SM-1 (5 g, 27.93 mmol) in ethanol (50 mL) were added sulfur (890 mg, 27.93 mmol), propionaldehyde (1.62 mg, 27.93 mmol) and diethylamine (7.75 mL, 55.85 mmol), and the mixture was stirred at 70° C. for 6 hours. After the reaction completed, the reaction mixture was concentrated under reduced pressure to obtain a residue, and the residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate: hexane) to obtain 2.2 g of Intermediate 1.

Yield: 31%, 1H NMR (300 MHz, DMSO-$d_6$): δ 7.8 (d, 2H), 7.6 (d, 2H), 7.53 (d, J=8.8 Hz, 2H), 6.9 (brs, 2H), 6.4 (s, 1H), 2.2 (s, 3H) and LC-MS (M+H): 252.07.

Step-2: Synthesis of (4-chlorophenyl)(2-isothiocyanato-5-methylthiophen-3-yl)methanone (Intermediate 2)

[Chem. 98]

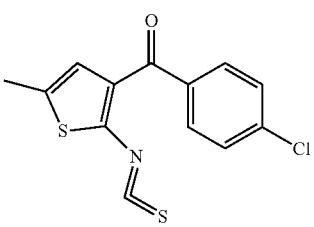

To a solution of thiophosgene (0.1 mL, 1.03 mmol) in water (3 mL) was added a solution of Intermediate 1 (200 mg, 0.79 mmol) in dichloromethane (5 mL) at 0° C., and the mixture was stirred at the same temperature for one hour and at room temperature for 2 hours. After the reaction completed, the reaction mixture was quenched with ice-water, extracted with dichloromethane, washed with brine. The organic layer was dried over anhydrous sodium sulfate and filtered, and the filtrate was concentrated under reduced pressure to obtain a crude compound. The crude compound was triturated with hexane to obtain 180 mg of Intermediate 2. Intermediate 2 (LC-MS (M+H): 293.99) was used in the next Step without further purification.

Step-3: Synthesis of N-(3-(4-chlorobenzoyl)-5-methylthiophen-2-yl)-1-(4-methoxybenzyl)hydrazinecarbothioamide (Intermediate 3)

[Chem. 99]

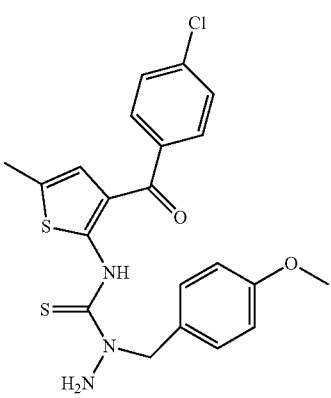

To a solution of Intermediate 2 (300 mg, 1.02 mmol) in tetrahydrofuran (10 mL) was added triethylamine (0.42 mL, 3.07 mmol), followed by (4-methoxybenzyl)hydrazine.HCl (155 mg, 1.02 mmol), and the mixture was stirred at 0° C. for one hour and at room temperature for 16 hours. After the reaction completed, the reaction mixture was concentrated under reduced pressure to obtain a residue. The residue was triturated with hexane to obtain 200 mg of Intermediate 3.

Yield: 44%, $^1$H NMR (300 MHz, DMSO-$d_6$): δ 10.6 (brs, 2H), 7.78-7.6 (m, 4H), 7.41-7.24 (m, 3H), 5.22 (s, 2H), 3.75 (s, 3H), 2.3 (s, 3H) and LC-MS (M+H): 445.99.

Step-4: Synthesis of 5-(4-chlorophenyl)-3-(4-methoxybenzyl)-7-methyl-1H-thieno[2,3-e][1,2,4]triazepine-2(3H)-thione (Intermediate 4)

[Chem. 100]

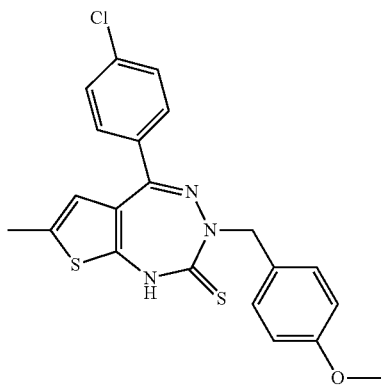

4

To a stirred solution of Intermediate 3 (2 g, 4.49 mmol) in ethanol (50 mL) was added p-toluenesulfonic acid (100 mg, 0.52 mmol), and the mixture was stirred at 100° C. for 16 hours. After the reaction completed, the reaction mixture was concentrated under reduced pressure to obtain a crude compound. The crude compound was purified by silica gel column chromatography (eluted with 30% ethyl acetate: hexane) to obtain 900 mg of Intermediate 4.

Yield: 47%, $^1$H NMR (300 MHz, DMSO-$d_6$): δ 11.1 (s, 1H), 7.55 (d, 2H), 7.3 (m, 4H), 6.85 (d, 2H), 5.05 s, 2H), 3.75 (s, 3H), 3.38 (s, 3H) and LC-MS (M+H): 428.26.

Step-5: Synthesis of 5-(4-chlorophenyl)-3-(4-methoxybenzyl)-7-methyl-2-(methylthio)-3H-thieno[2,3-e][1,2,4]triazepine (Intermediate 5)

[Chem. 101]

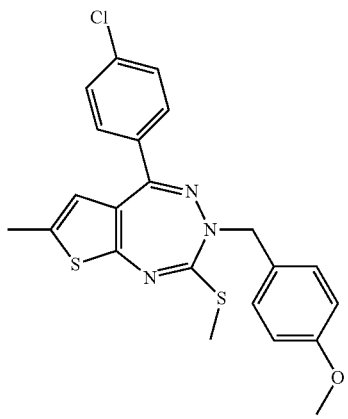

5

To a stirred solution of Intermediate 4 (200 mg, 0.46 mmol) in tetrahydrofuran (10 mL) was added NaH (21 mg, 0.5 mmol) at 0° C., and the mixture was stirred at room temperature for one hour. Methyl iodide (0.03 mg, 0.5 mmol) was added at the same temperature, and the mixture was stirred at room temperature for one hour. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain 80 mg of Intermediate 5.

Yield: 39%, $^1$H NMR (300 MHz, DMSO-$d_6$): δ 7.33-7.2 (m, 5H), 6.85 (d, J=14.1 Hz, 2H), 6.23 (brs, 1H), 4.71 (s, 2H), 3.8 (s, 3H), 2.5 (s, 3H), 2.37 (s, 3H), LC-MS (M+H): 442.27.

Step-6: Synthesis of 4-(4-chlorophenyl)-6-(4-methoxybenzyl)-2,9-dimethyl-6H-thieno[2,3-e][1,2,4]triazolo[3,4-c][1,2,4]triazepine (Compound of Example 65)

[Chem. 102]

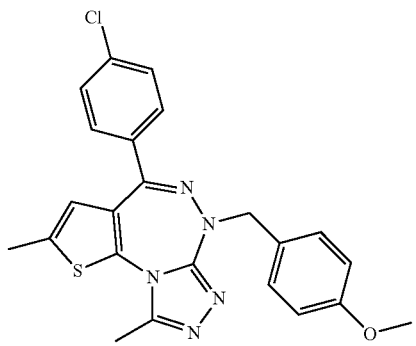

To a stirred solution of Intermediate 5 (500 mg, 1.13 mmol) in ethanol (20 mL) were added acetic hydrazide (525 mg, 3.4 mmol) and p-toluenesulfonic acid (50 mg, 0.11 mmol), and the mixture was stirred at 100° C. for 12 hours. After the reaction completed, the reaction mixture was concentrated under reduced pressure to obtain a crude compound. The crude compound was purified by silica gel column chromatography (eluted with 40% ethyl acetate: hexane) to obtain the compound of Example 65 (480 mg, LCMS purity: 58%), which was further purified by preparative HPLC to obtain 130 mg of the compound of Example 65.

Yield: 32%, $^1$H NMR (400 MHz, DMSO-$d_6$): δ 7.36 (d, J=16.8 Hz, 1H), 7.31 (brs, 4H), 6.86 (d, J=8.4 Hz, 2H), 6.39 (s, 1H), 4.95 (s, 2H), 3.8 (s, 3H), 2.6 (s, 3H), 2.47 (s, 3H) and LC-MS: (M+H): 450.02.

Synthetic Scheme of the compound of Example 66

[Chem. 103]

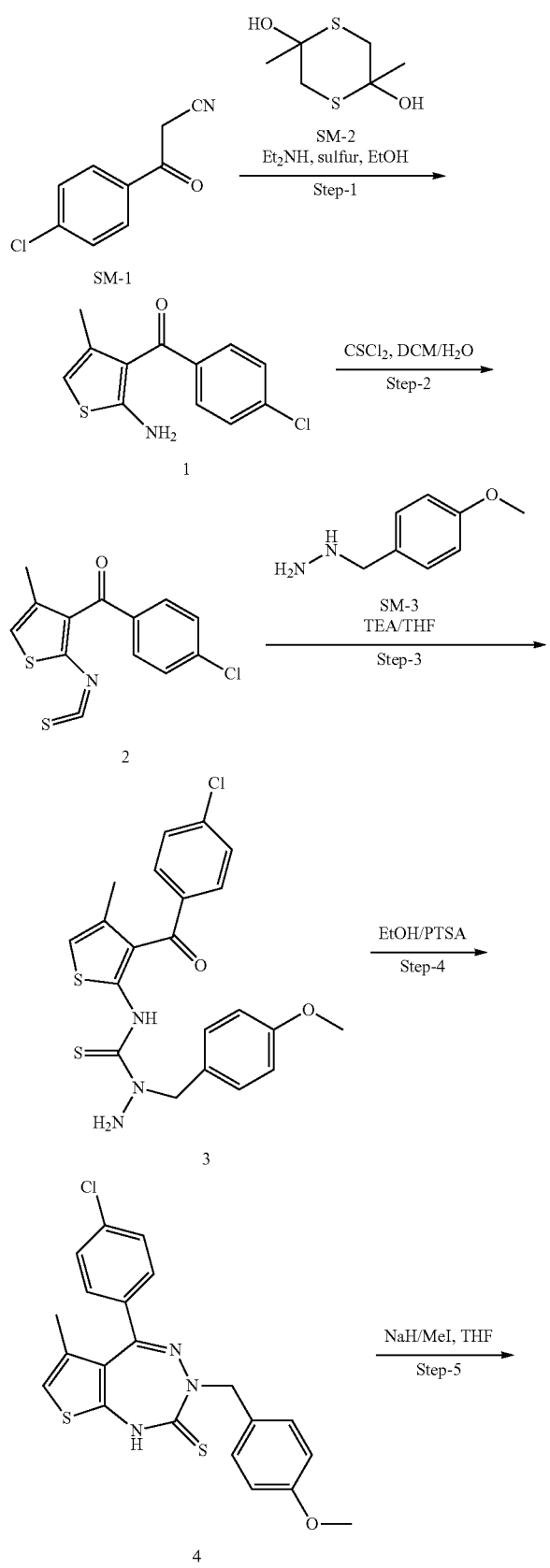

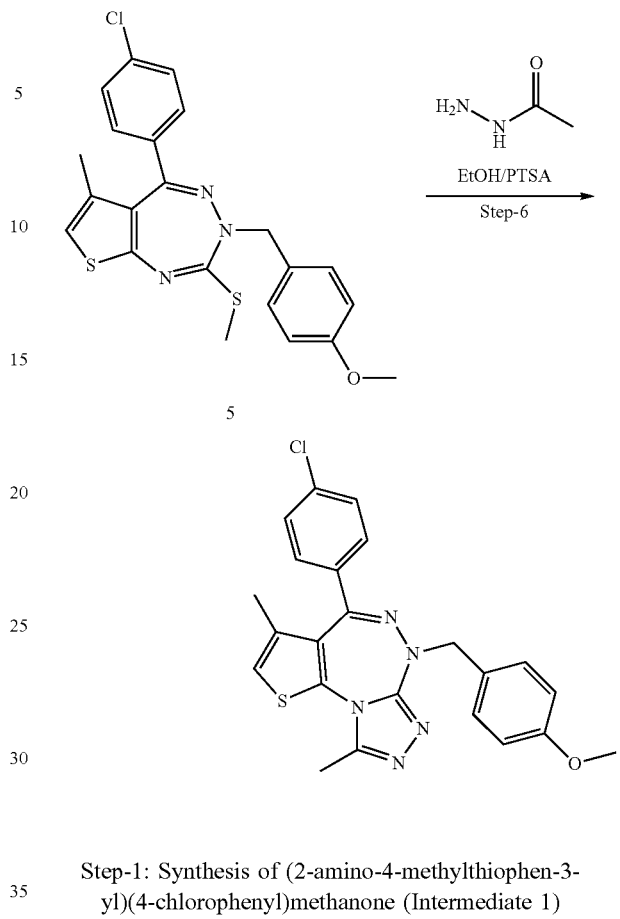

Step-1: Synthesis of (2-amino-4-methylthiophen-3-yl)(4-chlorophenyl)methanone (Intermediate 1)

[Chem. 104]

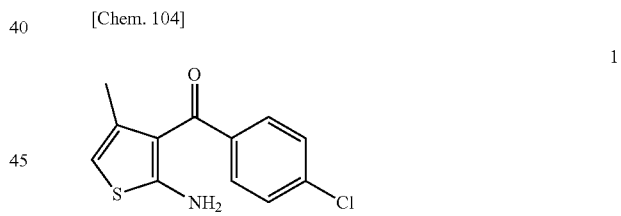

To a solution of SM-1 (2 g, 11.13 mmol) in ethanol (10 mL) were added SM-2 (1 g, 5.56 mmol) and diethylamine (1.2 mL, 11.62 mmol), and the mixture was stirred at 50° C. for 16 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate: hexane) to obtain 550 mg of Intermediate 1.

Yield: 20%, $^1$H NMR (400 MHz, DMSO-$d_6$) δ 1.55 (d, J=0.98 Hz, 3H), 5.97 (d, J=0.98 Hz, 1H), 7.40-7.45 (m, 2H), 7.47-7.53 (m, 2H), 8.06 (brs, 2H) and LC-MS: (M+H): 252.07.

Step-2: Synthesis of (4-chlorophenyl)(2-isothiocyanato-4-methylthiophen-3-yl)methanone (Intermediate 2)

[Chem. 105]

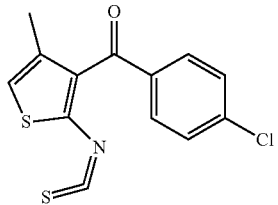

To a solution of thiophosgene (0.48 mL, 6.18 mmol) in water (6 mL) was added a solution of Intermediate 1 (1.2 g, 4.76 mmol) in dichloromethane (100 mL) at 0° C., and the mixture was stirred at the same temperature for one hour and at room temperature for 12 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with 15% ethyl acetate:hexane) to obtain 530 mg of Intermediate 2.

Yield: 38%, $^1$HNMR (300 MHz, DMSO-$d_6$) δ 2.12 (s, 1H), 5.99 (s, 1H), 7.67 (d, J=8.07 Hz, 1H), 7.81 (d, J=8.07 Hz, 1H) and LC-MS (M+H): 294.08.

Step-3: Synthesis of N-(3-(4-chlorobenzoyl)-4-methylthiophen-2-yl)-1-(4-methoxybenzyl)hydrazinecarbothioamide (Intermediate 3)

[Chem. 106]

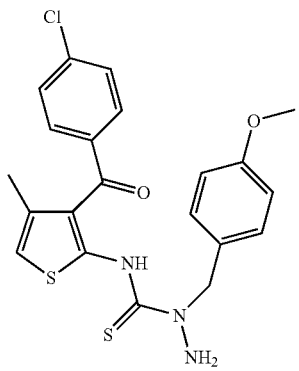

To a stirred solution of Intermediate 2 (700 mg, 2.38 mmol) in tetrahydrofuran (50 mL) was added triethylamine (0.3 mL, 2.38 mmol), followed by (4-methoxybenzyl)hydrazine hydrochloride (449 mg, 3.28 mmol), and the mixture was stirred at 0° C. for one hour and at room temperature for 16 hours. After the reaction completed, the reaction mixture was concentrated under reduced pressure to obtain a residue. The residue was triturated with hexane to obtain 600 mg of Intermediate 3.

Yield: 56%, $^1$H NMR (400 MHz, DMSO-$d_6$) δ 1.74 (s, 3H), 3.74 (s, 3H), 5.19 (s, 2H), 6.64 (d, J=0.98 Hz, 1H), 6.92 (d, J=8.80 Hz, 2H), 7.28 (d, J=8.80 Hz, 2H), 7.58 (s, 3H), 9.93 (brs, 1H) and LC-MS (M+H): 446.23.

Step-4: Synthesis of 5-(4-chlorophenyl)-3-(4-methoxybenzyl)-6-methyl-1H-thieno[2,3-e][1,2,4]triazepine-2(3H)-thione (Intermediate 4)

[Chem. 107]

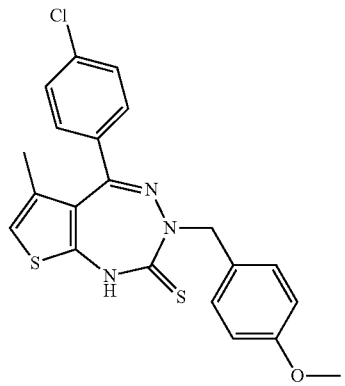

To a solution of Intermediate 3 (600 mg, 1.34 mmol) in ethanol (50 mL) was added p-toluenesulfonic acid (46 mg, 0.28 mmol), and the mixture was stirred at 100° C. for 16 hours. After the reaction completed, the reaction mixture was concentrated under reduced pressure to obtain a crude compound. The crude compound was purified by silica gel column chromatography (eluted with 30% ethyl acetate:hexane) to obtain 300 mg of Intermediate 4.

Yield: 52%, 1H NMR (300 MHz, DMSO-$d_6$) δ 1.50 (s, 3H), 3.72 (s, 3H), 5.04 (brs, 2H), 6.82-6.91 (m, 3H), 7.13 (d, J=8.44 Hz, 2H), 7.22 (d, J=8.80 Hz, 2H), 7.49 (d, J=8.80 Hz, 2H), 11.06 (s, 1H) and LC-MS (M+H): 428.19.

Step-5: Synthesis of 5-(4-chlorophenyl)-3-(4-methoxybenzyl)-6-methyl-2-(methylthio)-3H-thieno[2,3-e][1,2,4]triazepine (Intermediate 5)

[Chem. 108]

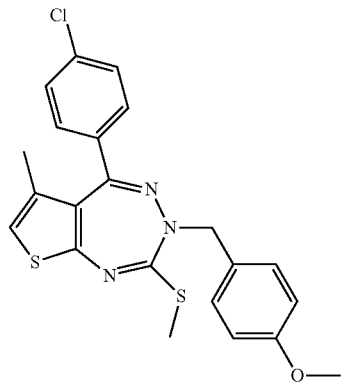

To a stirred solution of Intermediate 4 (300 mg, 0.7 mmol) in tetrahydrofuran (10 mL) was added sodium hydride (34 mg, 1.4 mmol) at 0° C., and the mixture was stirred at room temperature for one hour. Methyl iodide (0.05 mL, 0.77 mmol) was added thereto at the same temperature, and the mixture was stirred at room temperature for one hour. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain 290 mg of Intermediate 5.

Yield: 94%, $^1$H NMR (300 MHz, DMSO-$d_6$) δ 1.52 (s, 3H), 2.48 (s, 3H), 3.73 (s, 3H), 4.67 (brs, 2H), 6.90 (brd, J=6.58 Hz, 3H), 7.17 (d, J=8.04 Hz, 2H), 7.27 (d, J=8.04 Hz, 2H), 7.47 (d, J=8.41 Hz, 2H) and LC-MS (M+H): 442.23.

Step-6: Synthesis of 4-(4-chlorophenyl)-6-(4-methoxybenzyl)-3,9-dimethyl-6H-thieno[2,3-e][1,2,4]triazolo[3,4-c][1,2,4]triazepine (Compound of Example 66)

[Chem. 109]

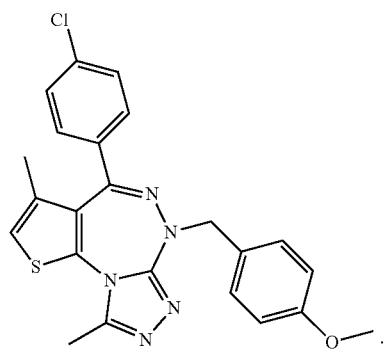

To a stirred solution of Intermediate 5 (290 mg, 0.65 mmol) in ethanol (20 mL) were added acetic hydrazide (241 mg, 3.25 mmol) and p-toluenesulfonic acid (22 mg, 0.13 mmol), and the mixture was stirred at 100° C. for 12 hours. After the reaction completed, the reaction mixture was concentrated under reduced pressure to obtain a crude compound. The crude compound was triturated with diethyl ether to obtain 300 mg of the compound of Example 66.

Yield: 16%, $^1$HNMR (400 MHz, DMSO-$d_6$) δ 1.58 (s, 3H), 2.55 (s, 3H), 3.73 (s, 3H), 4.72 (s, 1H), 4.92 (s, 1H), 6.89 (d, J=8.80 Hz, 2H), 7.30-7.36 (m, 5H), 7.50 (d, J=8.80 Hz, 2H) and LC-MS (M+H): 449.95.

Synthetic Scheme of the Compound of Example 67

[Chem. 110]

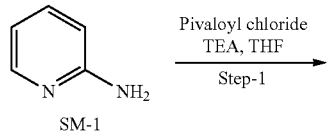

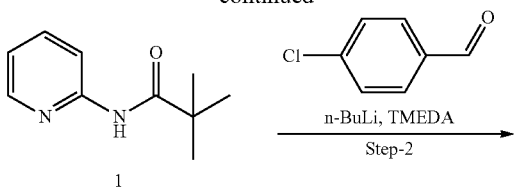

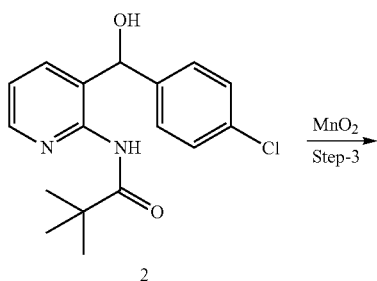

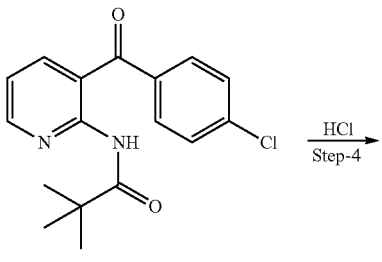

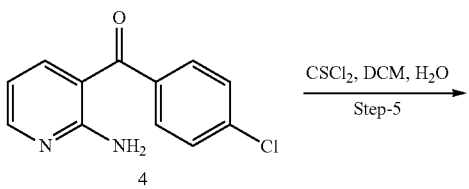

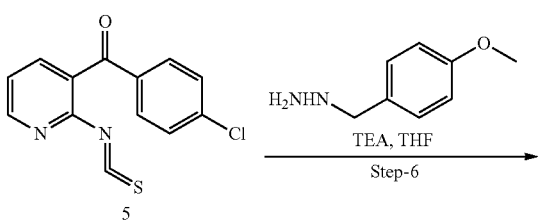

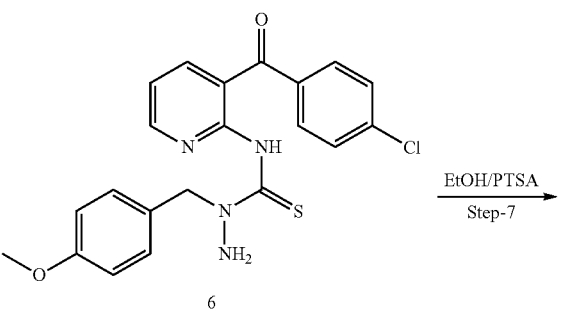

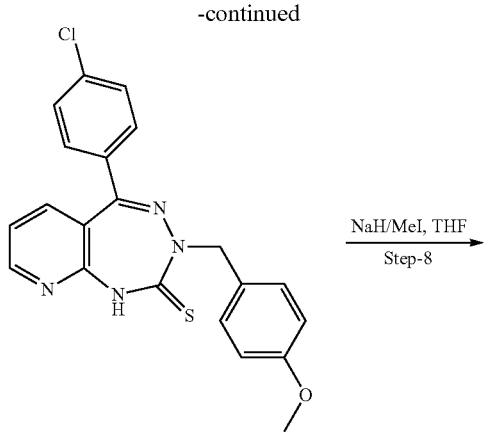

7

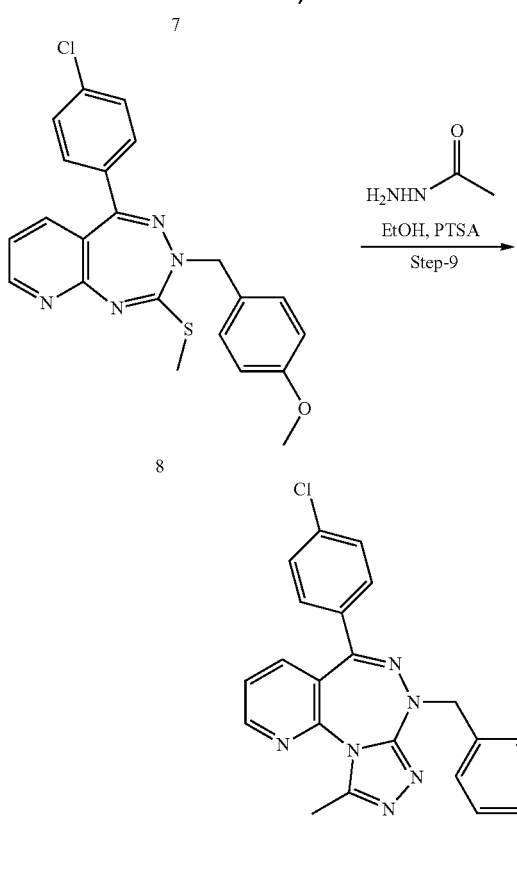

8

Step-1: Synthesis of N-(pyridin-2-yl)pivalamide (Intermediate 1)

[Chem. 111]

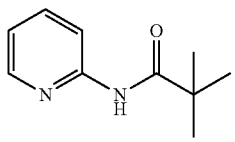

1

To a solution of SM-1 (2 g, 21.25 mmol) in tetrahydrofuran (20 mL) were added pivaloyl chloride (2.6 mL, 21.46 mmol) and triethylamine (1.2 mL, 11.62 mmol), and the mixture was stirred at room temperature for 16 hours. After the reaction completed, the reaction mixture was diluted with water and extracted with ethyl acetate. The combined organic layers were dried over anhydrous sodium sulfate and filtered, and the filtrate was distilled off under reduced pressure to obtain 500 mg of Intermediate 1 (550 mg, Y: 20%) as an off-white solid. Intermediate 1 was confirmed by $^1$H-NMR and LC-MS.

Yield: 20%, $^1$H NMR (300 MHz, DMSO-$d_6$) δ 1.23 (s, 9H), 7.09 (dd, J=6.76, 5.30 Hz, 1H), 7.72-7.81 (m, 1H), 8.04 (d, J=8.41 Hz, 1H), 8.28-8.34 (m, 1H), 9.73 (brs, 1H) and LC-MS (M+1): 179.29.

Step-2: Synthesis of N-(3-((4-chlorophenyl)(hydroxy)methyl)pyridin-2-yl)pivalamide (Intermediate 2)

[Chem. 112]

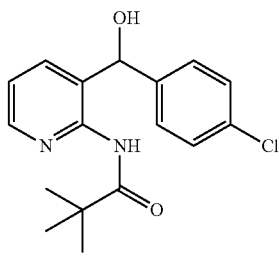

2

To a solution of Intermediate 1 (500 mg, 3.06 mmol) and TMEDA (0.9 mL, 9.20 mmol) in tetrahydrofuran (10 mL) was added n-butyllithium (1.6 M, 5.75 mL, 9.20 mmol) at −78° C., and the mixture was gradually warmed to room temperature and stirred for 2 hours. A solution of 4-chlorobenzaldehyde (1.29 g, 9.20 mmol) in tetrahydrofuran (5 mL) was added thereto at −70° C., and the mixture was stirred at room temperature for 18 hours. After the reaction completed, the reaction mixture was quenched with ice-water, extracted with ethyl acetate and washed with brine. The organic layer was dried over anhydrous sodium sulfate and filtered, and the filtrate was concentrated under reduced pressure to obtain a crude compound. The crude compound was purified by silica gel column chromatography (eluted with 50% ethyl acetate:hexane) to obtain 140 mg of Intermediate 2.

Yield: 16%, $^1$H NMR (300 MHz, DMSO-$d_6$) δ 1.14 (s, 7H), 5.80 (d, J=4.77 Hz, 1H), 6.22 (d, J=4.40 Hz, 1H), 7.21-7.37 (m, 5H), 7.86 (dd, J=7.70, 1.83 Hz, 1H), 8.33 (dd, J=4.77, 1.83 Hz, 1H), 9.45 (s, 1H) and LC-MS (M+1): 319.28.

Step-3: Synthesis of N-(3-(4-chlorobenzoyl)pyridin-2-yl)pivalamide (Intermediate 3)

[Chem. 113]

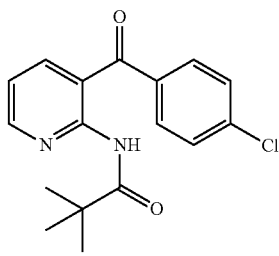

3

To a solution of Intermediate 2 (140 mg, 0.44 mmol) in tetrahydrofuran (10 mL) was added manganese dioxide (880 mg, 10.12 mmol), and the mixture was stirred at room temperature for 16 hours. After the reaction completed, the reaction mixture was filtered through a celite pad, and the filtrate was concentrated under reduced pressure to obtain a crude compound. The crude compound was triturated with hexane to obtain 80 mg of Intermediate 3, which was confirmed by LC-MS (M+1): 317.13 and used in the next Step without further purification.

Step-4: Synthesis of (2-aminopyridin-3-yl)(4-chlorophenyl)methanone (Intermediate 4)

[Chem. 114]

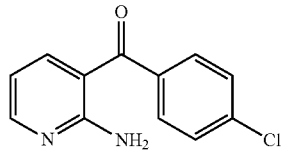

4

To a solution of Intermediate 3 (80 mg, 0.25 mmol) in water (1 mL) was added conc. hydrochloric acid (1 mL) at 0° C., and the mixture was stirred at 100° C. for 24 hours. After the reaction completed, the reaction mixture was concentrated under reduced pressure to obtain a residue. The residue was diluted with water, made basic with a saturated sodium bicarbonate solution and extracted with ethyl acetate. The combined organic layers were dried over anhydrous sodium sulfate and filtered, and the filtrate was distilled off under reduced pressure to obtain a crude compound. The crude compound was triturated with hexane to obtain 50 mg of Intermediate 4.

Yield: 86%, $^1$H NMR (400 MHz, DMSO-d$_6$) δ 6.62 (dd, J=7.83, 4.89 Hz, 1H), 7.56-7.62 (m, 6H), 7.67 (dd, J=7.83, 1.96 Hz, 1H), 8.25 (dd, J=4.89, 1.96 Hz, 1H) and LC-MS (M+1): 233.06.

Step-5: Synthesis of (4-chlorophenyl)(2-isothiocyanatopyridin-3-yl)methanone (Intermediate 5)

[Chem. 115]

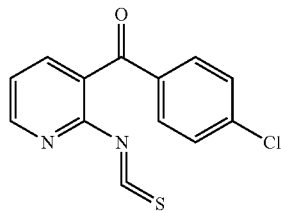

5

To a solution of thiophosgene (0.84 mL, 11.17 mmol) in water (15 mL) was added a solution of Intermediate 4 (2 g, 8.59 mmol) in dichloromethane (75 mL) at 0° C., and the mixture was stirred at 0° C. for one hour and at room temperature for 16 hours.

After the reaction completed, the reaction mixture was quenched with ice-water, 25 extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with 30% ethyl acetate: hexane) to obtain 1 g of Intermediate 5.

Yield: 43%, $^1$H NMR (400 MHz, DMSO-d$_6$) δ 7.61 (dd, J=7.83, 4.89 Hz, 2H), 7.68-7.71 (m, 1H), 7.81-7.86 (m, 2H), 8.11 (dd, J=7.83, 1.47 Hz, 1H), 8.70 (dd, J=4.89, 1.47 Hz, 1H) and LC-MS (M+1): 275.02.

Step-6: Synthesis of N-(3-(4-chlorobenzoyl)pyridin-2-yl)-1-(4-methoxybenzyl)hydrazinecarbothioamide (Intermediate 6)

[Chem. 116]

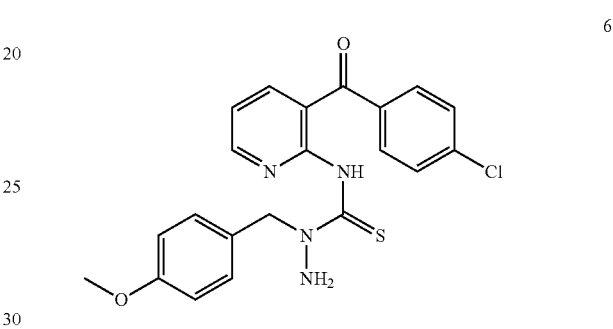

6

To a solution of Intermediate 5 (1 g, 3.63 mmol) in tetrahydrofuran (30 mL) was added (4-methoxybenzyl)hydrazine (552 mg, 3.63 mmol), and the mixture was stirred at 0° C. for one hour and at room temperature for 12 hours. After the reaction completed, the reaction mixture was concentrated under reduced pressure to obtain a residue. The residue was triturated with hexane to obtain 1.4 g of Intermediate 6 (LC-MS: 57%), which was confirmed by LC-MS (M+1): 426.99 and used in the next Step without further purification.

Step-7: Synthesis of 5-(4-chlorophenyl)-3-(4-methoxybenzyl)-1H-pyrido[2,3-e][1,2,4]triazepine-2(3H)-thione (Intermediate 7)

[Chem. 117]

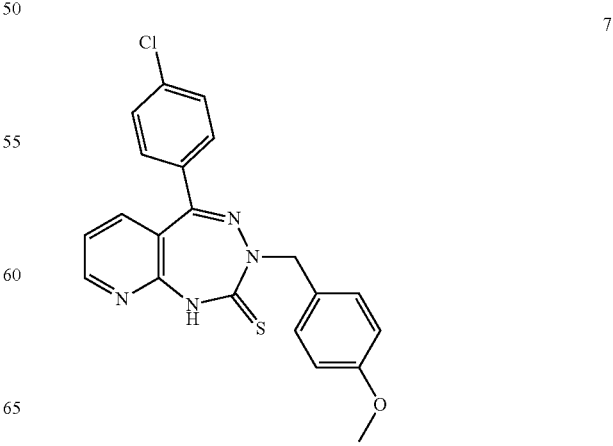

7

To a solution of Intermediate 6 (1.4 g, LC-MS: 57%) in ethanol (50 mL) was added p-toluenesulfonic acid (113 mg, 0.65 mmol), and the mixture was stirred at 100° C. for 24 hours. After the reaction completed, the reaction mixture was concentrated under reduced pressure to obtain a residue, and the residue was diluted with water and extracted with ethyl acetate. The combined organic layers were dried over anhydrous sodium sulfate and filtered, and the filtrate was distilled off under reduced pressure to obtain a crude compound. The crude compound was triturated with 10% ethyl acetate/dichloromethane to obtain 380 mg of Intermediate 7.

Yield: 56%, $^1$H NMR (400 MHz, DMSO-$d_6$) δ 3.71 (s, 3H), 5.19 (s, 2H), 6.86 (d, J=8.31 Hz, 2H), 7.19-7.27 (m, 3H), 7.29 (d, J=8.31 Hz, 2H), 7.51 (d, J=8.31 Hz, 3H), 8.51 (dd, J=4.89, 1.47 Hz, 1H), 10.42 (s, 1H) and LC-MS (M+1): 409.22.

Step-8: Synthesis of 5-(4-chlorophenyl)-3-(4-methoxybenzyl)-2-(methylthio)-3H-pyrido[2,3-e][1,2,4]triazepine (Intermediate 8)

[Chem. 118]

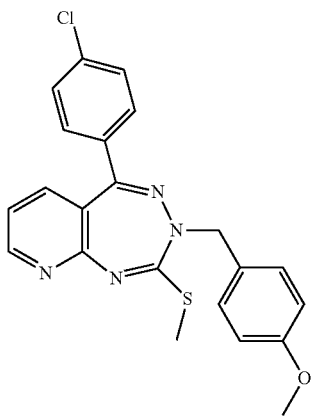

8

To a solution of Intermediate 7 (350 mg, 0.85 mmol) in tetrahydrofuran (20 mL) was added sodium hydride (42 mg, 1.71 mmol) at 0° C., and the mixture was stirred at room temperature for one hour. Methyl iodide (0.06 mL, 1.79 mmol) was added thereto at 0° C., and the mixture was stirred at room temperature for 3 hours. After the reaction completed, the reaction mixture was poured into ice-cold water and extracted with ethyl acetate. The combined organic layers were dried over anhydrous sodium sulfate and filtered, and the filtrate was distilled off under reduced pressure to obtain 355 mg of a crude compound of Intermediate 8.

Yield: 96%: $^1$H NMR (400 MHz, DMSO-$d_6$) δ 2.54 (s, 3H), 3.71 (s, 3H), 4.67 (s, 2H), 6.86 (d, J=8.31 Hz, 2H), 7.10 (dd, J=7.83, 4.89 Hz, 1H), 7.22 (d, J=8.31 Hz, 2H), 7.33 (d, J=8.31 Hz, 2H), 7.44 (dd, J=7.83, 1.96 Hz, 1H), 7.49 (d, J=8.31 Hz, 2H), 8.57 (dd, J=4.65, 1.71 Hz, 1H) and LC-MS (M+1): 423.26.

Step-9: Synthesis of 5-(4-chlorophenyl)-7-(4-methoxybenzyl)-10-methyl-7H-pyrido[2,3-e][1,2,4]triazolo[3,4-c][1,2,4]triazepine (Compound of Example 67)

[Chem. 119]

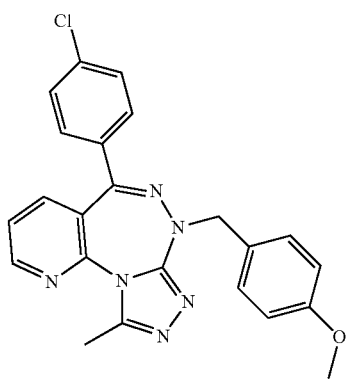

To a solution of Intermediate 8 (350 mg, 0.82 mmol) in ethanol (30 mL) were added acetohydrazide (295 mg, 4.1 mmol) and p-toluenesulfonic acid (28 mg, 0.16 mmol), and the mixture was stirred at 100° C. for 16 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain a crude compound. The crude compound was triturated with diethyl ether to obtain a crude compound, which was further purified by preparative HPLC to obtain 130 mg of the compound of Example 67.

Yield: 37%, 1H NMR (400 MHz, DMSO-$d_6$) δ 2.59 (s, 3H), 3.72 (s, 3H), 4.85 (s, 2H), 6.88 (d, J=8.80 Hz, 2H), 7.32 (d, J=8.31 Hz, 2H), 7.40-7.46 (m 2H), 7.47-7.53 (m, 3H), 7.70 (dd, J=7.83, 1.96 Hz, 1H), 8.73 (dd, J=4.65, 1.71 Hz, 1H) and LC-MS (M+1): 431.19.

Synthetic Scheme of the Compound of Example 68

[Chem. 120]

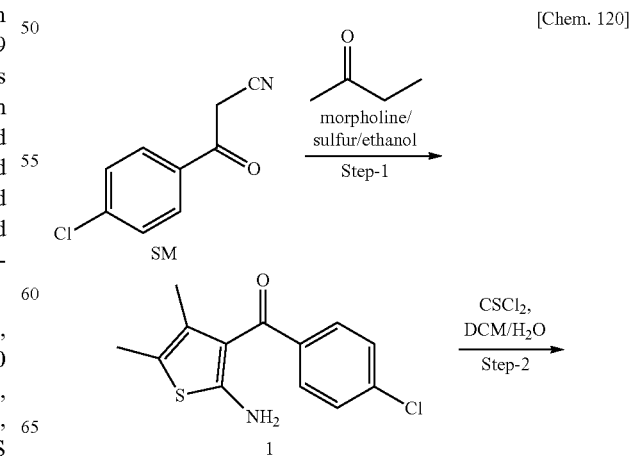

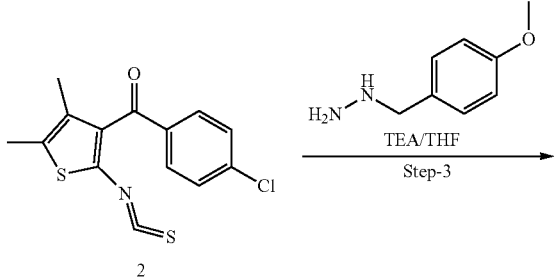

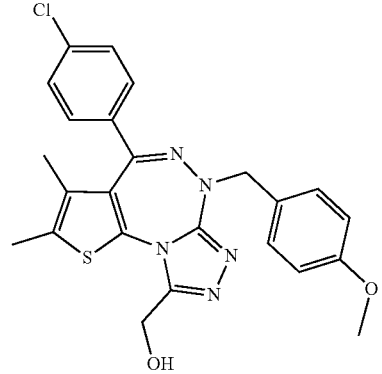

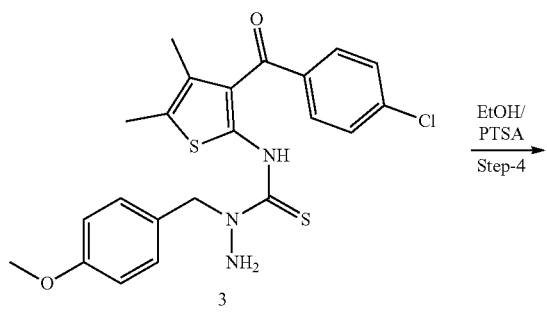

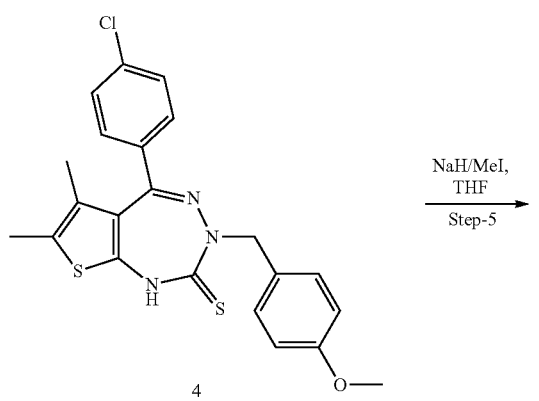

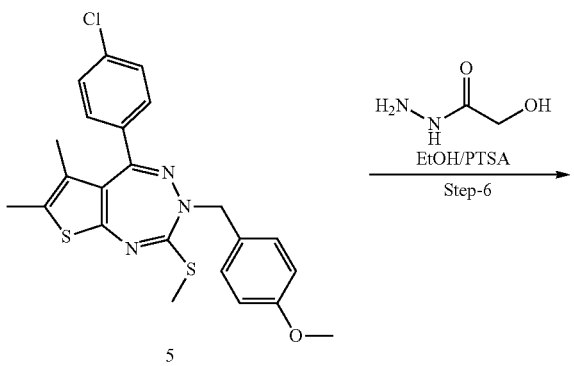

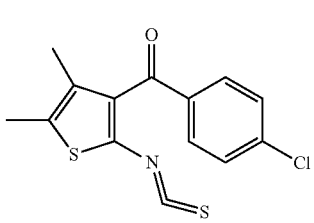

Step-1: Synthesis of (2-amino-4,5-dimethylthiophen-3-yl)(4-chlorophenyl)methanone (Intermediate 1)

[Chem. 121]

To a solution of SM (1 g, 5.56 mmol) in ethanol (20 mL) were added butan-2-one (0.5 mL, 5.56 mmol), sulfur (178 mg, 5.56 mmol) and morpholine (0.45 mL, 5.56 mmol), and the mixture was stirred at 70° C. for 16 hours. After the reaction completed, the reaction mixture was concentrated under reduced pressure to obtain a crude residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate: hexane) to obtain Intermediate 1 (800 mg).

Yield: 54%, $^1$H NMR (300 MHz, DMSO-$d_6$) δ 1.43 (s, 3H), 2.09 (s, 3H), 7.36-7.45 (m, 2H), 7.49-7.55 (m, 2H), 7.88 (brs, 2H) and LC-MS (M+1): 266.06.

Step-2: Synthesis of (4-chlorophenyl)(2-isothiocyanato-4,5-dimethylthiophen-3-yl)methanone (Intermediate 2)

[Chem. 122]

To a solution of thiophosgene (0.3 mL, 3.92 mmol) in water (10 mL) was added a solution of Intermediate 1 (800 mg, 3.01 mmol) in dichloromethane (20 mL) at 0° C., and the mixture was stirred at the same temperature for one hour and at room temperature for 4 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was triturated with hexane to obtain Intermediate 2 (750 mg).

Yield: 81%, $^1$H NMR (300 MHz, CDCl$_3$) δ 2.04 (s, 3H), 2.33 (s, 3H), 7.45-7.52 (m, 2H), 7.76-7.81 (m, 2H). and LC-MS (M+1): 308.16.

Step-3: Synthesis of N-(3-(4-chlorobenzoyl)-4,5-dimethylthiophen-2-yl)-1-(4-methoxybenzyl)hydrazinecarbothioamide (Intermediate 3)

[Chem. 123]

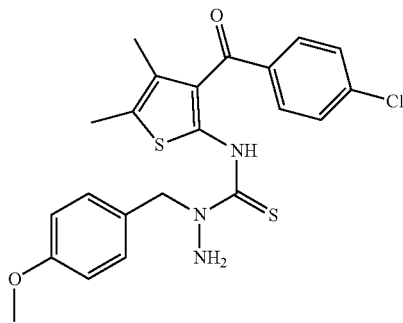

3

To a solution of Intermediate 2 (750 mg, 2.43 mmol) in tetrahydrofuran (50 mL) was added triethylamine (0.68 mL, 4.87 mmol), followed by (4-methoxybenzyl)hydrazine hydrochloride (553 mg, 2.93 mmol), and the mixture was stirred at 0° C. for one hour and at room temperature for one hour. After the reaction completed, the reaction mixture was filtered and washed with diethyl ether to obtain Intermediate 3 (650 mg), which was confirmed by LC-MS (M+1): 460.19 and used in the next Step without further formation.

Step-4: Synthesis of 5-(4-chlorophenyl)-3-(4-methoxybenzyl)-6,7-dimethyl-1H-thieno[2,3-e][1,2,4]triazepin e-2(3H)-thione (Intermediate 4)

[Chem. 124]

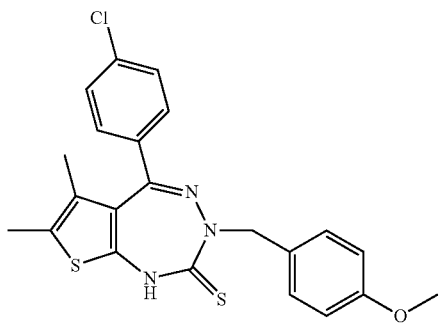

4

To a solution of Intermediate 3 (650 mg, 1.41 mmol) in ethanol (20 mL) was added p-toluenesulfonic acid (24 mg, 0.14 mmol), and the mixture was stirred at 100° C. for 16 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 30% ethyl acetate:hexane) to obtain Intermediate 4 (450 mg).

Yield: 72%, $^1$H NMR (300 MHz, DMSO-d$_6$) δ 1.38 (s, 3H), 2.23 (s, 311), 3.72 (s, 3H), 5.01 (brs, 2H), 6.87 (d, J=8.44 Hz, 2H), 7.13 (d, J=8.44 Hz, 2H), 7.23 (d, J=8.44 Hz, 2H), 7.47 (d, J=8.44 Hz, 2H), 11.00 (s, 1H) and LC-MS (M+1): 442.23.

Step-5: Synthesis of 5-(4-chlorophenyl)-3-(4-methoxybenzyl)-6,7-dimethyl-2-(methylthio)-3H-thieno[2,3-e][1,2,4]triazepine (Intermediate 5)

[Chem. 125]

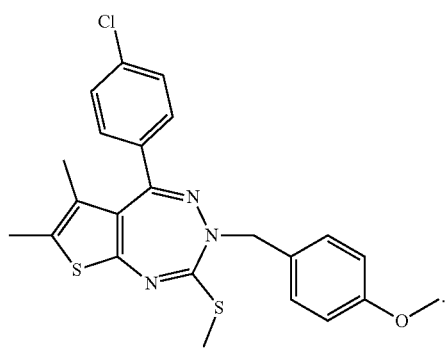

5

To a solution of Intermediate 4 (450 mg, 1.02 mmol) in tetrahydrofuran (20 mL) was added NaH (45 mg, 1.12 mmol) at 0° C., and the mixture was stirred at room temperature for one hour. Methyl iodide (0.07 mL, 1.12 mmol) was added thereto at 0° C., and the mixture was stirred at room temperature for one hour. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain Intermediate 5 (310 mg).

Yield: 67%, $^1$H NMR (400 MHz, DMSO-d$_6$) δ 1.40 (s, 3H), 2.24 (s, 3H), 2.47 (s, 3H), 3.73 (s, 3H), 4.70 (brs, 2H), 6.89 (d, J=8.31 Hz, 2H), 7.17 (d, J=8.31 Hz, 2H), 7.28 (d, J=8.31 Hz, 2H), 7.47 (d, J=8.80 Hz, 2H) and LC-MS (M+1): 456.27.

Step-6: Synthesis of (4-(4-chlorophenyl)-6-(4-methoxybenzyl)-2,3-dimethyl-6H-thieno[2,3-e][1,2,4]triazolo[3,4-c][1,2,4]triazepin-9-yl)methanol (Compound of Example 68)

[Chem. 126]

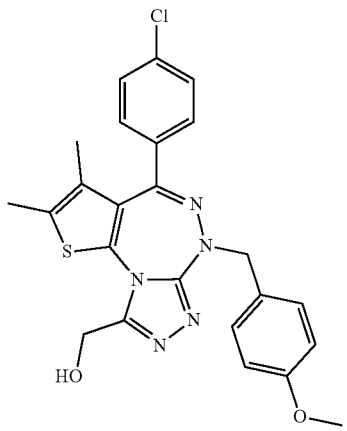

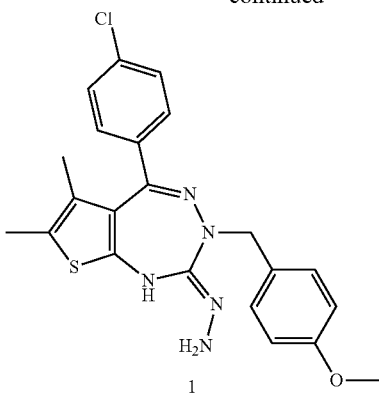

To a solution of Intermediate 5 (310 mg, 0.68 mmol) in ethanol (20 mL) were added 2-hydroxyacetohydrazide (306 mg, 3.4 mmol) and p-toluenesulfonic acid (24 mg, 0.13 mmol), and the mixture was stirred at 100° C. for 16 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 3% methanol/dichloromethane) to obtain 400 mg of a compound, which was further purified by preparative HPLC to obtain the compound of Example 68 (68 mg).

Yield: 20%, $^1$H NMR (400 MHz, DMSO-$d_6$) δ 1.47 (s, 3H), 2.34 (s, 3H), 3.73 (s, 3H), 4.58 (dd, J=13.21, 6.36 Hz, 1H), 4.66-4.76 (m, 2H), 4.96 (d, J=13.21 Hz, 1H), 5.79 (t, J=5.38 Hz, 1H), 6.89 (d, J=8.31 Hz, 2H), 7.33 (dd, J=8.56, 1.71 Hz, 4H), 7.50 (d, J=8.80 Hz, 2H) and LC-MS (M+1): 480.01.

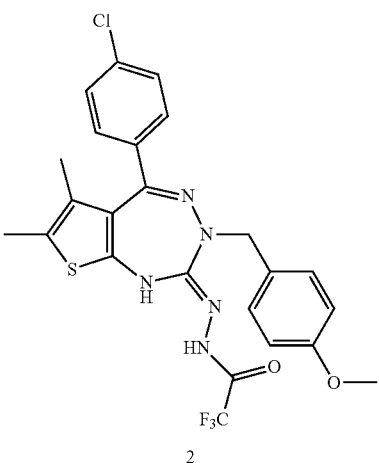

Synthetic Scheme of the Compound of Example 69

[Chem. 127]

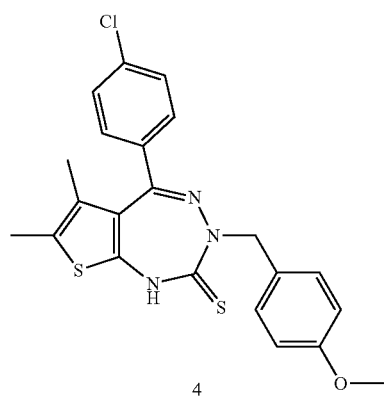

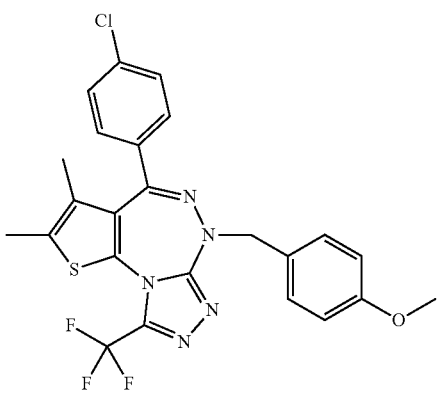

Step-1: Synthesis of (E)-5-(4-chlorophenyl)-2-hydrazino-3-(4-methoxybenzyl)-6,7-dimethyl-2,3-dihydro-1H-thieno[2,3-e][1,2,4]triazepine (Intermediate 1)

[Chem. 128]

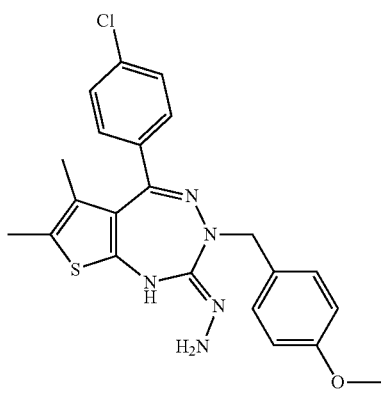

1

To a solution of hydrazine monohydrate (0.04 mL, 0.68 mmol) in dichloromethane (5 mL) were added Intermediate 4 (100 mg, 0.22 mmol), triethylamine (0.16 mL, 1.13 mmol) and $HgCl_2$ (154 mg, 0.56 mmol) at 0° C., and the mixture was stirred at room temperature for 48 hours. After the reaction completed, the reaction mixture was diluted with ethyl acetate, washed with water and a brine solution, dried over anhydrous sodium sulfate, and filtered. The filtrate was distilled off under reduced pressure to obtain a crude Intermediate 1 (80 mg), which was confirmed by LC-MS (M+1): 440.17 and used in the next Step without further purification.

Step-2: Synthesis of (E)-N'-(5-(4-chlorophenyl)-3-(4-methoxybenzyl)-6,7-dimethyl-1H-thieno[2,3-e][1,2,4]triazepin-2(3H)-ylidene)-2,2,2-trifluoroacetohydrazide (Intermediate 2)

[Chem. 129]

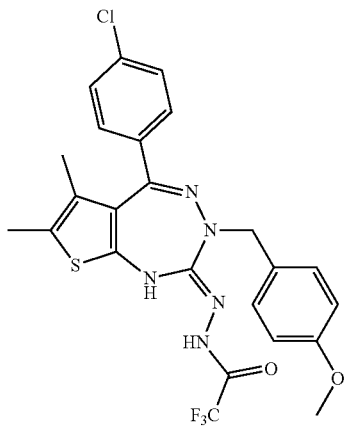

2

To a solution of Intermediate 1 (80 mg, 0.18 mmol) in dichloromethane (5 mL) were added DIPEA (0.05 mL, 0.27 mmol) and anhydrous trifluoroacetic acid (0.03 mL, 0.21 mmol) at 0° C., and the mixture was stirred at room temperature for 3 hours. After the reaction completed, the reaction mixture was diluted with ethyl acetate, washed with water and a brine solution, dried over anhydrous sodium sulfate, and filtered. The filtrate was distilled off under reduced pressure to obtain a crude Intermediate 2 (80 mg), which was confirmed by LC-MS (M+1): 536.15 and used without further purification.

Step-3: Synthesis of 4-(4-chlorophenyl)-6-(4-methoxybenzyl)-2,3-dimethyl-9-(trifluoromethyl)-6H-thieno[2,3-e][1,2,4]triazolo[3,4-c][1,2,4]triazepine (Compound of Example 69)

[Chem. 130]

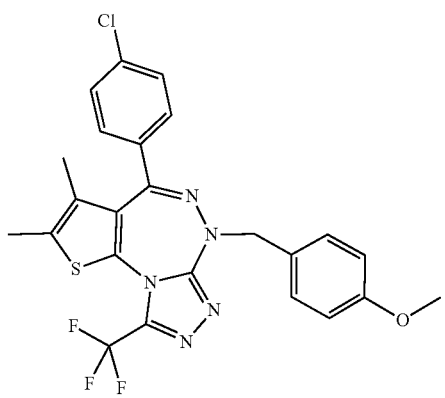

To a stirred solution of Intermediate 2 (400 mg, 0.74 mmol) in tetrahydrofuran (10 mL) was added acetic acid (5 mL) at 0° C., and the mixture was stirred at room temperature for 24 hours. After the reaction completed, the reaction mixture was concentrated under reduced pressure to obtain a residue. The residue was diluted with ethyl acetate, washed with saturated sodium bicarbonate, dried over anhydrous sodium sulfate, and filtered. The filtrate was distilled off under reduced pressure to obtain a crude compound. The crude compound was purified by preparative HPLC to obtain the compound of Example 69 (51 mg).

Yield: 20%, 1H NMR (400 MHz, $CDCl_3$) δ 1.52 (s, 3H), 2.38 (s, 311), 3.81 (s, 3H), 4.88 (d, J=13.69 Hz, 1H), 5.07 (d, J=13.69 Hz, 1H), 6.87 (d, J=8.31 Hz, 2H), 7.27-7.37 (m, 6H) and LC-MS (M+1): 518.20.

Synthetic Scheme of the Compound of Example 70

[Chem. 131]

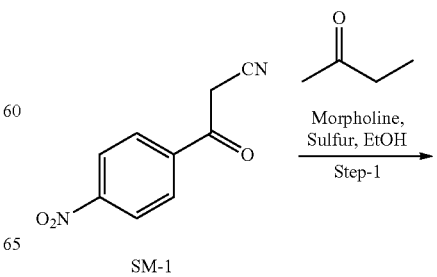

SM-1

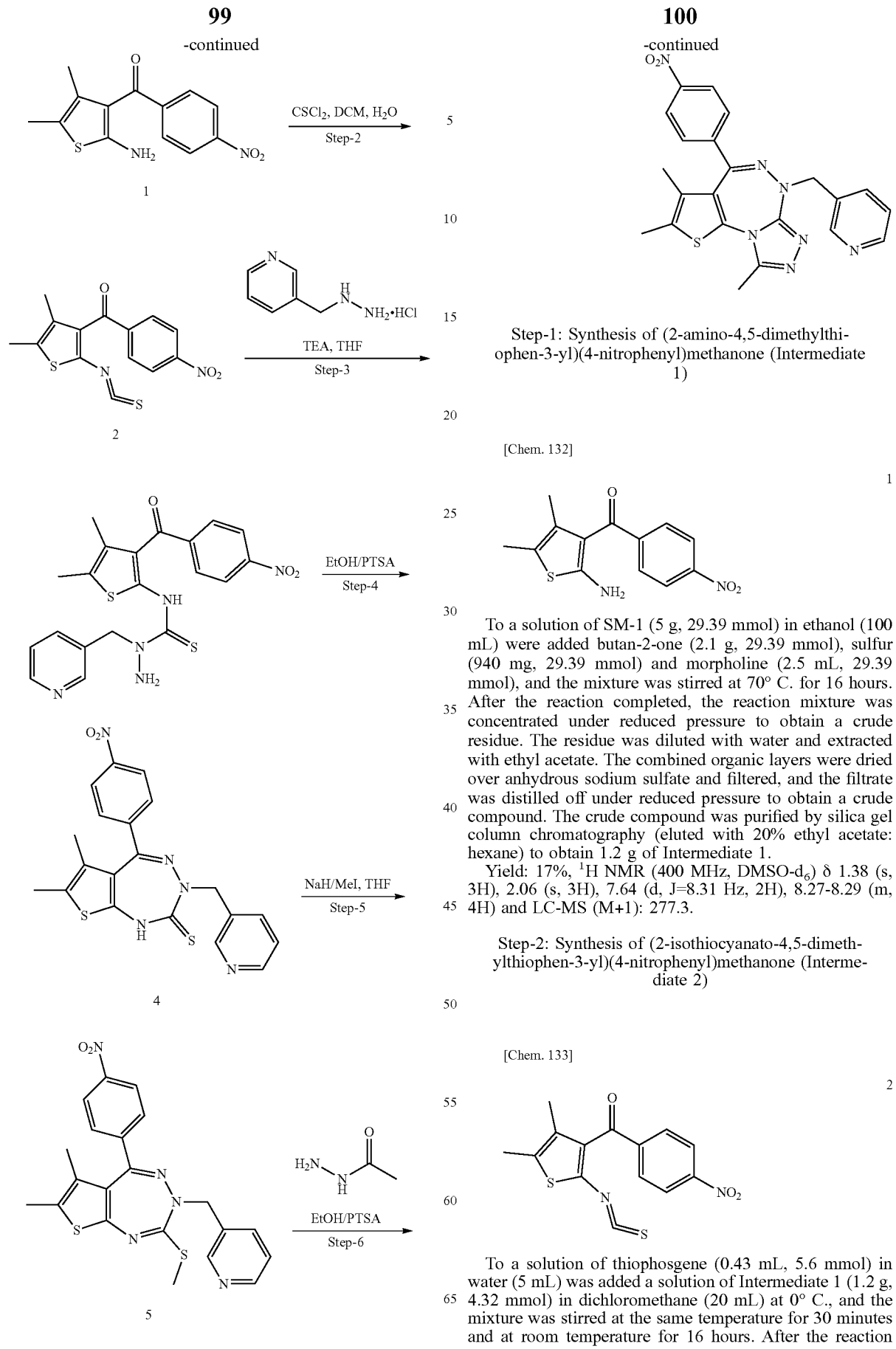

Step-1: Synthesis of (2-amino-4,5-dimethylthiophen-3-yl)(4-nitrophenyl)methanone (Intermediate 1)

[Chem. 132]

To a solution of SM-1 (5 g, 29.39 mmol) in ethanol (100 mL) were added butan-2-one (2.1 g, 29.39 mmol), sulfur (940 mg, 29.39 mmol) and morpholine (2.5 mL, 29.39 mmol), and the mixture was stirred at 70° C. for 16 hours. After the reaction completed, the reaction mixture was concentrated under reduced pressure to obtain a crude residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate: hexane) to obtain 1.2 g of Intermediate 1.

Yield: 17%, $^1$H NMR (400 MHz, DMSO-$d_6$) δ 1.38 (s, 3H), 2.06 (s, 3H), 7.64 (d, J=8.31 Hz, 2H), 8.27-8.29 (m, 4H) and LC-MS (M+1): 277.3.

Step-2: Synthesis of (2-isothiocyanato-4,5-dimethylthiophen-3-yl)(4-nitrophenyl)methanone (Intermediate 2)

[Chem. 133]

To a solution of thiophosgene (0.43 mL, 5.6 mmol) in water (5 mL) was added a solution of Intermediate 1 (1.2 g, 4.32 mmol) in dichloromethane (20 mL) at 0° C., and the mixture was stirred at the same temperature for 30 minutes and at room temperature for 16 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with dichloromethane) to obtain Intermediate 2 (600 mg).

Yield: 43%, $^1$H NMR (400 MHz, DMSO-$d_6$) δ 2.03 (s, 3H), 2.37 (s, 3H), 8.00-8.05 (m, 2H), 8.40 (d, J=8.80 Hz, 2H) and LC-MS (M+1): Mass not ionized.

Step-3: Synthesis of N-(4,5-dimethyl-3-(4-nitrobenzoyl)thiophen-2-yl)-1-(pyridin-3-ylmethyl)hydrazinecarbothioamide (Intermediate 3)

[Chem. 134]

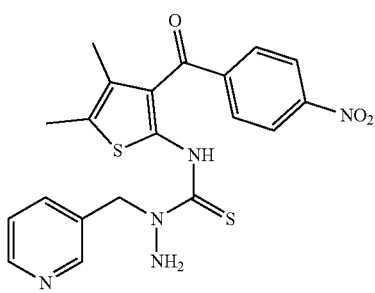

3

To a solution of Intermediate 2 (1.3 g, 4.08 mmol) in tetrahydrofuran (50 mL) was added triethylamine (0.26 mL, 4.49 mmol), followed by SM-3 (712 mg, 4.49 mmol), and the mixture was stirred at 0° C. for one hour and at room temperature for one hour. After the reaction completed, the reaction mixture was concentrated under reduced pressure to obtain a residue. The residue was triturated with hexane to obtain Intermediate 3 (1.5 g), which was confirmed by LC-MS (M+1): 442.19 and used in the next Step without further purification.

Step-4: Synthesis of 6,7-dimethyl-5-(4-nitrophenyl)-3-(pyridin-3-ylmethyl)-1H-thieno[2,3-e][1,2,4]triazepine-2(3H)-thione (Intermediate 4)

[Chem. 135]

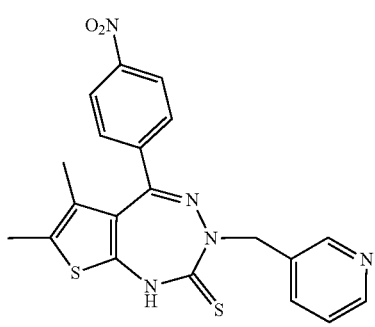

4

To a solution of Intermediate 3 (1.5 g, 3.4 mmol) in ethanol (200 mL) was added p-toluenesulfonic acid (117 mg, 0.68 mmol), and the mixture was stirred at 100° C. for 16 hours. After the reaction completed, the reaction mixture was concentrated under reduced pressure to obtain a residue. The residue was diluted with ethyl acetate and washed with a saturated sodium hydrogen carbonate aqueous solution and brine, dried over anhydrous sodium sulfate, and filtered. The filtrate was distilled off under reduced pressure to obtain a crude compound. The crude compound was purified by silica gel column chromatography (40% ethyl acetate: hexane) to obtain a crude compound, which was purified by preparative HPLC to obtain Intermediate 4 (260 mg).

Yield: 18%, $^1$H NMR (400 MHz, DMSO-$d_6$) δ 1.36 (s, 3H), 2.36 (s, 3H), 7.13 (t, J=7.34 Hz, 1H), 7.20-7.26 (m, 2H), 7.97-8.03 (m, 3H), 8.38-8.43 (m, 3H).

Step-5: Synthesis of 6,7-dimethyl-2-(methylthio)-5-(4-nitrophenyl)-3-(pyridin-3-ylmethyl)-3H-thieno[2,3-e][1,2,4]triazepine (Intermediate 5)

[Chem. 136]

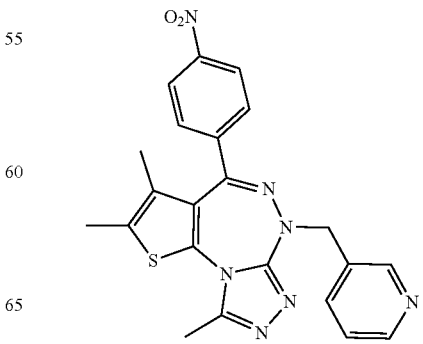

5

To a solution of Intermediate 4 (500 mg, LC-MS: 26%) in tetrahydrofuran (20 mL) was added NaH (57 mg, 2.34 mmol) at 0° C., and the mixture was stirred at room temperature for one hour. Methyl iodide (0.09 mL, 1.41 mmol) was added thereto at the same temperature, and the mixture was stirred at room temperature for one hour. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound of Intermediate 5 (550 mg, LC-MS: 24%), which was used in the next Step without further purification.

Step-6: Synthesis of 2,3,9-trimethyl-4-(4-nitrophenyl)-6-(pyridin-3-ylmethyl)-6H-thieno[2,3-e][1,2,4]triazolo[3,4-c][1,2,4]triazepine

[Chem. 137]

To a solution of Intermediate 5 (550 mg, LC-MS: 24%) in ethanol (50 mL) were added acetohydrazide (462 mg, 6.25 mmol) and p-toluenesulfonic acid (43 mg, 0.25 mmol), and the mixture was stirred at 100° C. for 16 hours. After the reaction completed, the reaction mixture was concentrated under reduced pressure to obtain a residue. The residue was diluted with ethyl acetate, washed with a saturated sodium hydrogen carbonate aqueous solution and brine, dried over anhydrous sodium sulfate, and filtered. The filtrate was distilled off under reduced pressure to obtain a crude compound, which was further purified by preparative HPLC to obtain the compound of Example 70 (58 mg).

Y: 43%, $^1$H NMR (400 MHz, DMSO-$d_6$) δ 1.44 (s, 3H), 2.36 (s, 3H), 2.55 (s, 3H), 4.87 (d, J=14.18 Hz, 1H), 5.08 (d, J=13.69 Hz, 1H), 7.39 (m, 1H), 7.58 (d, J=8.80 Hz, 2H), 7.80-7.86 (m, 1H), 8.28 (d, J=8.80 Hz, 2H), 8.50 (dd, J=4.89, 1.47 Hz, 1H), 8.65 (d, J=1.96 Hz, 1H) and LC-MS (M+1): 446.4.

Synthetic Scheme of the Compound of Example 71

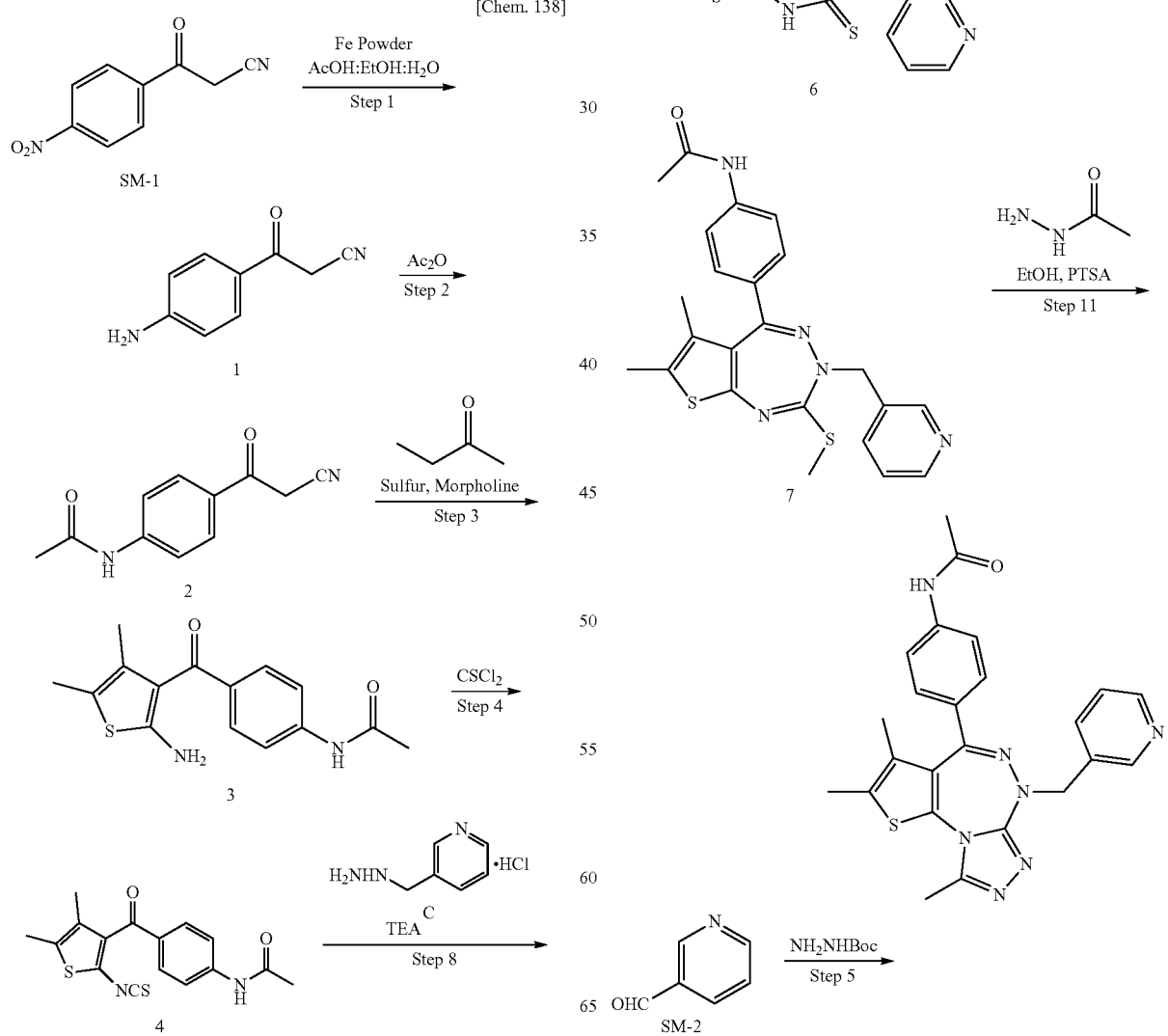

[Chem. 138]

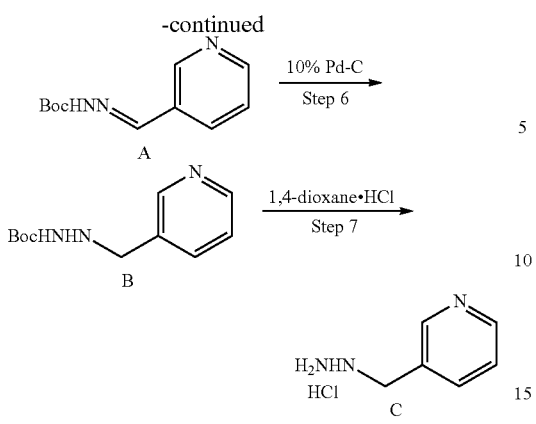

Step-1: Synthesis of 3-(4-aminophenyl)-3-oxopropanenitrile (Intermediate 1)

[Chem. 139]

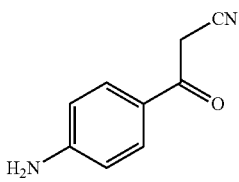

1

To a solution of SM (1 g, 5.2 mmol) in acetic acid:EtOH:water (1:1:0.5.35 mL) was added iron powder (3.89 g, 12.6 mmol) in portions, and the mixture was stirred at room temperature for 3 hours. After the reaction completed, the reaction mixture was filtered through a celite pad and washed with ethyl acetate, and the filtrate was distilled off under reduced pressure to obtain a residue. The residue was diluted with ethyl acetate, and washed with a saturated sodium bicarbonate solution, water and brine. The organic layer was dried over anhydrous sodium sulfate and filtered, and the filtrate was distilled off under reduced pressure to obtain Intermediate 1 (400 mg).

Yield: 48%, H NMR (400 MHz, DMSO-$d_6$) δ 4.47 (s, 2H), 6.29 (s, 2H), 6.57 (d, J=8.80 Hz, 2H), 7.64 (d, J=8.31 Hz, 2H) and LC-MS (M+1): 161.05.

Step-2: Synthesis of N-(4-(2-cyanoacetyl)phenyl)acetamide (Intermediate 2)

[Chem. 140]

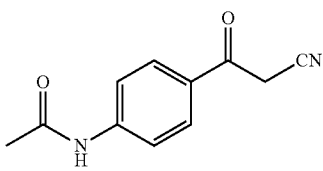

2

To a solution of cooled (0° C.) acetic anhydride (1.2 mL) was added Intermediate 1 (300 mg, 1.8 mmol), and the mixture was stirred at room temperature for one hour. After the reaction completed, the reaction mixture was concentrated under reduced pressure to obtain a solid. The solid was diluted with iced water, and the liquid was made basic with a saturated sodium hydrogen carbonate solution and filtered through Buechner funnel. The solid was washed with water and diethyl ether, and dried under reduced pressure to obtain Intermediate 2 (200 mg).

Yield: 53%, $^1$HNMR (400 MHz, DMSO-$d_6$) δ 2.10 (s, 3H), 4.68 (s, 2H), 7.74 (d, J=8.31 Hz, 2H), 7.90 (d, J=8.80 Hz, 2H), 10.36 (s, 1H) and LC-MS: 203.09.

Step-3: Synthesis of N-(4-(2-amino-4,5-dimethylthiophen-3-carbonyl)phenyl)acetamide (Intermediate 3)

[Chem. 141]

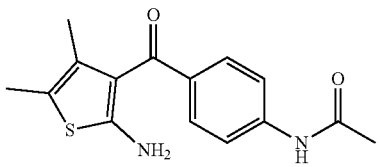

3

To a solution of Intermediate 2 (200 mg, 1 mmol) in ethanol (5 mL) were added butan-2-one (0.1 mL, 1 mmol), sulfur (32 mg, 1 mmol) and morpholine (0.1 mL, 1 mmol), and the mixture was stirred at 70° C. for 20 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (20% ethyl acetate: hexane) to obtain Intermediate 3 (200 mg).

Yield: 69%, $^1$HNMR (400 MHz, DMSO-$d_6$) δ 1.52 (s, 3H), 2.07 (s, 6H), 7.38 (d, J=8.31 Hz, 2H), 7.52 (s, 2H), 7.64 (d, J=8.31 Hz, 2H), 10.14 (s, 1H) and LC-MS (M+1): 289.23.

Step-4: Synthesis of N-(4-(2-isothiocyanato-4,5-dimethylthiophen-3-carbonyl)phenyl)acetamide (Intermediate 4)

[Chem. 142]

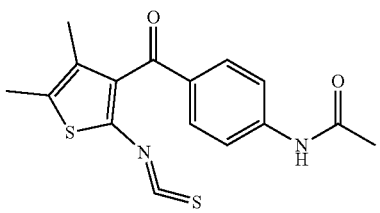

4

To a solution of thiophosgene (0.04 mL, 0.52 mmol) in water (5 mL) was added a solution of Intermediate 3 (100 mg, 0.4 mmol) in dichloromethane (10 mL) at 0° C., and the mixture was stirred at the same temperature for one hour and at room temperature for one hour. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with dichloromethane) to obtain Intermediate 4 (80 mg), which was confirmed by LC-MS (M+1): 331.16 and used in the next Step without further purification.

Step-5: Synthesis of tert-butyl 2-(pyridin-3-ylmethylene)hydrazinecarboxylate (Compound A)

[Chem. 143]

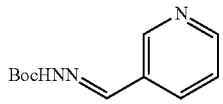

A

To a solution of SM-2 (58 g, 542 mmol) in methanol (600 mL) was added tert-butyl carbazate (86 g, 650 mmol), and the mixture was stirred at 70° C. for 16 hours. After the reaction completed, the reaction mixture was concentrated under reduced pressure to obtain a crude compound. The crude compound was triturated with diethyl ether to obtain Compound A (100 g).
Yield: 83%, $^1$H NMR (400 MHz, CDCl$_3$) δ 1.55 (s, 9H), 7.31 (dd, J=7.83, 4.89 Hz, 1H), 7.91 (s, 1H), 8.07-8.15 (m, 2H), 8.58 (dd, J=4.89, 1.47 Hz, 1H), 8.75 (d, J=1.96 Hz, 1H) and LC-MS (M+1): 222.12.

Step-6: Synthesis of tert-butyl 2-(pyridin-3-ylmethyl)hydrazinecarboxylate (Compound B)

[Chem. 144]

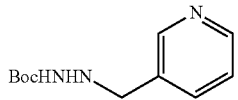

B

To a solution of Compound A (100 g, 452 mmol) in methanol (500 mL) was added 10% Pd/C (20 g), and the mixture was stirred under hydrogen atmosphere with 50 psi balloon pressure at room temperature for 16 hours. After the reaction completed, the reaction mixture was filtered through a celite pad and concentrated under reduced pressure to obtain Compound B (70 g).
Yield: 69%, $^1$H NMR (400 MHz, CDCl$_3$) δ 1.46 (s, 9H), 4.02 (s, 2H), 4.27 (s, 1H), 6.10 (s, 1H), 7.24-7.30 (m, 1H), 7.69 (d, J=7.82 Hz, 1H), 8.52-8.59 (in, 2H) and LC-MS (M+1): 224.17.

Step-7: Synthesis of 3-(hydrazinylmethyl)pyridine hydrochloride (Compound C)

[Chem. 145]

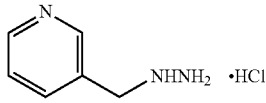

C

To a solution of Compound B (70 g, 313 mmol) in 1,4-dioxane (350 mL) was added 4N HCl in dioxane (1 L) at 5° C., and the mixture was stirred at room temperature for 72 hours. After the reaction completed, the reaction mixture was concentrated under reduced pressure to obtain Compound C (48 g).
Yield: 96%, $^1$H NMR (400 MHz, DMSO-d$_6$) δ 4.32 (s, 2H), 8.11 (dd, J=8.07, 5.62 Hz, 1H), 8.33-8.42 (m, 2H), 8.67 (d, J=7.82 Hz, 1H), 8.91 (d, J=5.87 Hz, 1H), 8.97 (s, 1H) and LC-MS: No mass ionization.

Step-8: Synthesis of N-(4-(4,5-dimethyl-2-(1-(pyridin-3-ylmethyl)hydrazinecarbothioamide)thiophen-3-carbonyl)phenyl)acetamide (Intermediate 5)

[Chem. 146]

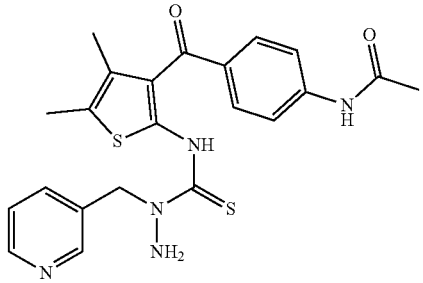

5

To a solution of Intermediate 4 (80 g, 0.24 mmol) in tetrahydrofuran (5 mL) were added triethylamine (0.1 mL, 4.49 mmol), followed by Compound C (71 mg, 0.36 mmol), and the mixture was stirred at 0° C. for one hour and at room temperature for 20 hours. After the reaction completed, the reaction mixture was concentrated under reduced pressure to obtain Intermediate 5 (100 mg), which was confirmed by LC-MS (M+1): 454.2 and used in the next Step without further purification.

Step-9: Synthesis of N-(4-(6,7-dimethyl-3-(pyridin-3-ylmethyl)-2-thioxo-2,3-dihydro-1H-thieno[2,3-e][1,2,4]triazepin-5-yl)phenyl)acetamide (Intermediate 6)

[Chem. 147]

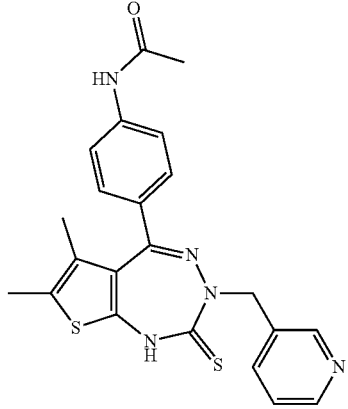

6

To a stirred solution of Intermediate 5 (600 mg, 1.32 mmol) in ethanol (30 mL) was added p-toluenesulfonic acid (23 mg, 0.13 mmol), and the mixture was stirred at 90° C. for 30 hours. After the reaction completed, the reaction mixture was concentrated under reduced pressure to obtain a crude compound of Intermediate 6 (500 mg), which was confirmed by LC-MS (M+1): 436.24 and used in the next Step without further purification.

Step-10: Synthesis of N-(4-(6,7-dimethyl-2-(methylthio)-3-(pyridin-3-ylmethyl)-3H-thieno[2,3-e][1,2,4]triazepin-5-yl)phenyl)acetamide (Intermediate 7)

[Chem. 148]

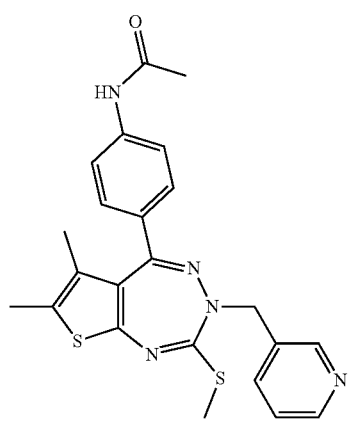

To a stirred solution of Intermediate 6 (20 g, LC-MS: 69%) in tetrahydrofuran (600 mL) was added NaH (2.2 g, 55.17 mmol) at 0° C., and the mixture was stirred at room temperature for one hour. Methyl iodide (1.75 mL, 27.58 mmol) was added thereto at 0° C., and the mixture was stirred at room temperature for 6 hours. After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound of Intermediate 7 (13 g), which was confirmed by LC-MS (M+): 450.27 and used in the next Step without further purification.

Step-11: Synthesis of N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide (Compound of Example 71)

[Chem. 149]

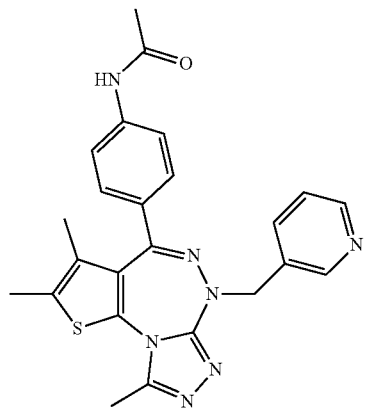

To a stirred solution of Intermediate 7 (9 g, LC-MS: 56%) in ethanol (500 mL) were added acethylhydrazine (2.96 g, 40.08 mmol) and p-toluenesulfonic acid (690 mg, 4 mmol), and the mixture was stirred at 10° C. for 48 hours. After the reaction completed, the reaction mixture was concentrated under reduced pressure to obtain a residue. The residue was diluted with ethyl acetate, washed with saturated sodium hydrogen carbonate and a brine solution, dried over anhydrous sodium sulfate and filtered. The filtrate was distilled off under reduced pressure to obtain 2.6 g of a crude compound (LC-MS: 48%), which was purified by preparative HPLC to obtain the compound of Example 71 (500 mg).

Yield: 9.7%, $^1$H NMR (400 MHz, DMSO-$d_6$) δ 1.49 (s, 3H), 2.04 (s, 3H), 2.36 (s, 3H), 2.54 (s, 3H), 4.76-4.83 (m, 1H), 4.95-5.04 (m, 1H), 7.24 (d, J=8.55 Hz, 2H), 7.37 (dd, J=7.45, 4.82 Hz, 1H), 7.61 (d, J=8.77 Hz, 2H), 7.81 (d, J=7.89 Hz, 1H), 8.48 (s, 1H), 8.62 (s, 1H), 10.12 (s, 1H) and LC-MS (M+1): 456.11.

Synthetic Scheme of the Compound of Example 72

[Chem. 150]

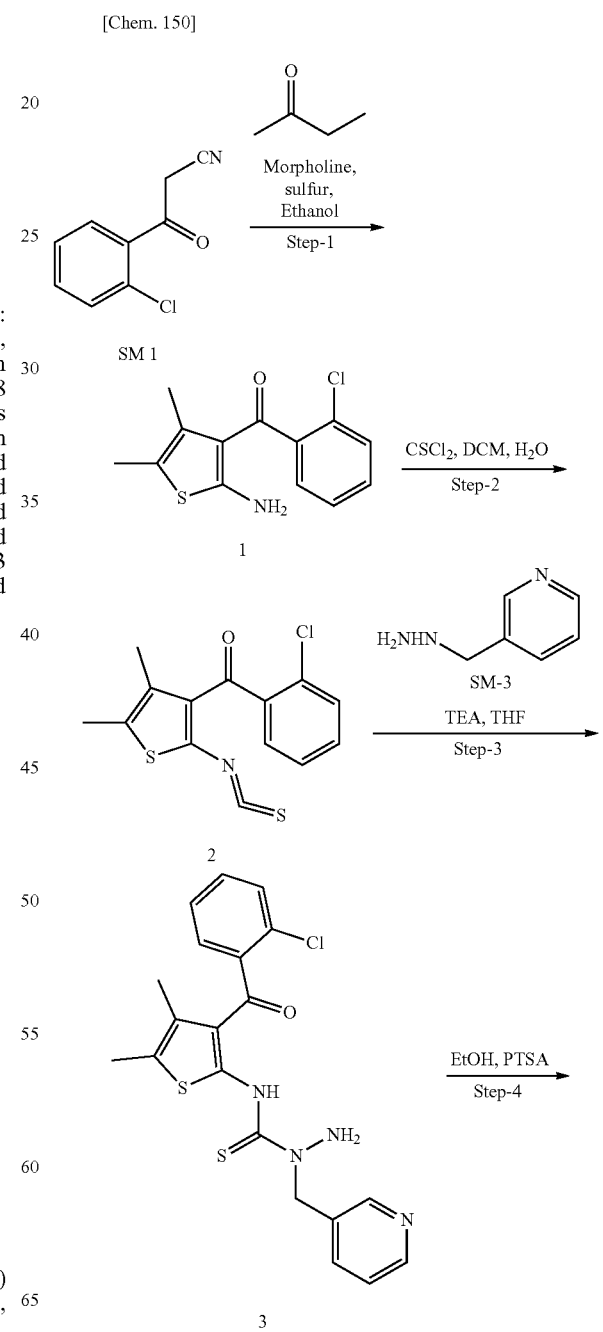

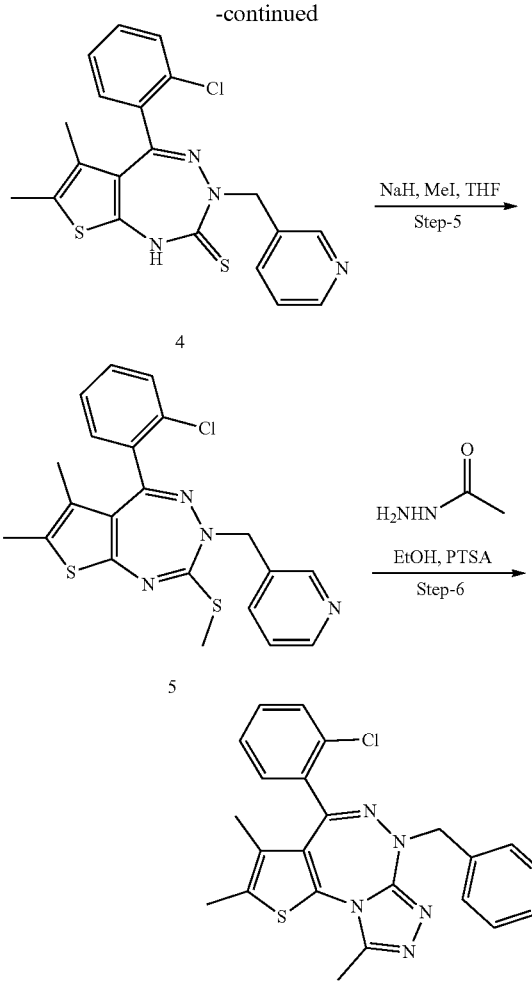

Step-1: Synthesis of (2-amino-4,5-dimethylthiophen-3-yl)(2-chlorophenyl)methanone (Intermediate 1)

[Chem. 151]

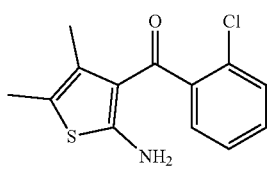

1

To a solution of SM1 (1 g, 5.56 mmol) in ethanol (20 mL) were added butan-2-one (0.5 mL, 5.56 mmol), sulfur (178 mg, 5.56 mmol) and morpholine (0.45 mL, 5.56 mmol), and the mixture was stirred at 70° C. for 16 hours. After the reaction completed, the reaction mixture was concentrated under reduced pressure to obtain a residue, and the residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain 400 mg of Intermediate 1 as a yellow solid (400 mg, Y: 27%).

Intermediate 1 was confirmed by $^1$H-NMR and LC-MS, and used in the next Step without further purification.

Y: 27%, $^1$H NMR (400 MHz, DMSO-$d_6$) δ 1.27 (s, 3H), 2.03 (s, 3H), 7.27 (dd, J=7.09, 1.71 Hz, 1H), 7.37-7.52 (m, 3H), 8.58 (s, 2H) and LC-MS (M+1): 266.13.

Step-2: Synthesis of (2-chlorophenyl)(2-isothiocyanato-4,5-dimethylthiophen-3-yl)methanone (Intermediate 2)

[Chem. 152]

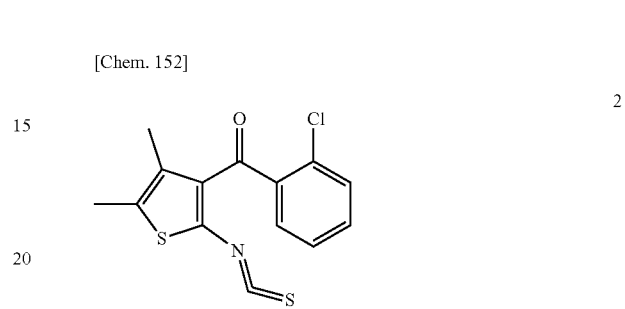

2

To a stirred solution of thiophosgene (0.15 mL, 1.95 mmol) in water (5 mL) was added a solution of Intermediate 1 (400 mg, 1.5 mmol) in dichloromethane (10 mL) at 0° C., and the mixture was stirred at 0° C. for one hour and at room temperature for 4 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was triturated with hexane to obtain 300 mg of Intermediate 2, which was confirmed by LC-MS (M+1): 308.06 and used in the next Step without further purification.

Step-3: Synthesis of N-(3-(2-chlorobenzoyl)-4,5-dimethylthiophen-2-yl)-1-(pyridin-3-ylmethyl)hydrazinecarbothioamide (Intermediate 3)

[Chem. 153]

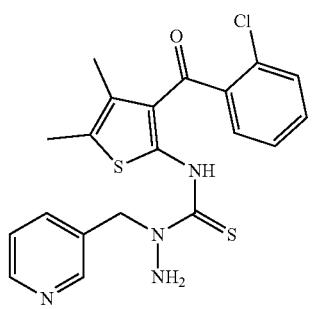

3

To a stirred solution of Intermediate 2 (300 mg, 0.97 mmol) in tetrahydrofuran (25 mL) was added triethylamine (0.27 mL, 1.95 mmol), followed by 3-(hydrazinylmethyl)pyridine dihydrochloride (230 mg, 1.17 mmol), and the mixture was stirred at 0° C. for one hour and at room temperature for one hour. After the reaction completed, the reaction mixture was concentrated under reduced pressure to obtain 400 mg of Intermediate 3, which was confirmed by LC-MS (M+1): 431.11 and used in the next Step without further purification.

Step-4: Synthesis of 5-(2-chlorophenyl)-6,7-dimethyl-3-(pyridin-3-ylmethyl)-1H-thieno[2,3-e][1,2,4]triazepine-2(3H)-thione (Intermediate 4)

[Chem. 154]

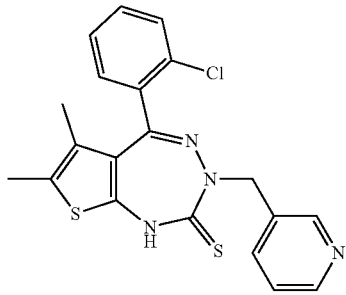

To a stirred solution of Intermediate 3 (1.8 g, 4.1 mmol) in ethanol (40 mL) was added p-toluenesulfonic acid (72 mg, 0.41 mmol), and the mixture was stirred at 100° C. for 16 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain a crude compound. The crude compound was triturated with diethyl ether to obtain 400 mg of Intermediate 4.

Yield: 23%, $^1$H NMR (400 MHz, DMSO-$d_6$) δ 1.23 (s, 3H), 2.17 (s, 3H), 5.09 (brs, 2H), 6.84 (d, J=7.82 Hz, 1H), 7.32-7.40 (m, 2H), 7.44-7.50 (m, 2H), 7.71-7.76 (m, 1H), 8.45-8.57 (m, 2H), 11.36 (s, 1H)

Step-5: Synthesis of 5-(2-chlorophenyl)-6,7-dimethyl-2-(methylthio)-3-(pyridin-3-ylmethyl)-3H-thieno[2,3-e][1,2,4]triazepine (Intermediate 5)

[Chem. 155]

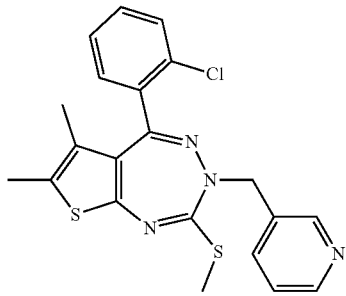

To a stirred solution of Intermediate 4 (400 mg, 0.96 mmol) in tetrahydrofuran (10 mL) was added sodium hydride (43 mg, 1.06 mmol) at 0° C., and the mixture was stirred at room temperature for one hour. Methyl iodide (0.06 mL, 1.06 mmol) was added thereto at the same temperature, and the mixture was stirred at room temperature for 2 hours. After the reaction completed, the reaction mixture was poured into ice-cold water, and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 30% ethyl acetate: hexane) to obtain 300 mg of Intermediate 5.

Yield: 72%, $^1$H NMR (400 MHz, CDCl$_3$) δ 1.32 (s, 3H), 2.22 (s, 3H), 2.55 (s, 3H), 4.81 (s, 2H), 6.96 (d, J=7.34 Hz, 1H), 7.17 (td, J=7.21, 1.71 Hz, 1H), 7.24-7.31 (m, 3H), 7.74 (d, J=7.82 Hz, 1H), 8.53 (d, J=4.89 Hz, 1H), 8.68 (d, J=1.47 Hz, 1H) and LC-MS (M+1): 427.19.

Step-6: Synthesis of 4-(2-chlorophenyl)-2,3,9-trimethyl-6-(pyridin-3-ylmethyl)-6H-thieno[2,3-e][1,2,4]triazolo[3,4-c][1,2,4]triazepine (Compound of Example 72)

[Chem. 156]

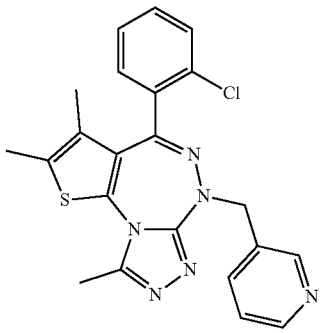

To a stirred solution of Intermediate 5 (300 mg, 0.7 mmol) in ethanol (10 mL) were added acetohydrazide (260 mg, 3.5 mmol) and p-toluenesulfonic acid (24 mg, 0.14 mmol), and the mixture was stirred at 100° C. for 16 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain a crude compound of Example 72, which was further purified by preparative HPLC to obtain 160 mg of Example 72.

Yield: 52%, 1H NMR (400 MHz, CDCl$_3$) δ 1.42 (s, 3H), 2.32 (s, 3H), 2.63 (s, 3H), 5.06 (s, 2H), 7.11 (d, J=7.34 Hz, 1H), 7.22-7.25 (m, 1H), 7.32 (d, J=3.91 Hz, 3H), 7.83 (d, J=7.82 Hz, 1H), 8.55 (d, J=3.91 Hz, 1H), 8.72 (s, 1H) and LC-MS (M+1): 435.13.

Synthetic Scheme of the Compound of Example 73

[Chem. 157]

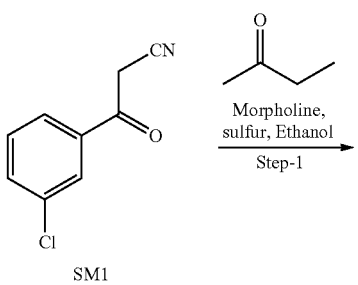

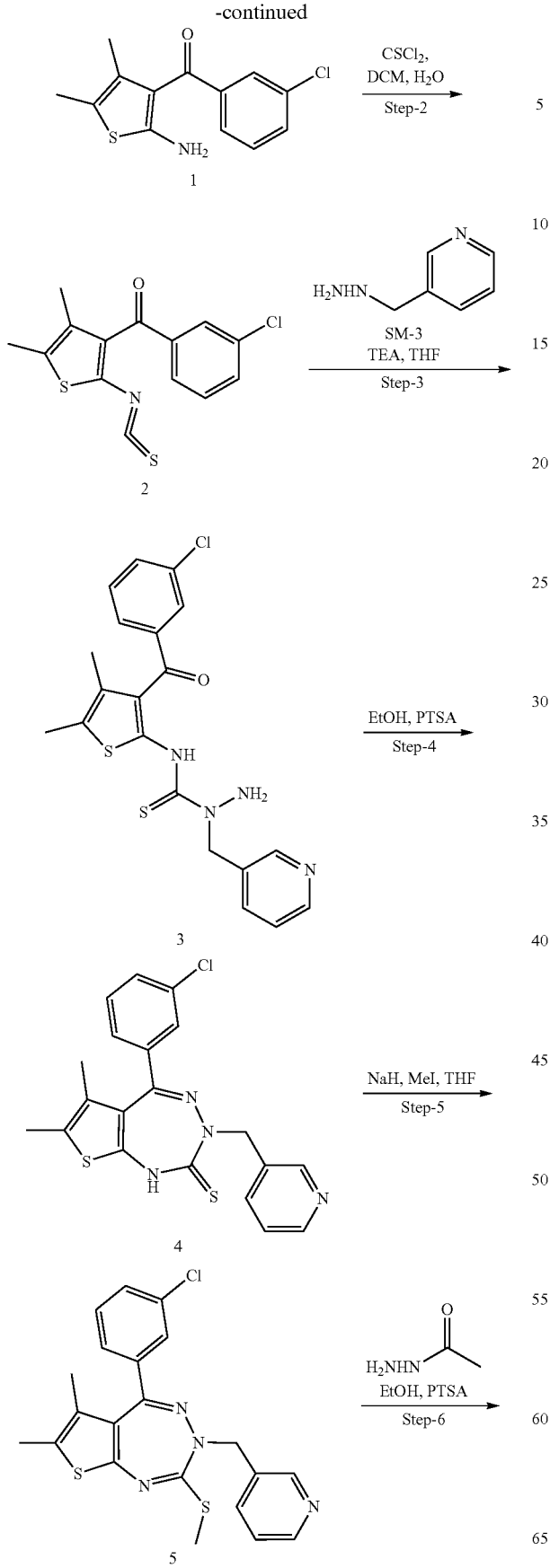

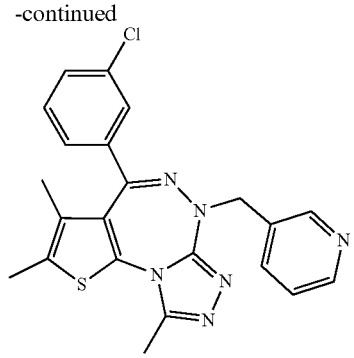

Step-1: Synthesis of (2-amino-4,5-dimethylthiophen-3-yl)(3-chlorophenyl)methanone (Intermediate 1)

[Chem. 158]

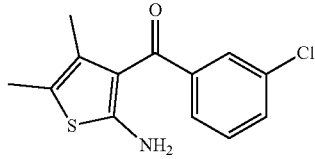

To a solution of SM1 (1 g, 5.56 mmol) in ethanol (20 mL) were added butan-2-one (0.5 mL, 5.56 mmol), sulfur (178 mg, 5.56 mmol) and morpholine (0.45 mL, 5.56 mmol), and the mixture was stirred at 70° C. for 16 hours. After the reaction completed, the reaction mixture was concentrated under reduced pressure to obtain a residue, and the residue was diluted with water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 20% ethyl acetate:hexane) to obtain 200 mg of Intermediate 1.

Yield: 14%, $^1$H NMR (400 MHz, CDCl$_3$) δ 1.54 (s, 3H), 2.13 (s, 3H), 6.55 (br s, 2H), 7.31-7.45 (m, 3H), 7.48 (d, J=1.47 Hz, 1H) and LC-MS (M+1): 266.1

Step-2: Synthesis of (3-chlorophenyl)(2-isothiocyanato-4,5-dimethylthiophen-3-yl)methanone (Intermediate 2)

[Chem. 159]

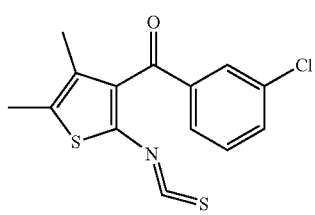

To a stirred solution of thiophosgene (1 mL, 13.68 mmol) in water (30 mL) was added a solution of Intermediate 1 (2.8 g, 10.52 mmol) in dichloromethane (50 mL) at 0° C., and the mixture was stirred at 0° C. for one hour and at room temperature for 4 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was triturated with hexane to obtain 2 g of Intermediate 2.

Yield: 61%, $^1$H NMR (400 MHz, CDCl$_3$) δ 2.05 (s, 3H), 2.34 (s, 3H), 7.42-7.48 (m 1H), 7.58 (dq, J=7.89, 1.12 Hz, 1H), 7.67-7.73 (m, 1H), 7.81 (t, J=1.96 Hz, 1H) and LC-MS (M+1): 308.06.

Step-3: Synthesis of N-(3-(3-chlorobenzoyl)-4,5-dimethylthiophen-2-yl)-1-(pyridin-3-ylmethyl)hydrazinecarbothioamide (Intermediate 3)

[Chem. 160]

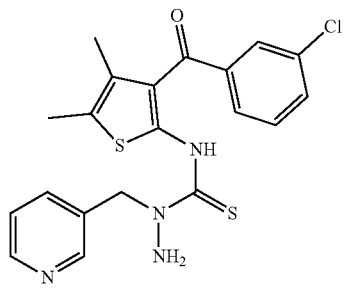

3

To a stirred solution of Intermediate 2 (2 g, 6.49 mmol) in tetrahydrofuran (100 mL) was added triethylamine (1.8 mL, 12.98 mmol), followed by SM-2 (1.9 g, 9.74 mmol), and the mixture was stirred at 0° C. for one hour and at room temperature for one hour. After the reaction completed, the reaction mixture was concentrated under reduced pressure to obtain 1.54 g of Intermediate 3, which was confirmed by LC-MS (M+1): 431.18 and used in the next Step without further purification.

Step-4: Synthesis of 5-(3-chlorophenyl)-6,7-dimethyl-3-(pyridin-3-ylmethyl)-1H-thieno[2,3-e][1,2,4]triazepine-2(3H)-thione (Intermediate 4)

[Chem. 161]

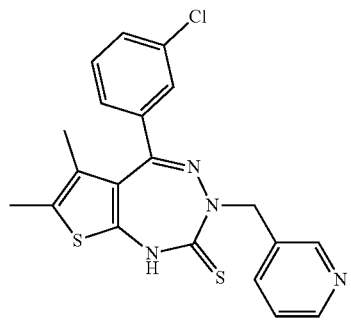

4

To a stirred solution of Intermediate 3 (1.5 g, 3.48 mmol) in ethanol (40 mL) was added p-toluenesulfonic acid (60 mg, 0.34 mmol), and the mixture was stirred at 100° C. for 16 hours. After the reaction completed, the reaction mixture was concentrated under reduced pressure to obtain a residue, and the residue was diluted with ethyl acetate, washed with a saturated sodium bicarbonate solution and a brine solution, dried over anhydrous sodium sulfate, and filtered. The filtrate was distilled off under reduced pressure to obtain 1.4 g of Intermediate 4, which was confirmed by LC-MS (M+1): 413.3 and used in the next Step without further purification.

Step-5: Synthesis of 5-(3-chlorophenyl)-6,7-dimethyl-2-(methylthio)-3-(pyridin-3-ylmethyl)-3H-thieno[2,3-e][1,2,4]triazepine (Intermediate 5)

[Chem. 162]

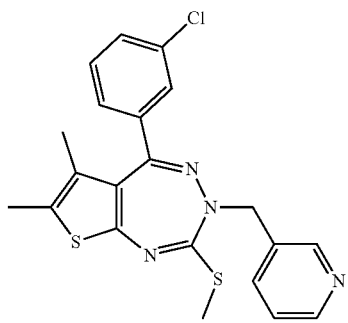

5

To a stirred solution of Intermediate 4 (1.4 g, 3.38 mmol) in tetrahydrofuran (30 mL) was added sodium hydride (149 mg, 3.72 mmol) at 0° C., and the mixture was stirred at room temperature for one hour. Methyl iodide (0.23 mL, 3.72 mmol) was added thereto at 0° C., and the mixture was stirred at room temperature for 2 hours.

After the reaction completed, the reaction mixture was poured into ice-cold water and extracted with ethyl acetate. The combined organic layers were dried over anhydrous sodium sulfate and filtered, and the filtrate was distilled off under reduced pressure to obtain a crude compound. The crude compound was purified by silica gel column chromatography (eluted with 30% ethyl acetate:hexane) to obtain 400 mg of Intermediate 5.

Yield: 27%, $^1$H NMR (400 MHz, CDCl$_3$) δ 1.44 (s, 3H), 2.27 (s, 3H), 2.52 (s, 3H), 4.79 (brs, 2H), 7.07 (d, J=7.34 Hz, 1H), 7.18-7.21 (m, 1H), 7.24-7.29 (m, 2H), 7.31-7.37 (m, 1H), 7.71 (d, J=7.82 Hz, 1H), 8.52-8.55 (m, 1H), 8.66 (d, J=0.98 Hz, 1H) and LC-MS (M+1): 427.10.

Step-6: Synthesis of 4-(3-chlorophenyl)-2,3,9-trimethyl-6-(pyridin-3-ylmethyl)-6H-thieno[2,3-e][1,2,4]triazolo[3,4-c][1,2,4]triazepine (Compound of Example 73)

[Chem. 163]

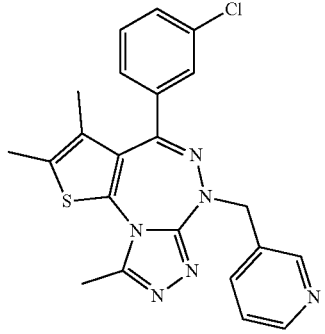

To a stirred solution of Intermediate 5 (400 mg, 0.93 mmol) in ethanol (10 mL) were added acetohydrazide (346 mg, 4.68 mmol) and p-toluenesulfonic acid (32 mg, 0.18 mmol), and the mixture was stirred at 100° C. for 16 hours. After the reaction completed, the reaction mixture was concentrated under reduced pressure to obtain a residue. The residue was diluted with ethyl acetate, washed with a saturated sodium bicarbonate solution and a brine solution, dried over anhydrous sodium sulfate, and filtered. The filtrate was distilled off under reduced pressure to obtain a crude compound. The crude compound was purified by silica gel column chromatography (eluted with 2% methanol/dichloromethane) to obtain a crude compound, which was further purified by preparative HPLC to obtain 200 mg of the compound of Example 73.

Yield: 49%, $^1$H NMR (400 MHz, CDCl$_3$) δ 1.54 (s, 3H), 2.38 (s, 3H), 2.63 (s, 3H), 4.91-4.97 (m, 1H), 5.13-5.18 (m, 1H), 7.16-7.23 (m, 1H), 7.27-7.31 (m, 3H), 7.36-7.41 (m, 1H), 7.77 (d, J=7.82 Hz, 1H), 8.54 (dd, J=4.89, 1.47 Hz, 1H), 8.69 (d, J=1.47 Hz, 1H) and LC-MS (M+1): 435.13.

Synthetic Scheme of the Compound of Example 74

[Chem. 164]

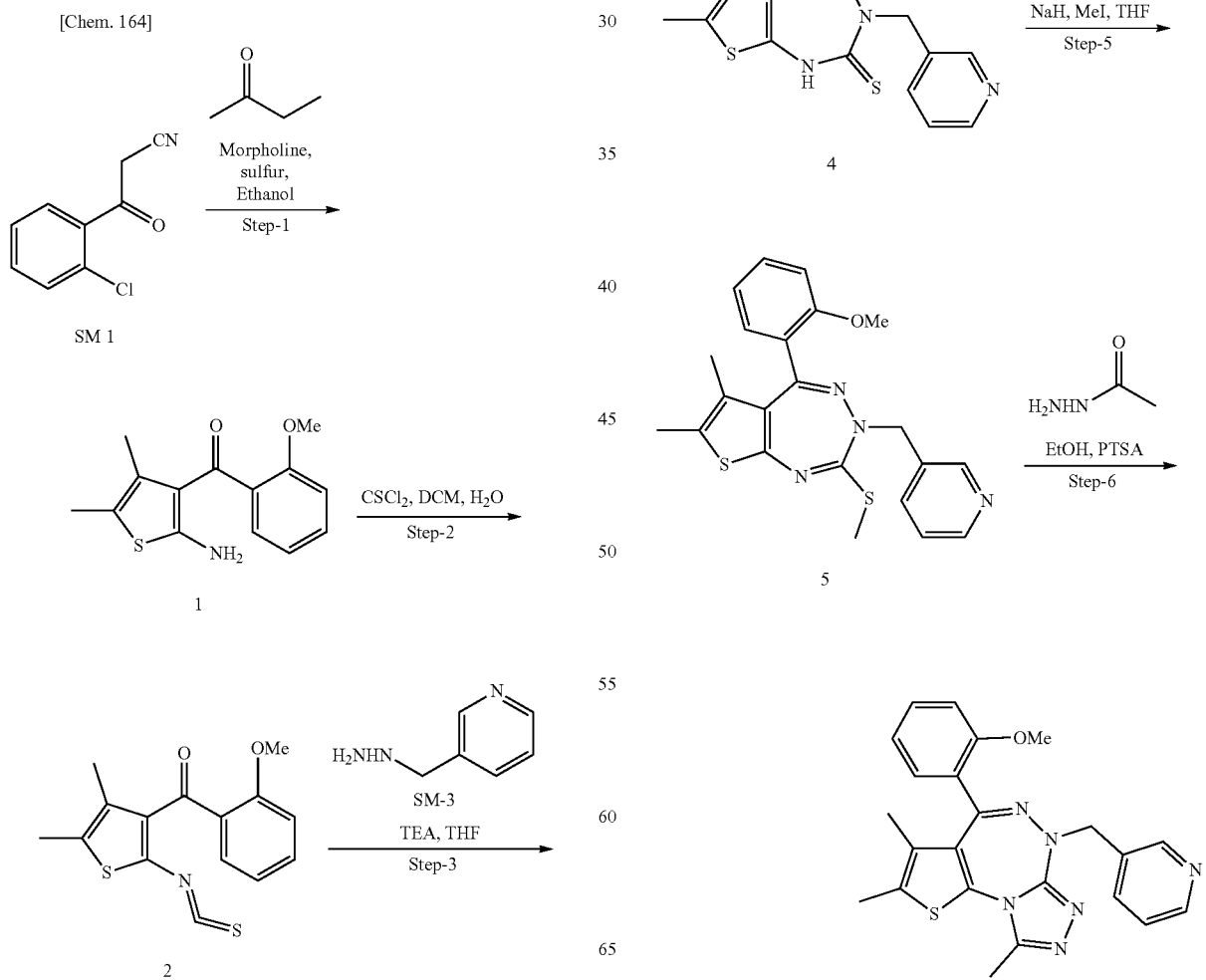

Step-1: Synthesis of (2-amino-4,5-dimethylthiophen-3-yl)(2-methoxyphenyl)methanone (Intermediate 1)

[Chem. 165]

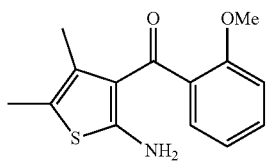

1

A solution of SM1 (5 g, 28.54 mmol) in ethanol (100 mL) were added butan-2-one (2.46 g, 34.25 mmol), sulfur (1 g, 34.25 mmol) and morpholine (2.98 g, 34.25 mmol), and the mixture was stirred at 70° C. for 16 hours. After the reaction completed, the reaction mixture was concentrated under reduced pressure to obtain a residue, and the residue was diluted with water and extracted with ethyl acetate. The combined organic layers were dried over anhydrous sodium sulfate and filtered, and the filtrate was distilled off under reduced pressure to obtain 5 g of Intermediate 1, which was confirmed by LC-MS (M+1): 262.1 and used in the next Step without further purification.

Step-2: Synthesis of (2-isothiocyanato-4,5-dimethylthiophen-3-yl)(2-methoxyphenyl)methanone (Intermediate 2)

[Chem. 166]

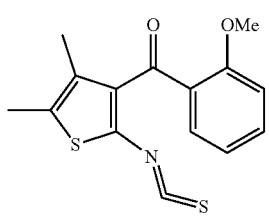

2

To a solution of thiophosgene (1.5 mL, 20.77 mmol) in water (50 mL) was added a solution of Intermediate 1 (5 g, 13.85 mmol) in dichloromethane (100 mL) at 0° C., and the mixture was stirred at 0° C. for one hour and at room temperature for 16 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with 10% ethyl acetate:hexane) to obtain 3.5 g of Intermediate 2.

Yield: 85%, $^1$H NMR (400 MHz, DMSO-$d_6$) δ 2.03 (s, 3H), 2.32 (s, 3H), 3.73 (s, 3H), 7.07-7.12 (m, 1H), 7.19 (d, J=8.31 Hz, 1H), 7.43 (dd, J=7.58, 1.71 Hz, 1H), 7.54-7.59 (m, 1H) and LC-MS (M+1): 304.1.

Step-3: Synthesis of N-(3-(2-methoxybenzoyl)-4,5-dimethylthiophen-2-yl)-1-(pyridin-3-ylmethyl)hydrazine carbothioamide (Intermediate 3)

[Chem. 167]

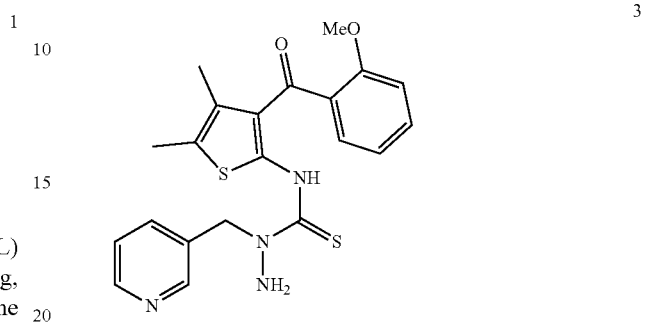

3

To a solution of Intermediate 2 (3.5 g, 11.55 mmol) in tetrahydrofuran (50 mL) was added triethylamine (3.2 mL, 23.1 mmol), followed by SM-2 (2.75 g, 17.3 mmol), and the mixture was stirred at 0° C. for one hour and at room temperature for 16 hours. After the reaction completed, the reaction mixture was concentrated under reduced pressure to obtain a crude compound. The crude compound was triturated with hexane to obtain 5 g of Intermediate 3, which was confirmed by LC-MS (M+1): 427.2 and used in the next Step without further purification.

Step-4: Synthesis of 5-(2-methoxyphenyl)-6,7-dimethyl-3-(pyridin-3-ylmethyl)-1H-thieno[2,3-e][1,2,4]triazepine-2(3H)-thione (Intermediate 4)

[Chem. 168]

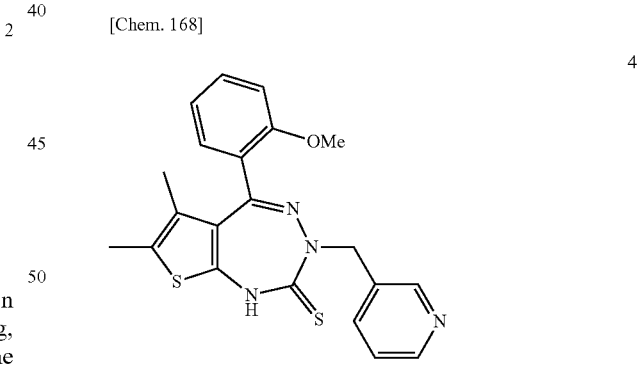

4

To a stirred solution of Intermediate 3 (5 g, 11.73 mmol) in ethanol (300 mL) was added p-toluenesulfonic acid (403 mg, 2.3 mmol), and the mixture was stirred at 100° C. for 16 hours. After the reaction completed, the reaction mixture was concentrated under reduced pressure to obtain a residue. The residue was diluted with ethyl acetate, washed with a saturated sodium bicarbonate solution and a brine solution, dried over anhydrous sodium sulfate, and filtered. The filtrate was distilled off under reduced pressure to obtain 3 g (LC-MS: 60%) of Intermediate 4, which was confirmed by LC-MS (M+1): 409.2 and used in the next Step without further purification.

Step-5: Synthesis of 5-(2-methoxyphenyl)-6,7-dimethyl-2-(methylthio)-3-(pyridin-3-ylmethyl)-3H-thieno[2,3-e][1,2,4]triazepine (Intermediate 5)

[Chem. 169]

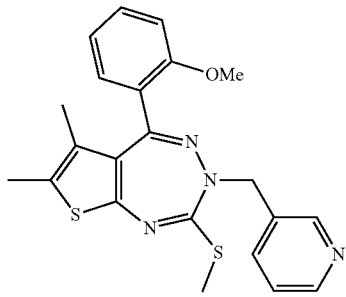

To a stirred solution of Intermediate 4 (1.5 g, 3.6 mmol) in tetrahydrofuran (30 mL) was added sodium hydride (172 mg, 7.2 mmol) at 0° C., and the mixture was stirred at room temperature for one hour. Methyl iodide (1 g, 7.2 mmol) was added thereto at 0° C., and the mixture was stirred at room temperature for 4 hours. After the reaction completed, the reaction mixture was poured into ice-cold water and extracted with ethyl acetate. The combined organic layers were dried over anhydrous sodium sulfate, and filtered. The filtrate was distilled off under reduced pressure to obtain 1.52 g of a residue of Intermediate 5, which was used in the next Step without further purification.

Step-6: Synthesis of 4-(2-methoxyphenyl)-2,3,9-trimethyl-6-(pyridin-3-ylmethyl)-6H-thieno[2,3-e][1,2,4]triazolo[3,4-c][1,2,4]triazepine (Compound of Example 74)

[Chem. 170]

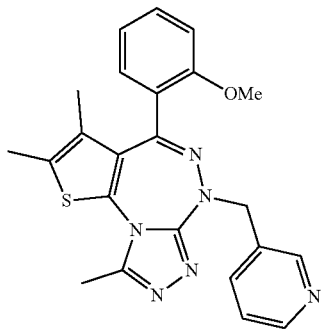

To a stirred solution of Intermediate 5 (1.5 g, 3.55 mmol) in ethanol (70 mL) were added acetohydrazide (932 mg, 12.6 mmol) and p-toluenesulfonic acid (64 mg, 0.35 mmol), and the mixture was stirred at 100° C. for 16 hours. After the reaction completed, the reaction mixture was concentrated under reduced pressure to obtain a residue. The residue was diluted with ethyl acetate, washed with a saturated sodium bicarbonate solution and a brine solution, dried over anhydrous sodium sulfate, and filtered. The filtrate was distilled off under reduced pressure to obtain a crude compound, which was further purified by preparative HPLC to obtain 50 mg of the compound of Example 74.

Yield: 3%, $^1$H NMR (400 MHz, DMSO-d$_6$) δ 1.36 (s, 3H), 2.29 (s, 3H), 2.55 (s, 3H), 3.52 (s, 3H), 4.88 (s, 2H), 6.93-7.08 (m, 3H), 7.36-7.45 (m, 2H), 7.81 (d, J=7.82 Hz, 1H), 8.50 (s, 1H), 8.63 (s, 1H) and LC-MS (M+1): 431.21.

Synthetic Scheme of the Compound of Example 75

[Chem. 171]

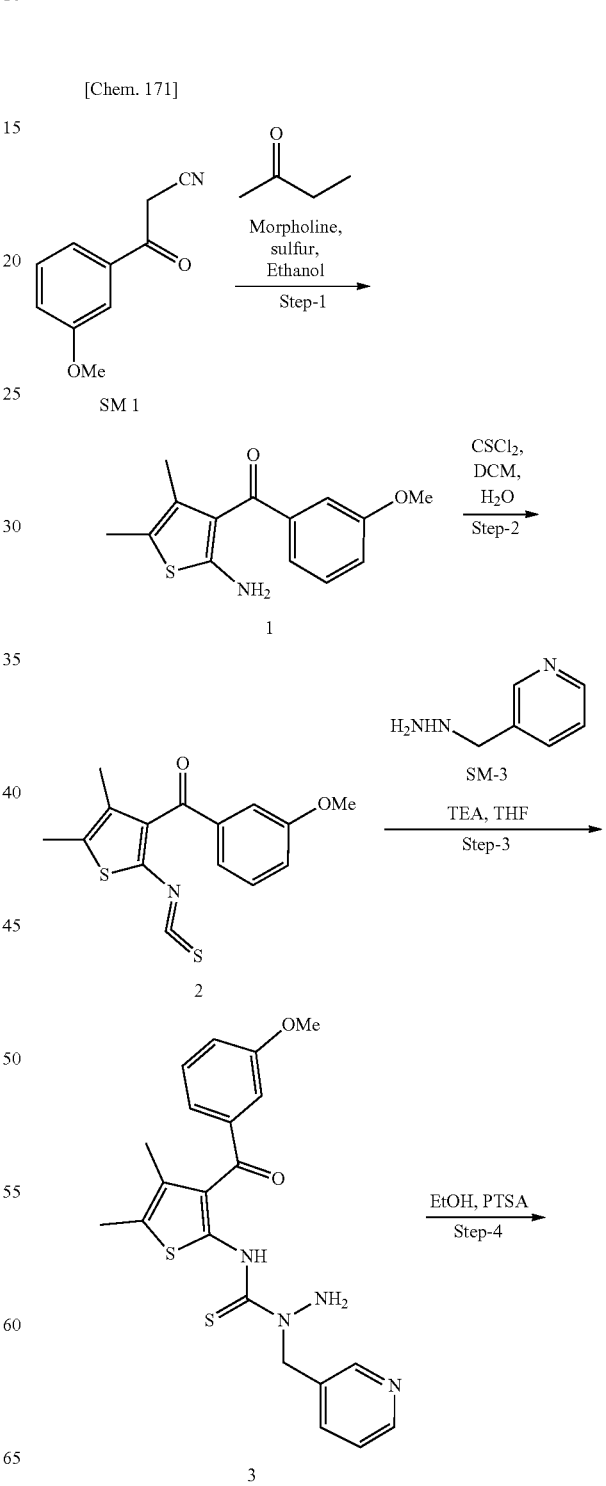

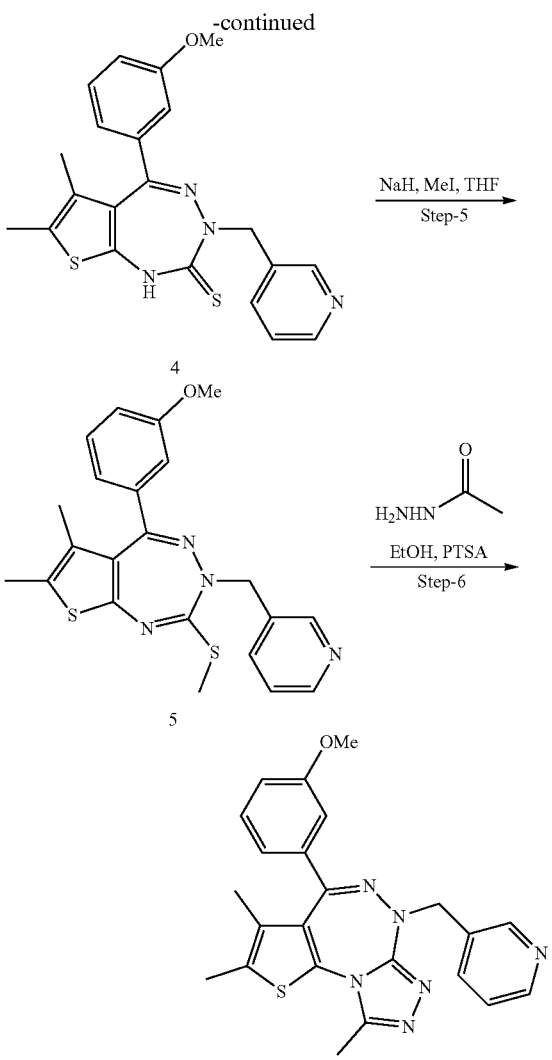

Step-1: Synthesis of (2-amino-4,5-dimethylthiophen-3-yl)(3-methoxyphenyl)methanone (Intermediate 1)

[Chem. 172]

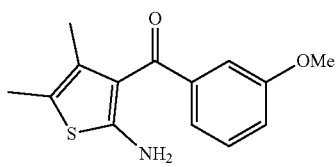

To a stirred solution of SM1 (5 g, 28.54 mmol) in ethanol (100 mL) were added butan-2-one (2.46 g, 34.25 mmol), sulfur (1 g, 34.25 mmol) and morpholine (2.98 g, 34.25 mmol), and the mixture was stirred at 70° C. for 16 hours. After the reaction completed, the reaction mixture was concentrated under reduced pressure to obtain a residue. The residue was diluted with water and extracted with ethyl acetate. The combined organic layers were dried over anhydrous sodium sulfate and filtered, and the filtrate was distilled off under reduced pressure to obtain 5 g of Intermediate 1, which was confirmed by LC-MS (M+1): 262.1 and used in the next Step without further purification.

Step-2: Synthesis of (2-isothiocyanato-4,5-dimethylthiophen-3-yl)(3-methoxyphenyl)methanone (Intermediate 2)

[Chem. 173]

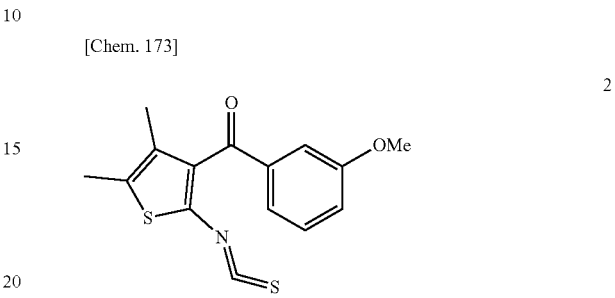

To a solution of thiophosgene (1.5 mL, 20.77 mmol) in water (50 mL) was added a solution of Intermediate 1 (5 g, 13.85 mmol) in dichloromethane (100 mL) at 0° C., and the mixture was stirred at the same temperature for one hour and at room temperature for 16 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain a crude compound. The crude compound was purified by silica gel column chromatography (eluted with 10% ethyl acetate:hexane) to obtain 2 g of Intermediate 2.

Yield: 34%, $^1$H NMR (400 MHz, CDCl$_3$) δ 2.01 (s, 3H), 2.33 (s, 3H), 3.88 (s, 3H), 7.14-7.19 (m, 1H), 7.33-7.44 (m, 3H) and LC-MS (M+1): 304.1.

Step-3: Synthesis of N-(3-(3-methoxybenzoyl)-4,5-dimethylthiophen-2-yl)-1-(pyridin-3-ylmethyl)hydrazine carbothioamide (Intermediate 3)

[Chem. 174]

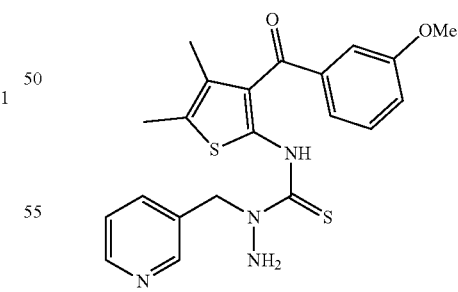

To a stirred solution of Intermediate 2 (2 g, 6.6 mmol) in tetrahydrofuran (30 mL) was added triethylamine (1.83 mL, 13.2 mmol), followed by SM-2 (2 g, 13.2 mmol), and the mixture was stirred at 0° C. for one hour and at room temperature for 16 hours. After the reaction completed, the reaction mixture was concentrated under reduced pressure to obtain a crude compound. The crude compound was triturated with hexane to obtain 3 g of Intermediate 3, which was confirmed by LC-MS (M+1): 427.1 and used in the next Step without further purification.

Step-4: Synthesis of 5-(3-methoxyphenyl)-6,7-dimethyl-3-(pyridin-3-ylmethyl)-1H-thieno[2,3-e][1,2,4]triaz epine-2(3H)-thione (Intermediate 4)

[Chem. 175]

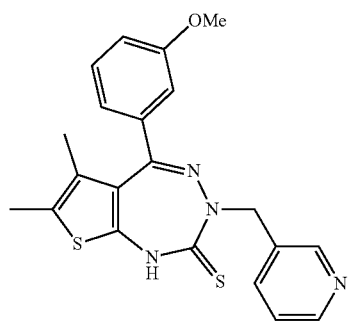

To a stirred solution of Intermediate 3 (3 g, 7.04 mmol) in ethanol (150 mL) was added p-toluenesulfonic acid (242 mg, 1.4 mmol), and the mixture was stirred at 100° C. for 16 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain 2.7 g (LC-MS: 47%) of Intermediate 4, which was confirmed by LC-MS (M+1): 409.27 and used in the next Step without further purification.

Step-5: Synthesis of 5-(3-methoxyphenyl)-6,7-dimethyl-2-(methylthio)-3-(pyridin-3-ylmethyl)-3H-thieno[2,3-e][1,2,4]triazepine (Intermediate 5)

[Chem. 176]

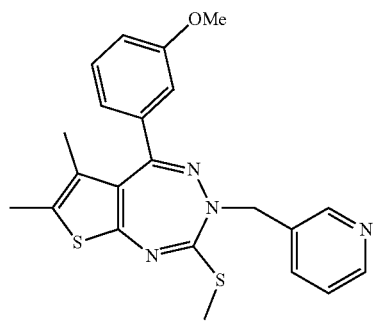

To a stirred solution of Intermediate 4 (2.7 g, 6.61 mmol) in tetrahydrofuran (70 mL) was added sodium hydride (317 mg, 13.23 mmol) at 0° C., and the mixture was stirred at room temperature for one hour. Methyl iodide (1.4 g, 9.9 mmol) was added thereto at 0° C., and the mixture was stirred at room temperature for 4 hours. After the reaction completed, the reaction mixture was poured into ice-cold water and extracted with ethyl acetate. The combined organic layers were dried over anhydrous sodium sulfate and filtered, and the filtrate was distilled off under reduced pressure to obtain 2.6 g of a crude compound of Intermediate 5, which was used in the next Step without further purification.

Step-6: Synthesis of 4-(3-methoxyphenyl)-2,3,9-trimethyl-6-(pyridin-3-ylmethyl)-6H-thieno[2,3-e][1,2,4]triazolo[3,4-c][1,2,4]triazepine (Compound of Example 75)

[Chem. 177]

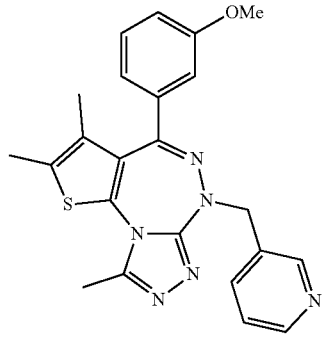

To a stirred solution of Intermediate 5 (2.6 g, crude) in ethanol (100 mL) were added acetohydrazide (4.5 mg, 61.5 mmol) and p-toluenesulfonic acid (211 mg, 1.23 mmol), and the mixture was stirred at 100° C. for 30 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain a crude compound, which was further purified by preparative HPLC to obtain 120 mg of the compound of Example 75.

Yield: 16%, $^1$H NMR (400 MHz, DMSO-$d_6$) δ 1.46 (s, 3H), 2.35 (s, 3H), 2.55 (s, 3H), 3.73 (s, 3H), 4.77-4.86 (m, 1H), 4.96-5.04 (m, 1H), 6.80-6.87 (m, 2H), 7.05 (dd, J=7.83, 2.45 Hz, 1H), 7.29-7.40 (m, 2H), 7.79-7.84 (m, 1H), 8.49 (dd, J=4.89, 1.47 Hz, 1H), 8.64 (d, J=1.47 Hz, 1H) and LC-MS (M+1): 431.18.

Synthetic Scheme of the Compound of Example 76

[Chem. 178]

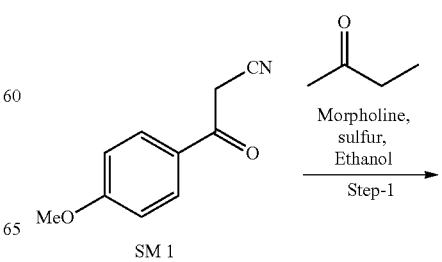

129
-continued

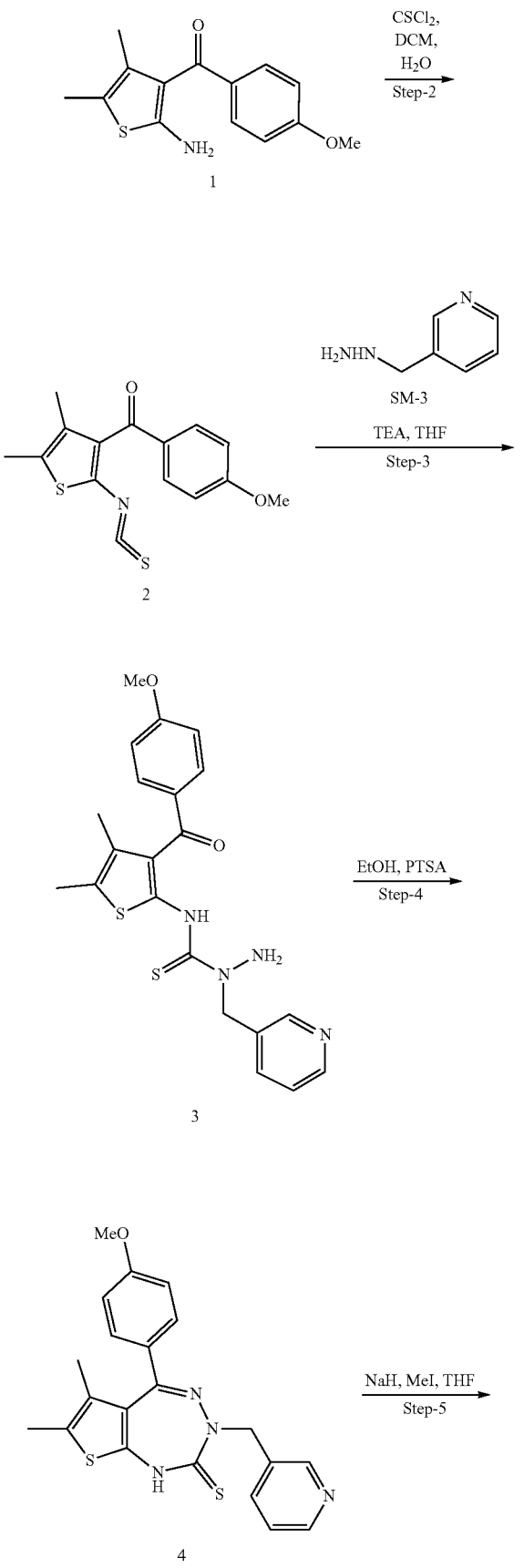

130
-continued

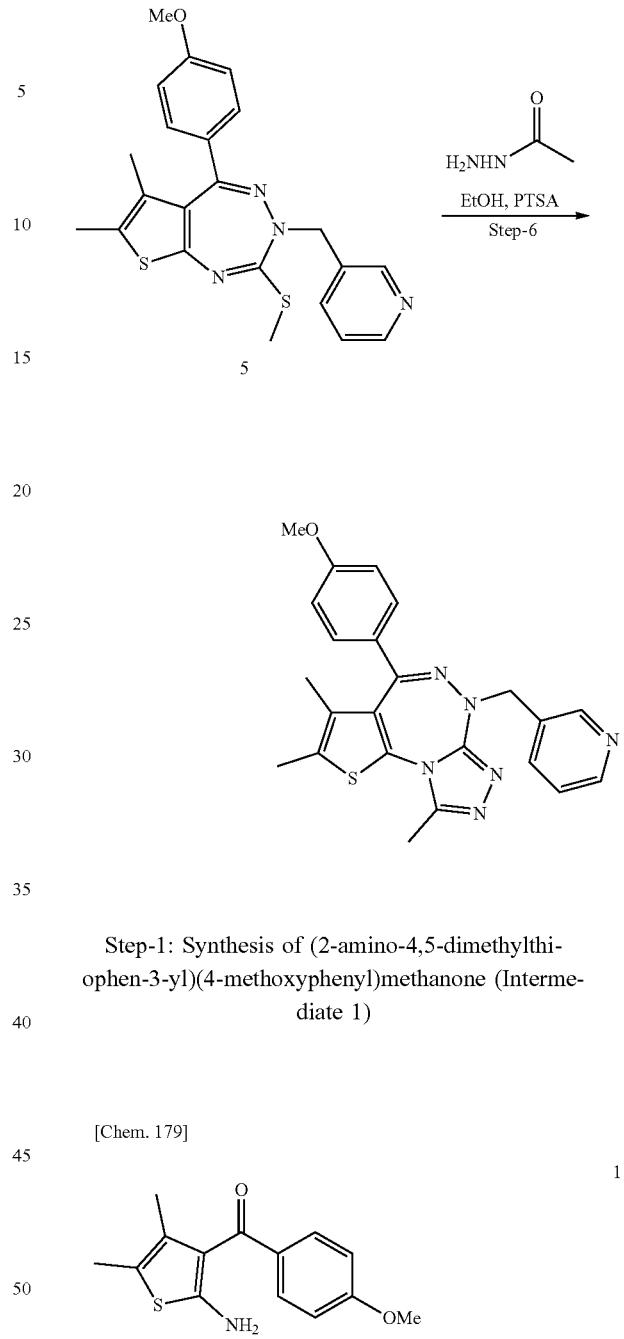

Step-1: Synthesis of (2-amino-4,5-dimethylthiophen-3-yl)(4-methoxyphenyl)methanone (Intermediate 1)

[Chem. 179]

To a solution of SM1 (5 g, 28.54 mmol) in ethanol (100 mL) were added butan-2-one (2.46 g, 34.25 mmol), sulfur (1 g, 34.25 mmol) and morpholine (2.98 g, 34.25 mmol), and the mixture was stirred at 55° C. for 25 hours. After the reaction completed, the reaction mixture was filtered and washed with ethanol to obtain 3.5 g of Intermediate 1.

Yield: 46%, $^1$H NMR (400 MHz, CDCl$_3$) δ 1.65 (s, 3H), 2.15 (s, 3H), 3.86 (s, 3H), 5.96 (br s, 2H), 6.88-6.94 (m, 2H), 7.53-7.60 (m, 2H) and LC-MS (M+1): 262.18.

Step-2: Synthesis of (2-isothiocyanato-4,5-dimethylthiophen-3-yl)(4-methoxyphenyl)methanone (Intermediate 2)

[Chem. 180]

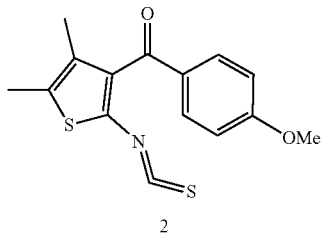

2

To a solution of thiophosgene (1.55 mL, 20.11 mmol) in water (30 mL) was added a solution of Intermediate 1 (3.5 g, 13.4 mmol) in dichloromethane (70 mL) at 0° C., and the mixture was stirred at 0° C. for 30 minutes and at room temperature for 16 hours. After the reaction completed, the reaction mixture was quenched with ice-water, extracted with dichloromethane and washed with brine. The organic layer was dried over anhydrous sodium sulfate and filtered, and the filtrate was concentrated under reduced pressure to obtain 3.8 g of Intermediate 2, which was used in the next Step without further purification.

Step-3: Synthesis of N-(3-(4-methoxybenzoyl)-4,5-dimethylthiophen-2-yl)-1-(pyridin-3-ylmethyl)hydrazine carbothioamide (Intermediate 3)

[Chem. 181]

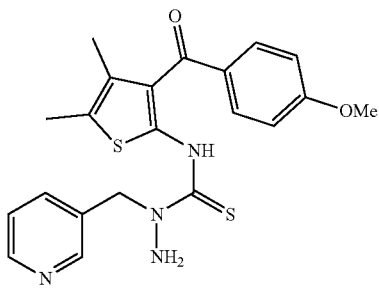

3

To a stirred solution of Intermediate 2 (3.8 g, 12.54 mmol) in tetrahydrofuran (50 mL) was added triethylamine (12.6 mL, 18.81 mmol), followed by SM-2 (3 g, 18.8 mmol), and the mixture was stirred at 0° C. for one hour and at room temperature for 16 hours. After the reaction completed, the reaction mixture was concentrated under reduced pressure to obtain a crude compound. The crude compound was triturated with hexane to obtain 4 g of Intermediate 3, which was confirmed by LC-MS (M+1): 427.4 and used in the next Step without further purification.

Step-4: Synthesis of 5-(4-methoxyphenyl)-6,7-dimethyl-3-(pyridin-3-ylmethyl)-1H-thieno[2,3-e][1,2,4]triazepine-2(3H)-thione (Intermediate 4)

[Chem. 182]

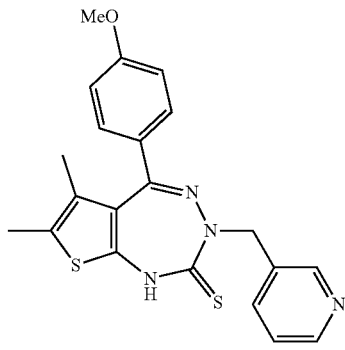

4

To a stirred solution of Intermediate 3 (4 g, 9.3 mmol) in ethanol (200 mL) was added p-toluenesulfonic acid (320 mg, 1.86 mmol), and the mixture was stirred at 100° C. for 16 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain 3.5 g of Intermediate 4, which was confirmed by LC-MS (M+1): 409.3 and used in the next Step without further purification.

Step-5: Synthesis of 5-(4-methoxyphenyl)-6,7-dimethyl-2-(methylthio)-3-(pyridin-3-ylmethyl)-3H-thieno[2,3-e][1,2,4]triazepine (Intermediate 5)

[Chem. 183]

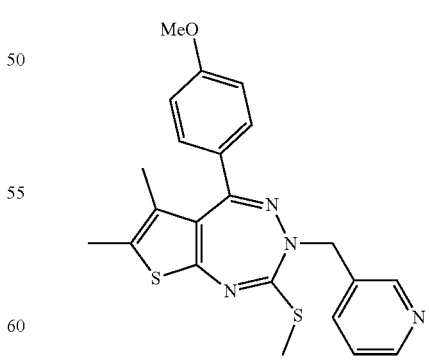

5

To a stirred solution of Intermediate 4 (3.5 g, 8.57 mmol) in tetrahydrofuran (100 mL) was added sodium hydride (514 mg, 21.44 mmol) at 0° C., and the mixture was stirred at room temperature for one hour. Methyl iodide (1.81 g, 12.85 mmol) was added thereto at 0° C., and the mixture was stirred at room temperature for 4 hours. After the reaction completed, the reaction mixture was poured into ice-cold water and extracted with ethyl acetate. The combined organic layers were dried over anhydrous sodium sulfate and filtered, and the filtrate was distilled off under reduced pressure to obtain 3.2 g (LC-MS: 35%) of Intermediate 5, which was confirmed by LC-MS (M+1): 423.14 and used in the next Step without further purification.

Step-6: Synthesis of 4-(4-methoxyphenyl)-2,3,9-trimethyl-6-(pyridin-3-ylmethyl)-6H-thieno[2,3-e][1,2,4]triazolo[3,4-c][1,2,4]triazepine (Compound of Example 76)

[Chem. 184]

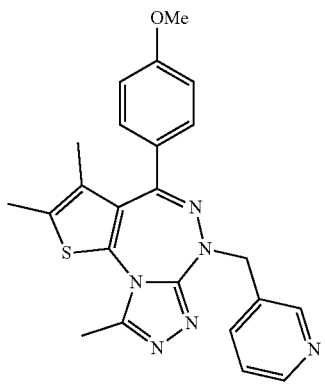

To a stirred solution of Intermediate 5 (3 g, 7.09 mmol) in ethanol (70 mL) were added acetohydrazide (5.25 g, 71 mmol) and p-toluenesulfonic acid (243 mg, 1.4 mmol), and the mixture was stirred at 100° C. for 30 hours. After the reaction completed, the reaction mixture was concentrated under reduced pressure to obtain a residue. The residue was diluted with ethyl acetate, washed with saturated sodium bicarbonate and a brine solution, dried over anhydrous sodium sulfate, and filtered. The filtrate was distilled off under reduced pressure to obtain a crude compound. The crude compound was purified by silica gel column chromatography (eluted with 2% methanol/dichloromethane) to obtain a crude compound, which was further purified by preparative HPLC to obtain 280 mg of the compound of Example 76.

Yield: 24%, $^1$H NMR (400 MHz, DMSO-$d_6$) δ 1.49 (s, 3H), 2.36 (s, 3H), 2.55 (s, 3H), 3.78 (s, 3H), 4.76-4.83 (m, 1H), 4.96-5.02 (m, 1H), 6.96 (d, J=8.80 Hz, 2H), 7.23 (d, J=8.80 Hz, 2H), 7.37 (dd, J=7.58, 5.14 Hz, 1H), 7.80 (dd, J=7.82, 1.96 Hz, 1H), 8.48 (dd, J=4.89, 1.47 Hz, 1H), 8.62 (d, J=1.47 Hz, 1H).

Synthesis of the Compounds of Examples 77 to 79

Example 77

Synthesis of 3-((4-(4-chlorophenyl)-2,3,9-trimethyl-6H-thieno[2,3-e][1,2,4]triazolo[3,4-c][1,2,4]triazepin-6-yl)methyl)picolinonitrile (Compound of Example 77)

[Chem. 185]

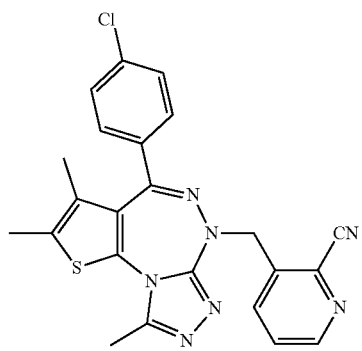

The title compound was synthesized according to the general method of coupling reaction using the compound of Example 1.

Yield: 20.5%, $^1$H NMR (400 MHz, CDCl$_3$) δ 1.58 (is, 3H), 2.39 (s, 3H), 2.63 (s, 3H), 5.11-5.17 (m, 1H), 5.31-5.38 (m, 1H), 7.36 (s, 4H), 7.50 (dd, J=8.07, 4.65 Hz, 1H), 8.15-8.19 (m, 1H), 8.64 (dd, J=4.89, 1.47 Hz, 1H) and LC-MS (M+1): 460.25.

Example 78

Synthesis of 4-(4-chlorophenyl)-2,3,9-trimethyl-6-((2-(trifluoromethyl)pyridin-3-yl)methyl)-6H-thieno[2,3-e][1,2,4]triazolo[3,4-c][1,2,4]triazepine (Compound of Example 78)

[Chem. 186]

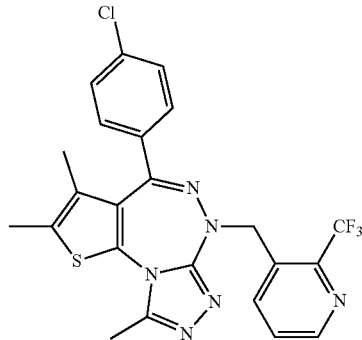

The title compound was synthesized according to the general method of coupling reaction using the compound of Example 1.

Yield: 47%, $^1$H NMR (400 MHz, CDCl$_3$) δ 1.57 (s, 3H), 2.40 (s, 3H), 2.64 (s, 3H), 5.17 (d, J=15.16 Hz, 1H), 5.42 (d, J=15.16 Hz, 1H), 7.22-7.25 (m, 2H), 7.30-7.32 (m, 2H), 7.47

(dd, J=7.82, 4.89 Hz, 1H), 8.06 (d, J=7.82 Hz, 1H), 8.64 (d, J=3.42 Hz, 1H) and LC-MS (M+1): 503.26.

Example 79

Synthesis of 6-((2-bromopyridin-3-yl)methyl)-4-(4-chlorophenyl)-2,3,9-trimethyl-6H-thieno[2,3-e][1,2,4]triazolo[3,4-c][1,2,4]triazepine (Compound of Example 79)

[Chem. 187]

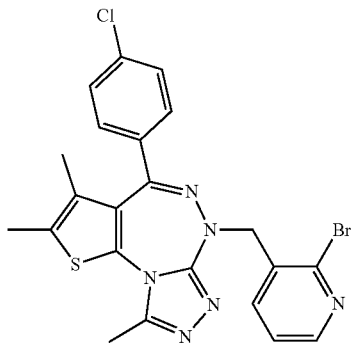

The title compound was synthesized according to the general method of coupling reaction using the compound of Example 1.

Yield: 8.3%, ¹H NMR (400 MHz, CDCl₃) δ 1.56 (s, 3H), 2.40 (s, 3H), 2.65 (s, 3H), 5.03 (d, J=15.16 Hz, 2H), 5.28 (d, J=14.67 Hz, 2H), 7.21-7.27 (m, 1H), 7.32-7.37 (m, 4H), 7.81 (dd, J=7.58, 1.71 Hz, 1H), 8.31 (dd, J=4.89, 1.96 Hz, 1H) and LC-MS (M+1): 513.0.

Synthetic Scheme of the Compound of Example 80

[Chem. 188]

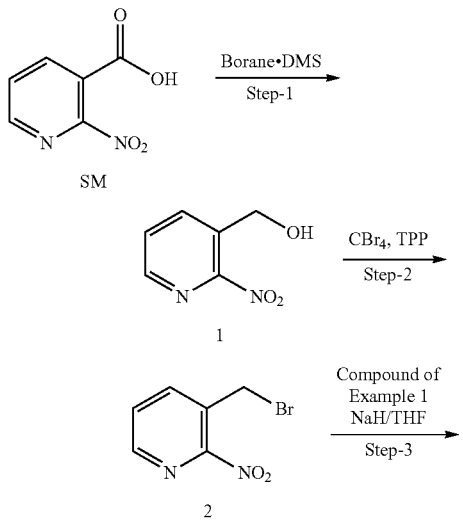

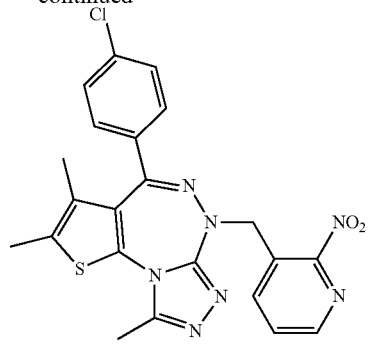

Step-1 Synthesis of (2-nitropyridin-3-yl)methanol

[Chem. 189]

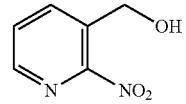

1

To a stirred solution of SM (100 mg, 5.58 mmol) in tetrahydrofuran (5 mL) was added borane DMS (0.1 mL), and the mixture was stirred at 50° C. for 5 hours.

After the reaction completed, the reaction mixture was poured into ice-cold water and extracted with ethyl acetate. The combined organic layers were dried over anhydrous sodium sulfate and filtered, and the filtrate was distilled off under reduced pressure to obtain Intermediate 1 (50 mg) (LC-MS: 84.2%). Intermediate 1 was confirmed by LC-MS (M+1) and used in the next Step without further purification.

Step-2: Synthesis of 3-(bromomethyl)-2-nitropyridine

[Chem. 190]

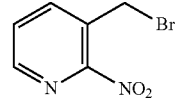

2

To a stirred solution of Intermediate 1 (520 mg, 3.37 mmol) in dichloromethane (20 mL) were added CBr4 (2.2 g, 6.75 mmol) and TPP (1.77 g, 6.75 mmol), and the mixture was stirred at room temperature for 4 hours. After the reaction completed, the reaction mixture was poured into ice-cold water and extracted with dichloromethane. The combined organic layers were dried over anhydrous sodium sulfate and filtered, and the filtrate was evaporated under reduced pressure to obtain a crude compound. The crude compound was purified by silica gel column chromatography (eluted with 30% ethyl acetate/petroleum ether) to obtain Intermediate 2 (500 mg).

Yield: 68%, ¹H NMR (400 MHz, CDCl₃) δ 4.73 (s, 2H), 7.64 (dd, J=7.83, 4.40 Hz, 1H), 8.10 (dd, J=7.58, 1.71 Hz, 1H), 8.54 (dd, J=4.65, 1.71 Hz, 1H) and LC-MS did not ionize.

Step-3: Synthesis of 4-(4-chlorophenyl)-2,3,9-trimethyl-6-((2-nitropyridin-3-yl)methyl)-6H-thieno[2,3-e][1,2,4]triazolo[3,4-c][1,2,4]triazepine (Compound of Example 80)

[Chem. 19]

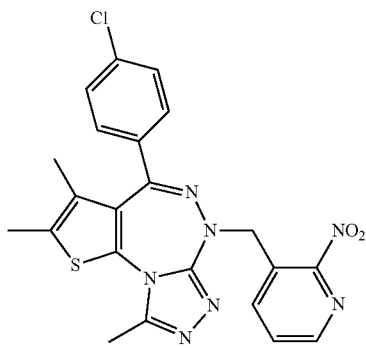

The title compound was synthesized according to the general method of coupling reaction using the compound of Example 1 and 3-(bromomethyl)-2-nitropyridine.

Yield: 8.3%, $^1$H NMR (400 MHz, DMSO-$d_6$) δ 1.49 (s, 3H), 2.38 (s, 3H), 2.54 (s, 3H), 5.03 (d, J=14.67 Hz, 1H), 5.28 (d, J=14.67 Hz, 1H), 7.24 (d, J=8.4 Hz, 2H), 7.48 (d, J=8.4 Hz, 2H), 7.84 (dd, J=7.58, 4.65 Hz, 1H), 8.27 (dd, J=7.82, 1.47 Hz, 1H), 8.55 (dd, J=4.65, 1.71 Hz, 1H) and LC-MS (M+1): 480.22.

Synthetic Scheme of the compound of Example 81

[Chem. 192]

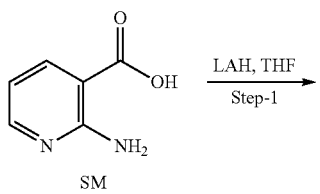

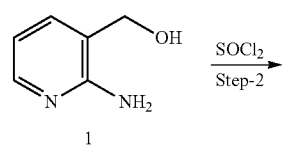

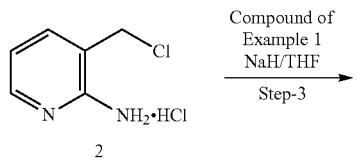

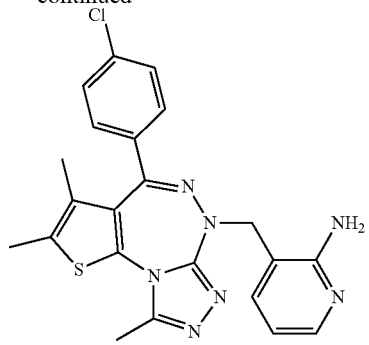

Step-1: Synthesis of (2-aminopyridin-3-yl)methanol

[Chem. 193]

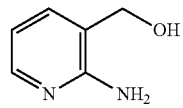

To a stirred solution of SM (10 g, 72.4 mmol) in tetrahydrofuran (100 mL) was added LAH (5.5 g, 144.9 mmol), and the mixture was stirred at 70° C. for 12 hours. After the reaction completed, the reaction mixture was cooled to room temperature, quenched with iced water, and subsequently added an aqueous 15% NaOH solution. Next, the reaction mixture was stirred at room temperature for 15 minutes. The mixture was filtered through a celite pad, and washed with tetrahydrofuran and 5% methanol/dichloromethane. The combined filtrates were concentrated under reduced pressure to obtain Intermediate 1 (6.8 g).

Yield: 88%, $^1$H NMR (400 MHz, CDCl$_3$) δ 2.53-2.68 (m, 1H), 4.62 (s, 2H), 4.99 (brs, 2H), 6.61 (dd, J=7.09, 5.14 Hz, 1H), 7.27-7.33 (m, 1H), 7.98 (d, J=4.40 Hz, 1H) and LC-MS (M+1): 125.2.

Step-2: Synthesis of 3-(chloromethyl)pyridin-2-amine hydrochloride

[Chem. 194]

To a stirred solution of thionyl chloride (1.4 mL, 19 mmol) in tetrahydrofuran (20 mL) was added Intermediate 1 (47 mg, 1.16 mmol) in tetrahydrofuran (10 mL) at 0° C., and the mixture was stirred at room temperature for one hour. After the reaction completed, the reaction mixture was distilled off under reduced pressure to obtain Intermediate 2 (2.2 g).

Yield: 78%, $^1$H NMR (400 MHz, CDCl$_3$) δ 4.60 (s, 2H), 6.88 (t, J=6.60 Hz, 1H), 7.46 (brs, 1H), 7.85 (d, J=6.36 Hz, 1H) and LC-MS: mass not ionized.

139

Step-3: Synthesis of 3-((4-(4-chlorophenyl)-2,3,9-trimethyl-6H-thieno[2,3-e][1,2,4]triazolo[3,4-c][1,2,4]triazepin-6-yl)methyl)pyridin-2-amine (Compound of Example 81)

[Chem. 195]

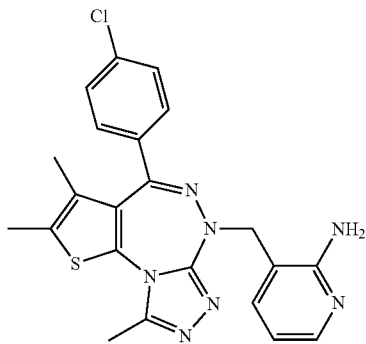

The title compound was synthesized according to the general method of coupling reaction using the compound of Example 1 and 3-(chloromethyl)pyridin-2-amine hydrochloride.

Yield: 3.7%, $^1$H NMR (400 MHz, DMSO-$d_6$) δ 1.48 (s, 3H), 2.36 (s, 3H), 2.54 (s, 3H), 4.63 (d, J=14.18 Hz, 1H), 4.83 (d, J=13.69 Hz, 1H), 5.74-5.79 (m, 2H), 6.55 (dd, J=7.34, 4.89 Hz, 1H), 7.33 (d, J=8.31 Hz, 2H), 7.42 (dd, J=7.34, 1.96 Hz, 1H), 7.49 (d, J=8.80 Hz, 2H), 7.88 (dd, J=5.14, 1.71 Hz, 1H) and LC-MS (M+1): 450.25.

Example 82

Synthesis of N-(3-((4-(4-chlorophenyl)-2,3,9-trimethyl-6H-thieno[2,3-e][1,2,4]triazolo[3,4-c][1,2,4]triazepin-6-yl)methyl)pyridin-2-yl)acetamide (Compound of Example 82)

[Chem. 196]

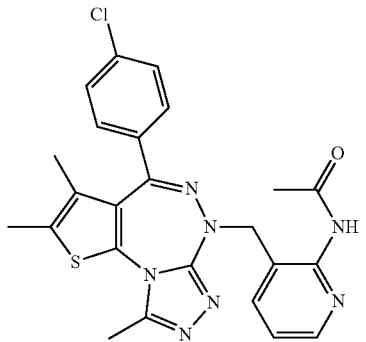

The title compound was synthesized according to the general method of coupling reaction using the compound of Example 1.

Yield: 8.3%, $^1$HNMR (400 MHz, DMSO-$d_6$) δ 1.51 (s, 3H), 1.92 (s, 3H), 2.37 (s, 3H), 2.54 (s, 3H), 4.71 (d, J=14.67 Hz, 1H), 4.99 (d, J=15.65 Hz, 1H), 7.21-7.27 (m, 3H), 7.44-7.49 (m, 2H), 7.71-7.79 (m, 1H), 8.33 (dd, J=4.89, 1.96 Hz, 1H), 10.12 (s, 1H) and LC-MS (M+1): 492.23.

Example 83

Synthesis of methyl 3-((4-(4-chlorophenyl)-2,3,9-trimethyl-6H-thieno[2,3-e][1,2,4]triazolo[3,4-c][1,2,4]triazepin-6-yl)methyl)picolinate (Compound of Example 83)

[Chem. 197]

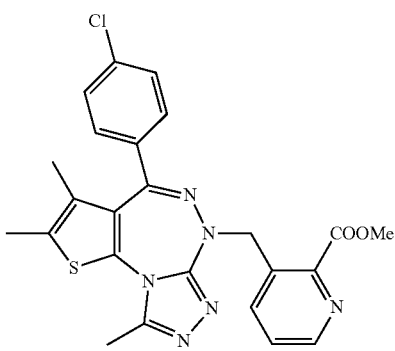

The title compound was synthesized according to the general method of coupling reaction using the compound of Example 1.

Yield: 47%, $^1$H NMR (400 MHz, DMSO-$d_6$) δ 1.47 (s, 3H), 2.37 (s, 3H), 2.54 (s, 3H), 3.48 (s, 3H), 4.97 (d, J=13.69 Hz, 1H), 5.19 (d, J=14.18 Hz, 1H), 7.21 (d, J=8.31 Hz, 2H), 7.47 (d, J=8.80 Hz, 2H), 7.58 (dd, J=7.82, 4.40 Hz, 1H), 7.99-8.04 (m, 1H), 8.55 (dd, J=4.89, 1.47 Hz, 1H) and LC-MS (M+1): 493.26.

Example 84

Synthesis of 3-((4-(4-chlorophenyl)-2,3,9-trimethyl-6H-thieno[2,3-e][1,2,4]triazolo[3,4-c][1,2,4]triazepin-6-yl)methyl)picolinic acid (Compound of Example 84)

[Chem. 198]

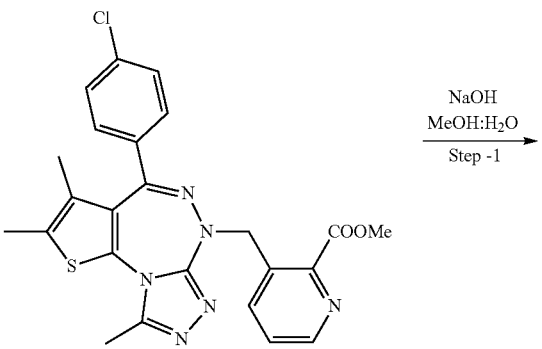

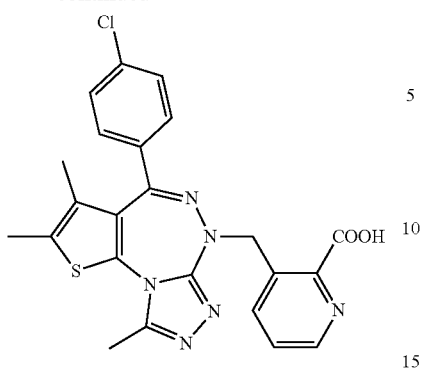

To a stirred solution of the compound of Example 83 (600 mg, 1.2 mmol) in methanol:water (4:1, 30 mL) was added NaOH (97 mg, 2.43 mmol) and the mixture was stirred at room temperature for 2 hours. After the reaction completed, the reaction mixture was poured into ice-cold water, neutralized with citric acid (pH=7) and extracted with ethyl acetate. The combined organic layers were dried over anhydrous sodium sulfate and filtered, and the filtrate was distilled off under reduced pressure to obtain a crude compound. The crude compound was purified by preparative HPLC to obtain the compound of Example 84 (41 mg).

Yield: 8.5%, $^1$H NMR (400 MHz, CD$_3$OD) δ1.51 (s, 3H), 2.37 (s, 3H), 2.62 (s, 3H), 5.21-5.62 (m, 2H), 7.15-7.54 (m, 5H), 7.97 (brs, 1H), 8.53 (brs, 1H) and LC-MS (M+1): 479.0.

Example 85

Synthesis of 3-((4-(4-chlorophenyl)-2,3,9-trimethyl-6H-thieno[2,3-e][1,2,4]triazolo[3,4-c][1,2,4]triazepin-6-yl)methyl)-N-ethylpicolinamide (Compound of Example 85)

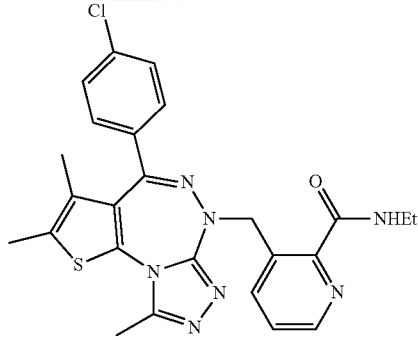

To a solution of the compound of Example 84 (700 mg, 1.46 mmol) in DMF (20 mL) were added EDC.HCl (97 mg, 2.43 mmol) and HOBT (31 mg, 0.22 mmol), and the mixture was stirred at room temperature for 30 minutes, followed by DIPEA (56 mg, 0.43 mmol) and ethylamine (0.21 ml, 0.42 mmol), and the mixture was stirred at room temperature for 16 hours. After the reaction completed, the reaction mixture was poured into ice-cold water and extracted with ethyl acetate. The combined organic layer was dried over sodium sulfate and filtered, and the filtrate was distilled off under reduced pressure to obtain a crude compound. The crude compound was purified by preparative HPLC to obtain the compound of Example 85 (204 mg).

Yield: 27%, $^1$H NMR (400 MHz, DMSO-d$_6$) δ 1.04 (t, J=7.34 Hz, 3H), 1.49 (s, 3H), 2.36 (s, 3H), 2.54 (s, 3H), 3.12-3.22 (m, 2H), 5.21 (d, J=15.16 Hz, 1H), 5.44 (d, J=14.67 Hz, 1H), 7.27 (d, J=8.80 Hz, 2H), 7.47 (d, J=8.80 Hz, 2H), 7.51-7.56 (m, 1H), 7.86 (d, J=6.85 Hz, 1H), 8.52 (dd, J=4.40, 1.47 Hz, 1H), 8.59 (t, J=5.87 Hz, 1H) and LC-MS (M+1): 506.34.

Example 86

Synthesis of (3-((4-(4-chlorophenyl)-2,3,9-trimethyl-6H-thieno[2,3-e][1,2,4]triazolo[3,4-c][1,2,4]triazepin-6-yl)methyl)pyridin-2-yl)methanol (Compound of Example 86)

[Chem. 199]

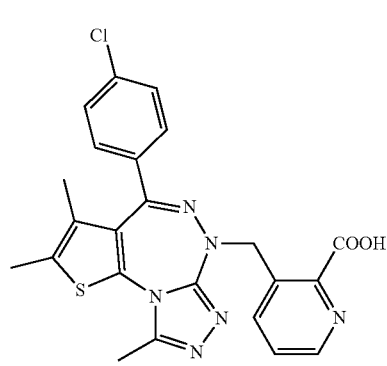

EDC·HCl, HOBt
DIPEA/DMF
―――――――→
Step-1

[Chem. 200]

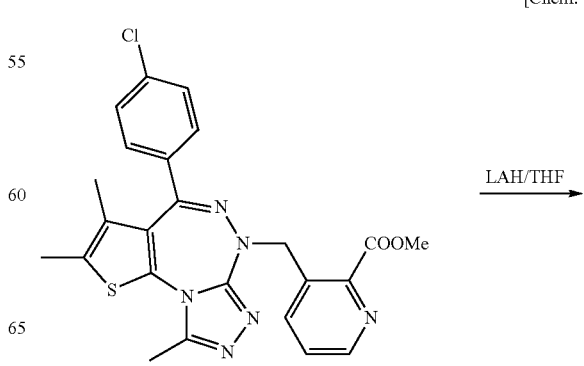

LAH/THF
―――――→

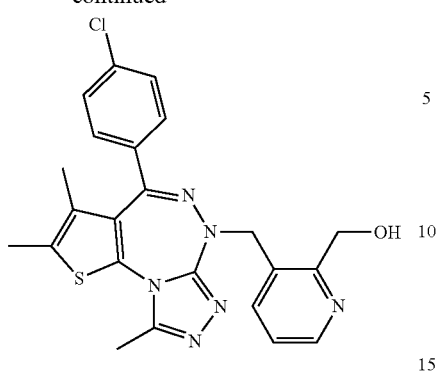

To a solution of the compound of Example 83 (350 mg, 0.7 mmol) in tetrahydrofuran (10 mL) was added LAH (57 mg, 1.4 mmol) at 0° C., and the mixture was stirred at room temperature for 6 hours. After the reaction completed, the reaction mixture was poured into ice-cold water and extracted with ethyl acetate. The combined organic layers were dried over anhydrous sodium sulfate and filtered, and the filtrate was evaporated under reduced pressure to obtain a crude compound. The crude compound was purified by preparative HPLC to obtain the compound of Example 86 (31 mg).

Yield: 9.4%, $^1$H NMR (400 MHz, DMSO-$d_6$) δ 1.48 (s, 3H), 2.36 (s, 3H), 2.54 (s, 3H), 4.67 (d, J=5.38 Hz, 2H), 4.93 (d, J=14.67 Hz, 1H), 5.13-5.20 (m, 2H), 7.27-7.34 (m, 3H), 7.49 (d, J=8.80 Hz, 2H), 7.74 (d, J=6.36 Hz, 1H), 8.43 (d, J=3.42 Hz, 1H) and LC-MS (M+1): 465.29.

Synthetic Scheme of the Compound of Example 87

[Chem 201]

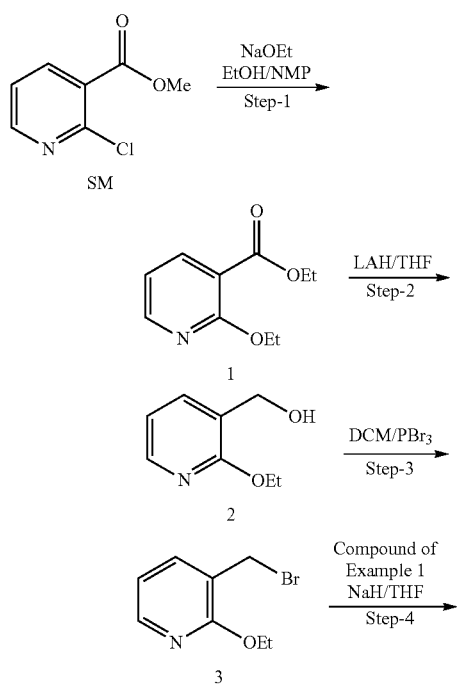

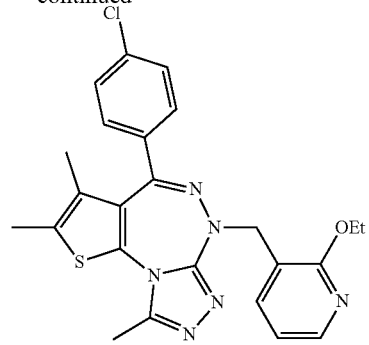

Step-1: Synthesis of ethyl 2-ethoxynicotinate

[Chem. 202]

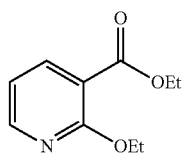

To a solution of SM (500 mg, 2.91 mmol) in NMP (9 mL) were added ethanol (3 mL) and NaOEt (0.39 mg, 5.82 mmol), and the mixture was stirred at 90° C. for 16 hours. After the reaction completed, the reaction mixture was poured into ice-cold water and extracted with ethyl acetate. The combined organic layers were dried over anhydrous sodium sulfate and filtered, and the filtrate was evaporated under reduced pressure to obtain a crude compound. The crude compound was purified by silica gel column chromatography (eluted with 10% ethyl acetate:hexane) to obtain Intermediate 1 (100 mg).

Yield: 9.4%, $^1$H NMR (400 MHz, DMSO-$d_6$) δ 1.25-1.6 (m, 6H), 4.35 (q, J=7.2 Hz, 2H), 4.48 (q, J=6.8 Hz, 2H), 6.91 (dd, J=5.2 & 7.6H, 1H), 8.11-8.13 (m. 1H), 8.26-8.28 (m, 1H) and LC-MS (M+1): 196.0.

Step-2: Synthesis of (2-ethoxypyridin-3-yl)methanol

[Chem. 203]

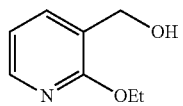

To a stirred solution of Intermediate 1 (100 mg, 0.51 mmol) in tetrahydrofuran (5 mL) was added LAH (22 mg, 0.71 mmol) at 0° C., and the mixture was stirred at room temperature for 2 hours. After the reaction completed, the reaction mixture was quenched with a saturated sodium sulfate solution and extracted with ethyl acetate. The combined organic layers were dried over anhydrous sodium sulfate and filtered, and the filtrate was distilled off under reduced pressure to obtain Intermediate 2 (40 mg), which was confirmed by LC-MS (M+1): 154.08 and used in the next Step without further purification.

Step-3: 3-(bromomethyl)-2-ethoxypyridine

[Chem. 204]

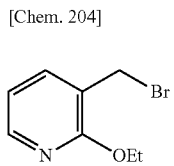

3

To a stirred solution of Intermediate 2 (400 mg, 0.26 mmol) in dichloromethane (2 mL) was added PBr$_3$ (0.1 mL, 1.05 mmol) at 0° C., and the mixture was stirred at room temperature for one hour. After the reaction completed, the reaction mixture was poured into a saturated sodium hydrogen carbonate solution and extracted with dichloromethane. The combined organic layers were dried over anhydrous sodium sulfate and filtered, and the filtrate was distilled off under reduced pressure to obtain Intermediate 3 (25 mg), which was confirmed by LC-MS (M+1): 215.96 and used in the next Step without further purification.

Step-4: Synthesis of 4-(4-chlorophenyl)-6-((2-ethoxypyridin-3-yl)methyl)-2,3,9-trimethyl-6H-thieno[2,3-e][1,2,4]triazolo[3,4-c][1,2,4]triazepine (Compound of Example 87)

[Chem. 205]

The title compound was synthesized according to the general method of coupling reaction using the compound of Example 1 and 3-(bromomethyl)-2-ethoxypyridine.

Yield: 41%, $^1$H NMR (400 MHz, CDCl$_3$) δ 1.35 (t, J=7.09 Hz, 3H), 1.60 (s, 3H), 2.41 (s, 3H), 2.65 (s, 3H), 4.40 (q, J=7.34 Hz, 2H), 4.95-5.02 (m, 1H), 5.13-5.21 (m, 1H), 6.82 (dd, J=7.34, 4.89 Hz, 1H), 7.31-7.36 (m, 4H), 7.57-7.62 (m, 1H), 8.08 (dd, J=4.89, 1.96 Hz, 1H) and LC-MS (M+1): 479.26.

Synthetic Scheme of the Compound of Example 88

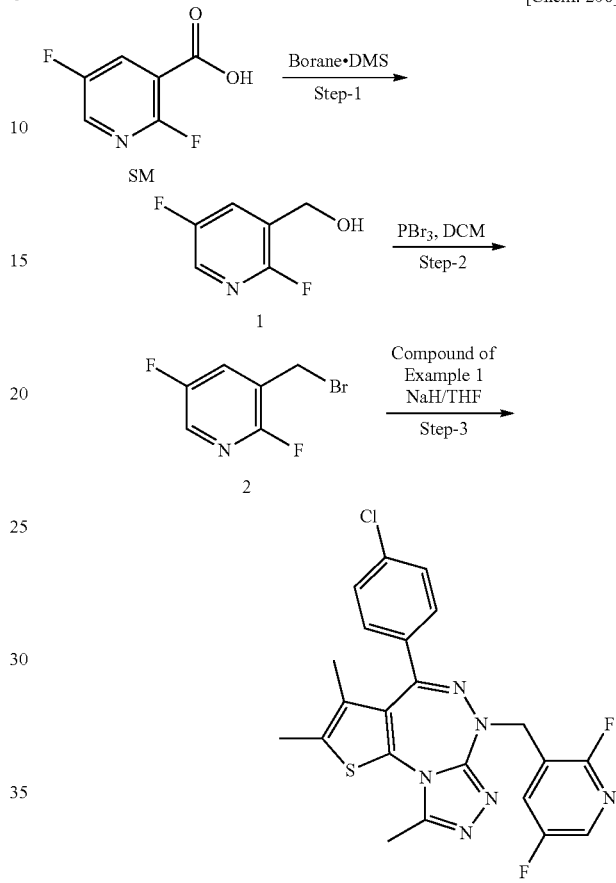

Step-1: Synthesis of (2,5-difluoropyridin-3-yl)methanol

[Chem. 207]

To a stirred solution of SM (200 mg, 1.25 mmol) in THF (10 mL) was added borane dimethylsulfide (0.18 mL), and the mixture was stirred at 50° C. for 5 hours. After the reaction completed, the reaction mixture was quenched with a saturated ammonium chloride solution and extracted with ethyl acetate. The combined organic layers were dried over anhydrous sodium sulfate and filtered, and the filtrate was distilled off under reduced pressure to obtain an intermediate (100 mg).

Yield: 80%, $^1$H NMR (400 MHz, CDCl$_3$) δ 4.76 (s, 2H), 7.67-7.71 (m, 1H), 7.94 (brs, 1H) and LC-MS (M+1): 145.96.

Step-2: Synthesis of
3-(bromomethyl)-2,5-difluoropyridine

[Chem. 208]

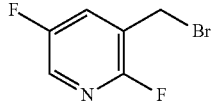

To a stirred solution of Intermediate 1 (100 mg, 0.68 mmol) in dichloromethane (10 mL) was added PBr$_3$ (0.2 g, 2.1 mmol) at 0° C., and the mixture was stirred at room temperature for 5 hours. After the reaction completed, the reaction mixture was quenched with a saturated sodium hydrogen carbonate solution and extracted with dichloromethane. The combined organic layers were dried over anhydrous sodium sulfate and filtered, and the filtrate was distilled off under reduced pressure to obtain Intermediate 2 (40 mg), which was used in the next Step without further purification.

Step-3: Synthesis of 4-(4-chlorophenyl)-6-((2,5-difluoropyridin-3-yl)methyl)-2,3,9-trimethyl-6H-thieno[2,3-e][1,2,4]triazolo[3,4-c][1,2,4]triazepine (Compound of Example 88)

[Chem. 209]

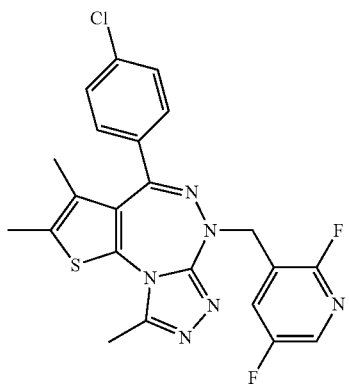

The title compound was synthesized according to the general method of coupling reaction using the compound of Example 1 and 3-(bromomethyl)-2,5-difluoropyridine.

Yield: 46%, $^1$H NMR (400 MHz, DMSO-d$_6$) δ 1.48 (s, 3H), 2.37 (s, 3H), 2.56 (s, 3H), 4.80-4.88 (m, 1H), 4.98-5.06 (m, 1H), 7.32-7.38 (m, 2H), 7.52 (d, J=8.80 Hz, 2H), 7.95 (td, J=7.70, 3.18 Hz, 1H), 8.22 (dd, J=2.93, 1.96 Hz, 1H) and LC-MS (M+1): 471.21.

Synthetic Scheme of the Compound of Example 89

[Chem. 210]

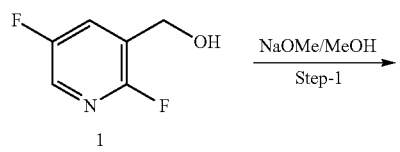

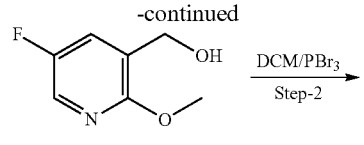

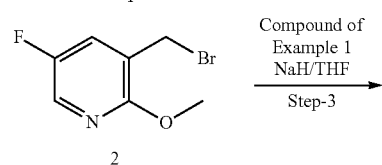

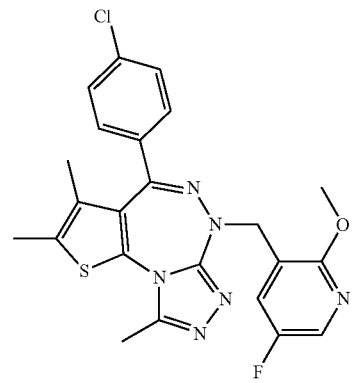

Step-1: Synthesis of
(5-fluoro-2-methoxypyridin-3-yl)methanol

[Chem. 211]

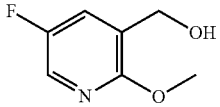

To a solution of Compound 1 (100 mg, 0.68 mmol) in methanol (5 mL) was added a 30% sodium methoxide solution (0.15 mL, 0.82 mmol), and the mixture was stirred at 75° C. for 24 hours. After the reaction completed, the reaction mixture was concentrated under reduced pressure to obtain a residue. The residue was diluted with ethyl acetate, washed with water and a brine solution, dried over anhydrous sodium sulfate, and filtered. The filtrate was distilled off under reduced pressure to obtain a crude compound. The crude compound was triturated with n-pentane to obtain Intermediate 1 (60 mg).

Yield: 55%, $^1$H NMR (400 MHz, CDCl$_3$) δ 2.20 (d, J=6.36 Hz, 1H), 3.96 (s, 3H), 4.64 (d, J=6.36 Hz, 2H), 7.43 (dd, J=7.82, 2.93 Hz, 1H), 7.91 (d, J=2.93 Hz, 1H) and LC-MS (M+1): 158.04.

Step-2: Synthesis of
3-(bromomethyl)-5-fluoro-2-methoxypyridine

[Chem. 212]

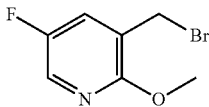

To a solution of Intermediate 1 (60 mg, 0.37 mmol) in dichloromethane (5 mL) was added PBr$_3$ (0.1 mL, 1.05 mmol) at 0° C., and the mixture was stirred at room temperature for 5 hours. After the reaction completed, the reaction mixture was quenched with a saturated sodium hydrogen carbonate solution and extracted with dichloromethane. The combined organic layer was dried over anhydrous sodium sulfate and filtered, and the filtrate was distilled off under reduced pressure to obtain Intermediate 2 (40 mg), which was used in the next Step without further purification.

Step-3: Synthesis of 4-(4-chlorophenyl)-6-((5-fluoro-2-methoxypyridin-3-yl)methyl)-2,3,9-trimethyl-6H-thieno[2,3-e][1,2,4]triazolo[3,4-c][1,2,4]triazepine (compound of Example 89)

[Chem. 213]

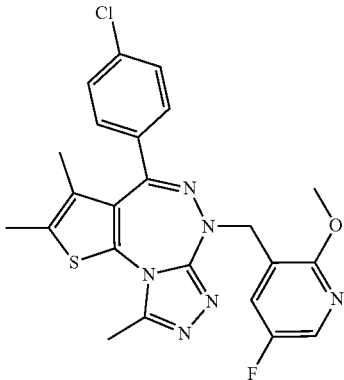

The title compound was synthesized according to the general method of coupling reaction using the compound of Example 1 and 3-(bromomethyl)-5-fluoro-2-methoxypyridine.

Yield: 14.2%, $^1$H NMR (400 MHz, DMSO-d$_6$) δ 1.52 (s, 3H), 2.38 (s, 3H), 2.56 (s, 3H), 3.91 (s, 3H), 4.77 (d, J=13.69 Hz, 1H), 4.95 (s, 1H), 7.34 (d, J=8.80 Hz, 2H), 7.45 (dd, J=8.80, 2.93 Hz, 1H), 7.51 (d, J=8.80 Hz, 2H), 8.10 (d, J=2.93 Hz, 1H) and LC-MS (M+1): 483.23.

Example 90: Synthesis of 6-((2-fluoropyridin-3-yl)methyl)-2,3,9-trimethyl-4-phenyl-6H-thieno[2,3-e][1,2,4]triazolo[3,4-c][1,2,4]triazepine (Compound of Example 90)

[Chem. 214]

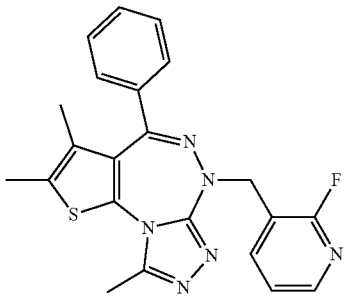

The title compound was synthesized according to the general method of coupling reaction using the compound of Example 1.

Yield: 21.7%, $^1$H NMR (400 MHz, DMSO-d$_6$) δ 1.43 (s, 3H), 2.35 (s, 3H), 2.56 (s, 3H), 4.80-4.89 (m, 1H), 4.98-5.05 (m, 1H), 7.27-7.32 (m, 2H), 7.36-7.44 (m, 3H), 7.45-7.52 (m, 1H), 7.95-8.05 (m, 1H), 8.19 (d, J=4.40 Hz, 1H) and LC-MS: 419.25.

Example 91

Synthesis of 4-(4-chlorophenyl)-2,3,9-trimethyl-N-phenyl-6H-thieno[2,3-e][1,2,4]triazolo[3,4-c][1,2,4]triazepine-6-carboxamide (Compound of Example 91)

[Chem. 215]

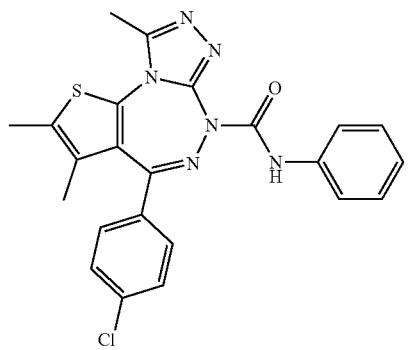

The title compound was synthesized according to the general method of coupling reaction using the compound of Example 1 and phenylcarbamic acid bromide (16 mg, 23.1%).

1H NMR (400 MHz, CDCl3) δ 8.85 (s, 1H), 7.61 (d, J=8.0 Hz, 2H), 7.53 (d, J=8.3 Hz, 2H), 7.44 (d, J=8.3 Hz, 2H), 7.36 (t, J=7.8 Hz, 2H), 7.13 (t, J=7.4 Hz, 1H), 2.69 (s, 3H), 2.40 (s, 3H), 1.63 (s, 3H); LCMS: 463 (M+1); HPLC: 98.09%.

Example 92: Synthesis of 4-(2,3,9-trimethyl-6-(pyridin-3-ylmethyl)-6H-thieno[2,3-e][1,2,4]triazolo[3,4-c][1,2,4]triazepin-4-yl)aniline (Compound of Example 92)

[Chem. 216]

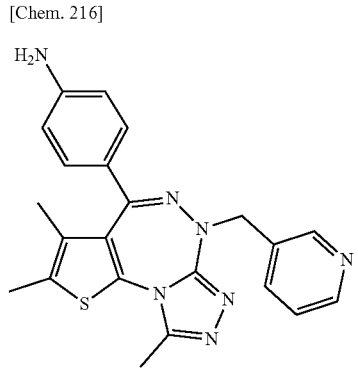 [SMILES: Cc1sc2c(c1C)C(c1ccc(N)cc1)=NN(Cc1cccnc1)c1nnc(C)n1-2]

The compound of Example 71 (N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide) was hydrolyzed with conc. sulfuric acid in THF to obtain Example 92.

$^1$H NMR (500 MHz, DMSO-d$_6$) δ 8.60 (d, J=1.5 Hz, 1H), 8.46 (dd, J=1.7 and 4.7 Hz, 1H), 7.77 (td, J=1.9 and 7.9 Hz, 1H), 7.38-7.34 (m, 1H), 6.98 (d, J=8.5 Hz, 2H), 6.51 (d, J=8.9 Hz, 2H), 5.62 (s, 2H), 4.94 (d, J=14 Hz, 1H), 4.75 (d, J=13.7 Hz, 1H), 2.53 (s, 3H), 2.36 (s, 3H), 1.58 (s, 3H).
Synthetic Schemes of Compounds of Examples 92, 93 and 105
[Chem. 217]
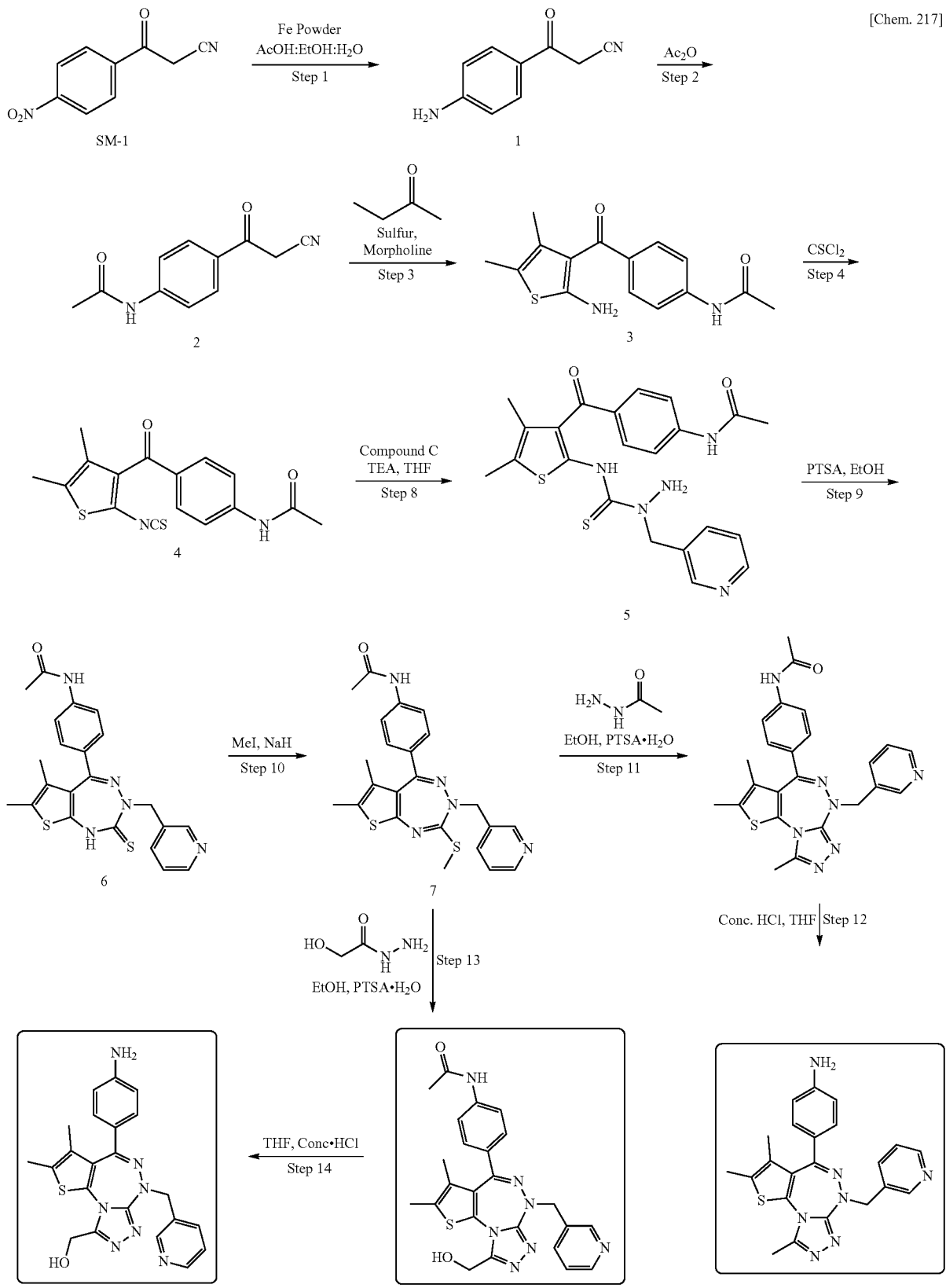

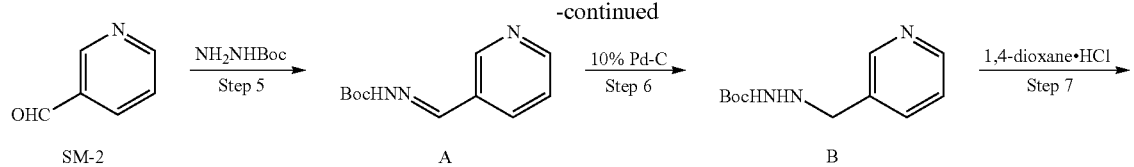

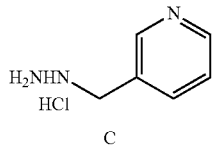

Note: The details of all the experiments and analyzes for the synthesis of the compound of Example 71 are shared.

Step 12: Synthesis of 4-(2,3,9-trimethyl-6-(pyridin-3-ylmethyl)-6H-thieno[2,3-e][1,2,4]triazolo[3,4-c][1,2,4]triazepin-4-yl)aniline (Compound of Example 92)

[Chem. 218]

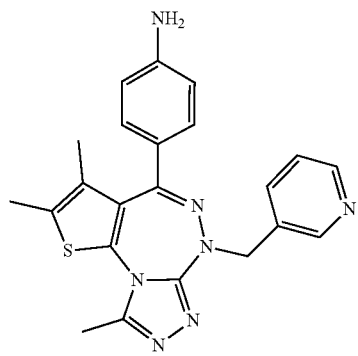

To a solution of the compound of Example 71 (10 g, 21.88 mmol) in THF (100 mL) was added conc. hydrochloric acid (100 mL), and the mixture was stirred at 70° C. for 16 hours. After the reaction completed, the reaction mixture was concentrated under reduced pressure to obtain a residue, and the residue was diluted with iced water and washed with ethyl acetate. The aqueous layer was made basic with a saturated sodium bicarbonate solution to obtain a solid, and the solid was filtered through Buechner funnel, washed with water and dried under highly vacuum for overnight to obtain a crude compound. The crude compound was triturated with ethyl acetate to obtain 6 g of the compound of Example 92.

Yield: 66%, $^1$HNMR (500 MHz, DMSO-$d_6$) δ 1.58 (s, 3H), 2.36 (s, 3H), 2.53 (s, 3H), 4.75 (d, J=13.73 Hz, 1H), 4.95 (d, J=14.04 Hz, 1H), 5.64 (brs, 2H), 6.51 (d, J=8.85 Hz, 2H), 6.99 (d, J=8.24 Hz, 2H), 7.36 (dd, J=7.63 & 4.88 Hz, 1H), 7.78 (d, J=7.93 Hz, 1H), 8.42-8.71 (m, 2H) and LC-MS (M+1): 416.24

Step 13: Synthesis of N-(4-(9-(hydroxymethyl)-2,3-dimethyl-6-(pyridin-3-ylmethyl)-6H-thieno[2,3-e][1,2,4]triazolo[3,4-c][1,2,4]triazepin-4-yl)phenyl)acetamide (Compound of Example 93)

[Chem. 219]

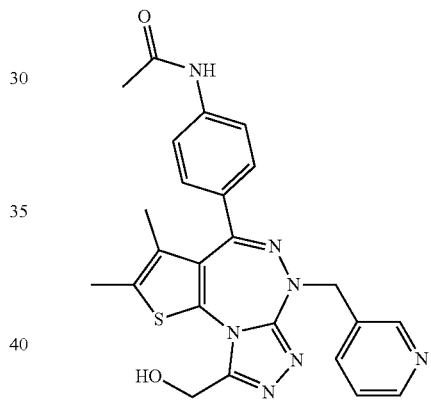

To a solution of Compound 7 (1.5 g, 3.34 mmol) in ethanol (50 mL) were added 2-hydroxyacetohydrazide (1.5 g, 16.7 mmol) and PTSA.H$_2$O (127 mg, 0.66 mmol), and the mixture was stirred at 100° C. for 40 hours. After the reaction completed, the reaction mixture was concentrated under reduced pressure to obtain a residue, and the residue was diluted with ethyl acetate and washed with a saturated sodium hydrogen carbonate solution and brine. The organic layer was dried over anhydrous sodium sulfate and filtered, and the filtrate was concentrated under reduced pressure to obtain a crude compound. The crude compound was purified by silica (100-200 mesh) column chromatography, eluted with 8% methanol/DCM, to obtain 600 mg of the compound of Example 93.

Yield: 40%, $^1$HNMR (500 MHz, DMSO-$d_6$) δ 1.49 (s, 3H), 2.04 (s, 3H), 2.35 (d, J=0.61 Hz, 3H), 4.59 (dd, J=13.43 & 6.41 Hz, 1H), 4.74 (dd, J=13.43 & 4.88 Hz, 1H), 4.82 (d, J=14.04 Hz, 1H), 5.02 (d, J=13.73 Hz, 1H), 5.80 (t, J=5.65 Hz, 1H), 7.24 (d, J=8.54 Hz, 2H), 7.33-7.40 (m, 1H), 7.61 (d, J=8.85 Hz, 2H), 7.82 (dt, J=7.86 & 1.87 Hz, 1H), 8.49

(dd, J=4.88 & 1.53 Hz, 1H), 8.64 (d, J=1.53 Hz, 1H), 10.14 (s, 1H) and LC-MS (M+1): 474.34

Step 14: Synthesis of (4-(4-aminophenyl)-2,3-dimethyl-6-(pyridin-3-ylmethyl)-6H-thieno[2,3-e][1,2,4]triazolo[3,4-c][1,2,4]triazepin-9-yl)methanol (Compound of Example 105)

[Chem. 220]

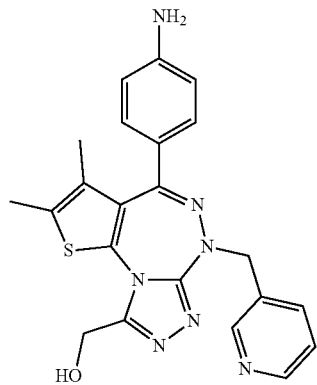

To a solution of the compound of Example 93 (250 mg, 0.52 mmol) in THF (10 mL) was added conc. hydrochloric acid (10 mL), and the mixture was stirred at 70° C. for 16 hours. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was triturated with diethyl ether and lyophilized to obtain 120 mg of the compound of Example 105.

Yield: 52%, $^1$H NMR (500 MHz, DMSO-$d_6$) δ 1.57 (d, J=0.61 Hz, 3H), 2.35 (d, J=0.61 Hz, 3H), 4.54-4.60 (m, 1H), 4.69-4.80 (m, 2H), 4.96 (d, J=14.04 Hz, 1H), 5.63 (s, 2H), 5.77 (t, J=5.65 Hz, 1H), 6.51 (d, J=8.85 Hz, 2H), 6.98 (d, J=8.24 Hz, 2H), 7.36 (ddd, J=7.78, 4.73 & 0.92 Hz, 1H), 7.78 (dt, J=7.86 & 1.87 Hz, 1H), 8.47 (dd, J=4.88 & 1.83 Hz, 1), 8.60 (d, J=1.53 Hz, 1H) and LC-MS (M+1): 432.35

Synthetic Scheme of the Compound of Example 94

[Chem. 221]

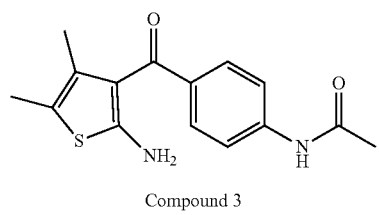

Compound 3

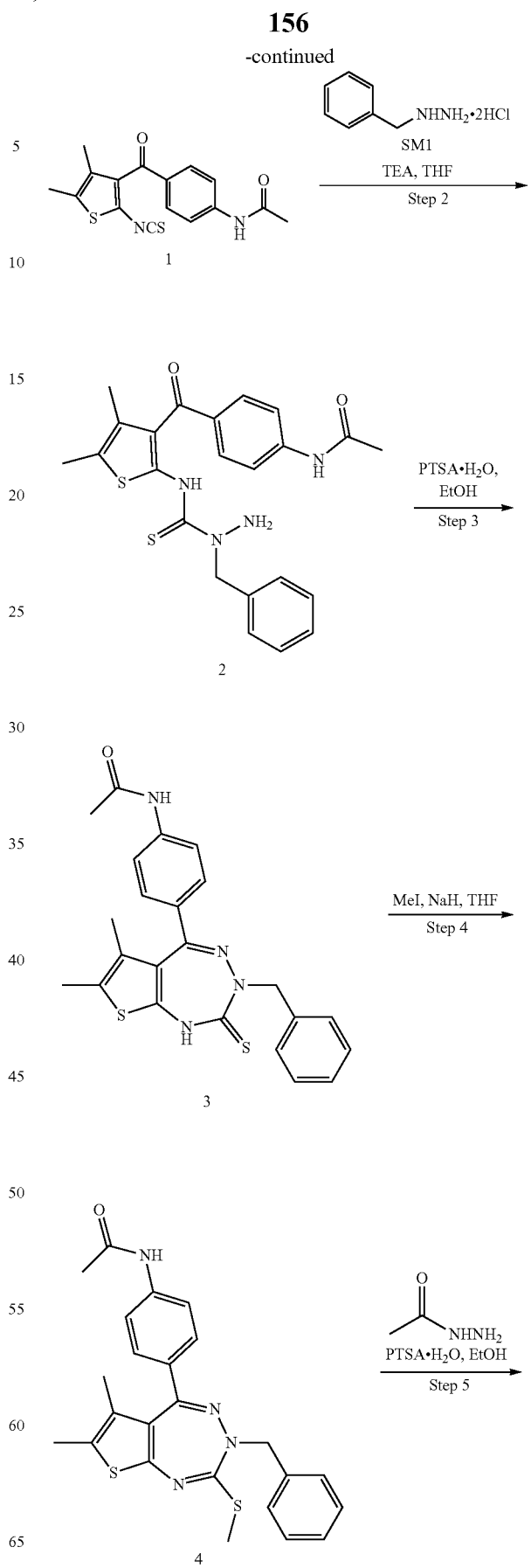

-continued

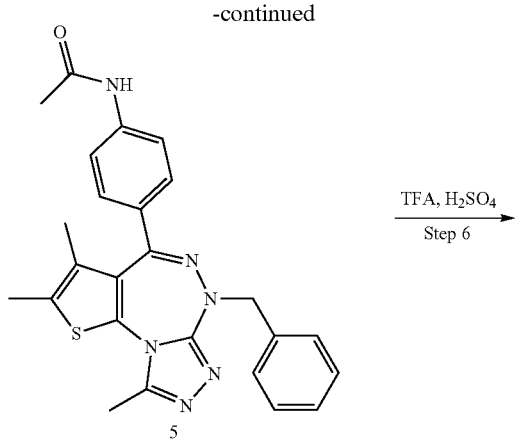
5

TFA, H₂SO₄
Step 6

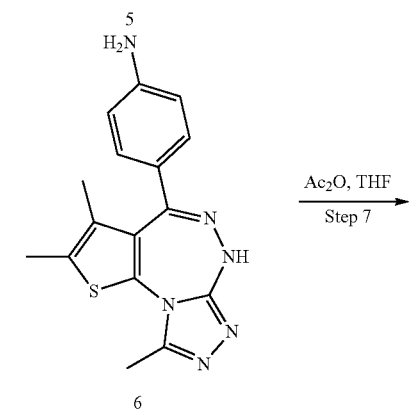
6

Ac₂O, THF
Step 7

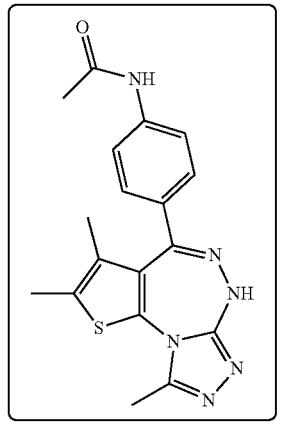

Step 1: Synthesis of N-(4-(2-isothiocyanato-4,5-dimethylthiophen-3-carbonyl)phenyl)acetamide (Compound 1)

[Chem. 222]

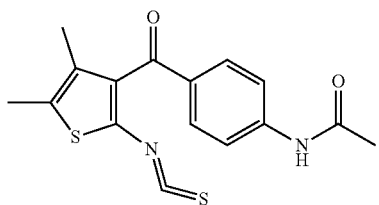
1

To a solution of thiophosgene (0.31 mL, 4.16 mmol) in water (10 mL) was added a solution of Compound 3 in Scheme of Example 71 (1 g, 3.47 mmol) in DCM (10 mL) at 0° C., and the mixture was stirred at the same temperature for one hour and at room temperature for one hour. After the reaction completed, the reaction mixture was quenched with ice-water, extracted with DCM and washed with brine. The organic layer was dried over anhydrous sodium sulfate and filtered, and the filtrate was concentrated under reduced pressure to obtain a crude compound. The crude compound was purified by silica gel column chromatography, eluted with DCM, to obtain 0.88 g of Compound 1, which was confirmed by LC-MS (purity: 43%) and used in the next Step without further purification. LC-MS (M+1): 331.19

Step 2: Synthesis of N-(4-(2-(1-benzylhydrazine-1-carbothioamide)-4,5-dimethylthiophen-3-carbonyl)phenyl)acetamide (Compound 2)

[Chem. 223]

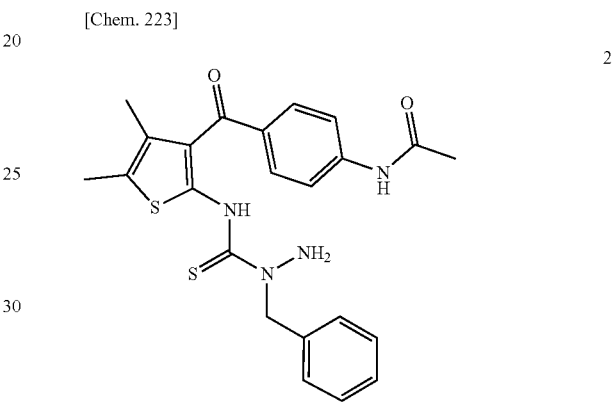
2

To a solution of Compound 1 (880 mg, LC-MS: 43%) in THF (30 mL) was added TEA (0.93 mL, 6.65 mmol), followed by a compound SM1 (518 mg, 2.66 mmol), and the mixture was stirred at 0° C. for one hour and at room temperature for one hour. After the reaction completed, the reaction mixture was concentrated under reduced pressure to obtain 1.8 g of Compound 2, which was confirmed by (LC-MS: 69%) and used in the next Step without further purification. LC-MS (M+1): 453.20

Step 3: Synthesis of N-(4-(3-benzyl-6,7-dimethyl-2-thioxo-2,3-dihydro-1H-thieno[2,3-e][1,2,4]triazepin-5-y 1)phenyl)acetamide (Compound 3)

[Chem. 224]

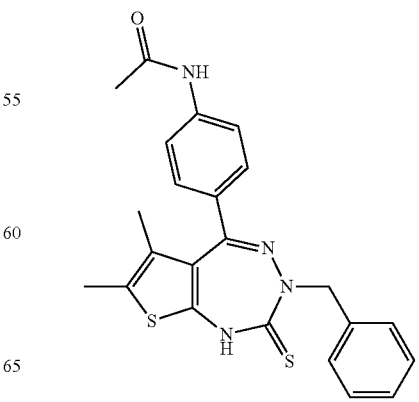
3

To a solution of Compound 2 (1.8 g, LC-MS: 69%) in ethanol (30 mL) was added PTSA.H$_2$O (151 mg, 0.79 mmol), and the mixture was stirred at 90° C. for 48 hours. After the reaction completed, the reaction mixture was concentrated under reduced pressure to obtain a residue, and the residue was diluted with water and extracted with ethyl acetate. The organic layer was dried over anhydrous sodium sulfate and filtered, and the filtrate was concentrated under reduced pressure to obtain a crude compound. The crude compound was purified by silica gel (100-200 mesh) column chromatography, eluted with 40% ethyl acetate/petroleum ether, to obtain Compound 3 (400 mg, LC-MS: 75%), which was used in the next Step without further purification. LC-MS (M+1): 435.07

Step 4: Synthesis of N-(4-(3-benzyl-6,7-dimethyl-2-(methylthio)-3H-thieno-[2,3-e][1,2,4]triazepin-5-yl)phenyl)acetamide (Compound 4)

[Chem. 225]

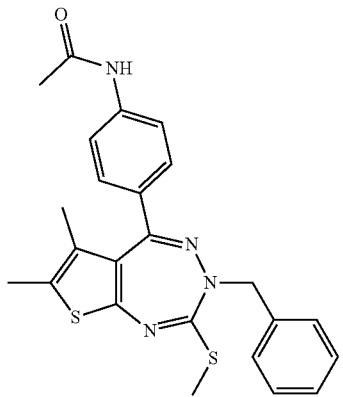

4

To a cooled (0° C.) solution of Compound 3 (5 g, LC-MS: 65.6%) in THF (30 mL) was added sodium hydride (358 mg, 8.95 mmol), and the mixture was stirred at room temperature for 30 minutes. Methyl iodide (0.46 mL, 8.21 mmol) was added thereto, and the mixture was stirred at room temperature for 4 hours. After the reaction completed, the reaction mixture was quenched with ice-cold water, extracted with ethyl acetate, and washed with water and brine. The organic layer was dried over anhydrous sodium sulfate and filtered, and the filtrate was concentrated under reduced pressure to obtain a crude compound. The crude compound was purified by silica gel (100-200 mesh) column chromatography, eluted with 30% ethyl acetate/petroleum ether, to obtain 2.46 g of Compound 4.

Yield: 73%, yield was calculated based on LC-MS purity of Compound 4

$^1$HNMR (400 MHz, DMSO-d$_6$) δ 1.41 (s, 3H), 2.04 (s, 3H), 2.24 (s, 3H), 2.46 (s, 3H), 4.59 (s, 1H), 4.83 (s, 1H), 7.06 (d, J=8.8 Hz, 2H), 7.25 (m, 5H), 7.57 (d, J=8.4 Hz, 2H), 10.11 (s, 1H) and LC-MS (M+1): 449.24

Step 5: Synthesis of N-(4-(6-benzyl-2,3,9-trimethyl-6H-thieno[2,3-e][1,2,4]-triazolo[3,4-c][1,2,4]triazepin-4-yl)phenyl)acetamide (Compound 5)

[Chem. 226]

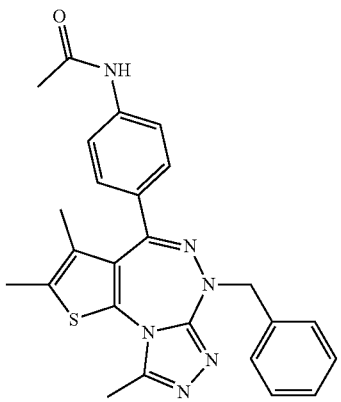

5

To a solution of Compound 4 (15 g, LC-MS: 83%) in ethanol (150 mL) were added PTSA.H$_2$O (630 mg, 3.34 mmol) and acetylhydrazine (6.14 g, 83 mmol), and the reaction mixture was stirred at 90° C. for 18 hours. After the reaction completed, the reaction mixture was concentrated under reduced pressure to obtain a residue. The residue was diluted with water and extracted with ethyl acetate. The organic layer was dried over anhydrous sodium sulfate and filtered, and the filtrate was concentrated under reduced pressure to obtain a crude compound. The crude compound was purified by comb flash instrument, eluted with 4% methanol/DCM, to obtain 8 g of Compound 5.

Yield: 63%, yield was calculated based on the purity of Compound 4

$^1$HNMR (400 MHz, DMSO-d$_6$) δ 1.50 (s, 3H), 2.04 (s, 3H), 2.07 (s, 3H), 2.36 (s, 3H), 2.53 (s, 3H), 4.75 (d, J=14 Hz, 1H), 4.99 (d, J=14 Hz, 1H), 7.22-728 (m, 3H), 7.33 (t, J=7.6 Hz, 2H), 7.38 (d, J=8.8 Hz, 2H), 10.12 (s, 1H) and LC-MS (M+1): 457.24

Step 6: Synthesis of 4-(2,3,9-trimethyl-6H-thieno[2,3-e][1,2,4]triazolo[3,4-c][1,2,4]triazepin-4-yl)aniline (Compound 6)

[Chem. 227]

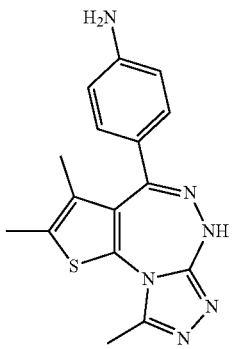

6

To a solution of Compound 5 (7 g, 15.35 mmol) in TFA (70 mL) was added sulfuric acid (7 mL) in a seal tube, and the reaction mixture was stirred at 100° C. for 18 hours.

After the reaction completed, the reaction mixture was quenched with a cooled saturated sodium hydrogen carbonate solution and extracted with ethyl acetate. The organic layer was dried over anhydrous sodium sulfate and filtered. The filtrate was concentrated under reduced pressure to obtain a crude compound, and it was triturated with acetonitrile. The solid was filtered and dried to obtain 2.6 g of Compound 6.

Yield: 53%, $^1$HNMR (400 MHz, DMSO-$d_6$) δ 1.59 (s, 3H), 2.35 (s, 3H), 2.51 (s, 3H, merged in DSMO peak), 5.54 (s, 2H), 6.53 (d, J=8.8 Hz, 2H), 7.08 (d, J=8 Hz, 2H), 9.44 (s, 1H) and LC-MS (M+1): 324.90

Step 7: Synthesis of the Compound of Example 94

N-(4-(2,3,9-trimethyl-6H-thieno[2,3-e][1,2,4]triazolo[3,4-c][1,2,4]triazepin-4-yl)phenyl)acetamide

[Chem. 228]

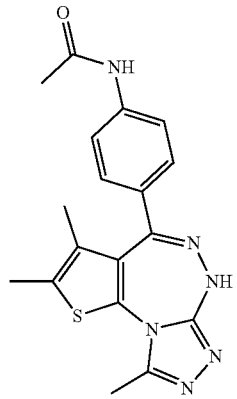

Acetic anhydride (26 mL) was added to Compound 6 (2.6 g, 8.02 mmol) at 0° C., and the reaction mixture was stirred at the same temperature for 2 hours. After the reaction completed, a solid precipitated in the reaction mixture was filtered, washed with acetic anhydride and hexane, and dried under highly vacuum to obtain a crude compound (solid). The crude compound (solid) was suspended in an aqueous saturated sodium bicarbonate solution. The mixture was stirred for 5 minutes, filtered, washed with water and dried under vacuum to obtain a solid. The solid was triturated with acetonitrile and filtered. The solid was washed with hexane and dried under highly vacuum to obtain 2.4 g of the compound of Example 94.

Yield: 81%, $^1$HNMR (400 MHz, DMSO-$d_6$) δ 1.52 (s, 3H), 2.05 (s, 3H), 2.35 (s, 3H), 2.42-2.47 (m, 3H), 7.35 (d, J=8.56 Hz, 2H), 7.63 (d, J=8.80 Hz, 2H), 9.72 (s, 1H), 10.13 (s, 1H) and LC-MS (M+1): 367.17

Synthetic Scheme of the Compounds of Examples 95, 106, 108 and 109

[Chem. 229]

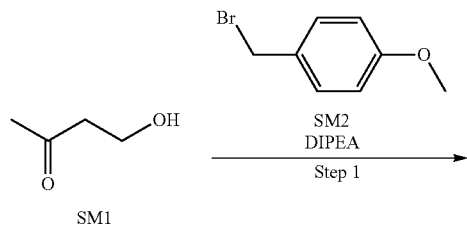

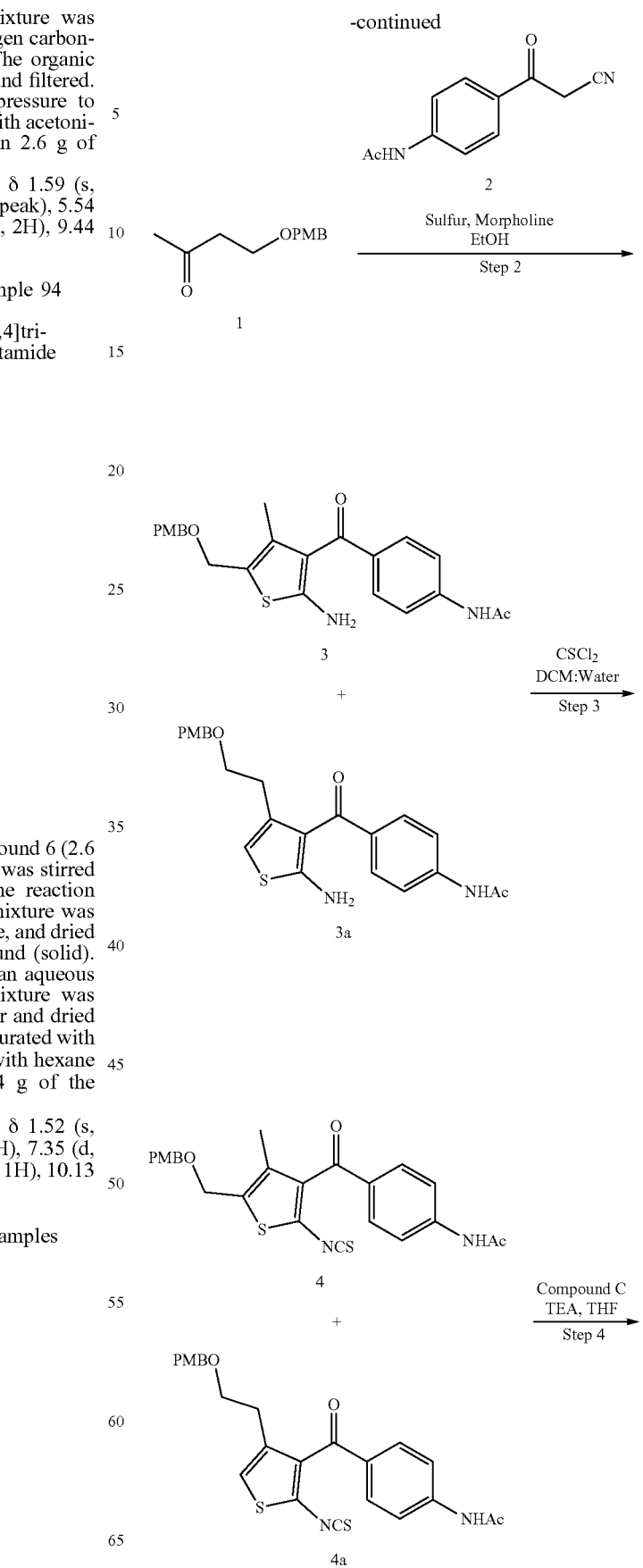

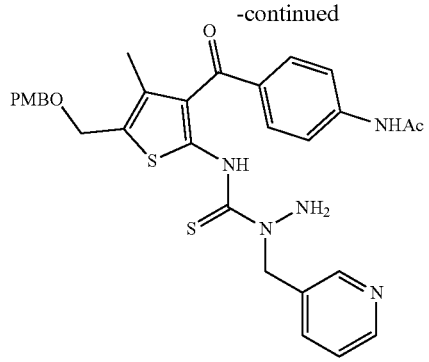
5
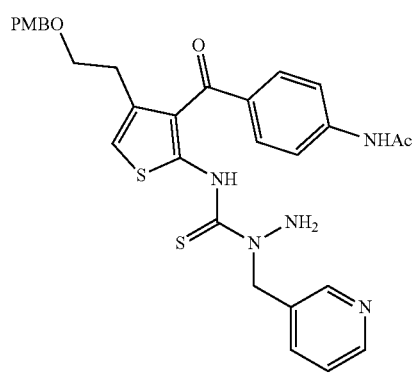
5a
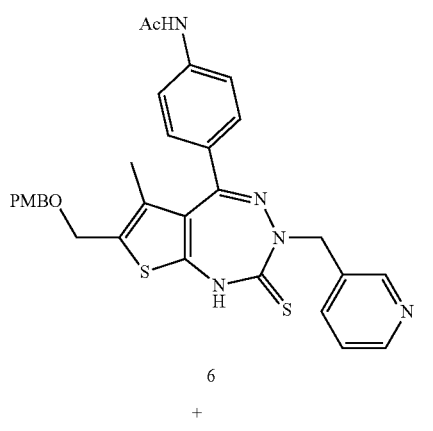
6
+
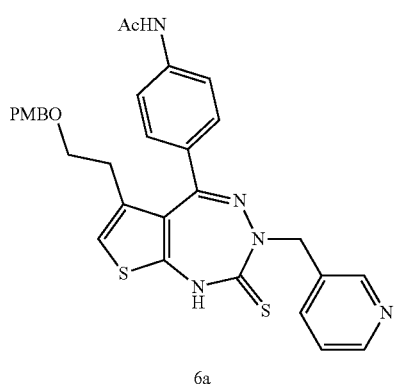
6a
PTSA·H₂O, EtOH
Step 5 →
MeI, NaH, THF
Step 6 →
[Chem. 229]
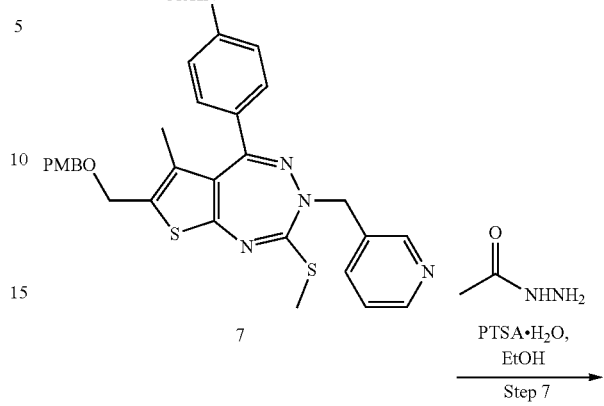
7
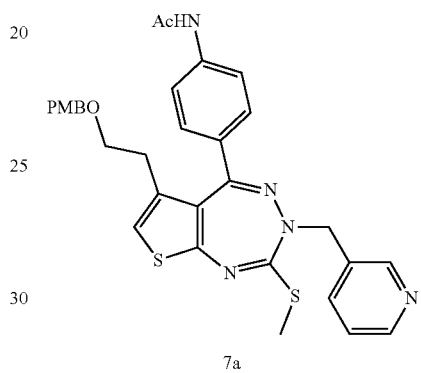
7a
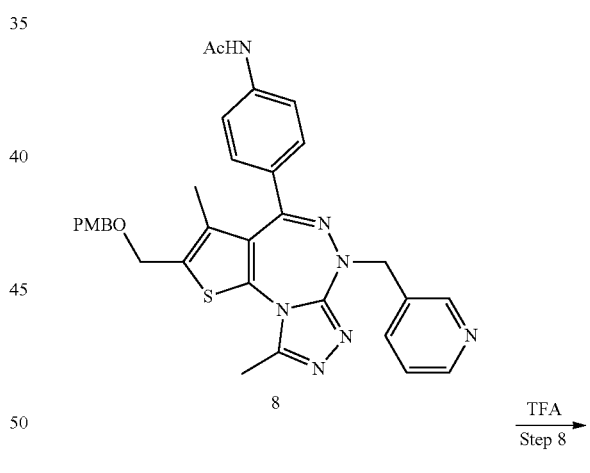
8
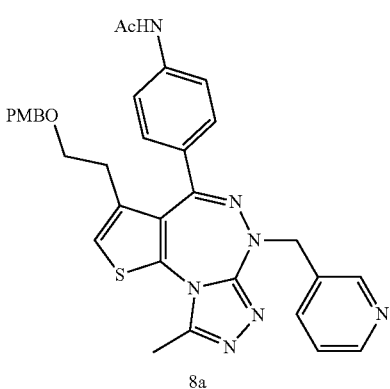
8a
PTSA·H₂O, EtOH
Step 7 →
TFA
Step 8 →

-continued

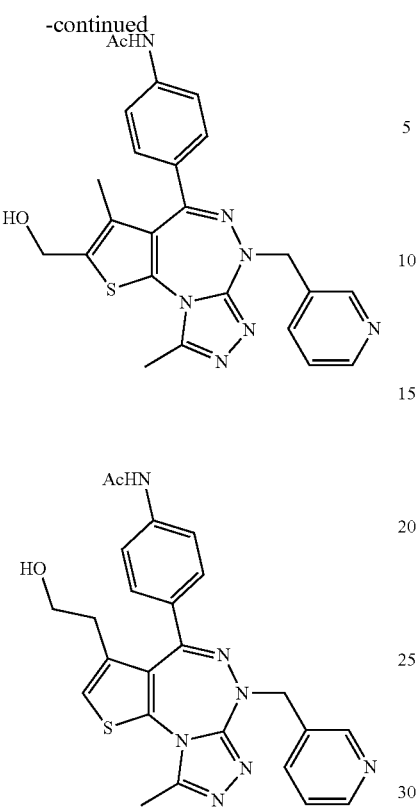

Step 1: Synthesis of 4-((4-methoxybenzyl)oxy)butan-2-one

[Chem. 230]

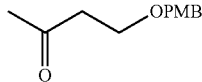

To a solution of compound SM1 (20 g, 113.49 mmol) in DIPEA (39.5 mL, 226.98 mmol) was added 4-methoxybromobenzyl (18 mL, 124.83 mmol), and the mixture was stirred at 120° C. for 10 hours. After the reaction completed, the reaction mixture was quenched with ice-water and extracted with ethyl acetate. The organic layer was washed with water and a brine solution. The organic layer was dried over anhydrous sodium sulfate and filtered, and the filtrate was concentrated under reduced pressure to obtain a crude compound. The crude compound was purified by silica gel (60-120 mesh) column chromatography, eluted with 10% ethyl acetate/petroleum ether, to obtain 31 g of Compound 1.

Yield: 66%, 1HNMR (500 MHz, CDCl$_3$) δ 2.16 (s, 3H), 2.69 (t, J=6.0 Hz, 2H), 2.70 (t, J=6.5 Hz, 2H), 3.79 (s, 3H), 4.43 (s, 2H), 6.87 (d, J=6.5 Hz, 2H), 7.24 (d, J=6.5 Hz, 2H) and GC-MS: 208.2

Step 2: Syntheses of N-(4-(2-amino-4-(2-((4-methoxybenzyl)oxy)ethyl)thiophen-3-carbonyl)phenyl)acetamide (Compound 3a) and N-(4-(2-amino-5-(((4-methoxybenzyl)oxy)methyl)-4-methylthiophen-3-carbonyl)phenyl)acetamide (Compound 3)

[Chem. 231]

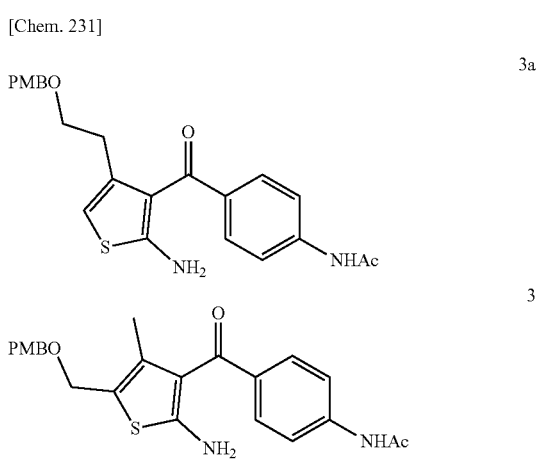

To a solution of Compound 2 (5 g, 24.75 mmol) in Scheme of Example 71 in ethanol (100 mL) were added Compound 1 (10.3 g, 49.5 mmol), morpholine (25 mL) and sulfur (0.972 mg, 24.75 mmol), and the mixture was stirred at 70° C. for 18 hours.

After the reaction completed, the reaction mixture was quenched with ice-water and extracted with ethyl acetate. The organic layer was washed with water and a brine solution, dried over anhydrous sodium sulfate and filtered, and the filtrate was concentrated under reduced pressure to obtain a crude compound. The crude compound was purified by column chromatography using silica gel (60-120 mesh), eluted with 50% ethyl acetate/petroleum ether, to obtain 4.3 g of Compounds 3 and 3a (LC-MS: 47%). The crude Compounds 3 and 3a were purified by preparative HPLC and two fractions were collected. The both fractions were lyophilized and confirmed by 1HNMR and LC-MS.

Fraction 1 (Compound 3a): 40 mg: N-(4-(2-amino-4-(2-((4-methoxybenzyl)oxy)ethyl)thiophen-3-carbonyl)phenyl)acetamide (Compound 3a)

1HNMR (500 MHz, DMSO-d$_6$) δ 2.07 (s, 3H), 2.32 (t, J=7 Hz, 2H), 3.25 (t, J=7 Hz, 2H), 3.70 (s, 3H), 4.16 (s, 2H), 6.09 (s, 1H), 6.84 (d, J=8 Hz, 2H), 7.08 (d, J=8 Hz, 2H), 7.38 (s, 1H), 7.42 (d, J=8 Hz, 2H), 7.66 (d, J=8 Hz, 2H), 10.17 (s, 1H) and LC-MS (M+1): 424.97

Fraction 2 (Compound 3): 150 mg: N-(4-(2-amino-5-(((4-methoxybenzyl)oxy)-methyl)-4-methylthiophen-3-carbonyl)phenyl)acetamide (Compound 3)

1HNMR (500 MHz, DMSO-d$_6$) δ 1.56 (s, 3H), 2.07 (s, 3H), 3.74 (s, 3H), 4.37 (d, J=6.5 Hz, 2H), 6.90 (d, J=8.5 Hz, 2H), 7.23 (d, J=8.5 Hz, 2H), 7.40 (d, J=8.5 Hz, 2H), 7.62 (s, 2H), 7.65 (d, J=8.5 Hz, 2H), 10.15 (s, 1H) and LC-MS (M+1): 425.15

Step 3: Synthesis of N-(4-(2-isothiocyanato-4-(2-((4-methoxybenzyl)oxy)ethyl)thiophen-3-carbonyl)phenyl) acetamide (Compound 4a) and N-(4-(2-isothiocyanato-5-(((4-methoxybenzyl)oxy)methyl)-4-methylthiophen-3-carbonyl)phenyl)acetamide (Compound 4)

[Chem. 232]

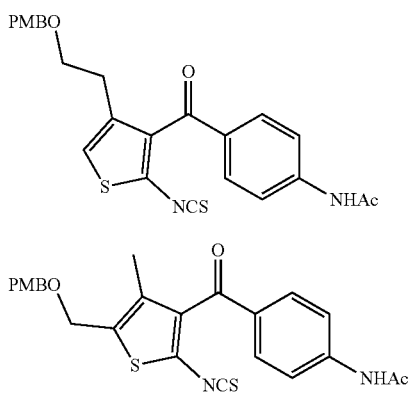

To a cooled (0° C.) solution of thiophosgene (3.25 mL, 25.58 mmol) in water (200 mL) was added Compound 3 (18 g, LC-MS: 37%) in DCM (400 mL), and the mixture was stirred at 0° C. for one hour and at room temperature for one hour. After the reaction completed, the reaction mixture was quenched with ice-water, extracted with DCM. The organic layer was dried over anhydrous sodium sulfate and filtered, and the filtrate was concentrated under reduced pressure to obtain 11 g. LC-MS analysis showed 14% of Compound 4 and 12% of Compound 4a in MS. The crude compound was used in the next Step without further purification. Compounds 4 and 4a (LC-MS, M+1): 467.07

Step 4: Syntheses of N-(4-(4-(2-((4-methoxybenzyl)oxy)ethyl)-2-(1-(pyridin-3-ylmethyl)hydrazine-1-carbothioamide)thiophen-3-carbonyl)phenyl)acetamide (Compound 5a) and N-(4-(5-(((4-methoxybenzyl)oxy)methyl)-4-methyl-2-(1-(pyridin-3-ylmethyl)hydrazine-1-carbothioamide)thiophen-3-carbonyl)phenyl)acetamide (Compound 5)

[Chem. 233]

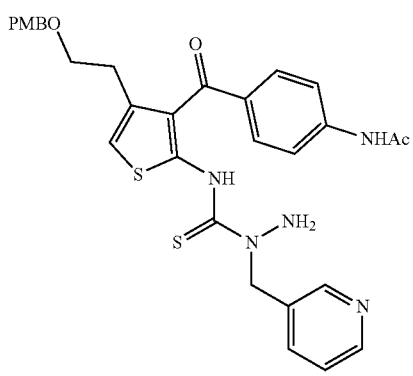

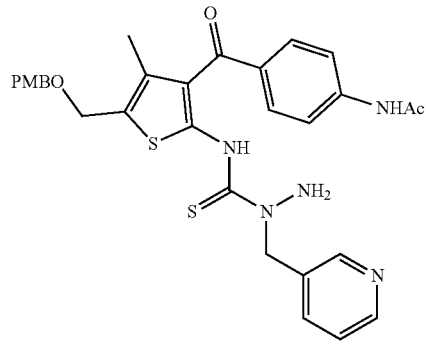

To a solution of Compounds 4 and 4a (8 g, LC-MS: 14% and 12%) in THF (160 mL) was added triethylamine (6.05 mL, 42.91 mmol), followed by Compound C (3.36 g, 17.16 mmol), and the mixture was stirred at 0° C. for one hour and at room temperature for 16 hours. After the reaction completed, the reaction mixture was concentrated under reduced pressure to obtain 9.2 g. LC-MS analysis showed 22% of Compound 5 and 11% of Compound 5a. The product was used in the next Step without further purification. LC-MS (M+1): 590.21

Step 5: Syntheses of N-(4-(6-(2-((4-methoxybenzyl)oxy)ethyl)-3-(pyridin-3-ylmethyl)-2-thioxo-2,3-dihydro-1H-thieno[2,3-e][1,2,4]triazepin-5-yl)phenyl) acetamide (Compound 6 a) and N-(4-(7-(((4-methoxybenzyl)oxy)methyl)-6-methyl-3-(pyridin-3-ylmethyl)-2-thioxo-2,3-dihydro-1H-thieno[2,3-e][1,2,4]triazepin-5-yl)phenyl)acetamide (Compound 6)

[Chem. 234]

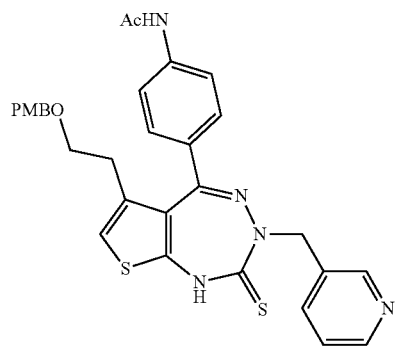

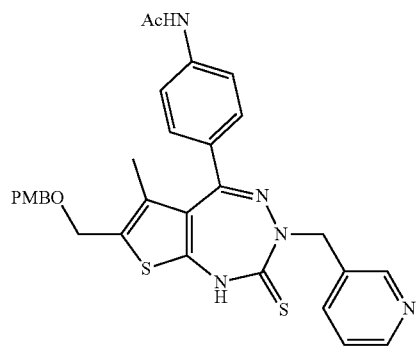

To a solution of Compounds 5 and 5a (9.2 g, LC-MS: 22 and 11%) in ethanol (200 mL) was added PTSA.H$_2$O (296 mg, 1.56 mmol), and the mixture was stirred at 80° C. for 48 hours. After the reaction completed, the reaction mixture was concentrated under reduced pressure to obtain a residue. The residue was diluted with water, extracted with ethyl acetate and washed with water and brine. The organic layer was dried over anhydrous sodium sulfate and filtered, and the filtrate was concentrated under reduced pressure to obtain a crude compound. The crude compound was purified by silica gel (100-200 mesh) column chromatography, followed by purification with grace instrument, eluted with 0.1% formic acid (in 35% acetonitrile in water), to obtain 3.1 g. LC-MS analysis showed 14% of Compound 6 and 41% of Compound 6a. The products were used in the next Step without further purification. LC-MS (M+1): 572.13

Note: Compound 5 was decomposed during the reaction, and showed low formation of Compound 6 in LC-MS.

Step 6: Syntheses of N-(4-(6-(2-((4-methoxybenzyl)oxy)ethyl)-2-(methylthio)-3-(pyridin-3-ylmethyl)-3H-thieno[2,3-e][1,2,4]triazepin-5-yl)phenyl)acetamide (Compound 7a) and N-(4-(7-(((4-methoxybenzyl)oxy)methyl)-6-methyl-2-(methylthio)-3-(pyridin-3-ylmeth yl)-3H-thieno[2,3-e][1,2,4]triazepin-5-yl)phenyl)acetamide (Compound 7)

[Chem. 235]

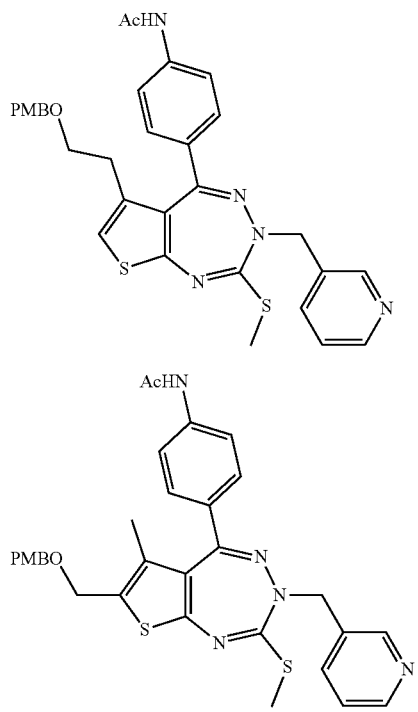

To a cooled (0° C.) solution of Compounds 6 and 6a (3.1 g, LC-MS: 14% and 41%) in THF (100 mL) was added sodium hydride (540 mg, 13.57 mmol), and the mixture was stirred at room temperature for 30 minutes. Methyl iodide (0.17 mL, 2.71 mmol) was added thereto, and the mixture was stirred at room temperature for 4 hours. After the reaction completed, the reaction mixture was quenched with ice-cold water, extracted with ethyl acetate and washed with water and brine. The organic layer was dried over anhydrous sodium sulfate and filtered, and the filtrate was concentrated under reduced pressure to obtain a crude compound. The crude compound was purified by combi instrument, eluted with 2% methanol/DCM, to obtain 1.6 g. LC-MS analysis showed 24% of Compound 7 and 57% of Compound 7a. The products were used in the next Step without further purification. LC-MS (M+1): 586.21

Step 7: Syntheses of 4-(3-(2-((4-methoxybenzyl)oxy)ethyl)-9-methyl-6-(pyridin-3-ylmethyl)-6H-thieno[2,3-e][1,2,4]triazolo[3,4-c][1,2,4]triazepin-4-yl)aniline (Compound 8a) and N-(4-(2-(((4-methoxybenzyl)oxy)methyl)-3,9-dimethyl-6-(pyridin-3-ylmethyl)-6H-thieno[2,3-e][1,2,4]triazolo[3,4-c][1,2,4]triazepin-4-yl)phenyl)acetamide (Compound 8)

[Chem. 236]

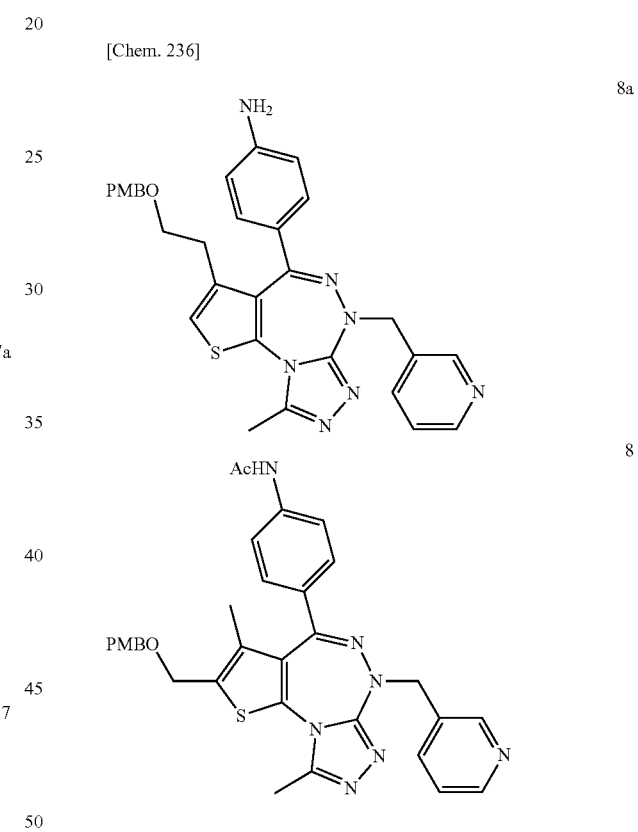

To a solution of Compounds 7 and 7a (1.6 g, LC-MS: 24% and 57%) in ethanol (50 mL) were added PTSA.H$_2$O (103 mg, 0.54 mmol) and acetohydrazide (1.01 g, 13.67 mmol), and the reaction mixture was stirred at 90° C. for 18 hours. After the reaction completed, the reaction mixture was concentrated under reduced pressure to obtain a residue, and the residue was diluted with water and extracted with ethyl acetate. The organic layer was dried over anhydrous sodium sulfate and filtered, and the filtrate was concentrated under reduced pressure to obtain a crude compound. The crude compound was purified by preparative HPLC and lyophilized to obtain two fractions, details of which are as follows.

Fraction 1 (Compound 8a): 420 mg: 4-(3-(2-((4-methoxybenzyl)oxy)ethyl)-9-methyl-6-(pyridin-3-ylmethyl)-6H-thieno[2,3-e][1,2,4]triazolo[3,4-c][1,2,4]triazepin-4-yl)aniline $^1$HNMR (400 MHz, DMSO-d$_6$) δ 1.91-1.98 (m, 1H), 2.04 (s, 3H), 2.39-2.46 (m, 1H), 2.57 (s, 3H), 3.13-3.17 (m, 2H), 3.72 (s, 3H), 4.08 (d, J=6.8 Hz, 2H), 4.79 (d, J=14 Hz, 1H), 4.97 (d, J=14 Hz, 1H), 6.84 (d, J=8.4 Hz, 2H), 7.06 (d, J=8.4 Hz, 2H), 7.19 (d, J=8.8 Hz, 2H), 7.29-7.32 (m, 1H), 7.39 (s, 1H), 7.59 (d, J=8.8 Hz, 2H), 7.76 (d, J=8 Hz, 1H), 8.46-8.47 (m, 1H), 8.61 (d, J=1.6 Hz, 1H), 10.14 (s, 1H) and LC-MS (M−1): 591.74

Fraction 2 (Compound 8): 140 mg: N-(4-(2-(((4-methoxybenzyl)oxy)methyl)-3,9-dimethyl-6-(pyridin-3-ylmethyl)-6H-thieno[2,3-e][1,2,4]triazolo[3,4-c][1,2,4]triazepin-4-yl)phenyl)acetamide (Compound 8)

$^1$HNMR (400 MHz, DMSO-d$_6$) δ 1.49 (s, 3H), 2.04 (s, 3H), 2.55 (s, 3H), 3.74 (s, 3H), 4.52 (s, 2H), 4.62 (d, J=2.8 Hz, 2H), 4.81 (d, J=14 Hz, 1H), 4.99 (d, J=14 Hz, 1H), 6.92 (d, J=6.4 Hz, 2H), 7.23 (d, J=8.8 Hz, 2H), 7.28 (d, J=8.8 Hz, 2H), 7.35-7.38 (m, 1H), 7.60 (d, J=8.8 Hz, 2H), 7.80 (d, J=8 Hz, 1H), 8.47 (m, 1H), 8.62 (d, J=1.6 Hz, 1H), 10.14 (s, 1H) and LC-MS (M+1): 594.97

Step 8: N-(4-(2-(hydroxymethyl)-3,9-dimethyl-6-(pyridin-3-ylmethyl)-6H-thieno[2,3-e][1,2,4]triazolo[3,4-c][1,2,4]triazepin-4-yl)phenyl)acetamide (Compound of Example 95)

[Chem. 237]

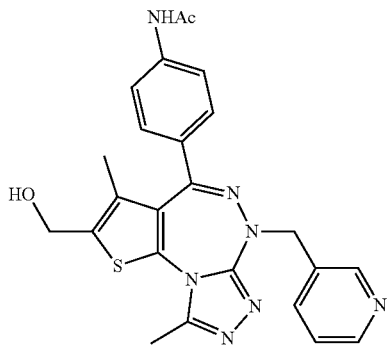

Compound 8 (80 mg, 0.134 mmol) was added to TFA (2.5 mL) in a seal tube, and the mixture was stirred at 40° C. for 18 hours. After the reaction completed, the reaction mixture was cooled to room temperature, added dropwise to a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was purified by preparative HPLC and lyophilized to obtain 17 mg of the compound of Example 95.

Yield: 27%, $^1$H NMR (400 MHz, DMSO-d$_6$) δ 1.50 (s, 3H), 2.04 (s, 3H), 2.56 (m, 3H), 4.62 (d, J=10.0 Hz, 2H), 4.80 (d, J=13.94 Hz, 1H), 5.00 (d, J=13.94 Hz, 1H), 5.79 (s, 1H), 7.24 (d, J=8.56 Hz, 2H), 7.38 (dd, J=7.82, 4.89 Hz, 1H), 7.61 (d, J=8.80 Hz, 2H), 7.80-7.83 (m, 1H), 8.48 (dd, J=4.65, 1.71 Hz, 1H), 8.62 (d, J=1.47 Hz, 1H), 10.14 (s, 1H) and LC-MS (M−1): 472.24

Compound of Example 109: N-(4-(3-(2-hydroxyethyl)-9-methyl-6-(pyridin-3-ylmethyl)-6H-thieno[2,3-e][1,2,4]triazolo[3,4-c][1,2,4]triazepin-4-yl)phenyl)acetamide (Compound of Example 109)

[Chem. 238]

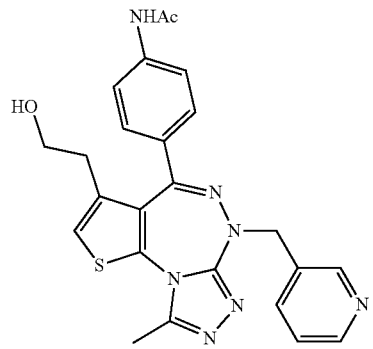

Compound 8a (300 mg, 0.505 mmol) was added to TFA (5 mL) in a seal tube, and the mixture was stirred at 40° C. for 18 hours. After the reaction completed, the reaction mixture was cooled to room temperature, added dropwise to a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was purified by preparative HPLC to obtain 28 mg of the compound of Example 109.

Yield: 11%, $^1$HNMR (500 MHz, DMSO-d$_6$) δ 1.85-1.92 (m, 1H), 2.04 (s, 3H), 2.23-2.29 (m, 1H), 2.51 (s, 3H), 3.22-3.25 (m, 2H), 4.52 (t, J=9.5 Hz, 1H), 4.83 (d, J=14.5 Hz, 1H), 4.99 (d, J=14.0 Hz, 1H), 7.19 (t, J=8.5 Hz, 2H), 7.35-7.39 (m, 2H). 7.59 (d, J=8.5 Hz, 2H), 7.77-7.80 (m, 1H), 8.48 (dd, J=4.5, 1.5 Hz, 1H), 8.62 (d, J=1.5 Hz, 1H), 10.14 (brs, 1H) and LC-MS (M+1): 474.19

Step 9: Synthesis of 2-(4-(4-aminophenyl)-9-methyl-6-(pyridin-3-ylmethyl)-6H-thieno[2,3-e][1,2,4]triazolo[3,4-c][1,2,4]triazepin-3-yl)ethane-1-ol (Compound of Example 108)

[Chem. 239]

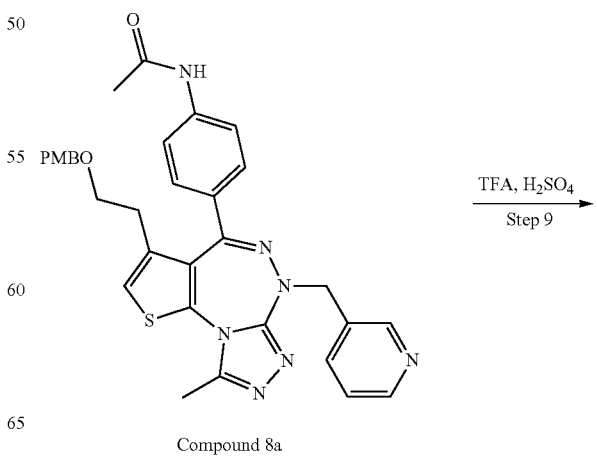

Compound 8a

-continued

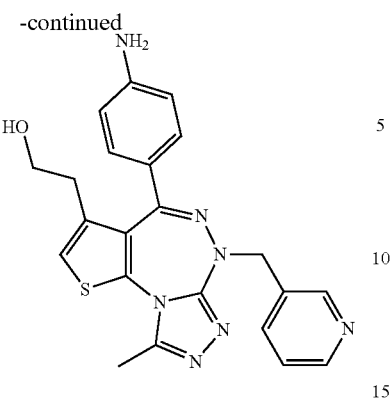

Compound 8a (600 mg, LC-MS: 52.57%) in TFA (10 mL) was added to sulfuric acid (0.1 mL) at room temperature, and the reaction mixture was stirred at 120° C. for 16 hours in a seal tube. After the reaction completed, the reaction mixture was cooled to room temperature, added dropwise to a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was purified by preparative HPLC and lyophilized to obtain 60 mg of the compound of Example 108.

Yield: 23%, yield was calculated based on the purity of Compound 8a $^1$HNMR (400 MHz, DMSO-d6) δ 2.05-2.10 (m, 1H), 2.31-2.38 (m, 1H), 2.56 (s, 3H), 3.23-3.26 (m, 2H), 4.51 (s, 1H), 4.78 (d, J=14.25 Hz, 1H), 4.94 (d, J=14.25 Hz, 1H), 5.61 (s, 2H), 6.49 (d, J=8.77 Hz, 2H), 6.94 (d, J=8.33 Hz, 2H), 7.32-7.36 (m, 2H), 7.75 (d, J=7.89 Hz, 1H), 8.46 (dd, J=4.82, 1.53 Hz, 1H), 8.59 (d, J=1.75 Hz, 1H) and LC-MS (M+1): 432.22

Step 10: Synthesis of (4-(4-aminophenyl)-3,9-dimethyl-6-(pyridin-3-ylmethyl)-6H-thieno[2,3-e][1,2,4]triazolo[3,4-c][1,2,4]triazepin-2-yl)methanol (Compound of Example 10)

[Chem. 240]

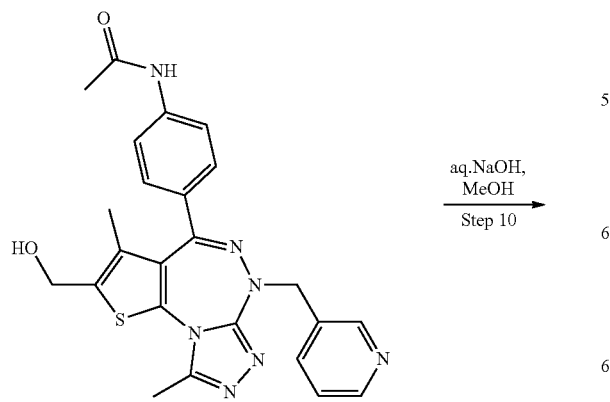

aq.NaOH, MeOH
Step 10

-continued

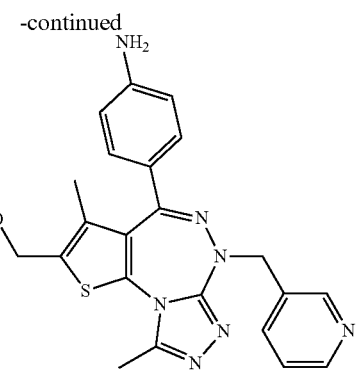

To a solution of the compound of Example 95 (30 mg, 0.063 mmol) in methanol:water (2:1, 4.5 mL) was added sodium hydroxide (150 mg) at room temperature, and the reaction mixture was stirred at 90° C. for 18 hours. After the reaction completed, the reaction mixture was diluted with water and extracted with 10% methanol/DCM. The organic layer was dried over sodium sulfate and filtered, and the filtrate was concentrated under reduced pressure to obtain a crude compound. The crude compound was triturated with diethyl ether and dried under highly vacuum to obtain 13 mg of the compound of Example 106.

Yield: 48%, $^1$HNMR (500 MHz, DMSO-d$_6$) δ 1.58 (s, 3H), 2.56 (s, 3H), 4.58-4.67 (m, 2H), 4.75 (d, J=14 Hz, 1H), 4.95 (d, J=14 Hz, 1H), 5.62 (s, 2H), 5.76 (t, J=5.5 Hz, 1H), 6.50 (d, J=9 Hz, 2H), 6.98 (d, J=8.5 Hz, 2H), 7.34-7.36 (m, 1H), 7.76-7.78 (m, 1H), 8.45-8.47 (m, 1H), 8.59 (d, J=1.5 Hz, 2H) and LC-MS: 432.19

Synthetic Scheme of the Compounds of Examples 96 and 107

[Chem. 241]

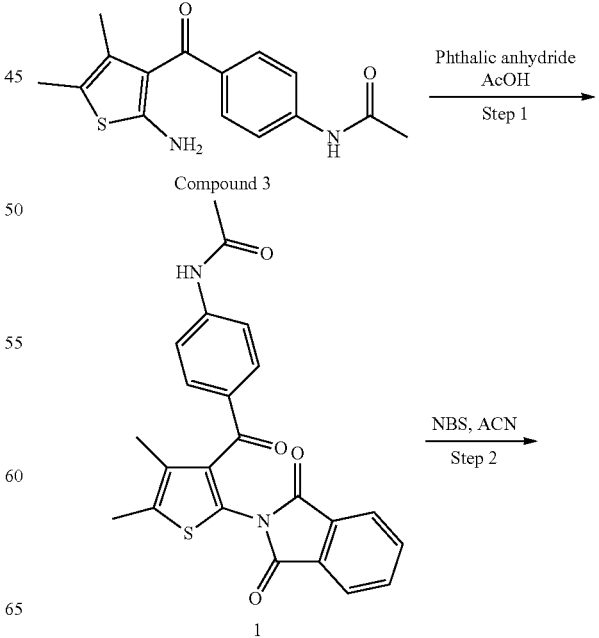

Phthalic anhydride
AcOH
Step 1

Compound 3

NBS, ACN
Step 2

1

175
-continued
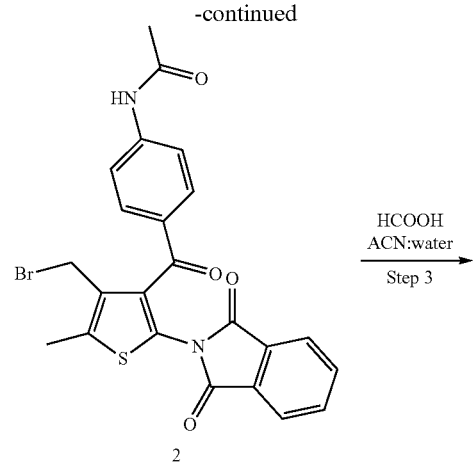
2
HCOOH
ACN:water
Step 3
→
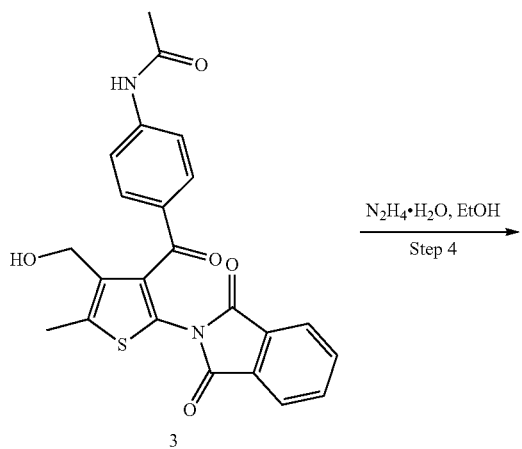
3
N₂H₄·H₂O, EtOH
Step 4
→
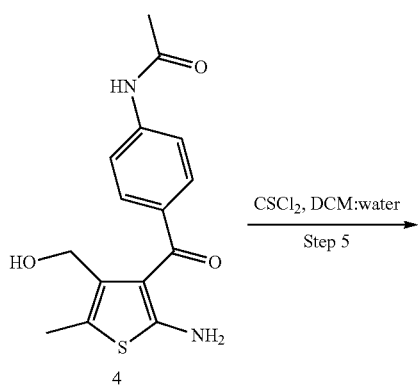
4
CSCl₂, DCM:water
Step 5
→
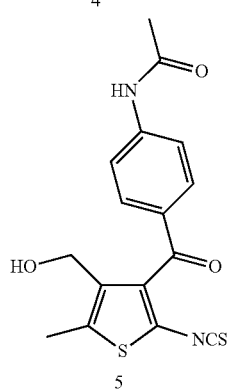
5
Compound C
TEA, THF
Step 6
→
176
-continued
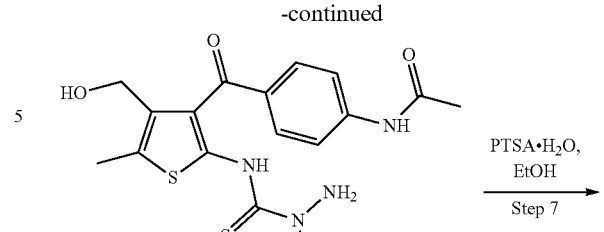
6
PTSA·H₂O, EtOH
Step 7
→
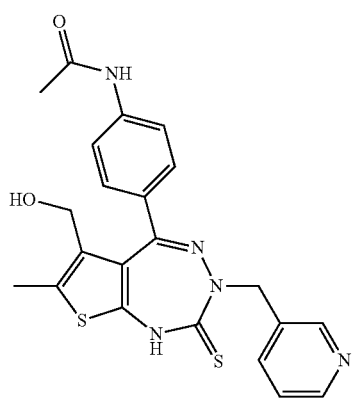
7
NaH, MeI
THF
Step 8
→
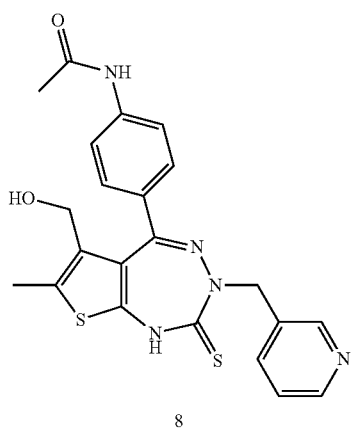
8
AcNHNH₂
PTSA·H₂O, EtOH
Step 9
→
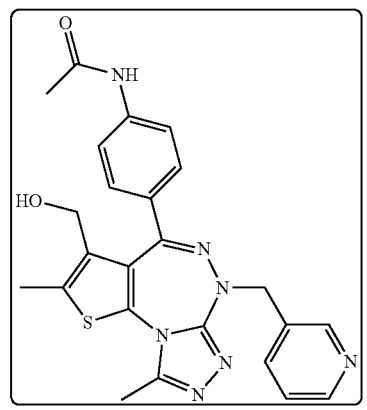
Conc·HCl, THF
Step 10
→

-continued

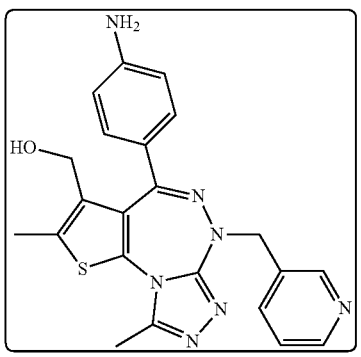

Step 1: Synthesis of N-(4-(2-(1,3-dioxoisoindolin-2-yl)-4,5-dimethylthiophen-3-carbonyl)phenyl)acetamide (Compound 1)

[Chem. 242]

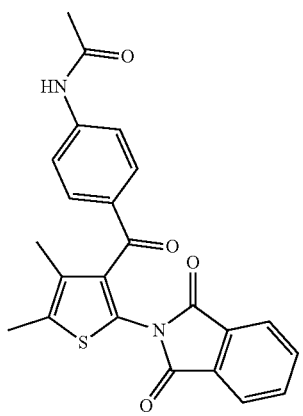

1

To a stirred solution of Compound 3 in Scheme of Example 100 (1 g, 3.47 mmol) in acetic acid (20 mL) was added phthalic anhydride (617 mg, 4.16 mmol), and the mixture was stirred at 120° C. for 16 hours. After the reaction completed, the reaction mixture was concentrated under reduced pressure to obtain a residue. The residue was diluted with water, made basic with saturated sodium hydrogen carbonate and extracted with ethyl acetate. The organic layer was washed with water and a brine solution, dried over anhydrous sodium sulfate, and filtered. The filtrate was distilled off under reduced pressure to obtain a crude compound. The crude compound was triturated with diethyl ether to obtain 1 g of Compound 1.

Yield: 69%, $^1$HNMR (400 MHz, CDCl$_3$) δ 2.06 (s, 3H), 2.13 (s, 3H), 2.41 (s, 3H), 7.19 (s, 1H), 7.44 (d, J=8 Hz, 1H), 7.66-7.69 (m, 2H), 7.72 (dd, J=2 & 7.2 Hz, 2H), 7.77-7.79 (m, 2H) and LC-MS (M+1): 419.15

Step 2: Synthesis of N-(4-(4-(bromomethyl)-2-(1,3-dioxoisoindolin-2-yl)-5-methylthiophen-3-carbonyl)phenyl)acetamide (Compound 2)

[Chem. 243]

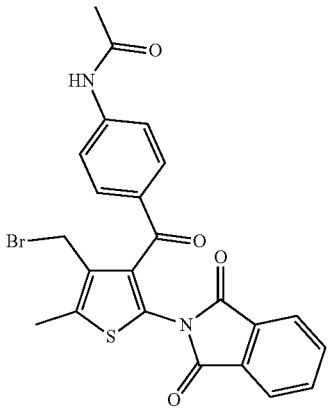

2

To a stirred solution of Compound 1 (700 mg, 1.67 mmol) in acetonitrile (20 L) was added NBS (596 mg, 3.349 mmol), and the mixture was stirred at 90° C. for 16 hours. After the reaction completed, the reaction mixture was concentrated under reduced pressure to obtain a residue. The residue was diluted with water, extracted with ethyl acetate, washed with water and a brine solution, dried over anhydrous sodium sulfate, and filtered. The filtrate was distilled off under reduced pressure to obtain 700 mg of Compound 2 (LC-MS: 45%), which was used in the next Step without further purification. LC-MS (M+1): 499.04

Step 3: Synthesis of N-(4-(2-(1,3-dioxoisoindolin-2-yl)-4-(hydroxymethyl)-5-methylthiophen-3-carbonyl)phenyl)acetamide (Compound 3)

[Chem. 244]

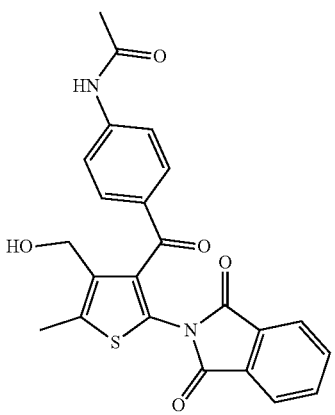

3

To a solution of Compound 2 (800 mg, LC-MS: 36.6%1 in acetonitrile:water (1:1, 10 mL) was added formic acid (1 mL) at room temperature, and the mixture was stirred at 60° C. for 16 hours. After the reaction completed, the reaction mixture was quenched with water, extracted with ethyl acetate and washed with brine. The organic layer was dried over anhydrous sodium sulfate and filtered, and the filtrate was distilled off under reduced pressure to obtain a crude compound. The crude compound was purified by combi flash instrument, eluted with 3% methanol/DCM, to obtain 100 mg of Compound 3 (LC-MS: 78%), which was used in the next Step without further purification. LC-MS (M+1): 433.28.

Step 4: Synthesis of N-(4-(2-amino-4-(hydroxymethyl)-5-methylthiophen-3-carbonyl)phenyl)acetamide (Compound 4)

[Chem. 245]

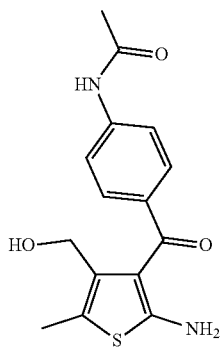

4

To a solution of Compound 3 (110 mg, LC-MS: 78%) in ethanol (5 mL) was added hydrazinehydrate (1 mL) at room temperature, and the mixture was stirred at room temperature for 16 hours. After the reaction completed, the reaction mixture was concentrated under reduced pressure to obtain a residue, and the residue was diluted with ethyl acetate and washed with water and brine. The organic layer was dried over anhydrous sodium sulfate and filtered, and the filtrate was distilled off under reduced pressure to obtain a crude compound. The crude compound was triturated with diethyl ether to obtain 40 mg of Compound 4.

Yield: 50%, $^1$HNMR (400 MHz, DMSO-$d_6$) δ 2.08 (s, 3H), 2.199 (s, 3H), 3.91 (d, J=6.0 Hz, 2H), 4.36 (t, J=4.8 Hz, 1H), 7.09 (s, 2H), 7.46 (d, J=8.4 Hz, 2H), 7.62 (d, J=8.8 Hz, 2H), 10.17 (s, 1H) and LC-MS (M+1): 305.12

Step 5: Synthesis of N-(4-(4-(hydroxymethyl)-2-isothiocyanato-5-methylthiophen-3-carbonyl)phenyl)acetamide (Compound 5)

[Chem. 246]

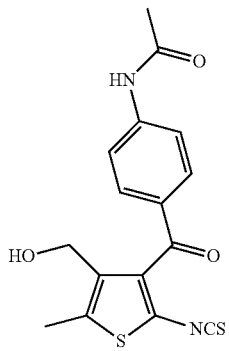

5

To a cooled solution (0° C.) of thiophosgene (0.06 mL, 0.74 mmol) in water (2 mL) was added Compound 4 (150 mg, LC-MS: 64%) in DCM (10 mL), and the mixture was stirred at 0° C. for one hour and at room temperature for one hour. After the reaction completed, the reaction mixture was quenched with ice-water and extracted with DCM. The organic layer was dried over anhydrous sodium sulfate and filtered, and the filtrate was concentrated under reduced pressure to obtain 100 mg of a crude Compound 5 (LC-MS purity: 27%), which was used in the next Step without further purification. LC-MS: 345.21

Step 6: Synthesis of N-(4-(4-(hydroxymethyl)-5-methyl-2-(1-(pyridin-3-ylmethyl)hydrazine-1-carbothioamide)thiophen-3-carbonyl)phenyl)acetamide (Compound 6)

[Chem. 247]

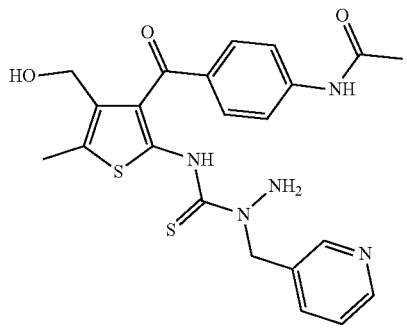

6

To a solution of Compound 5 (100 mg, LC-MS: 27%) in THF (5 mL) was added TEA (0.1 mL, 0.72 mmol), followed by Compound C (57 mg, 0.28 mmol) in Scheme of Example 71 at 0° C., and the mixture was stirred at room temperature for 16 hours. After the reaction completed, the reaction mixture was concentrated under reduced pressure to obtain 150 mg of Compound 6 (LC-MS purity: 53%), which was used in the next Step without further purification. LC-MS (M+1): 470.10

Step 7: Synthesis of N-(4-(6-(hydroxymethyl)-7-methyl-3-(pyridin-3-ylmethyl)-2-thioxo-2,3-dihydro-1H-thieno[2,3-e][1,2,4]triazepin-5-yl)phenyl)acetamide (Compound 7)

[Chem. 248]

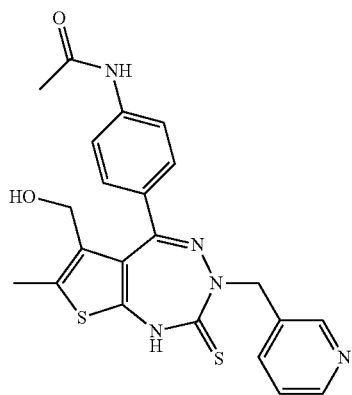

7

To a solution of Compound 6 (1.5 g, LC-MS: 62%) in ethanol (50 mL) was added PTSA.H$_2$O (122 mg, 0.63 mmol), and the reaction mixture was stirred at 90° C. for 4 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude compound. The crude compound was purified by silica gel (100-200 mesh) column chromatography, eluted with 8% methanol/DCM, to obtain 500 mg of Compound 7 (LC-MS purity: 58%), which was used in the next Step without further purification. LC-MS (M+1): 452.12

Step 8: Synthesis of N-(4-(6-(hydroxymethyl)-7-methyl-2-(methylthio)-3-(pyridin-3-ylmethyl)-3H-thieno[2,3-e][1,2,4]triazepin-5-yl)phenyl)acetamide (Compound 8)

[Chem. 249]

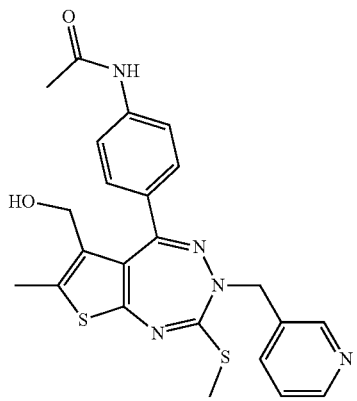

8

To a cooled (0° C.) solution of Compound 7 (500 mg, LC-MS: 58%) in THF (20 mL) was added sodium hydride (111 mg, 2.27 mmol), and the mixture was stirred at room temperature for 30 minutes. Methyl iodide (0.04 mL, 0.55 mmol) was added thereto, and the mixture was stirred at room temperature for one hour. After the reaction completed, the reaction mixture was quenched with ice-cold water, extracted with ethyl acetate and washed with water and brine. The organic layer was dried over anhydrous sodium sulfate and filtered, and the filtrate was concentrated under reduced pressure to obtain 300 mg of a crude Compound 8 (LC-MS purity: 29%), which was used in the next Step without further purification. LC-MS (M+1): 466.14

Step 9: Synthesis of N-(4-(3-(hydroxymethyl)-2,9-dimethyl-6-(pyridin-3-ylmethyl)-6H-thieno[2,3-e][1,2,4]triazolo[3,4-c][1,2,4]triazepin-4-yl)phenyl)acetamide (compound of Example 96)

[Chem. 250]

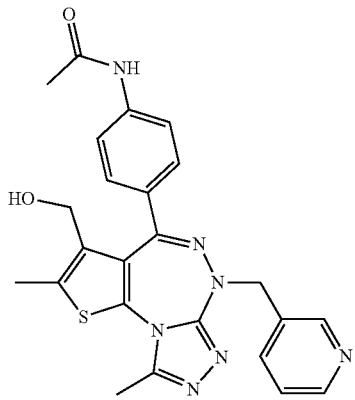

To a solution of Compound 8 (300 mg, LC-MS: 29%) in ethanol (10 mL) were added PTSA.H$_2$O (25 mg, 0.13 mmol) and acetylhydrazine (240 mg, 3.22 mmol), and the reaction mixture was stirred at 90° C. for 30 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude compound. The crude compound was purified by combi flash, eluted with 10% methanol/DCM, to obtain 200 mg of a compound (LC-MS: 34% of compound mass of Example 96), which was further purified by preparative HPLC to obtain 10 mg of the compound of Example 96.

Yield: 11%, yield was calculated based on the purity of Compound 8

$^1$HNMR (400 MHz, DMSO-d$_6$) δ 2.04 (s, 3H), 2.46 (s, 3H), 2.55 (s, 3H), 3.53 (dd, J=12.72 & 6.36 Hz, 1H), 4.05 (dd, J=12.59 & 3.79 Hz, 1H), 4.69 (dd, J=6.11 & 3.91 Hz, 1H), 4.78-4.85 (m, 1H), 5.01 (d, J=14.43 Hz, 1H), 7.24 (d, J=8.56 Hz, 2H), 7.34 (dd, J=7.70 & 4.77 Hz, 1H), 7.57 (d, J=8.80 Hz, 2H), 7.81 (dd, J=7.82, 1.71 Hz, 1H), 8.47 (dd, J=4.77 & 1.59 Hz, 1H), 8.64 (d, J=1.71 Hz, 1H), 10.13 (s, 1H) and LC-MS (M−1): 472.24

183

Step 10: Synthesis of (4-(4-aminophenyl)-2,9-dimethyl-6-(pyridin-3-ylmethyl)-6H-thieno[2,3-e][1,2,4]triazolo[3,4-c][1,2,4]triazepin-3-yl)methanol (Compound of Example 107)

[Chem. 251]

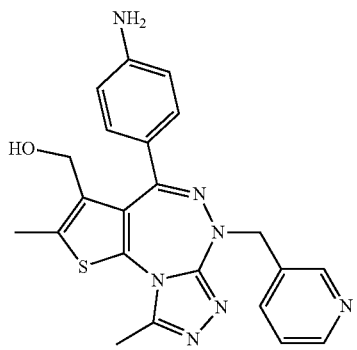

To a solution of the compound of Example 96 (350 mg, LC-MS: 75%) in THF (10 mL) was added conc. hydrochloric acid (5 mL), and the mixture was stirred at 60° C. for 16 hours. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was purified by grace instrument, eluted with 0.1% formic acid (in 15% acetonitrile in water), to obtain 200 mg of the compound of Example 107 (LC-MS: 87%), which was further purified by preparative HPLC to obtain 50 mg of the compound of Example 107.

Yield: 20%, yield was calculated based on the purity of the compound of Example 96

$^1$HNMR (500 MHz, DMSO-$d_6$) δ 2.48 (s, 3H), 2.53 (s, 3H), 3.71 (dd, J=12.51, 5.80 Hz, 1H), 4.08 (dd, J=12.51, 3.97 Hz, 1H), 4.67 (t, J=4.27 Hz, 1H), 4.76 (d, J=14.34 Hz, 1H), 4.96 (d, J=14.34 Hz, 1H), 5.57 (s, 2H), 6.49 (d, J=8.85 Hz, 2H), 6.99 (d, J=8.54 Hz, 2H), 7.31 (dd, J=7.5, 4.5 Hz, 1H), 7.77-7.78 (m, 1H), 8.45 (dd, J=4.88, 1.53 Hz, 1H), 8.61 (d, J=1.83 Hz, 1H) and LC-MS (M+1): 432.19

Synthetic Scheme of the compounds of Examples 97 and 101

[Chem. 252]

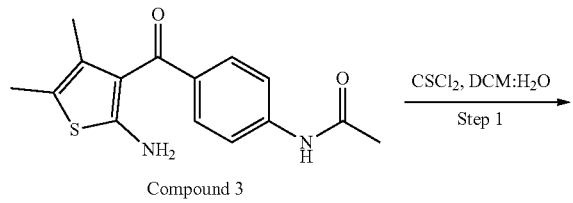

Compound 3

184

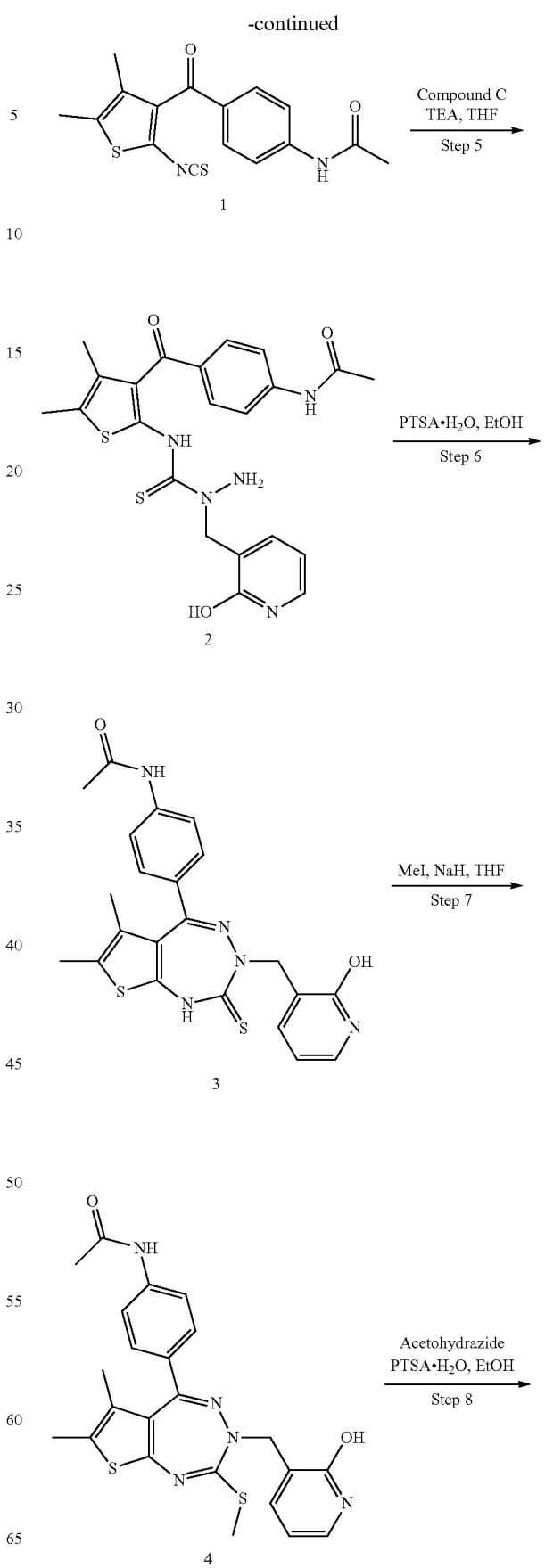

-continued

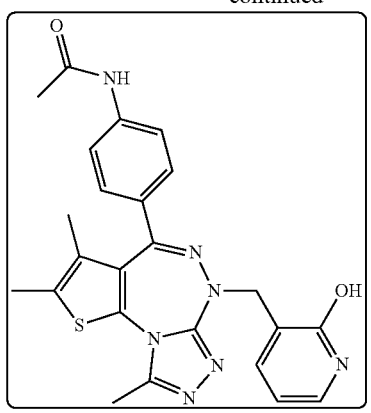

THF, Conc•HCl
Step 9

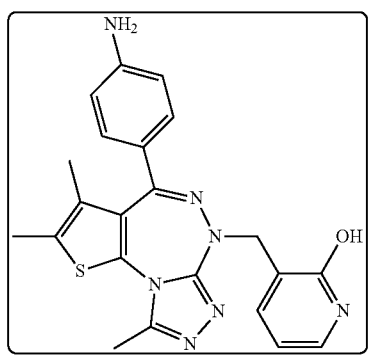

[Chem. 253]

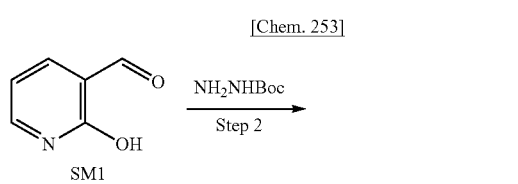

Step 2

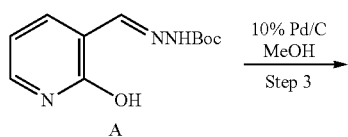

10% Pd/C
MeOH
Step 3

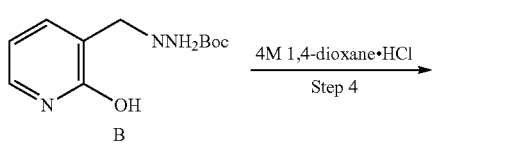

4M 1,4-dioxane•HCl
Step 4

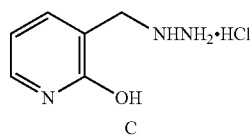

Step 1: Synthesis of N-(4-(2-isothiocyanato-4,5-dimethylthiophen-3-carbonyl)phenyl)acetamide (Compound 1)

[Chem. 254]

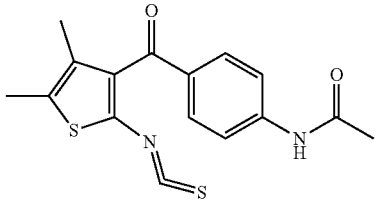

1

To a solution of thiophosgene (2 mL, 26.04 mmol) in water (20 mL) was added a solution of Compound 3 in Scheme of Example 71 (5 g, 17.36 mmol) in DCM (20 mL) at 0° C., and the mixture was stirred at the same temperature for one hour and at room temperature for one hour. After the reaction completed, the reaction mixture was quenched with ice-water, extracted with DCM and washed with brine. The organic layer was dried over anhydrous sodium sulfate and filtered, and the filtrate was concentrated under reduced pressure to obtain a crude Compound 1 (LC-MS: 83%), which was used in the next step without further purification. LC-MS (M+1): 331.19

Step 2: Synthesis of tert-butyl(Z)-2-((2-hydroxypyridin-3-yl)methylene)hydrazine-1-carboxylate (Compound A)

[Chem. 255]

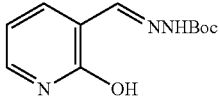

A

To a solution of SM1 (10 g, 81.3 mmol) in methanol (150 mL) was added tert-butyl carbazate (11.8 g, 89.43 mmol), and the mixture was stirred at room temperature for 6 hours. After the reaction completed, methanol was concentrated under reduced pressure to obtain a crude compound. The crude compound was triturated with diethyl ether to obtain 13 g of Compound A.
Y: 67.5%, $^1$HNMR (400 MHz, DMSO-$d_6$) δ 1.45 (s, 9H), 6.27 (t, J=6.5 Hz, 1H), 7.44 (d, J=6 Hz, 1H), 7.85 (d, J=6.5 Hz, 1H), 8.13 (s, 1H) and LC-MS (M+1): 238.15.

Step 3: Synthesis of tert-butyl 2-((2-hydroxypyridin-3-yl)methyl)hydrazine-1-carboxylate (Compound B)

[Chem. 256]

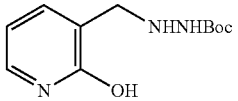

B

To a solution of Compound A (5 g, 21.1 mmol) in methanol (100 mL) was added 10% Pd/C (1 g), and the reaction mixture was stirred under a balloon pressure for 72 hours. After the reaction completed, the reaction mixture was filtered through a celite pad and washed with methanol, and the filtrate was concentrated under reduced pressure to obtain a crude compound. The crude compound was triturated with diethyl ether to obtain 2.5 g of Compound B.

Y: 67.5%, $^1$HNMR (400 MHz, DMSO-$d_6$) δ 1.35 (s, 9H), 3.60 (d, J=5.2 Hz, 2H), 4.76 (d, J=4 Hz, 1H), 6.13 (t, J=6.8 Hz, 1H), 7.24-7.25 (m, 1H), 7.39-7.41 (m, 1H), 8.25 (s, 1H), 11.51 (s, 1H) and LC-MS (M+1): 240.20 (de-boc mass).

Step 4: Synthesis of 3-(hydrazinylmethyl)pyridin-2-ol hydrochloride (Compound C)

[Chem. 257]

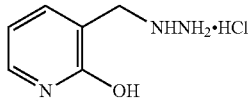

C

To a solution of Compound B (2.5 g, 10.46 mmol) in 1,4-dioxane (30 mL) was added 4M 1,4-dioxane.HCl (30 mL) at 10° C., and the reaction mixture was stirred at room temperature for 72 hours. After the reaction completed, the reaction mixture was concentrated under reduced pressure to obtain a crude compound. The crude compound was triturated with diethyl ether to obtain 2 g of Compound C.

Y: 67.5%, $^1$HNMR (400 MHz, DMSO-$d_6$) δ 3.88 (s, 2H), 6.26 (d, J=6.8 Hz, 1H), 7.42 (dd, J=6.4 & 2 Hz, 1H), 7.53 (dd, J=6.4 & 2 Hz, 1H), 12.00 (brs, 1H) and LC-MS (M+1): 140.23

Step 5: Synthesis of N-(4-(2-(1-((2-hydroxypyridin-3-yl)methyl)hydrazine-1-carbothioamide)-4,5-dimethylthiophen-3-carbonyl)phenyl)acetamide (Compound 2)

[Chem. 258]

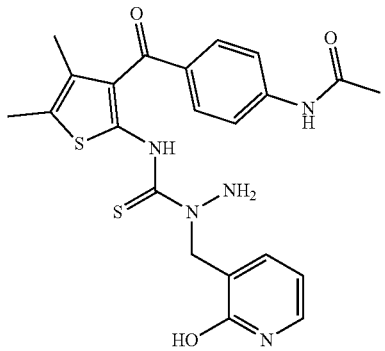

2

To a solution of Compound 1 (3 g, LC-MS: 83%) in THF (60 mL) was added TEA (3.2 mL, 22.72 mmol), followed by Compound C (1.92 g, 9.09 mmol) at 0° C., and the mixture was stirred at room temperature for 16 hours. After the reaction completed, the reaction mixture was concentrated under reduced pressure to obtain a crude compound. The crude compound was triturated with diethyl ether to obtain 5 g of Compound 2 (LC-MS: 84%), which was used in the next Step without further purification. LC-MS (M+1): 470.24.

Step 6: Synthesis of N-(4-(3-((2-hydroxypyridin-3-yl)methyl)-6,7-dimethyl-2-thioxo-2,3-dihydro-1H-thieno[2,3-e][1,2,4]triazepin-5-yl)phenyl)acetamide (Compound 3)

[Chem. 259]

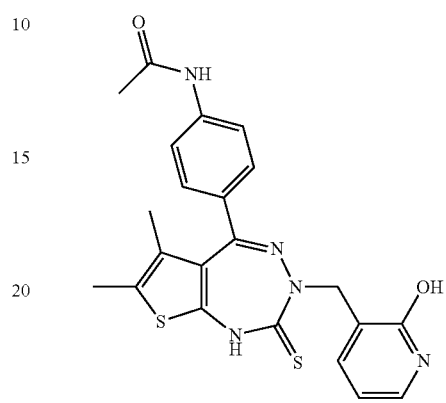

3

To a solution of Compound 2 (5 g, LC-MS: 84%) in ethanol (60 mL) was added PTSA.$H_2O$ (405 mg, 2.13 mmol), and the mixture was stirred at 90° C. for 16 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude compound. The crude compound was purified by flash column chromatography, eluted with 6% methanol/DCM, to obtain 2.5 g of Compound 3 (LC-MS: 55%), which was used in the next Step without further purification. LC-MS (M+1): 452.25.

Step 7: Synthesis of N-(4-(3-((2-hydroxypyridin-3-yl)methyl)-6,7-dimethyl-2-(methylthio)-3H-thieno[2,3-e][1,2,4]triazepin-5-yl)phenyl)acetamide (Compound 4)

[Chem. 260]

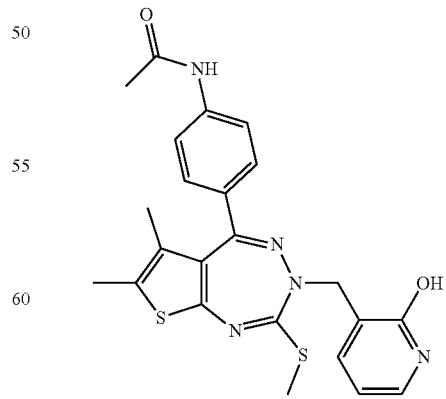

7

To a cooled (0° C.) solution of Compound 3 (20 g, LC-MS: 73%) in THF (600 mL) was added sodium hydride (3.54 g, 88.69 mmol), and the mixture was stirred at room temperature for 30 minutes. Methyl iodide (1.93 mL, 31.04 mmol) was added thereto, and the mixture was stirred at room temperature for 3 hours. After the reaction completed, the reaction mixture was quenched with ice-cold water, extracted with ethyl acetate and washed with water and brine. The organic layer was dried over anhydrous sodium sulfate and filtered, and the filtrate was concentrated under reduced pressure to obtain a crude Compound 4. The crude compound was triturated with ethyl acetate to obtain 6 g of Compound 4.

Y: 40%, yield was calculated based on the purity of Compound 3

$^1$HNMR (400 MHz, DMSO-$d_6$) δ 1.46 (s, 3H), 2.05 (s, 3H), 2.24 (s, 3H), 2.46 (s, 3H), 4.32 (brs, 1H), 4.66 (brs, 1H), 6.19 (t, J=6.8 Hz, 1H), 7.17 (d, J=28 Hz, 2H), 7.08 (d, J=6.4 Hz, 2H), 7.61 (d, J=8.4 Hz, 2H), 10.13 (brs, 1H), 11.69 (brs, 1H) and LC-MS (M+1): 466.21.

Step 8: Synthesis of N-(4-(6-((2-hydroxypyridin-3-yl)methyl)-2,3,9-trimethyl-6H-thieno[2,3-e][1,2,4]triazolo[3,4-c][1,2,4]triazepin-4-yl)phenyl)acetamide (Compound of Example 97)

[Chem. 261]

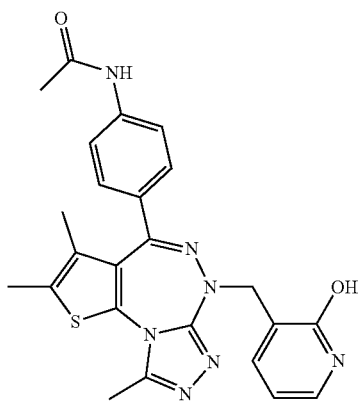

To a solution of Compound 4 (6 g, 12.9 mmol) in ethanol (200 mL) were added PTSA.H$_2$O (490 mg, 2.58 mmol) and acetylhydrazine (4.8 g, 64.51 mmol), and the reaction mixture was stirred at 90° C. for 16 hours. After the reaction completed, the reaction mixture was concentrated under reduced pressure to obtain a residue. The residue was diluted with water and extracted with 10% methanol/DCM. The organic layer was dried over anhydrous sodium sulfate and filtered, and the filtrate was concentrated under reduced pressure to obtain a crude compound. The crude compound was purified by grace instrument, eluted with 0.1% formic acid/25% acetonitrile in water, to obtain 1.4 g of the compound of Example 97 (LC-MS: 87%), which was further purified by SFC to obtain 720 mg of the compound of Example 97.

Yield: 11%, $^1$H NMR (400 MHz, DMSO-$d_6$) δ 1.53 (s, 3H), 2.05 (s, 3H), 2.36 (s, 3H), 2.54 (s, 3H), 4.51 (d, J=15.13 Hz, 1H), 4.83 (d, J=14.91 Hz, 1H), 6.19 (t, J=6.69 Hz, 1H), 7.27-7.40 (m, 4H), 7.62 (d, J=8.77 Hz, 2H), 10.12 (s, 1H), 11.62 (brs, 1H) and LC-MS (M+1): 474.16

Step 9: Synthesis of 3-((4-(4-aminophenyl)-2,3,9-trimethyl-6H-thieno[2,3-e][1,2,4]triazolo[3,4-c][1,2,4]triazepin-6-yl)methyl)pyridin-2-ol (Compound of Example 101)

[Chem. 262]

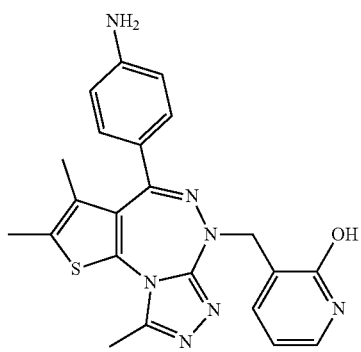

To a solution of the compound of Example 97 (3 g, LC-MS: 31%) in THF (30 mL) was added conc. hydrochloric acid (30 mL), and the mixture was stirred at 70° C. for 8 hours. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate, and filtered. The filtrate was distilled off under reduced pressure to obtain 500 mg of a crude compound (LC-MS: 81%). The compound of Example 101 (92 mg) was obtained by preparative HPLC purification.

Yield: 11%, yield was calculated based on the purity of the compound of Example 97

$^1$H NMR (500 MHz, DMSO-$d_6$) δ 1.62 (s, 3H), 2.37 (s, 3H), 2.53 (s, 3H), 4.46 (d, J=15.56 Hz, 1H), 4.75 (d, J=15.26 Hz, 1H), 5.61 (s, 2H), 6.17 (t, J=6.71 Hz, 1H), 6.52 (d, J=8.54 Hz, 2H), 7.04 (d, J=8.24 Hz, 2H), 7.26-7.33 (m, 2H), 11.58 (brs, 1H) and LC-MS (M+1): 432.15

Synthetic Scheme of the Compounds of Examples 98 and 102

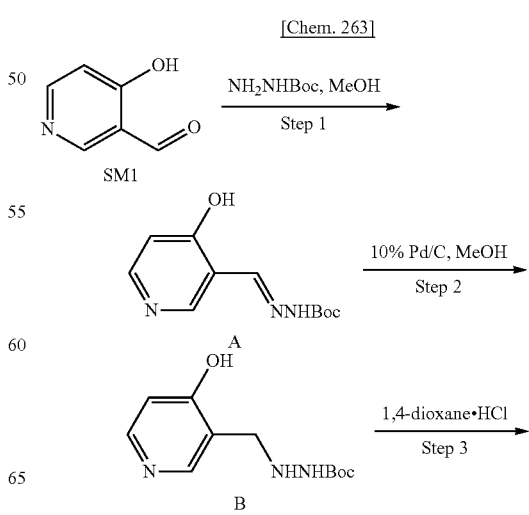

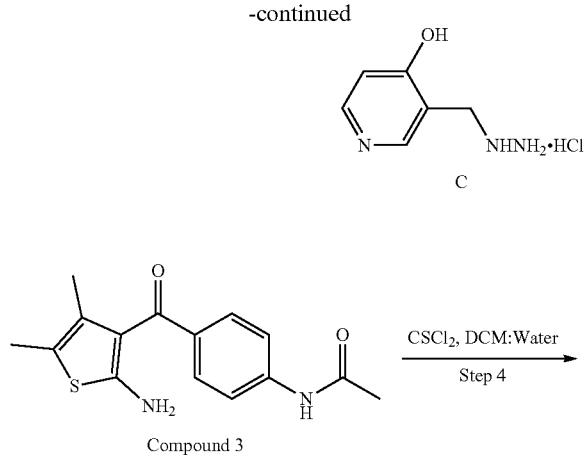
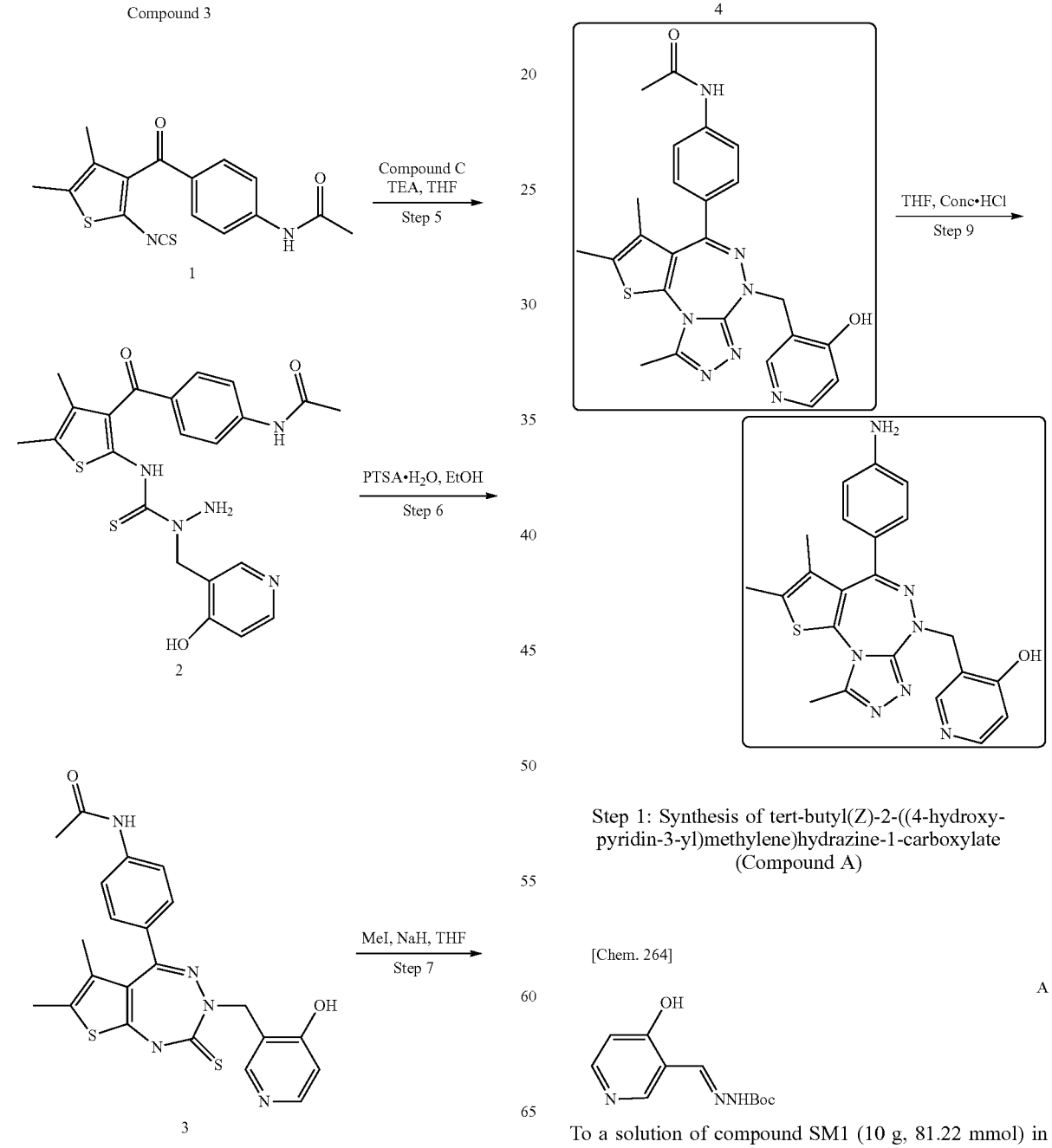
Step 1: Synthesis of tert-butyl(Z)-2-((4-hydroxy-pyridin-3-yl)methylene)hydrazine-1-carboxylate (Compound A)
[Chem. 264]
To a solution of compound SM1 (10 g, 81.22 mmol) in methanol (200 mL) was added tert-butyl carbazate (11.8 g, 89.34 mmol), and the mixture was stirred at room temperature for 16 hours. After the reaction completed, methanol was concentrated under reduced pressure to obtain a crude compound. The crude compound was triturated with diethyl ether to obtain 16 g of Compound A.

Yield: 83%, ¹HNMR (400 MHZ, DMSO-$d_6$) δ 1.45 (s, 9H), 6.22 (s, 1H), 7.68 (s, 1H), 8.04 (s, 1H), 8.12 (s, 1H), 10.82 (brs, 1H), 11.77 (brs, 1H) and LC-MS (M+1): 238.05

Step 2: Synthesis of tert-butyl 2-((4-hydroxypyridin-3-yl)methyl)hydrazine-1-carboxylate (CompoundB)

[Chem. 265]

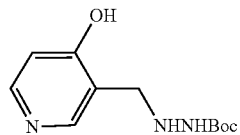

B

To a solution of Compound A (16 g, 67.51 mmol) in methanol (500 mL) was added 10% Pd/C (4 g), and the reaction mixture was stirred in a Parr shaker at room temperature under a hydrogen pressure of 80 psi for 48 hours. After the reaction completed, the reaction mixture was filtered through a celite pad and washed with methanol, and the filtrate was concentrated under reduced pressure to obtain a crude compound. The crude compound was triturated with methanol, and the solid was filtered, washed with diethyl ether and dried under highly vacuum to obtain 9.2 g of Compound B.

Yield: 57%, ¹HNMR (500 MHz, DMSO-d6) δ1.36 (s, 9H), 3.57 (s, 2H), 4.74 (s, 1H), 6.04 (s, 1H), 7.61 (brs, 2H), 8.24 (brs, 1H), 11.33 (s, 1H) and LC-MS (M+1): 240.06.

Step 3: Synthesis of 3-(hydrazinylmethyl)pyridin-4-ol hydrochloride (Compound C)

[Chem. 266]

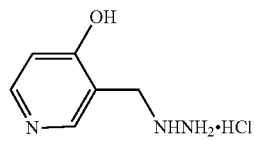

C

To a solution of Compound B (9.2 g, 38.49 mmol) in 1,4-dioxane (50 mL) was added 1,4 dioxane.HCl (4M, 50 mL) at 10° C., and the reaction mixture was stirred at room temperature for 16 hours. After the reaction completed, the reaction mixture was concentrated under reduced pressure to obtain a crude compound. The crude compound was triturated with diethyl ether to obtain 9 g of Compound C (with excessive salts). Compound C was confirmed by ¹H NMR and used in the next step without further purification.

1HNMR (500 MHz, DMSO-$d_6$) δ 4.04 (s, 3H), 7.33 (d, J=6.5 Hz, 1H), 8.45 (t, J=9.75 Hz, 2H), 11.52 (s, 1H).

Step 4: Synthesis of N-(4-(2-isothiocyanato-4,5-dimethylthiophen-3-carbonyl)phenyl)acetamide (Compound 1)

[Chem. 267]

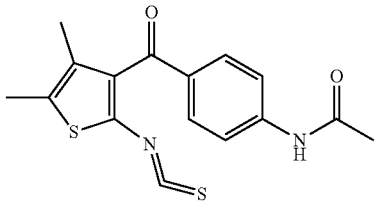

1

To a solution of thiophosgene (10 mL, 130.2 mmol) in water (250 mL) was added a solution of Compound 3 in Scheme of Example 71 (50 g, 173 mmol) in DCM (500 mL) at 0° C., and the mixture was stirred at the same temperature for one hour and at room temperature for one hour. After the reaction completed, the reaction mixture was quenched with ice-water, extracted with DCM and washed with brine. The organic layer was dried over anhydrous sodium sulfate and filtered, and the filtrate was concentrated under reduced pressure to obtain a crude compound. The crude compound was purified by silica gel column chromatography, eluted with DCM, to obtain 40 g of Compound 1. LC-MS (M+1): 331.09

Yield: 70%, used in the next Step without further purification.

Step 5: Synthesis of N-(4-(2-(1-((4-hydroxypyridin-3-yl)methyl)hydrazine-1-carbothioamide)-4,5-dimethylthiophen-3-carbonyl)phenyl)acetamide (Compound 2)

[Chem. 268]

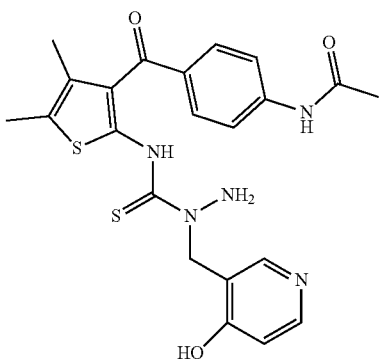

2

To a solution of Compound 1 (40 g, 120.8 mmol) in THF (200 mL) was added triethylamine (21.3 mL, 151.51 mmol), followed by Compound C (12.78 g, 60.6 mmol), and the mixture was stirred at 0° C. for one hour and at room temperature for 24 hours.

After the reaction completed, the reaction mixture was concentrated under reduced pressure to obtain 80 g (LC-MS: 42%) of a crude Compound 2, which was used in the next Step without further purification. LC-MS (M+1): 470.20

Step 6: Synthesis of N-(4-(3-((4-hydroxypyridin-3-yl)methyl)-6,7-dimethyl-2-thioxo-2,3-dihydro-1H-thieno[2,3-e][1,2,4]triazepin-5-yl)phenyl)acetamide (Compound 3)

[Chem. 269]

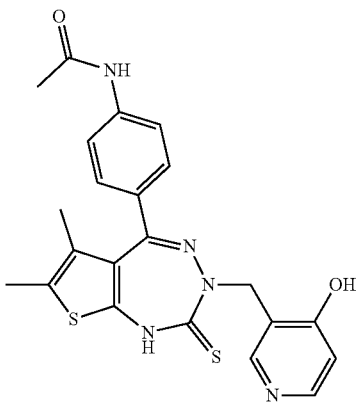

To a solution of Compound 2 (80 g, LC-MS: 42%) in ethanol (400 mL) was added PTSA.H$_2$O (1.6 g, 8.52 mmol), and the mixture was stirred at 90° C. for 18 hours. After the reaction completed, the reaction mixture was concentrated under reduced pressure to obtain a residue. The residue was diluted with water and extracted with ethyl acetate. The organic layer was dried over anhydrous sodium sulfate and filtered, and the filtrate was concentrated under reduced pressure to obtain a crude compound. The crude compound was purified by silica gel (100-200 mesh) column chromatography, eluted with 3% methanol/DCM, to obtain 50 g of Compound 3 (LC-MS: 72%), which was used in the next step without further purification. LC-MS (M+1): 452.15

Step 7: Synthesis of N-(4-(3-((4-hydroxypyridin-3-yl)methyl)-6,7-dimethyl-2-(methylthio)-3H-thieno[2,3-e][1,2,4]triazepin-5-yl)phenyl)acetamide (Compound 4)

[Chem. 270]

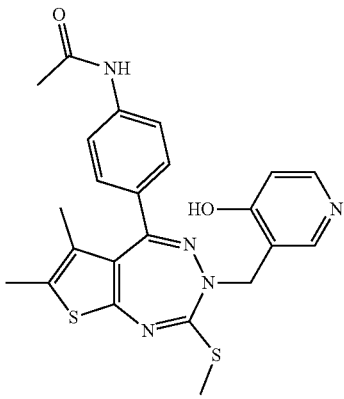

To a cooled (0° C.) solution of Compound 3 (50 g, LC-MS: 72%) in THF (1,000 mL) was added sodium hydride (8.85 g, 221 mmol), and the mixture was stirred at room temperature for 30 minutes. Methyl iodide (5.5 mL, 88.65 mmol) was added thereto, and the mixture was stirred at room temperature for 4 hours. After the reaction completed, the reaction mixture was quenched with ice-cold water, extracted with ethyl acetate, washed with water and brine, dried over anhydrous sodium sulfate, and filtered.

The filtrate was concentrated under reduced pressure to obtain a crude compound. The crude compound was purified by silica gel (100-200 mesh) column chromatography, eluted with 8% methanol/DCM, and two fractions were collected. Details are as follows.

Fraction 1: 7 g of Compound 4 (LC-MS: 92%)
Fraction 2: 20 g of Compound 4 (LC-MS: 59%)

The above-mentioned fractions were used in the next step without further purification.

$^1$HNMR (400 MHz, DMSO-d$_6$) δ 1.46 (s, 3H), 2.05 (s, 3H), 2.24 (s, 3H), 2.46 (s, 3H), 4.22 (brs, 1H), 4.66 (brs, 1H), 6.09 (dd, J=0.8 & 7.2 Hz, 1H), 7.18 (d, J=8.4 Hz, 2H), 7.50 (d, J=4 Hz, 1H), 7.60-7.65 (m, 3H), 10.14 (s, 1H), 11.31 (s, 1H) and LC-MS (M+1): 466.24.

Step 8: Synthesis of N-(4-(6-((4-hydroxypyridin-3-yl)methyl)-2,3,9-trimethyl-6H-thieno[2,3-e][1,2,4]triazolo[3,4-c][1,2,4]triazepin-4-yl)phenyl)acetamide (compound of Example 98)

[Chem. 271]

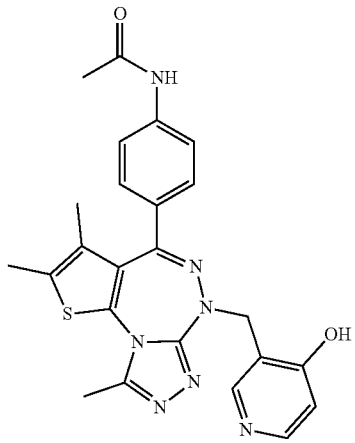

To a solution of Compound 4 (4 g, LC-MS: 92%) in ethanol (80 mL) were added PTSA.H$_2$O (326 mg, 1.72 mmol) and acetylhydrazine (1.9 g, 25.8 mmol), and the reaction mixture was stirred at 90° C. for 18 hours. After the reaction completed, the reaction mixture was concentrated under reduced pressure to obtain a residue, and the residue was diluted with water and extracted with ethyl acetate. The organic layer was dried over anhydrous sodium sulfate and filtered, and the filtrate was concentrated under reduced pressure to obtain a crude compound. The crude compound was purified by comb flash instrument, eluted with 12% methanol/DCM, to obtain 900 mg, which was further purified by preparative HPLC to obtain 255 mg of the compound of Example 98.

Yield: 4%, $^1$H NMR (400 MHz, DMSO-d$_6$) δ 1.53 (s, 3H), 2.05 (s, 3H), 2.36 (s, 3H), 2.54 (s, 3H), 4.51 (d, J=15.13 Hz, 1H), 4.83 (d, J=14.91 Hz, 1H), 6.19 (t, J=6.69 Hz, 1H), 7.27-7.40 (m, 4H), 7.62 (d, J=8.77 Hz, 2H), 10.12 (s, 1H), 11.62 (brs, 1H) and LC-MS (M+1): 474.20

Step 9: Synthesis of 3-((4-(4-aminophenyl)-2,3,9-trimethyl-6H-thieno[2,3-e][1,2,4]triazolo[3,4-c][1,2,4]triazepin-6-yl)methyl)pyridin-4-ol (Compound of Example 102)

[Chem. 272]

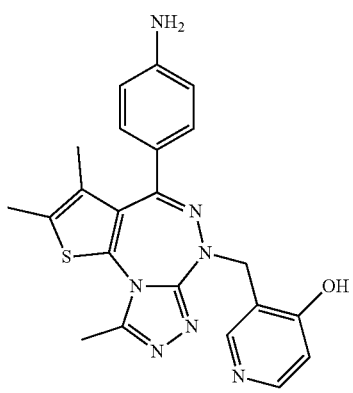

To a solution of the compound of Example 98 (200 mg, 0.42 mmol) in THF (10 mL) was added conc. hydrochloric acid (10 mL), and the mixture was stirred at 70° C. for 18 hours. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate, and filtered. The filtrate was distilled off under reduced pressure to obtain 150 mg of a crude compound, which was triturated with acetonitrile and filtered. The solid was dissolved in acetonitrile:water (8:2, 5 mL) and lyophilized to obtain 118 mg of the compound of Example 102.

Yield: 63%, $^1$H NMR (400 MHz, DMSO-$d_6$) δ 1.61 (s, 3H), 2.27-2.37 (m, 3H), 2.52 (s, 3H), 4.40 (d, J=14.43 Hz, 1H), 4.72 (d, J=14.67 Hz, 1H), 5.63 (brs, 2H), 6.09 (brs, 1H), 6.52 (d, J=8.80 Hz, 2H), 7.05 (d, J=8.31 Hz, 2H), 7.59 (brs, 2H), 11.31 (brs, 1H) and LC-MS (M+1): 432.15

Synthetic Scheme of the Compounds of Examples 99 and 103

[Chem. 273]

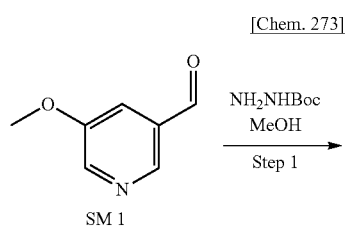

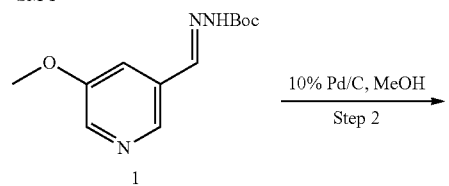

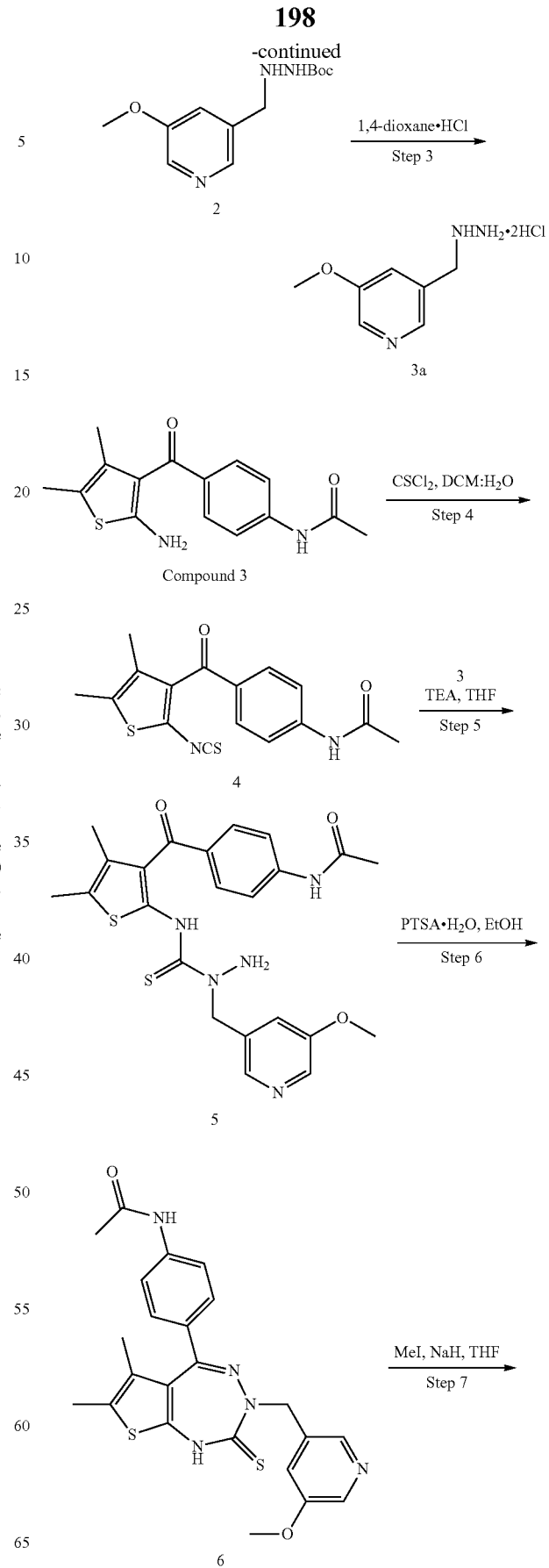

199
-continued

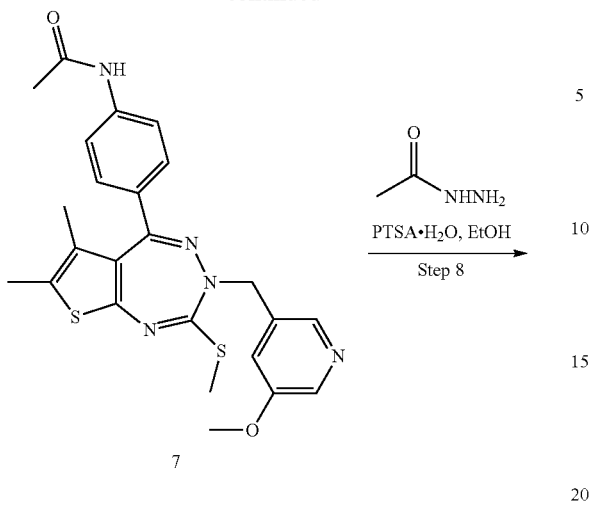
7

PTSA·H₂O, EtOH
Step 8

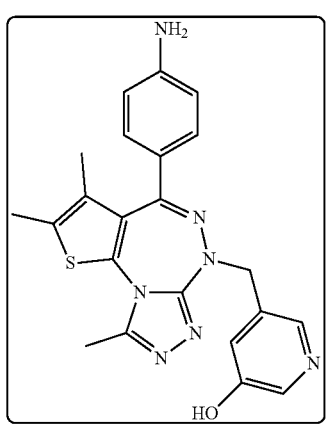
8

TFA, H₂SO₄
Step 9 i) Ac₂O, THF
ii) K₂CO₃, MeOH
Step 10 & 11

200
-continued

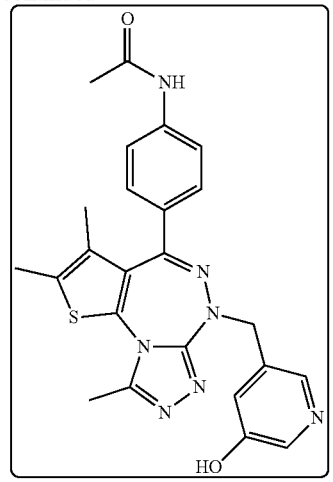

Step 1: Synthesis of tert-butyl (E)-2-((5-methoxy-pyridin-3-yl)methylene)-hydrazine-1-carboxylate (Compound 1)

[Chem. 274]

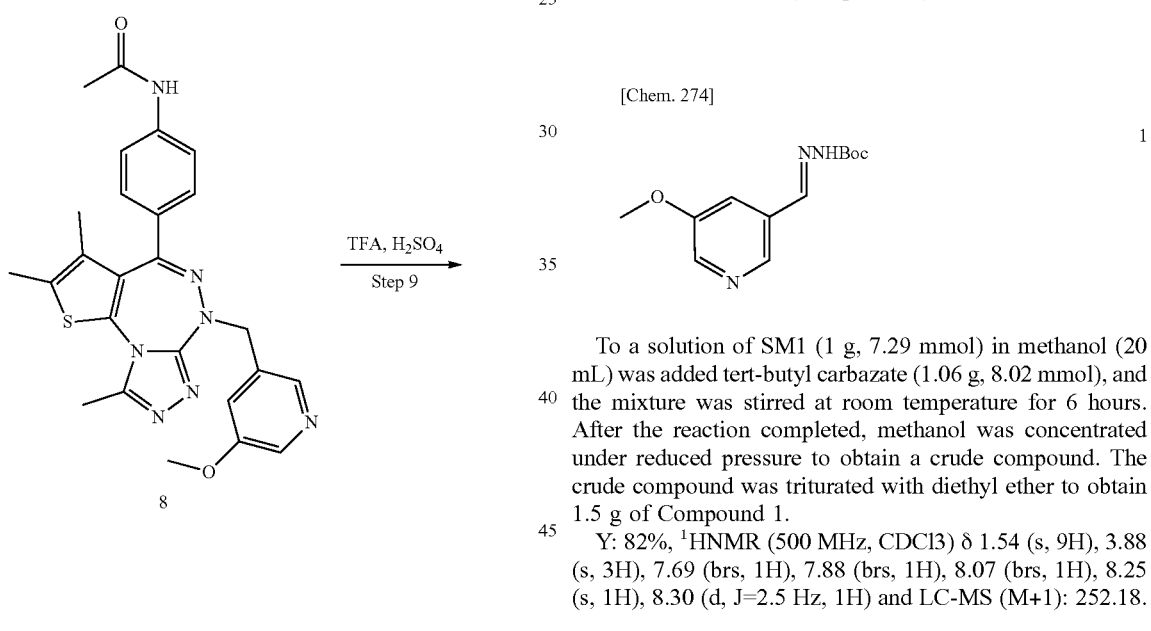

To a solution of SM1 (1 g, 7.29 mmol) in methanol (20 mL) was added tert-butyl carbazate (1.06 g, 8.02 mmol), and the mixture was stirred at room temperature for 6 hours. After the reaction completed, methanol was concentrated under reduced pressure to obtain a crude compound. The crude compound was triturated with diethyl ether to obtain 1.5 g of Compound 1.

Y: 82%, ¹HNMR (500 MHz, CDCl3) δ 1.54 (s, 9H), 3.88 (s, 3H), 7.69 (brs, 1H), 7.88 (brs, 1H), 8.07 (brs, 1H), 8.25 (s, 1H), 8.30 (d, J=2.5 Hz, 1H) and LC-MS (M+1): 252.18.

Step 2: Synthesis of tert-butyl 2-((5-methoxypyridin-3-yl)methyl)hydrazine-1-carboxylate (Compound 2)

[Chem. 275]

To a solution of Compound 1 (1.5 g, 5.97 mmol) in methanol (30 mL) was added 10% Pd/C (300 mg), and the reaction mixture was stirred under hydrogen balloon pressure at room temperature for 24 hours. After the reaction completed, the reaction mixture was filtered through a celite pad, washed with methanol and filtered, and the filtrate was concentrated under reduced pressure to obtain a crude compound. The crude compound was triturated with diethyl ether to obtain 1.2 g of Compound 2.

Y: 82%, $^1$HNMR (400 MHz, CDCl$_3$) δ 1.46 (s, 9H), 3.86 (s, 3H), 4.01 (s, 2H), 6.03 (s, 1H), 7.24 (s, 1H), 8.18 (s, 1H), 8.23 (d, J=2.8 Hz, 1H) and LC-MS (M+1): 254.12

Step 3: Synthesis of 3-(hydrazinylmethyl)-5-methoxypyridine (Compound 3)

[Chem. 276]

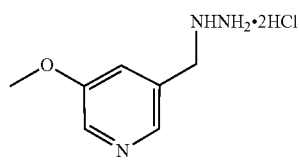

3a

To a solution of Compound 2 (6.5 g, 25.6 mmol) in 1,4-dioxane (100 mL) was added 4M 1,4 dioxane.HCl (200 mL) at 10° C., and the reaction mixture was stirred at room temperature for 24 hours. After the reaction completed, the reaction mixture was concentrated under reduced pressure to obtain a crude compound. The crude compound was triturated with diethyl ether to obtain 5.5 g of Compound 3a.

Y: 96%, $^1$HNMR (500 MHz, DMSO-d$_6$) δ 4.00 (s, 3H), 4.26 (s, 2H), 8.28 (s, 1H), 8.54 (s, 1H), 8.66 (d, J=2.5 Hz, 1H), 9.52 (brs, 3H) and LC-MS (M+1): 154.41

Step 4: Synthesis of N-(4-(2-isothiocyanato-4,5-dimethylthiophen-3-carbonyl)phenyl)acetamide (Compound 4)

[Chem. 277]

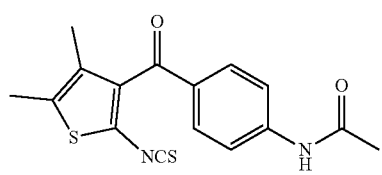

4

To a cooled (0° C.) solution of thiophosgene (4 mL, 52.08 mmol) in water (100 mL) was added Compound 3 in Scheme of Example 71 (10 g, 34.7 mmol) in DCM (400 mL), and the mixture was stirred at 0° C. for one hour and at room temperature for one hour. After the reaction completed, the reaction mixture was quenched with ice-water and extracted with DCM. The organic layer was dried over anhydrous sodium sulfate and filtered, and the filtrate was concentrated under reduced pressure to obtain 8 g of a crude Compound 5.

Y: 70%, 1HNMR (400 MHz, CDCl$_3$) δ 2.01 (s, 3H), 2.26 (s, 3H), 2.32 (s, 3H), 7.67 (d, J=8.4 Hz, 2H), 7.79-7.82 (m, 3H) and LC-MS (M+1): 330.90

Step 5: Synthesis of N-(4-(2-(1-((5-methoxypyridin-3-yl)methyl)hydrazine-1-carbothioamide)-4,5-dimethylthiophen-3-carbonyl)phenyl)acetamide (Compound 5)

[Chem. 278]

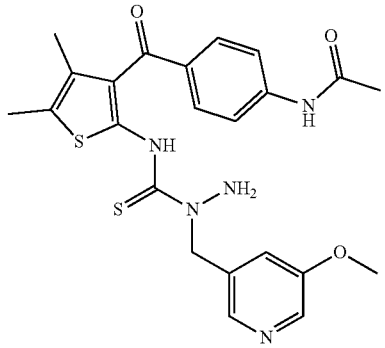

5

To a solution of Compound 4 (8 g, 24.24 mmol) in THF (160 mL) was added TEA (8.5 mL, 60.60 mmol), followed by Compound 3a (5.47 g, 24.24 mmol) at 0° C., and the mixture was stirred at room temperature for 16 hours. After the reaction completed, the reaction mixture was concentrated under reduced pressure to obtain a residue. The residue was diluted with ethyl acetate and washed with sodium bicarbonate and a brine solution. The organic layer was dried over anhydrous sodium sulfate and filtered, and the filtrate was concentrated under reduced pressure to obtain 12 g of Compound 5 (LC-MS: 76.2%), which was used in the next Step without further purification. LC-MS (M+1): 484.12

Step 6: Synthesis of N-(4-(3-((5-methoxypyridin-3-yl)methyl)-6,7-dimethyl-2-thioxo-2,3-dihydro-1H-thieno [2,3-e][1,2,4]triazepin-5-yl)phenyl)acetamide (Compound 6)

[Chem. 279]

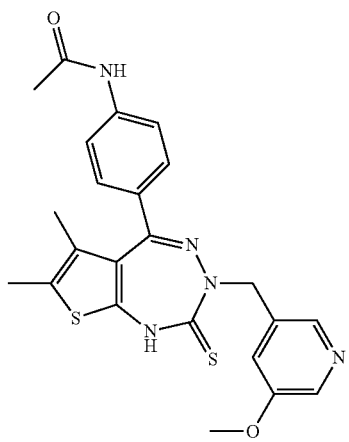

6

To a solution of Compound 5 (12 g, LC-MS: 76.2%) in ethanol (250 mL) was added PTSA.H$_2$O (944 mg, 4.49 mmol), and the reaction mixture was stirred at 90° C. for 16 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude compound. The crude compound was purified by silica gel (60-120 mesh) column chromatography, eluted with 10% methanol/DCM, to obtain 6 g of Compound 6 (LC-MS: 70%), which was used in the next Step without further purification. LC-MS (M+1): 466.17

Step 7: Synthesis of N-(4-(3-((5-methoxypyridin-3-yl)methyl)-6,7-dimethyl-2-(methylthio)-3H-thieno[2,3-e][1,2,4]triazepin-5-yl)phenyl)acetamide (Compound 7)

[Chem. 280]

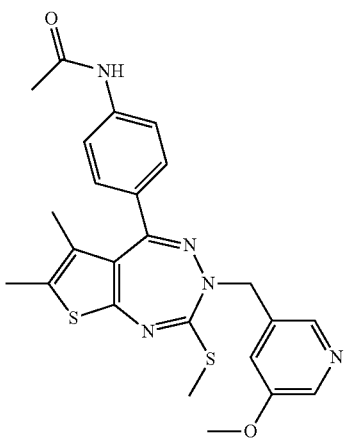

7

To a cooled (0° C.) solution of Compound 6 (6 g, LC-MS: 70%) in THF (100 mL) was added sodium hydride (1.29 g, 32.24 mmol), and the mixture was stirred at room temperature for 30 minutes. Methyl iodide (0.64 mL, 10.32 mmol) was added thereto, and the mixture was stirred at room temperature for 3 hours. After the reaction completed, the reaction mixture was quenched with ice-cold water, extracted with ethyl acetate and washed with water and brine. The organic layer was dried over anhydrous sodium sulfate and filtered, and the filtrate was concentrated under reduced pressure to obtain a crude compound. The crude compound was purified by silica gel (60-120 mesh) column chromatography, eluted with 8% methanol/DCM, to obtain 3 g of Compound 7 (LC-MS: 50.6%), which was used in the next Step without further purification.

¹HNMR (500 MHz, CDCl₃) δ 1.45 (s, 3H), 2.17 (s, 3H), 2.26 (s, 3H), 2.52 (s, 3H), 3.81 (s, 3H), 4.71 (brs, 1H), 4.89 (brs, 1H), 7.15 (d, J=8.5 Hz, 2H), 7.23 (s, 1H), 7.45 (d, J=8.5 Hz, 2H), 7.62 (s, 1H), 8.20-8.22 (m, 2H) and LC-MS (M+1): 494.15

Step 8: Synthesis of N-(4-(6-((5-methoxypyridin-3-yl)methyl)-2,3,9-trimethyl-6H-thieno[2,3-e][1,2,4]triazolo[3,4-c][1,2,4]triazepin-4-yl)phenyl)acetamide (Compound 8)

[Chem. 281]

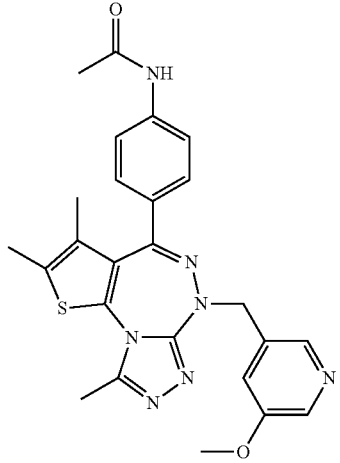

8

To a solution of Compound 7 (3 g, LC-MS: 50.6%) in ethanol (60 mL) were added PTSA.H₂O (240 mg, 1.25 mmol) and acetylhydrazine (2.3 g, 31.31 mmol), and the reaction mixture was stirred at 90° C. for 16 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude Compound 8. The crude Compound 8 was purified by grace instrument, eluted with 0.1% formic acid/25% acetonitrile in water, to obtain 1.5 g of Compound 8 (LC-MS: 68.6%), which was used in the next step without further purification. LC-MS (M+1): 488.24

Step 9: Synthesis of 5-((4-(4-aminophenyl)-2,3,9-trimethyl-6H-thieno[2,3-e][1,2,4]triazolo[3,4-c][1,2,4]triazepin-6-yl)methyl)pyridin-3-ol (Compound of Example 103)

[Chem. 282]

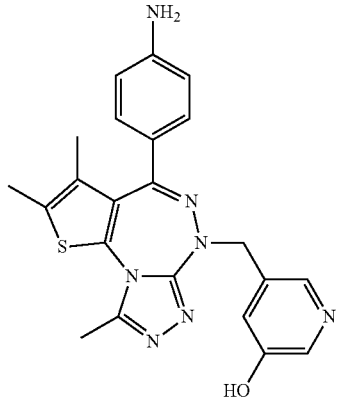

To a solution of Compound 8 (1.4 g, LC-MS: 68.6%) in a seal tube were added TFA (20 mL) and sulfuric acid (2 mL) at room temperature, and the mixture was stirred at 120° C. for 60 hours. LC-MS analysis showed 47% of the compound of Example 103 and 40% of deacetylated Compound 8. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate and filtered, and the filtrate was distilled off under reduced pressure to obtain 850 mg of a crude compound. The crude compound was purified by grace instrument, eluted with 0.1% formic acid/25% acetonitrile in water, to obtain 350 mg of the compound of Example 103 (HPLC: 85%) and 400 mg of a deacetylated Compound 8 (LC-MS: 98%). The above 350 mg was further purified by SFC to obtain 115 mg of the compound of Example 103.

Y: 13%, yield was calculated based on the purity of Compound 8

$^1$HNMR (400 MHz, DMSO-$d_6$) δ 1.59 (s, 3H), 2.36 (s, 3H), 2.53 (s, 3H), 4.63-4.67 (d, J=14.25 Hz, 1H), 4.88 (d, J=14.03 Hz, 1H), 5.60 (s, 2H), 6.51 (d, J=8.77 Hz, 2H), 7.00 (d, J=8.33 Hz, 2H), 7.13 (d, J=1.97 Hz, 1H), 8.01 (dd, J=14.58, 2.08 Hz, 2H), 9.93 (brs, 1H) and LC-MS (M+1): 432.15

Steps 10 and 11: Synthesis of N-(4-(6-((5-hydroxy-pyridin-3-yl)methyl)-2,3,9-trimethyl-6H-thieno[2,3-e][1,2,4]triazolo[3,4-c][1,2,4]triazepin-4-yl)phenyl)acetamide (Compound of Example 99)

[Chem. 283]

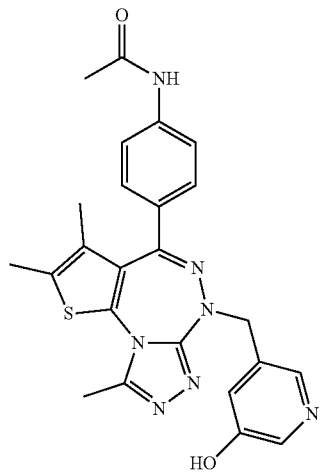

To a solution of the compound of Example 103 (500 mg, LC-MS: 82.84%) in THF (10 mL) was added acetic anhydride (0.2 mL) at 0° C., and the mixture was stirred at room temperature for 5 hours. After the reaction completed, the reaction mixture was concentrated under reduced pressure to obtain 600 mg of a crude compound (LC-MS: 62%, mass of N and O-acetylated product), which was used in the next Step without further purification. LC-MS (M+1): 516.23

[Chem. 284]

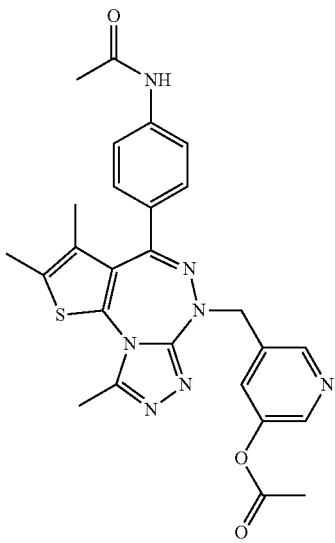

To the above-mentioned crude compound (600 mg, LC-MS: 62%, mass of N and O-acetylated product) in methanol (25 mL) was added potassium carbonate (322 mg) at 0° C., and the mixture was stirred at room temperature for 3 hours. After the reaction completed, the reaction mixture was concentrated under reduced pressure to obtain a residue, and the residue was diluted with ethyl acetate. The organic layer was washed with water and a brine solution, dried over anhydrous sodium sulfate and filtered, and the filtrate was concentrated under reduced pressure to obtain a crude compound. The crude compound was purified by grace, eluted with 0.1% formic acid/25% acetonitrile in water, to obtain 340 mg of a crude compound, which was purified by preparative HPLC to obtain 125 mg of the compound of Example 99.

Y: 27%, yield was calculated based on the purity of the compound of Example 103

$^1$HNMR (500 MHz, DMSO-$d_6$) δ 1.51 (s, 3H), 2.05 (s, 3H), 2.36 (s, 3H), 2.54 (s, 3H), 4.72 (d, J=14.04 Hz, 1H), 4.94 (d, J=14.04 Hz, 1H), 7.18 (t, J=2.25 Hz, 1H), 7.26 (d, J=8.54 Hz, 2H), 7.61 (d, J=8.85 Hz, 2H), 8.02 (d, J=2.75 Hz, 1H), 8.07 (d, J=1.53 Hz, 1H), 9.87 (s, 1H), 10.14 (s, 1H) and LC-MS (M+1): 474.40

Synthetic Scheme of the compounds of Examples 100 and 104

[Chem. 285]

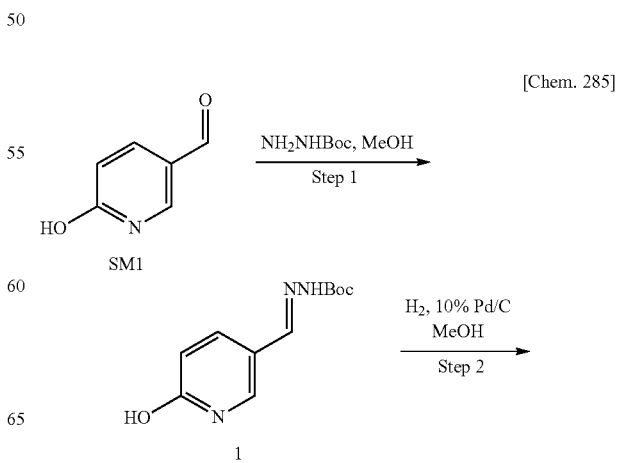

-continued
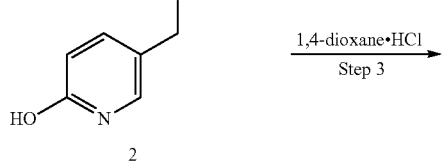
2
1,4-dioxane•HCl
Step 3
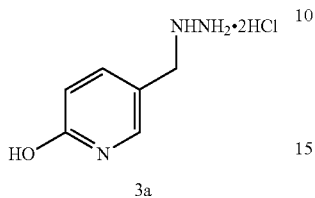
3a
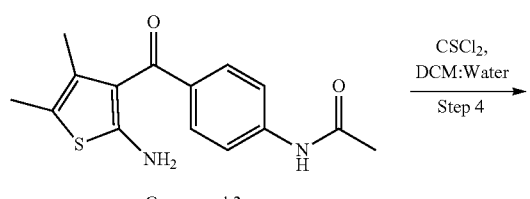
Compound 3
CSCl₂,
DCM:Water
Step 4
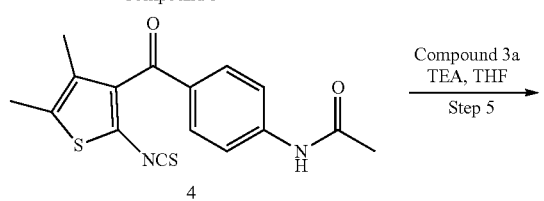
4
Compound 3a
TEA, THF
Step 5
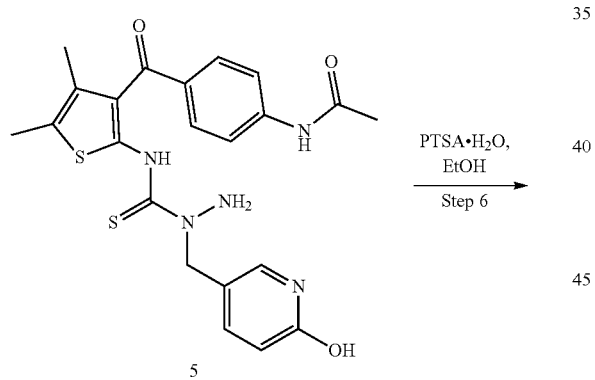
5
PTSA•H₂O,
EtOH
Step 6
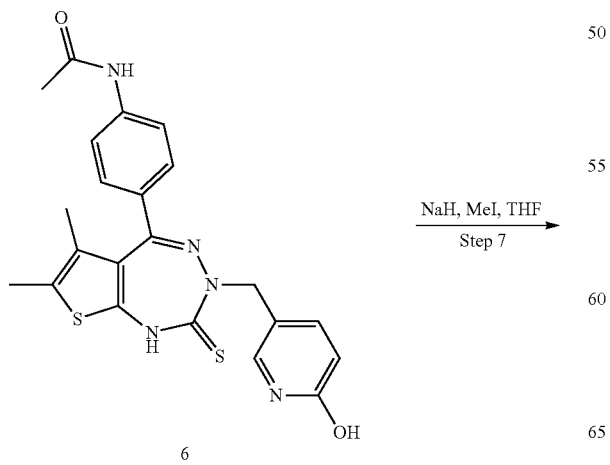
6
NaH, MeI, THF
Step 7
-continued
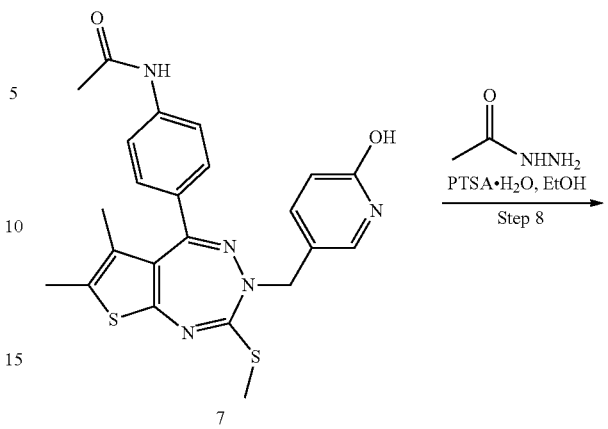
7
Step 8
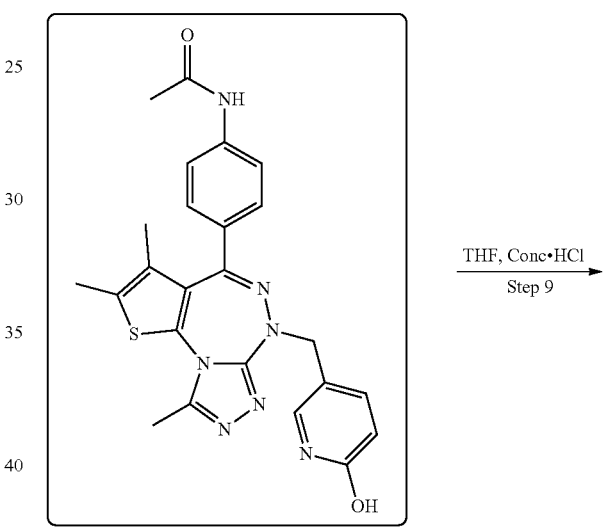
THF, Conc•HCl
Step 9
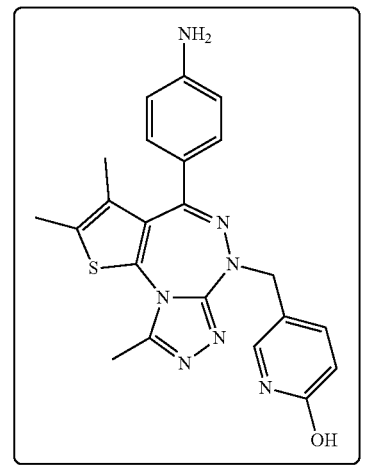 [SMILES: Cc1sc2c(c1C)C(c1ccc(N)cc1)=NN(Cc1ccc(O)nc1)c1nnc(C)n1-2]

Step 1: Synthesis of tert-butyl (E)-2-((6-hydroxy-pyridin-3-yl)methylene)hydrazine-1-carboxylate (Compound 1)

[Chem. 286]

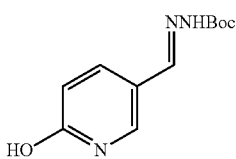

1

To a solution of SM1 (10 g, 81.3 mmol) in methanol (100 mL) was added tert-butyl carbazate (11.8 g, 89.43 mmol), and the mixture was stirred at room temperature for 16 hours. After the reaction completed, methanol was concentrated under reduced pressure to obtain a crude compound. The crude compound was triturated with diethyl ether to obtain 17 g of Compound 1.

Yield: 88%, $^1$HNMR (500 MHz, DMSO-$d_6$) δ 1.44 (s, 9H), 6.39 (d, J=9.5 Hz, 1H), 7.59 (d, J=2.5 Hz, 1H), 7.76-7.78 (m, 2H), 10.74 (s, 1H), 11.79 (s, 1H) and LC-MS (M+1): 238.31

Step 2: Synthesis of tert-butyl 2-((6-hydroxypyridin-3-yl)methyl)hydrazine-1-carboxylate (Compound 2)

[Chem. 287]

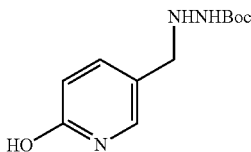

2

To a solution of Compound 1 (15 g, 34.32 mmol) in ethanol (150 mL) was added 10% Pd/C (1.5 g) at room temperature, and the mixture was stirred under hydrogen balloon pressure of 40 psi at room temperature for 8 hours. After the reaction completed, the reaction mixture was filtered through a celite pad and washed with methanol, and the filtrate was concentrated under reduced pressure to obtain a crude compound. The crude compound was washed with diethyl ether, filtered and dried to obtain 10 g of Compound 2.

Yield: 66%, $^1$HNMR (400 MHz, DMSO-$d_6$) δ 1.36 (s, 9H), 3.55 (d, J=3.6 Hz, 2H), 4.68 (d, J=4 Hz, 1H), 6.27 (d, J=9.6 Hz, 1H), 7.16 (s, 1H), 7.37 (dd, J=9.2 & 2.4 Hz, 1H), 8.17 (s, 1H), 11.39 (s, 1H) and LC-MS (M+1): 240.62

Step 3: Synthesis of 5-(hydrazinylmethyl)pyridin-2-ol dihydrochloride (Compound 3a)

[Chem. 288]

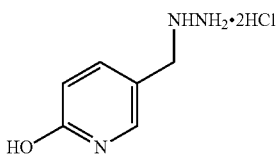

3a

To a solution of Compound 2 (10 g, 41.84 mmol) in 1,4-dioxane (25 mL) was added 4N hydrochloric acid in dioxane (75 mL) at 5° C., and the mixture was stirred at room temperature for 16 hours. After the reaction completed, the reaction mixture was concentrated under reduced pressure to obtain a crude compound. The crude compound was triturated with diethyl ether to obtain 9.5 g of Compound 3a (LC-MS: 67%), which was used in the next Step without further purification.

$^1$HNMR (500 MHz, DMSO-$d_6$) δ 3.84 (s, 2H), 6.47 (d, J=9.5 Hz, 1H), 6.83 (brs 2H), 7.50 (d, J=1.6 Hz, 1H), 7.57 (dd, J=2 and 7.2 Hz, 1H) and LC-MS (M+1): 140.02

Step 4: Synthesis of N-(4-(2-isothiocyanato-4,5-dimethylthiophen-3-carbonyl)phenyl)acetamide (Compound 4)

[Chem. 289]

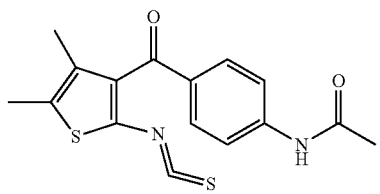

4

To a solution of thiophosgene (10 mL, 130.2 mmol) in water (250 mL) was added Compound 3 in Scheme of Example 71 (50 g, 173 mmol) in DCM (500 mL) at 0° C., and the mixture was stirred at the same temperature for one hour and at room temperature for one hour. After the reaction completed, the reaction mixture was quenched with ice-water, extracted with DCM and washed with brine. The organic layer was dried over anhydrous sodium sulfate and filtered, and the filtrate was concentrated under reduced pressure to obtain a crude compound. The crude compound was purified by silica gel column chromatography, eluted with DCM, to obtain 40 g of Compound 4 (LC-MS: 94%), which was used in the next Step without further purification.
LC-MS (M+1): 331.09

Step 5: Synthesis of N-(4-(2-(1-(((6-hydroxypyridin-3-yl)methyl)hydrazine-1-carbothioamide)-4,5-dimethylthiophen-3-carbonyl)phenyl)acetamide (Compound 5)

[Chem. 290]

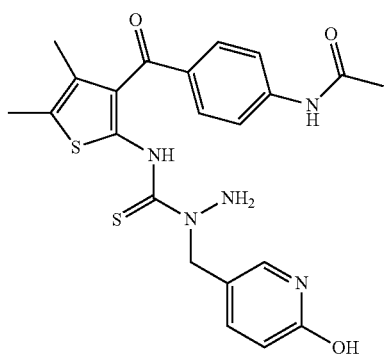

5

To a solution of Compound 4 (26 g, 78.78 mmol) in THF (260 mL) was added TEA (27.8 mL, 196.95 mmol), followed by Compound 3a (20 g, 94.53 mmol) at 0° C., and the mixture was stirred at room temperature for 16 hours. After the reaction completed, the reaction mixture was quenched with water, extracted with ethyl acetate and washed with water and brine. The organic layer was dried over anhydrous sodium sulfate and filtered, and the filtrate was concentrated under reduced pressure to obtain a crude Compound 5. The crude compound was triturated with diethyl ether, and the solid was filtered and dried under highly vacuum to obtain 35 g of Compound 5 (LC-MS: 59%), which was used in the next Step without further purification. LC-MS (M+1): 470.16

Step 6: Synthesis of N-(4-(3-((6-hydroxypyridin-3-yl)methyl)-6,7-dimethyl-2-thioxo-2,3-dihydro-1H-thieno[2,3-e][1,2,4]triazepin-5-yl)phenyl)acetamide (Compound 6)

[Chem. 291]

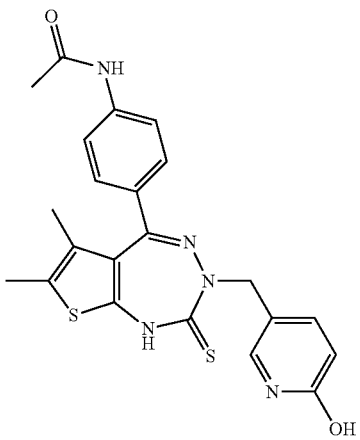

To a solution of Compound 5 (35 g, LC-MS: 59%) in ethanol (1,000 mL) was added PTSA.H$_2$O (2.83 g, 14.92 mmol), and the mixture was stirred at 90° C. for 18 hours. After the reaction completed, the reaction mixture was concentrated under reduced pressure to obtain a residue. The residue was diluted with water and extracted with ethyl acetate and washed with water and brine. The organic layer was dried over anhydrous sodium sulfate and filtered, and the filtrate was concentrated under reduced pressure to obtain a crude Compound 6. The crude compound was washed with diethyl ether, filtered and dried to obtain 30 g of Compound 6 (LC-MS: 64%), which was used in the next Step without further purification. LC-MS (M+1): 452.21

Step 7: Synthesis of N-(4-(3-((6-hydroxypyridin-3-yl)methyl)-6,7-dimethyl-2-(methylthio)-3H-thieno[2,3-e][1,2,4]triazepin-5-yl)phenyl)acetamide (Compound 7)

[Chem. 292]

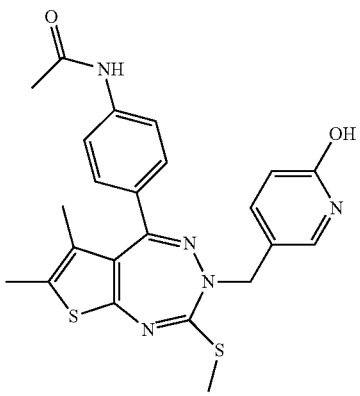

To a cooled (0° C.) solution of Compound 6 (30 g, LC-MS: 64%) in THF (600 mL) was added sodium hydride (6.6 g, 166.2 mmol), and the mixture was stirred at room temperature for 30 minutes. Methyl iodide (2.88 mL, 46.5 mmol) was added thereto at 0° C., and the mixture was stirred at room temperature for 2 hours. After the reaction completed, the reaction mixture was quenched with ice-cold water, extracted with ethyl acetate and washed with water and brine. The organic layer was dried over anhydrous sodium sulfate and filtered, and the filtrate was concentrated under reduced pressure to obtain a crude Compound 7. The crude compound was washed with ethyl acetate, and the solid was filtered and dried to obtain 16 g of Compound 7 (LC-MS: 84%), which was used in the next Step without further purification.

$^1$HNMR (400 MHz, DMSO-d$_6$) δ 1.40 (s, 3H), 2.05 (s, 3H), 2.22 (s, 3H), 2.45 (s, 3H), 4.31 (brs, 1H), 4.54 (brs, 1H), 6.29 (d, J=9.6 Hz, 1H), 7.13 (d, J=8.8 Hz, 2H), 7.38 (brs, 1H), 7.42 (dd, J=2.6 & 9.6 Hz, 1H), 7.61 (d, J=8.8 Hz, 2H), 10.13 (s, 1H), 11.49 (s, 1H) and LC-MS (M+1): 466.17

Step 8: Synthesis of N-(4-(6-((6-hydroxypyridin-3-yl)methyl)-2,3,9-trimethyl-6H-thieno[2,3-e][1,2,4]triazolo[3,4-c][1,2,4]triazepin-4-yl)phenyl)acetamide (Compound of Example 100)

[Chem. 293]

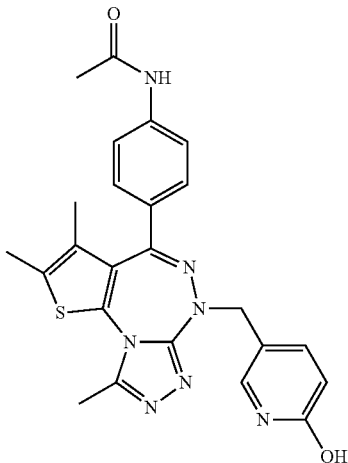

To a solution of Compound 7 (16 g, LC-MS: 84%) in ethanol (300 mL) were added acetohydrazide (12.72 g, 172 mmol) and PTSA.H$_2$O (1.3 g, 6.88 mmol), and the mixture was stirred at 80° C. for 48 hours. After the reaction completed, the reaction mixture was concentrated under reduced pressure to obtain a crude compound. The crude compound was diluted with ethyl acetate and washed with saturated sodium bicarbonate and a brine solution. The organic layer was dried over anhydrous sodium sulfate and filtered, and the filtrate was concentrated under reduced pressure to obtain a crude compound. The crude compound was washed with diethyl ether and dried under highly vacuum to obtain 14 g of the compound of Example 100 (LC-MS: 57%), which was used in the next Step without further purification.

$^1$HNMR (400 MHz, DMSO-d$_6$) δ 1.50 (s, 3H), 2.05 (s, 3H), 2.35 (s, 3H), 2.53 (s, 3H), 4.48 (d, J=13.59 Hz, 1H), 4.67 (d, J=13.15 Hz, 1H), 6.29 (d, J=9.43 Hz, 1H), 7.29 (d,

J=8.33 Hz, 2H), 7.44 (br s, 1H), 7.49 (dd, J=9.43, 2.41 Hz, 1H), 7.63 (d, J=8.55 Hz, 2H), 10.13 (s, 1H), 11.47 (brs, 1H) and LC-MS (M+1): 474.41

Step 9: Synthesis of N-(4-(6-((6-hydroxypyridin-3-yl)methyl)-2,3,9-trimethyl-6H-thieno[2,3-e][1,2,4]triazolo[3,4-c][1,2,4]triazepin-4-yl)phenyl)acetamide (Compound of Example 104)

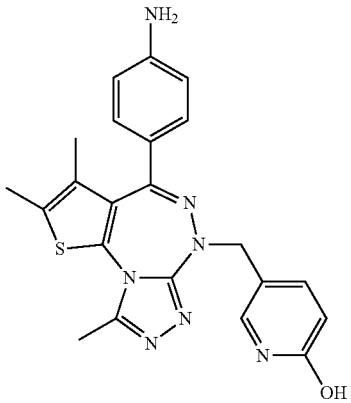

[Chem. 294]

To a solution of the compound of Example 100 (14 g, LC-MS: 57%) in THF (140 mL) was added dropwise conc. hydrochloric acid (70 mL) at 0° C., and the mixture was stirred at 70° C. for 16 hours. After the reaction completed, the reaction mixture was quenched with water and extracted with ethyl acetate. The aqueous layer was made basic with a saturated sodium hydrogen carbonate solution and extracted with ethyl acetate. The organic layer was washed with water and brine, dried over anhydrous sodium sulfate and filtered, and the filtrate was distilled off under reduced pressure to obtain a crude compound. The crude compound was purified by combi instrument, eluted with 8% methanol/DCM, to obtain 4.8 g of the compound of Example 104 (LC-MS: 80%). This was further purified by triturating with 20% methanol/acetonitrile, and the solid was filtered and dried under highly vacuum to obtain 3.35 g of the compound of Example 104.

Yield: 46%, $^1$HNMR (500 MHz, DMSO-$d_6$) δ 1.58 (s, 3H), 2.35 (s, 3H), 2.52 (s, 3H), 4.43 (d, J=13.43 Hz, 1H), 4.61 (d, J=13.43 Hz, 1H), 5.62 (s, 2H), 6.24-6.30 (m, 1H), 6.51-6.55 (m, 2H), 7.03 (d, J=8.24 Hz, 2H), 7.40 (s, 1H), 7.46 (dd, J=9.46 & 2.44 Hz, 1H), 11.46 (br s, 1H) and LC-MS (M+1): 432.15

<Salts and Crystals>
1. Crystallization of Free Materials

The compound of Example 71 (50 mg, HPLC: 93%, amorphous) was stirred with 200 μL of ethyl acetate at 20° C. to obtain crystals (seed crystals).

The compound of Example 71 (2.90 g) was dissolved in 120 mL of acetone under heating, filtered under reduced pressure (dust removing filtration) and washed with 10 mL of the same solvent twice. The filtrate and the washing solution were combined and concentrated under reduced pressure until it became 9.48 g. Seed crystals were added thereto and the mixture was stirred at 20° C. for 16 hours. The precipitated crystals were filtered under reduced pressure and washed with cold acetone to obtain 2.809 g of wet crystals. The crystals were dried under reduced pressure at 60° C. for 7 hours to obtain 2.512 g (87%, HPLC: 99.82%, containing 0.3% of acetone, mp. 162 to 165° C.).

2. Crystallization of p-Toluenesulfonic Acid Salts

The compound of Example 71 (229 mg (0.5 mmol)) and p-TsOH.H$_2$O (99.9 mg (1.05 eq)) were dissolved in 2.0 mL of ethanol under heating, and concentrated under reduced pressure to obtain 350 mg of a foamy residue. Among these, 50 mg was dissolved in 100 μL of 95% acetone containing water, and the mixture was stirred at 25° C. for 2 hours and allowed to stand at 25° C. for 16 hours. The precipitated crystals were filtered and washed with cold 95% acetone containing water. The crystals were dried under reduced pressure at 50° C. for 5 hours to obtain 32 mg (HPLC: 99.26%, containing 0.4% of acetone) of 1.0 tosylate (seed crystals).

The compound of Example 71 (2.00 g) was dissolved in 3.5 mL of 95% acetone containing water under heating, filtered under reduced pressure (dust removing filtration), and washed with 1.0 mL of the same solvent twice. The filtrate and the washing solution were combined, 831 mg (1.0 eq) of p-toluenesulfonic acid monohydrate was added thereto, and the mixture was dissolved under heating. Seed crystals were added thereto, and the mixture was stirred at 20° C. for 2 hours and allowed to stand at 3° C. for 16 hours. The precipitated crystals were filtered under reduced pressure, and washed with cold acetone to obtain 2.400 g of 1.0 p-toluenesulfonate (87%, HPLC: 99.05%). The crystals were dried under reduced pressure at 60° C. for 14.5 hours to obtain 2.354 g (86%, HPLC: 99.08%, containing 0.6% of acetone, mp. 217 to 219° C.).

3. Crystallization of Fumarates

The compound of Example 71 (2.00 g) was dissolved in 3.0 mL of 95% acetone containing water under heating, and the mixture was filtered under reduced pressure (dust removing filtration), washed with 1.0 mL of the same solvent twice.

The filtrate and the washing solution were combined, fumaric acid 507 mg (1.0 eq) was added thereto, and the mixture was dissolved under heating. The mixture was stirred at 60° C. to 20° C. for 2 hours and at 20° C. for 16 hours. The precipitated crystals were filtered under reduced pressure, and washed with cold 95% acetone containing water to obtain 1.992 g of 0.5 fumarate (HPLC: 98.91%). The crystals were dried under reduced pressure at 60° C. for 11 hours to obtain 1.954 g (87%, HPLC: 98.91%, containing <0.1% of acetone, mp. 157 to 159° C.).

4. Crystallization of succinates

The compound of Example 71 (46 mg (0.1 mmol)) and succinic acid (12 mg (1.00 eq)) was dissolved in 105 μL of 95% acetone containing water, and the mixture was stirred at 25° C. for 2 hours and allowed to stand at 25° C. for 16 hours. The precipitated crystals were filtered and washed with cold 95% acetone containing water. The crystals were air dried at 25° C. to obtain 27 mg of 0.5 succinate (HPLC: 98.99%) (seed crystals).

The compound of Example 71 (2.00 g) was dissolved in 95% acetone containing water (3.0 mL) under heating, and the mixture was filtered under reduced pressure (dust removing filtration) and washed with 1.0 mL of the same solvent twice. The filtrate and the washing solution were combined, 516 mg (1.0 eq) of succinic acid was added thereto, and the mixture was dissolved under heating. Seed crystals were added thereto, and the mixture was stirred at 35° C. to 25° C. for one hour and at 20° C. for 16 hours. The precipitated crystals were filtered under reduced pressure and washed with cold 95% acetone containing water to obtain 1.744 g of 0.5 succinate. The crystals were dried under reduced pressure at 60° C. for 7 hours to obtain 1.717 g (76%, HPLC: 99.22%, containing 0.2% of acetone, mp. 141 to 145° C.).

5. Crystallization of Maleates

The compound of Example 71 (229 mg (0.5 mmol)) and maleic acid (58 mg (1.00 eq)) were dissolved in 2.0 mL of ethanol under heating, and the mixture was concentrated under reduced pressure until it became 544 mg, and 350 μL of diethyl ether was added thereto and stirred at 25° C. for 3 hours. The precipitated crystals were filtered and washed with ethanol/diethyl ether (1/1), followed by with diethyl ether. The crystals were air dried at 25° C. to obtain 179 mg of 1.0 maleate (HPLC: 96.40%, containing 3% of ethanol) (seed crystals).

The compound of Example 71 (2.00 g) was dissolved in 3.0 mL of 95% acetone containing water under heating, and the mixture was filtered under reduced pressure (dust removing filtration) and washed with 1.0 mL of the same solvent twice. The filtrate and the washing solution were combined, 507 mg (1.0 eq) of maleic acid was added thereto, and the mixture was dissolved under heating. Seed crystals were added thereto, and the mixture was stirred at 20° C. for 16 hours. The precipitated crystals were filtered under reduced pressure and washed with cold acetone to obtain 1.648 g of maleate, which was a mixed crystal of 1.0 salt and 0.5 salt with 3:1. The crystals and the concentrated residue of the mother liquid were combined, 5.0 ml of 95% acetone containing water was added thereto, and the mixture was stirred at 60° C. for 1.5 hours. Thereafter, the mixture was gradually returned to room temperature and stirred at 20° C. for 16 hours. The precipitated crystals were filtered under reduced pressure, washed with cold 95% acetone containing water and dried under reduced pressure at 60° C. for 7 hours. 1.263 g (56%, HPLC: 98.98%, containing <0.1% of acetone, mp. 157 to 158° C.) of 0.5 maleate was obtained.

<Crystal Polymorph>

6. Crystallization of Hydrochlorides

1) Form I Hydrochloride Crystals

The compound of Example 71 (2.00 g, 4.37 mmol) was dissolved in 17.0 mL of ethanol under heating, and after dust removing filtration, 382 μL (1.05 eq) of conc. HCl was added thereto at 45° C., and the mixture was stirred at the same temperature for 2 hours, at 25° C. for 16 hours and at 3 C for 1.5 hours. The precipitated crystals were filtered and dried under reduced pressure at 60° C. for 6 hours to obtain 1.735 g of Form I 1.0 hydrochloride crystals [80%, HPLC: 98.87%, EtOH 0.8%, $H_2O$ 0.51%, mp 260-275° C., ion chromatography method Cl: 7.16% (calculated value: 7.19%)].

XRD 2θ (relative height): 8.330 (2.71), 8.937 (5.83), 10.290 (24.24), 10.550 (100.00), 13.405 (2.63), 15.457 (2.10), 16.065 (20.41), 16.727 (2.43), 17.044 (6.34), 17.192 (4.50), 17.485 (13.47), 18.001 (10.63), 18.608 (7.51), 19.120 (2.95), 20.588 (16.76), 21.236 (37.40), 21.555 (3.44), 21.945 (12.43), 22.408 (3.61), 22.722 (24.37), 23.433 (10.13), 24.140 (7.71), 24.913 (8.50), 25.228 (8.47), 25.524 (7.96), 25.958 (16.54).

IR (KBr), $cm^1$: 3424.48, 3221.50, 3050.83, 1676.32, 1596.77, 1523.49, 1428.51, 1405.85, 1368.73, 1314.25, 1279.54, 1260.74, 680.27, 597.34.

2) Form IV Hydrochloride Crystals

The compound of Example 71 (3.00 g, 6.55 mmol) was dissolved in 100 mL of methanol under heating, 2.46 mL (1.5 eq) of 4 mol/L HCl in ethyl acetate solution was added thereto, and the solvent was distilled off under reduced pressure to obtain 3.406 g of a foamy residue. Among these, 200 mg was weighed, dissolved in 0.40 mL of water, and allowed to stand at 25° C. for 16 hours. The precipitated crystals were filtered to obtain 157 mg of Form IV 1.0 hydrochloride crystals ($H_2O$ 9.56%, mp 262-275° C.).

XRD 2θ (relative height): 6.976 (19.38), 7.154 (42.47), 9.622 (100.00), 11.551 (14.74), 11.676 (16.99), 12.276 (15.32), 15.398 (14.74), 11.676 (16.99), 12.276 (15.32), 15.398 (14.44), 15.936 (16.47), 17.001 (22.01), 17.870 (11.25), 18.753 (16.82), 19.045 (11.57), 19.160 (16.60), 19.279 (53.90), 21.001 (15.78), 21.379 (21.54), 21.886 (55.75), 22.141 (22.46), 23.601 (18.58), 24.320 (21.71), 25.815 (17.80), 26.465 (32.16), 27.465 (23.68), 28.574 (33.71), 29.056 (22.72), 29.134 (16.87), 35.950 (12.44).

IR (KBr), $cm^{-1}$: 3407.60, 3224.40, 1676.32, 1598.22, 1575.56, 1558.68, 1523.49, 1428.51, 1405.85, 1369.69, 1314.73, 1279.54, 1260.25, 680.75, 604.57, 597.82.

3) Form II Hydrochloride Crystals

The compound of Example 71 (3.00 g, 6.55 mmol) was dissolved in 100 mL of methanol under heating, a solution of 4 mol/L HCl in ethyl acetate (2.46 mL (1.5 eq)) was added thereto, and the solvent was distilled off under reduced pressure to obtain 3.406 g of a foamy residue. Among these, 50 mg was weighed and dissolved in 0.15 mL of methanol, and allowed to stand at 25° C. for 24 hours. The precipitated crystals were filtered to obtain 25 mg of Form II 1.0 hydrochloride crystals ($H_2O$ 2.86%, mp 260-265° C.).

XRD 2θ (relative height): 8.453 (5.79), 9.094 (1.60), 10.625 (72.92), 10.706 (100.00), 16.091 (2.13), 16.188 (1.72), 16.848 (3.01), 17.174 (1.79), 18.110 (3.49), 18.699 (1.04), 20.696 (5.34), 21.372 (41.96), 22.080 (1.36), 22.807 (2.15), 23.497 (1.24), 23.599 (1.44), 24.962 (1.14), 25.359 (10.23), 25.965 (1.28).

IR (KBr), $cm^{-1}$: 3419.65, 3093.26, 2415.40, 2097.69, 1676.32, 1634.38, 1598.22, 1523.97, 1473.83, 1428.51, 1405.85, 1369.21, 1314.73, 1279.54, 1260.74, 1179.26, 1019.19, 962.79, 904.45, 841.29, 798.87, 748.25, 680.27, 597.82, 534.67, 522.13, 491.28, 468.14.

4) Form III hydrochloride crystals

The compound of Example 71 (3.00 g, 6.55 mmol) was dissolved in 100 mL of methanol under heating, a solution of 4 mol/L HCl in ethyl acetate (2.46 mL (1.5 eq)) was added thereto, and the solvent was distilled off under reduced pressure to obtain 3.406 g of a foamy residue. Among these, 50 mg was weighed and dissolved in 0.10 mL of water, and allowed to stand at 25° C. for 7 days. The precipitated crystals were filtered to obtain 15 mg (mp 260-265° C.) of Form III 1.0 hydrochloride crystals.

XRD 2θ (relative height): 8.481 (3.28), 9.045 (8.82), 10.374 (26.96), 10.374 (82.87), 10.702 (100.00), 13.481 (2.39), 15.479 (1.95), 16.167 (13.74), 16.882 (3.84), 17.118 (4.07), 17.605 (7.94), 18.070 (23.16), 18.728 (2.53), 19.262 (1.12), 20.723 (6.31), 21.355 (63.77), 22.089 (10.26), 22.398 (2.74), 22.651 (12.96), 22.834 (17.69), 23.558 (22.70), 24.155 (3.11), 24.281 (3.12). 24.956 (3.62), 25.041 (2.96), 25.232 (3.96), 25.389 (15.56), 25.698 (3.81)

IR (KBr), $cm^{-1}$: 3423.03, 3091.81, 1676.32, 1635.34, 1598.70, 1524.94, 1472.87, 1428.51, 1405.85, 1370.18, 1314.73, 1279.54, 1260.74, 1179.26, 845.15, 798.87, 748.25, 680.75, 597.82, 520.20.

5) Form I Hydrochloride Crystals

The compound of Example 71 (31.43 g, 68.68 mmol) was dissolved in 1,600 mL of acetone under heating, followed by dust removing filtration, and concentrated under reduced pressure at 50° C. until the residual liquid became 50.4 g. Then, 33.74 mL of 2.44 mol/L HCl (1.2 eq) was added thereto at 50° C., and the mixture was stirred at the same temperature for 61 hours, at 25° C. for 16 hours and at 3 C for 1.5 hours [61 mL (2V) of acetone was gradually added during stirring]. The precipitated crystals were filtered, and dried under reduced pressure at 60° C. for 5 hours to obtain 26.24 g of Form I 1.0 hydrochloride crystals (77%, HPLC: 99.74%, acetone 0.1%, mp 266-272° C.).

HPLC analysis conditions of the compound of Example 71 HPLC, 20 min: Column: X-Bridge C-18 (3.5 µm, 150× 4.6 mm i.d.; Waters Corporation), Eluent: A=10 mM ammonium acetate, B=acetonitrile, Flow rate: 1.0 mL/min, Temp.: 40° C., Detector: UV 280 nm. Gradient is as follow. A:B=90: 10 to 5:95 (12 min) to 2:98 (15 min) to 2:98 (20 min), 90:10 (20.1-30 min) HPLC system; Shimadzu LC-20A, Detector; Shimadzu SPD-20A, wave length; 280 nm

[Pharmacological Test]

BRD4 Inhibitory Activity Evaluation Test

In order to evaluate BRD4 inhibitory activity of the present compounds, BRD4-H4KAc4 binding assay was carried out by an amplified luminescence proximity homogeneous assay. The specific method is described below.

(Preparation of Reagents)

10×Assay buffer (500 mM HEPES, 1M NaCl, 0.5% CHAPS, 1% BSA, pH 7.4) HEPES (available from DOJINDO LABORATORIES, Cat No. GB10), NaCl (available from Wako Pure Chemical Industries, Ltd., Cat No. 191-01665), CHAPS (available from DOJINDO LABORATORIES, Cat No. C008) and BSA (available from Wako Pure Chemical Industries, Ltd., Cat No. 013-21275) were dissolved in MilliQ water, and the mixture was adjusted to pH 7.4. After adjustment of the pH, the solution was diluted in measuring cylinder with MilliQ water to prepare 10×Assay buffer with final concentrations of 500 mM HEPES, 1M NaCl, 0.5% CHAPS and 1% BSA solution.

1×Assay Buffer

10×Assay buffer was diluted with MilliQ water to 10-fold to prepare 1×Assay buffer.

1 mM H4KAc4 Peptide Stock Solution

H4KAc4 peptide (available from Toray Research Center, Inc., sequence SGRGK(Ac)GGK(Ac)GLGK(Ac)GGAK (Ac)RHR-K(Biotin)-NH2) was dissolved in 1×Assay buffer to prepare 1 mM H4KAc4 peptide stock solution.

250 nM H4KAc4 Peptide Solution 1 mM H4KAc4 peptide stock solution was diluted with 1×Assay buffer to 4,000-fold to prepare 250 nM H4KAc4 peptide solution.

250 nM BRD4 Solution

N-terminal His tag/C-terminal FLAG tag-fused type Recombinant BRD4 (44-168) protein (available from Active Motif, Cat No. 31380) was diluted with 1×Assay buffer to 1,250-fold to prepare 250 nM BRD4 solution.

Streptavidin Donor Beads 5 mg/mL of AlphaScreen streptavidin donor beads (available from PerkinElmer, Cat No. 6760002) was diluted with 1×Assay buffer to 50-fold to prepare 100 µg/mL of Streptavidin donor beads.

Nickel Chelate Acceptor Beads 5 mg/mL of AlphaScreen Nickel chelate acceptor beads (available from Perkin Elmer, Cat No. 6760619M) was diluted with 1×Assay buffer to 50-fold to prepare 100 µg/mL of Nickel chelate acceptor beads.

AlphaScreen Beads

100 µg/mL of Streptavidin donor beads and 100 µg/mL of Nickel chelate acceptor beads were mixed with equal amounts to prepare AlphaScreen beads.

1% DMSO Solution

DMSO (available from Wako Pure Chemical Industries, Ltd., Cat No. 049-07213) was diluted with 1×Assay buffer to 50-fold to prepare 1% DMSO solution.

Compound Solution

Each compound was dissolved in DMSO to prepare 5 mM stock solution.

Each 5 mM stock solution was diluted with 1×Assay buffer to 100-fold to prepare each 50 µM solution.

Each 50 µM solution was serially diluted with 1% DMSO solution to prepare 15 µM, 5 µM, 1.5 µM, 0.5 µM, 0.15 µM, 0.05 µM, 0.015 µM and 0.005 µM solution, respectively.

(Test Method and Measurement Method)

Experimental Procedure

1% DMSO solution (control) and 2 µL of each compound solution in each concentration were added to each well of AlphaPlate-384 (from PerkinElmer, Cat No. 6008350). Next, 2 µL of 250 nM BRD4 solution was added to each well of AlphaPlate-384. Further, 2 µL of 250 nM H4KAc4 peptide solution was added to each well of AlphaPlate-384. After addition of the 250 nM H4KAc4 peptide solution, the mixture was allowed to stand at room temperature under light shielding for 60 minutes, and 4 µL of AlphaScreen beads were added to each well of AlphaPlate-384. After addition of the AlphaScreen beads, the mixture was allowed to stand at room temperature under light shielding for 60 minutes, emission at 520-620 nm upon excitation at 680 nm was detected by EnVision multilabel counter (from PerkinElmer), and binding of BRD4 and H4KAc4 was detected. Incidentally, the evaluation of each compound was carried out in duplicate (2 well per 1 compound).

(Calculation of BRD4 Inhibition Rate)

The BRD4 inhibition rate (%) was calculated by the following equation using Microsoft EXCEL 2010.

BRD4 inhibition rate (%)=100−{(luminescence intensity average value of each compound added well)−(average value of luminescence intensity of blank well))/(average value of luminescence intensity of control well)−(average value of luminescence intensity of blank well)}×100

(Test Results and Consideration)

The BRD4 inhibition rates (%) for the compounds of Examples 1 to 91 as the test compounds are shown in Table 1.

As a result of the BRD4-H4KAc4 binding assay, the present compounds showed excellent BRD4 inhibitory activity.

TABLE 1

| Example | BRD4-H4KAc4 binding % of inhibition@10 uM |
|---|---|
| 1 | 99.9 |
| 2 | 100.1 |
| 3 | 100.3 |
| 4 | 100.3 |
| 5 | 100.3 |
| 6 | 100.3 |
| 7 | 99.8 |
| 8 | 100.1 |
| 9 | 100.1 |
| 10 | 100.1 |
| 11 | 100.0 |
| 12 | 100.2 |
| 13 | 100.2 |
| 14 | 100.2 |
| 15 | 22.3 |
| 16 | 100.2 |
| 17 | 69.7 |
| 18 | 100.2 |
| 19 | 96.6 |
| 20 | 82.2 |
| 21 | 100.2 |

TABLE 1-continued

| Example | BRD4-H4KAc4 binding % of inhibition@10 uM |
|---|---|
| 22 | 100.0 |
| 23 | 100.1 |
| 24 | 100.0 |
| 25 | 100.2 |
| 26 | 100.2 |
| 27 | 100.6 |
| 28 | 100.7 |
| 29 | 100.9 |
| 30 | 100.9 |
| 31 | 97.8 |
| 32 | 100.0 |
| 33 | 99.2 |
| 34 | 100.0 |
| 35 | 6.6 |
| 36 | 100.2 |
| 37 | 100.3 |
| 38 | 100.3 |
| 39 | 100.3 |
| 40 | 100.0 |
| 41 | — |
| 42 | 100.1 |
| 43 | 100.1 |
| 44 | 99.3 |
| 45 | 99.9 |
| 46 | 100.0 |
| 47 | 100.0 |
| 48 | 100.0 |
| 49 | 100.0 |
| 50 | 100.0 |
| 51 | 100.2 |
| 52 | 100.0 |
| 53 | 100.0 |
| 54 | 99.9 |
| 55 | 100.0 |
| 56 | 100.0 |
| 57 | 100.1 |
| 58 | 100.1 |
| 59 | 100.1 |
| 60 | 100.3 |
| 61 | 100.2 |
| 62 | 100.2 |
| 63 | 100.2 |
| 64 | 100.2 |
| 65 | 100.2 |
| 66 | 100.2 |
| 67 | 100.2 |
| 68 | 19.2 |
| 69 | 52.0 |
| 70 | 100.1 |
| 71 | 100.0 |
| 72 | 100.1 |
| 73 | 100.1 |
| 74 | 100.1 |
| 75 | 100.2 |
| 76 | 100.0 |
| 77 | 100.1 |
| 78 | 100.1 |
| 79 | 100.1 |
| 80 | 100.1 |
| 81 | 100.1 |
| 82 | 100.1 |
| 83 | 100.1 |
| 84 | 100.1 |
| 85 | 13.3 |
| 86 | 100.1 |
| 87 | 100.1 |
| 88 | 100.1 |
| 89 | 100.1 |
| 90 | 100.1 |
| 91 | 22.4 |

[Pharmacological Test]
NF-κB Inhibitory Activity Evaluation Test

In order to evaluate NF-κB inhibitory activity of the present compounds, NF-κB reporter gene assay was carried out. The specific method is described below.

(Preparation of Reagents)
Culture Medium

To Dulbecco's modified Eagle medium (available from Nacalai Tesque, Cat No. 08549-35) were added fatal bovine serum (available from Bio West, Cat No. S1820) and Penicillin-Streptomycin (available from Gibco, Cat No. 15140122), to prepare a culture medium with the final concentrations of 10% fatal bovine serum, 100 U/mL penicillin and 100 U/mL streptomycin.

TNF-α Solution

Gene recombinant human TNF-α (available from R&D systems, Cat No. 210-TA) was dissolved in D-PBS(−) (available from Wako Pure Chemical Industries, Ltd., Cat No. 293-72601) to prepare 100 μg/mL of TNF-α solution stock solution. 100 μg/mL of the TNF-α solution stock solution was diluted with the culture medium to prepare 10 ng/mL of TNF-α solution.

2% DMSO Solution

DMSO (available from Wako Pure Chemical Industries, Ltd., Cat No. 049-07213) was diluted to 50-fold with the culture medium to prepare 2% DMSO Solution Compound Solution Each compound was dissolved in DMSO to prepare 5 mM stock solution. Each 5 mM stock solution was diluted with the culture medium to 50-fold to prepare each 100 M solution.

Each 100 M solution was serially diluted with 2% DMSO solution to prepare 10 μM, 1 μM, and 0.1 M solution, respectively.

(Test Method and Measurement Method)
Experimental Procedure

A549/NF-κB-luc cells (available from Panomics, Cat No. LR0051) were prepared at 375,000 cells/mL in the culture medium. The 375,000 cells/mL A549/NF-κB-luc cell suspension was seeded at 80 μL each on a white 96-well plate (available from Greiner, Cat No. 655073). One hour after seeding the cells, 10 μL of 2% DMSO solution (control) and each compound solution in each concentration were added to each well of the 96-well plate. One hour after the addition of each compound solution, 10 ng/mL of the TNF-α solution (10 μL) was added to each well of the 96-well plate. Three hours after the addition of 10 ng/mL of the TNF-α solution, 100 μL of Steady-Glo reagent (available from Promega, Cat No. E2510) was added to each well of the 96-well plate. After 30 to 90 minutes of the addition of the Steady-Glo reagent, the luminescence intensity of each well was detected by EnVision multilabel counter (available from PerkinElmer).

(Calculation of NF-κB Inhibition Rate)

NF-κB inhibition rate (%) was calculated by the following equation using Microsoft EXCEL 2010.

$$NF\text{-}\kappa B \text{ inhibition rate (\%)}=100-\{(\text{luminescence intensity average value of each compound added well})-(\text{average value of luminescence intensity of blank well}))/(\text{average value of luminescence intensity of control well})-(\text{average value of luminescence intensity of blank well})\}\times 100$$

In addition, IC50 values were calculated from the calculated NF-κB inhibition rate (%) using curve fitting software XLfit (available from IDBS).

(Test Results and Consideration)

NF-κB inhibition rates (IC50 value) for the compounds of Examples 1 to 109 as the test compounds are shown in Table 2.

As a result of the NF-κB reporter gene assay, the present compounds showed NF-κB inhibitory activity.

TABLE 2

| Example | NF-κB activity IC50 (nM) |
|---------|--------------------------|
| 3 | 51.9 |
| 5 | 27.5 |
| 6 | 86.4 |
| 7 | 735.2 |
| 8 | 104.1 |
| 9 | 17.6 |
| 10 | 191.6 |
| 11 | 291.3 |
| 12 | 32.1 |
| 13 | 233.4 |
| 14 | 275.7 |
| 16 | 77.5 |
| 18 | 144.1 |
| 19 | 1321.8 |
| 21 | 30.3 |
| 22 | 33.6 |
| 23 | 157.9 |
| 24 | 1054.7 |
| 25 | 50.3 |
| 26 | 12.3 |
| 27 | 3101.5 |
| 29 | 265.1 |
| 31 | 150.2 |
| 33 | 87.2 |
| 34 | 611.7 |
| 36 | 401.1 |
| 38 | 106.4 |
| 39 | 620.0 |
| 40 | 699.2 |
| 42 | 1148.0 |
| 43 | 1833.2 |
| 44 | 9850.3 |
| 45 | 429.0 |
| 46 | 682.6 |
| 47 | 554.4 |
| 48 | 296.6 |
| 49 | 197.3 |
| 50 | 355.0 |
| 51 | 264.9 |
| 52 | 5232.6 |
| 53 | 2982.2 |
| 55 | 2763.3 |
| 56 | 942.3 |
| 57 | 558.0 |
| 58 | 728.4 |
| 60 | 1685.9 |
| 61 | 376.9 |
| 63 | 5235.9 |
| 64 | 5492.4 |
| 65 | 895.6 |
| 70 | 1833.7 |
| 71 | 633.7 |
| 73 | 246.2 |
| 74 | 2139.2 |
| 75 | 1926.8 |
| 77 | 1952.5 |
| 78 | 1260.0 |
| 79 | 741.9 |
| 80 | 1109.2 |
| 81 | 47.2 |
| 82 | 135.4 |
| 83 | 2818.3 |
| 86 | 95.3 |
| 87 | 1393.4 |
| 88 | 630.6 |
| 89 | 555.7 |
| 90 | 297.5 |
| 92 | 34.2 |

TABLE 2-continued

| Example | NF-κB activity IC50 (nM) |
|---------|--------------------------|
| 94 | 96.0 |
| 99 | 1644.4 |
| 103 | 288.6 |
| 104 | 3943.6 |
| 105 | 4832.8 |
| 106 | 1837.7 |
| 107 | 2317.4 |
| 108 | 4019.5 |

[Pharmacological Test]

*LPS-Induced IL-6 Production Model Test

In order to evaluate the inhibitory activity of inflammatory cytokine production in the present compounds, LPS-induced IL-6 production model evaluation was carried out. The specific method is described below.

(Preparation of Reagents)

LPS Solution

Lipopolysaccharides from *Escherichia coli* 055: B5 (available from Sigma Aldrich, Cat No. L2880) was dissolved in physiological saline (available from Otsuka Pharmaceutical Factory, Inc.) to prepare 100 μg/mL of LPS solution.

1% Methyl Cellulose Solution

An appropriate amount of methyl cellulose (available from Tokyo Chemical Industry Co., Ltd., Cat No. M0292) was weighted and dissolved in MilliQ water to prepare 1% methyl cellulose solution.

Administration Solutions Comprising the Compound

An appropriate amount of each compound was weighed, triturated with an agate mortar, and suspended or dissolved in 1% methyl cellulose solution to prepare 1 mg/mL solution.

(Test Method and Measurement Method)

Experimental Procedure

C57BL/6J mice (male, Purchaser: Charles River Laboratories Japan, Inc.) were weighted, before divided into normal group, control group and each compound-administered group based on the measured body weight using a random number, wherein each group contained 6 samples. The mice were manually held in hands and forced orally administered the 1% methyl cellulose solution (normal and control group) or each administration solution comprising the compound (each compound-administered group) at a dose of 10 mL/kg into stomach using a feeding needle. After 30 minutes from administration of the 1% methyl cellulose solution or each compound administration solution, the mice were manually held in hands and intraperitoneally administered physiological saline (normal group) or LPS solution (control and each compound-administered group) at a dose of 1 mg/kg. After 60 minutes from administration of the LPS solution, whole blood was collected from the abdominal vena cava of each mouse under isoflurane inhalation anesthesia (available from Mylan Seiyaku Ltd.), and the mice were euthanized. The collected blood was allowed to stand at room temperature for one hour, and then centrifuged at 1,500 G for 10 minutes to collect a serum (supernatant). The collected serum was stored in a deep freezer set at −80° C. until the measurement of IL-6 in the serum. The IL-6 concentration in the serum of each mouse was measured by a commercially available kit (available from R&D systems, Cat No. M6000B), according to the protocol attached thereto.

(Calculation of IL-6 Production Inhibition Rate)

The IL-6 production inhibition rate (%) was calculated by the following equation using Microsoft EXCEL 2010.

IL-6 production inhibition rate (%)=100−{(average value of IL-6 concentration in serum of each compound-administered group)−(average value of IL-6 concentration in serum of normal group))/(average value of IL-6 concentration in serum of control group)−(average value of IL-6 concentration in serum of normal group)}×100

(Test Results and Consideration)

The IL-6 production inhibition rate for Example 4, 5, 25, 30, 31, 32, 38, 49, 71, 92, 93, 94 and various salts of Example 71 as the test compounds is shown in Table 3.

As a result of the LPS-induced IL-6 production model test, the present compounds showed IL-6 production inhibitory activity.

TABLE 3

| Example | LPS-induced IL-6 production (% Inhibition @ 10 mg/kg) |
|---|---|
| 5 | 77.5 |
| 25 | 26.3 |
| 31 | 57.5 |
| 38 | 20.2 |
| 49 | 17.9 |
| 71 | 79.0 |
| 92 | 71.0 |
| 94 | 45.7 |
| 1 Hydrochloride of 71 | 82.7 |
| 1 Maleate of 71 | 82.0 |
| 0.5 Fumarate of 71 | 83.0 |
| 0.5 Succinate of 71 | 83.0 |
| 1 Tosylate of 71 | 85.0 |

[Pharmacological Test]

Rat Type II Collagen-Induced Arthritis Model Evaluation Test

In order to evaluate the inhibitory action for autoimmune and inflammatory diseases of the present compounds, the evaluation of Rat type II collagen-induced arthritis model was carried out. The specific method is described below.

(Preparation of Reagents)

0.05 Mol/L Acetic Acid 0.1 mol/L acetic acid (available from Nacalai Tesque, Cat No. 37307-15) was diluted with MilliQ water to prepare 0.05 mol/L acetic acid.

Emulsion for Sensitization 0.05 mol/L acetic acid was added to bovine type II collagen (Collagen Research Center, Cat No. K42) so that it became 2 mg/mL on the day before primary sensitization and secondary sensitization, and the mixture was allowed to stand overnight in a refrigerator to dissolve the material. Immediately before sensitization, it was mixed with an equal amount of Freund's incomplete adjuvant (available from Difco, Cat No. 263910) to prepare an emulsion for sensitization.

1% Methyl Cellulose Solution

An appropriate amount of methyl cellulose (available from Tokyo Chemical Industry Co., Ltd., Cat No. M0292) was weighted and dissolved in MilliQ water to prepare 1% methyl cellulose solution.

Administration Solutions Comprising the Compound

An appropriate amount of each compound was weighed, triturated with an agate mortar, and suspended or dissolved in 1% methyl cellulose solution to prepare 6 mg/mL solution.

(Test Method and Measurement Method)

Experimental Procedure

LEW/CrlCrlj rats (female, purchased from Charles River Laboratories Japan, Inc.) were weighted on the day of primary sensitization (Day 0) and primary grouped to an arthritis non-induced group and an arthritis induced group based on the measured body weight using a random number. The rats (other than the arthritis non-induced group) were thereafter administrated the emulsion for sensitization (500 µL) into the skin of the dorsum (divided into 5 portions) under general anesthesia with isoflurane inhalation (available from Mylan Seiyaku Ltd.). Seven days after the primary sensitization (Day 7), the rats (other than the arthritis non-induced group) were manually held in hands and administered the emulsion for sensitization (100 µL) into the skin of the tail. On Day 12, the rats developing arthritis were selected, a random number was used to avoid difference in an average hind limb volume between the groups, and the arthritis induced group was secondary grouped to a control group and each compound-administered group, wherein each group contained 8 samples. The rats were forced orally administered 1% methyl cellulose solution (arthritis non-induced group and control group) or each administration solution comprising the compound (each compound-administered group) at a dose of 5 mL/kg into stomach using a feeding needle once a day from Day 12. The volume of both hind limbs of each rat was measured using a plethysmometer (from Unicom) on Day 0, 4, 7, 12, 14, 18 and 21.

(Calculation of Limb Edema Suppression Rate) The limb edema suppression rate (%) was calculated by the following equation using Microsoft EXCEL 2010.

Limb edema suppression rate (%)=100−{(average value of hind limb volume of each compound-administered group on Day 21)−(average value of hind limb volume of arthritis non-induced group on Day 21))/(average value of hind limb volume of control group on Day 21)−(average value of hind limb volume of arthritis non-induced group on Day 21)}×100

(Test Results and Consideration)

The limb edema suppression rate (%) for Examples 5, 25, 31, 38, 49 and 71 as the test compounds is shown in Table 4.

TABLE 4

| Example | Limb edema suppression rate(%) |
|---|---|
| 5 | 92.9 |
| 25 | 39.8 |
| 31 | 68.9 |
| 38 | 11.9 |
| 71 | 93.8 |

As a result of the evaluation of the type II collagen-induced arthritis model, the present compounds showed a limb edema suppression effect.

[Pharmacokinetics Test]

Pharmacokinetics Test in Rats

In order to evaluate the transition of plasma concentration of the present compound after oral administration, pharmacokinetics was evaluated in rats. The specific method is described below.

(Preparation of Reagents)

1% Methyl Cellulose Solution

An appropriate amount of methyl cellulose (available from Tokyo Chemical Industry Co., Ltd., Cat No. M0292) was weighted and dissolved in MilliQ water to prepare 1% methyl cellulose solution.

Administration Solutions Comprising the Compound

Appropriate amounts of Example 71 and various salts thereof were weighed, triturated with an agate mortar, and suspended or dissolved in 1% methyl cellulose solution to 2 mg/mL (as a converted quantity of Example 71 considering the correction of purify).

Standard Solution

Example 71 was dissolved in acetonitrile (available from Kishida Chemical Co., Ltd., Cat No. 140-00401) to 200 g/mL, which was used as a standard stock solution. The standard stock solution was serially diluted with acetonitrile to 1, 2, 4, 40, 200, 500, 800 and 1,000 g/mL, which were used as a standard solution for calibration curves.

Internal Standard Solution

Etizolam (available from Wako Pure Chemical Industries, Ltd., Cat No. 057-06811) was dissolved in acetonitrile (available from Kishida Chemical Co., Ltd., Cat No. 140-00401) to 200 g/mL, which was used as an internal standard stock solution. The internal standard stock solution was diluted with acetonitrile to 20 μg/mL, which was used as an internal standard solution.

Re-Dissolved Solution

An appropriate amount of ammonium formate (available from Kanto Chemical Co., Inc., Cat No. 01294-00) was weighed to prepare 10 mmol/L ammonium formate solution. 10 mmol/L ammonium formate solution and acetonitrile (available from Kishida Chemical Co., Ltd., Cat No. 140-00401) were mixed with a volume ratio of 7:3 to prepare a re-dissolved solution.

(Test Method and Measurement Method)

Experimental Procedure

LEW/CrlCrlj rats (male, purchased form Charles River Laboratories Japan, Inc.) were weighted, a random number based on the measured body weight was used to avoid difference in average body weight among groups, and the rats were divided into groups, wherein each groups contained 4 rats. The rats were manually held in hands and forced orally administered each administration solution comprising the compound at a dose of 5 mL/kg into stomach using a feeding needle. At 0.5, 1, 3, 6 and 24 hours after the administration of each administration solution comprising the compound, the rats were manually held in hands, and blood was collected from the jugular vein or subclavian vein using a heparin-treated injection syringe. The obtained blood was centrifuged at 1,500 G for 10 minutes, and plasma was collected as an actual sample. In addition, plasma was collected from rats before the administration of the compound in the same manner, which was used as blank plasma. The collected actual samples and blank plasma were stored in a freezer set at −70° C. until the measurement of the compound concentration. To 20 μL of each actual sample were added 20 μL of acetonitrile (available from Kishida Chemical Co., Ltd., Cat No. 140-00401), 100 μL of MilliQ water and 20 μL of the internal standard solution to prepare an analytical sample. In addition, to 20 μL of blank plasma were added 20 μL or 40 μL of acetonitrile (available from Kishida Chemical Co., Ltd., Cat No. 140-00401) and 100 μL of MilliQ water (a blank sample or a zero sample, respectively). A standard sample for a calibration curve was prepared by mixing 20 μL of blank plasma, 20 μL of the standard solution for a calibration curve in each concentration, 100 μL of MilliQ water and 20 μL of the internal standard solution. Whole amount of the prepared each sample was applied to a diatomaceous earth column for liquid-liquid extraction (available from Biotage, Cat No. 820-0200), tert-butyl methyl ether (available from Kanto Chemical Co., Inc., Cat No. 04418-5B) was added and eluted by natural dropping, and the obtained eluate was concentrated to dryness under a nitrogen stream. The residue was dissolved in the re-dissolved solution and 10 μL of each sample was injected into the LC/MS/MS apparatus.

(Calculation of Pharmacokinetics Parameter)

LC/MS/MS analysis was carried out under the following conditions. Analytical column: Hydrosphere C18, 3 μm, 2.0 mm I.D.×50 mm (from YMC, Cat No. HS12S03-0502WT)
Mobile phase A: 10 mmol/L ammonium formate
Mobile phase B: acetonitrile
Gradient conditions:

TABLE 5

| Time (min) | Mobile phase A | Mobile phase B |
|---|---|---|
| 0 | 70 | 30 |
| 1 | 70 | 30 |
| 6 | 10 | 90 |
| 7 | 10 | 90 |
| 7.01 | 70 | 30 |
| 10.5 | 70 | 30 |

Flow rate: 0.3 mL/min.
Column temperature: 50° C.
Peak area calculation, peak area ratio calculation, preparation of calibration and quantification used in calculating the concentration for the LC/MS/MS analysis were carried out by Analyst ver.1.6.2 (available from AB Sciex). In addition, by using the obtained concentration measurement results, these were analyzed by Non-compartmental model of a pharmacokinetics analysis program WinNonlin ver.6.1 (Pharsight Corporation), and the pharmacokinetics parameter was calculated.

(Test Results and Consideration)

Pharmacokinetics parameter for the above-mentioned Example 71 and various salts thereof (crystals) as the test compounds is shown in Table 6.

As a result of the pharmacokinetics evaluation, the present compounds showed excellent absorbability when orally administrated.

TABLE 6

| Test article | Animal No. | Concentration (ng/mL) | | | | | PK parameter | | | | | | |
| | | Sampling time (h) | | | | | $C_{max}$ | $T_{max}$ | $AUC_t$ | $AUC_{inf}$ | MRT | Kel | $T_{1/2}$ |
| | | 0.5 | 1 | 3 | 6 | 24 | (ng/mL) | (h) | (ng · h/mL) | (ng · h/mL) | (h) | (1/h) | (h) |
| Example 71 | Mean (n = 4) | 22.1 | 14.79 | 4.23 | 1.46 | NA | 22.40 | 0.75 | 42.28 | 61.82 | 1.82 | 0.55 | 1.31 |
| | SD | 20.9 | 10.49 | 0.73 | 0.38 | NA | 20.6 | 0.29 | 25.09 | NA | 0.46 | NA | NA |
| 1 Hydrochloride of Example 71 | Mean (n = 4) | 111.0 | 34.0 | 6.75 | 1.5 | NA | 111.0 | 0.50 | 114.07 | 105.65 | 1.12 | 0.57 | 1.24 |
| | SD | 37.1 | 16.0 | 1.75 | 0.17 | NA | 37.0 | 0.00 | 35.63 | 33.59 | 0.2 | 0.08 | 0.17 |
| 1 Maleate of Example 71 | Mean (n = 4) | 80.1 | 42.9 | 7.69 | 1.66 | NA | 80.1 | 0.50 | 115.41 | 118.01 | 1.27 | 0.64 | 1.09 |
| | SD | 12.1 | 4 | 1.17 | 0.1 | NA | 12.1 | 0.00 | 7.48 | 7.38 | 0.07 | 0.03 | 0.05 |

TABLE 6-continued

| | | Concentration (ng/mL) | | | | | PK parameter | | | | | | |
|---|---|---|---|---|---|---|---|---|---|---|---|---|---|
| | | Sampling time (h) | | | | | $C_{max}$ | $T_{max}$ | $AUC_t$ | $AUC_{inf}$ | MRT | Kel | $T_{1/2}$ |
| Test article | Animal No. | 0.5 | 1 | 3 | 6 | 24 | (ng/mL) | (h) | (ng · h/mL) | (ng · h/mL) | (h) | (1/h) | (h) |
| 0.5 Fumarate | Mean (n = 4) | 15.70 | 11.3 | 4.28 | 2.29 | NA | 15.70 | 0.50 | 31.38 | 54.47 | 1.63 | 0.35 | 3.02 |
| of Example 71 | SD | 10.6 | 7.2 | 1.83 | NA | NA | 10.60 | 0.00 | 19.74 | NA | 0.58 | NA | NA |
| 0.5 Succinate | Mean (n = 4) | 79.8 | 36.2 | 6.88 | 1.3 | NA | 79.8 | 0.50 | 104.34 | 106.41 | 1.30 | 0.64 | 1.10 |
| of Example 71 | SD | 56.3 | 17.5 | 2.47 | 0.12 | NA | 56.3 | 0.00 | 54.10 | 53.79 | 0.18 | 0.10 | 0.18 |
| 1 Tosylate | Mean (n = 4) | 62.1 | 34.7 | 7.04 | 2.46 | NA | 62.1 | 0.50 | 95.75 | 101.11 | 1.48 | 0.52 | 1.42 |
| of Example 71 | SD | 41.4 | 20.4 | 1.43 | 1.54 | NA | 41.4 | 0.00 | 48.59 | 48.8 | 0.25 | 0.14 | 0.35 |

BLQ: Below the lower limit of quantification (1.00 ng/mL)
NA: Not applicable,
NC: Not calculated

PREPARATION EXAMPLES

General Preparation Examples of the present compounds are shown below.

Preparation Example 1: Tablets

Within 150 mg

| Present compound | 1 mg |
|---|---|
| Lactose | 100 mg |
| Corn starch | 40 mg |
| Carboxymethyl cellulose calcium | 4.5 mg |
| Hydroxypropyl cellulose | 4 mg |
| Magnesium stearate | 0.5 mg |

A target tablet can be obtained by coating the tablet of the above-mentioned prescription using 3 mg of coating agents (for example, generally used coating agents such as hydroxypropylmethyl cellulose, macrogol, a silicone resin). A desired tablet can also be obtained by appropriately changing the present compound, the type of the additives and/or the amount of the additives.

Preparation Example 2: Capsules

Within 150 mg

| Present compound | 5 mg |
|---|---|
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the present compound, the type of the additives and/or the amount of the additives.

Preparation Example 3: Injections

Within 1 vial (5 mL)

| Present compound | 30 mg |
|---|---|
| Polysorbate 80 | 5 mg |
| Conc. glycerin | 100 mg |
| Water for injections | 5 mL |

A desired injection can be obtained by appropriately changing the present compound, the type of the additives and/or the amount of the additives.

INDUSTRIAL APPLICABILITY

The 6H-thieno[2,3-e][1,2,4]triazolo[3,4-c][1,2,4]triazepine derivatives or salts thereof of the present invention have BRD4 inhibitory activity, and thus, they are useful as medicaments, in particular, as prophylaxis or therapeutic agents for diseases associated with BRD4.

The invention claimed is:
1. A compound of formula (I):

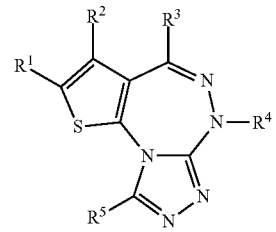

wherein
$R^1$ is H, halogen, $C_{1-6}$ alkyl, halo-$C_{1-6}$ alkyl, hydroxy-$C_{1-6}$ alkyl, $C_{1-6}$ alkoxy or halo-$C_{1-6}$ alkoxy;
$R^2$ is H, halogen, $C_{1-6}$ alkyl, halo-$C_{14}$ alkyl, hydroxy-$C_{1-6}$ alkyl, $C_{1-6}$ alkoxy or halo-$C_{1-6}$ alkoxy;
$R^3$ is substituted phenyl substituted with at least one substituent(s) selected from the group consisting of halogen, hydroxy, amino, nitro, cyano, carboxy, $C_{1-6}$ alkyl, halo-$C_{1-6}$ alkyl, hydroxy-$C_{1-6}$ alkyl, $C_{1-6}$ alkoxy, halo-$C_{1-6}$ alkoxy, —$NR^aR^b$, —OC(O)—$R^a$, —$NR^bC(O)$—$R^a$, —C(O)—$OR^a$ and —C(O)—$NR^bR^a$;
$R^4$ is unsubstituted pyridyl-$C_{1-6}$ alkyl;
$R^5$ is H, halogen, $C_{1-6}$ alkyl, halo-$C_{1-6}$ alkyl, hydroxy-$C_{1-6}$ alkyl, $C_{1-6}$ alkoxy, halo-$C_{1-6}$ alkoxy or hydroxy $C_{1-6}$ alkoxy;
$R^a$ is H, $C_{1-6}$ alkyl or halo-$C_{1-6}$ alkyl; and
$R^b$ is H, $C_{1-6}$ alkyl or halo-$C_{1-6}$ alkyl,
or a pharmaceutically acceptable salt thereof, provided that the following:
4-(4-chlorophenthyl)-2-ethyl-9-methyl-6-(pyridin-3-ylmethyl)-6H-thieno[2,3-e][1,2,4]triazolo[3,4-c][1,2,4]triazepine
4-(4-chlorophenyl)-2-ethyl-9-methyl-6-(pyridin-4-ylmethyl)-6H-thieno[2,3-e][1,2,4]triazolo[3,4-c][1,2,4]triazepine 4-(4-methoxyphenyl)-2,3,9-trimethyl-6-(pyridin-3-ylmethyl)-6H-thieno[2,3-e][1,2,4]triazolo[3,4-c][1,2,4]triazepine 4-(4-methoxyphenyl)-2,3,9-trimethyl-6-(pyridin-4-ylmethyl)-6H-thieno[2,3-e][1,2,4]triazolo[3,4-c][1,2,4]triazepine 4-(4-chlorophenyl)-2,3,9-trimethyl-6-(pyridin-3-ylmethyl)-6H-thieno[2,3-e][1,2,4]triazolo[3,4-c][1,2,4]triazepine 4-(4-chlorophenyl)-2,3,9-trimethyl-6-(pyridin-4-ylmethyl)-6H-thieno[2,3-e]-[1,2,4]triazolo[3,4-c][1,2,4]triazepine 4-((4-(4-chlorophenyl)-2-ethyl-9-methyl-6H-thieno[2,3-e][1,2,4]triazolo[3,4-c][1,2,4]triazepin-6-yl)methyl)pyridine 1-oxide 3-((4-(4-chlorophenyl)-2-ethyl-9-methyl-6H-thieno[2,3-e][1,2,4]triazolo[3,4-c][1,2,4]triazepin-6-yl)methyl)pyridine 1-oxide 4-(2-chlorophenyl)-2,3,9-trimethyl-6-(pyridin-4-ylmethyl)-6H-thieno[2,3-e][1,2,4]triazolo[3,4-c][1,2,4]triazepine 4-(2-chlorophenyl)-2,3,9-trimethyl-6-(pyridin-3-ylmethyl)-6H-thieno[2,3-e][1,2,4]triazolo[3,4-c][1,2,4]triazepine 3-((4-(4-chlorophenyl)-2,3,9-trimethyl-6H-thieno[2,3-e][1,2,4]triazolo[3,4-c][1,2,4]triazepin-6-yl)methyl)pyridine 1-oxide and 4-((4-(2-chlorophenyl)-2,3,9-trimethyl-6H-thieno[2,3-e][1,2,4]triazolo[3,4-c][1,2,4]triazepin-6-yl)methyl)pyridine 1-oxide are excluded.

2. The compound of formula (I) according to claim 1 or a pharmaceutically acceptable salt thereof, wherein $R^1$ is H, $C_{1-6}$ alkyl, halo-$C_{1-6}$ alkyl, or hydroxy-$C_{1-6}$ alkyl;

$R^2$ is H, $C_{1-6}$ alkyl, halo-$C_{1-6}$ alkyl, or hydroxy-$C_{1-6}$ alkyl;

$R^3$ is substituted phenyl substituted with at least one substituent(s) selected from the group consisting of halogen, amino, nitro, $C_{1-6}$ alkoxy, halo-$C_{1-6}$ alkoxy, —$NR^a R^b$, and —$NR^b C(O)$—$R^a$;

$R^4$ is pyridin-2-ylmethyl, pyridin-3-ylmethyl, or pyridin-4-ylmethyl;

$R^5$ is $C_{1-6}$ alkyl, halo-$C_{1-6}$ alkyl, or hydroxy-$C_{1-6}$ alkyl.

3. The compound of formula (I) according to claim 1 or a pharmaceutically acceptable salt thereof, wherein $R^1$ is $C_{1-6}$ alkyl;

$R^2$ is $C_{1-6}$ alkyl;

$R^3$ is substituted phenyl substituted with at least one substituent(s) selected from the group consisting of halogen, amino, and —$NR^b C(O)$—$R^a$;

$R^4$ is pyridin-2-ylmethyl, or pyridin-3-ylmethyl;

$R^5$ is $C_{1-6}$ alkyl;

$R^a$ is $C_{1-6}$ alkyl or halo-$C_{1-6}$.

4. The compound of formula (I) according to claim 1 or a pharmaceutically acceptable salt thereof, wherein $R^1$ is methyl;

$R^2$ is methyl;

$R^3$ is substituted phenyl substituted with at least one substituent(s) selected from the group consisting of amino and —$NR^b C(O)$—$R^a$;

$R^4$ is pyridin-3-ylmethyl;

$R^5$ is methyl;

$R^a$ is $C_{1-6}$ alkyl; and $R^b$ is H.

5. The compound according to claim 1 selected from:

4-(4-chlorophenyl)-2,3,9-trimethyl-6-(pyridin-2-ylmethyl)-6H-thieno[2,3-e][1,2,4]triazolo[3,4-c][1,2,4]triazepine 4-(4-chlorophenyl)-9-methyl-6-(pyridin-3-ylmethyl)-6H-thieno[2,3-e][1,2,4]triazolo[3,4-c][1,2,4]triazepine 4-(4-chlorophenyl)-9-methyl-6-(pyridin-2-ylmethyl)-6H-thieno[2,3-e][1,2,4]triazolo[3,4-c][1,2,4]triazepine 4-(4-chlorophenyl)-9-methyl-6-(pyridin-4-ylmethyl)-6H-thieno[2,3-e][1,2,4]triazolo[3,4-c][1,2,4]triazepine 2,3,9-trimethyl-4-(4-nitrophenyl)-6-(pyridin-3-ylmethyl)-6H-thieno[2,3-e][1,2,4]triazolo[3,4-c][1,2,4]triazepine N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide 4-(3-chlorophenyl)-2,3,9-trimethyl-6-(pyridin-3-ylmethyl)-6H-thieno[2,3-e][1,2,4]triazolo[3,4-c][1,2,4]triazepine 4-(2-methoxyphenyl)-2,3,9-trimethyl-6-(pyridin-3-ylmethyl)-6H-thieno[2,3-e][1,2,4]triazolo[3,4-c][1,2,4]triazepine 4-(3-methoxyphenyl)-2,3,9-trimethyl-6-(pyridin-3-ylmethyl)-6H-thieno[2,3-e][1,2,4]triazolo[3,4-c][1,2,4]triazepine 4-(2,3,9-trimethyl-6-(pyridin-3-ylmethyl)-6H-thieno[2,3-e][1,2,4]triazolo[3,4-c][1,2,4]triazepin-4-yl)aniline N-(4-(9-(hydroxymethyl)-2,3-dimethyl-6-(pyridin-3-ylmethyl)-6H-thieno[2,3-e][1,2,4]triazolo[3,4-c][1,2,4]triazepin-4-yl)phenyl)acetamide N-(4-(2-(hydroxymethyl)-3,9-dimethyl-6-(pyridin-3-ylmethyl)-6H-thieno[2,3-e][1,2,41]triazolo[3,4-c][1,2,4]triazepin-4-yl)phenylacetamide N-(4-(3-(hydroxymethyl)-2,9-dimethyl-6-(pyridin-3-ylmethyl)-6H-thieno[2,3-e][1,2,4]triazolo[3,4-c][1,2,4]triazepin-4-yl)phenyl)acetamide (4-(4-aminophenyl)-2,3-dimethyl-6-(pyridin-3-ylmethyl)-6H-thieno[2,3-e][1,2,4]triazolo[3,4-c][1,2,4]triazepin-9-yl)methanol (4-(4-aminophenyl)-3,9-dimethyl-6-(pyridin-3-ylmethyl)-6H-thieno[2,3-e][1,2,4]triazolo[3,4-c][1,2,4]triazepin-2-yl)methanol (4-(4-aminophenyl)-2,9-dimethyl-6-(pyridin-3-ylmethyl)-6H-thieno[2,3-e][1,2,4]triazolo[3,4-c][1,2,4]triazepin-3-yl)methanol 2-(4-(4-aminophenyl)-9-methyl-6-(pyridin-3-ylmethyl)-6H-thieno[2,3-e][1,2,4]triazolo[3,4-c][1,2,4]triazepin-3-yl)ethane-1-ol and N-(4-(3-(2-hydroxyethyl)-9-methyl-6-(pyridin-3-ylmethyl)-6H-thieno[2,3-e][1,2,4]triazolo[3,4-c][1,2,4]triazepin-4-yl)phenyl)acetamide or a pharmaceutically acceptable salt thereof.

6. A pharmaceutical composition comprising the compound according to claim 1 and a therapeutically inert carrier.

7. The compound according to claim 1 selected from:

N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide and 4-(2,3,9-trimethyl-6-(pyridin-3-ylmethyl)-6H-thieno[2,3-e][1,2,4]triazolo[3,4-c][1,2,4]triazepin-4-yl)aniline, or a pharmaceutically acceptable salt thereof.

8. A hydrochloride, maleate, succinate or tosylate of the compound selected from:

N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide and 4-(2,3,9-trimethyl-6-(pyridin-3-ylmethyl)-6H-thieno[2,3-e][1,2,4]triazolo[3,4-c][1,2,4]triazepin-4-yl)aniline.

9. A hydrochloride, maleate, succinate or tosylate of N-(4-(2,3,9-trimethyl-6-(pyridin-3-ylmethyl)-6H-thieno[2,3-e][1,2,4]triazolo[3,4-c][1,2,4]triazepin-4-yl)phenyl)acetamide.

* * * * *

UNITED STATES PATENT AND TRADEMARK OFFICE
CERTIFICATE OF CORRECTION

PATENT NO.        : 11,186,588 B2
APPLICATION NO.   : 16/617201
DATED             : November 30, 2021
INVENTOR(S)       : Hiroyuki Aono et al.

It is certified that error appears in the above-identified patent and that said Letters Patent is hereby corrected as shown below:

In the Claims

Column 228, Line 46, Claim 1:
"halo-$C_{14}$ alkyl"
Should read:
-- halo-$C_{1-6}$ alkyl --

Column 229, Line 52, Claim 3:
"halo-$C_{1-6}$"
Should read:
-- halo-$C_{1-6}$ alkyl --

Column 230, Line 29, Claim 5:
"[1,2,4l]triazolo"
Should read:
-- [1,2,4]triazolo --

Column 230, Line 30, Claim 5:
"phenylacetamide"
Should read:
-- phenyl)acetamide --

Signed and Sealed this
Eleventh Day of April, 2023

Katherine Kelly Vidal
*Director of the United States Patent and Trademark Office*